(12) United States Patent
Sato

(10) Patent No.: US 12,325,739 B2
(45) Date of Patent: *Jun. 10, 2025

(54) BISPECIFIC SARS-CoV-2 ANTIBODIES AND METHODS OF USE

(71) Applicant: Twist Bioscience Corporation, South San Francisco, CA (US)

(72) Inventor: Aaron Sato, Burlingame, CA (US)

(73) Assignee: Twist Bioscience Corporation, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/149,593

(22) Filed: Jan. 3, 2023

(65) Prior Publication Data

US 2023/0257448 A1   Aug. 17, 2023

Related U.S. Application Data

(60) Provisional application No. 63/296,087, filed on Jan. 3, 2022.

(51) Int. Cl.
*C07K 16/10* (2006.01)
*A61K 39/00* (2006.01)
*A61P 31/14* (2006.01)

(52) U.S. Cl.
CPC .......... *C07K 16/1003* (2023.08); *A61P 31/14* (2018.01); *A61K 2039/545* (2013.01); *C07K 2317/31* (2013.01); *C07K 2317/35* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,368,823 A | 11/1994 | McGraw et al. |
| 5,474,796 A | 12/1995 | Brennan |
| 5,534,507 A | 7/1996 | Cama et al. |
| 5,677,195 A | 10/1997 | Winkler et al. |
| 5,843,767 A | 12/1998 | Beattie |
| 6,013,440 A | 1/2000 | Lipshutz et al. |
| 6,028,189 A | 2/2000 | Blanchard |

(Continued)

FOREIGN PATENT DOCUMENTS

| CN | 101277758 A | 10/2008 |
| EP | 3030682 A2 | 6/2016 |

(Continued)

OTHER PUBLICATIONS

Mattioli et al. 2020. On the Challenges for the Diagnosis of SARS-CoV-2 Based on a Review of Current Methodologies. ACS Sensors 2020 5 (12), 3655-3677. DOI: 10.1021/acssensors.0c01382. p. 3658, 2nd paragraph (Year: 2020).*

(Continued)

*Primary Examiner* — Daniel E Kolker
*Assistant Examiner* — Hilary Ann Petrash
(74) *Attorney, Agent, or Firm* — Helene Laville; HEFIP, LLC

(57) ABSTRACT

Provided herein are methods and compositions relating to improved bispecific antibodies capable of binding and neutralizing SARS-CoV-2 variants.

6 Claims, 76 Drawing Sheets

(32 of 76 Drawing Sheet(s) Filed in Color)

Specification includes a Sequence Listing.

(56) References Cited

U.S. PATENT DOCUMENTS

| | | |
|---|---|---|
| 6,419,883 B1 | 7/2002 | Blanchard |
| 6,472,147 B1 | 10/2002 | Janda et al. |
| 6,492,107 B1 | 12/2002 | Kauffman et al. |
| 6,893,816 B1 | 5/2005 | Beattie |
| 7,163,660 B2 | 1/2007 | Lehmann |
| 7,202,264 B2 | 4/2007 | Ravikumar et al. |
| 8,198,071 B2 | 6/2012 | Goshoo et al. |
| 9,403,141 B2 | 8/2016 | Banyai et al. |
| 9,409,139 B2 | 8/2016 | Banyai et al. |
| 9,555,388 B2 | 1/2017 | Banyai et al. |
| 9,677,067 B2 | 6/2017 | Toro et al. |
| 9,745,619 B2 | 8/2017 | Rabbani et al. |
| 9,765,387 B2 | 9/2017 | Rabbani et al. |
| 9,833,761 B2 | 12/2017 | Banyai et al. |
| 9,839,894 B2 | 12/2017 | Banyai et al. |
| 9,889,423 B2 | 2/2018 | Banyai et al. |
| 9,895,673 B2 | 2/2018 | Peck et al. |
| 9,981,239 B2 | 5/2018 | Banyai et al. |
| 10,053,688 B2 | 8/2018 | Cox |
| 10,272,410 B2 | 4/2019 | Banyai et al. |
| 10,384,188 B2 | 8/2019 | Banyai et al. |
| 10,384,189 B2 | 8/2019 | Peck |
| 10,417,457 B2 | 9/2019 | Peck |
| 10,583,415 B2 | 3/2020 | Banyai et al. |
| 10,618,024 B2 | 4/2020 | Banyai et al. |
| 10,632,445 B2 | 4/2020 | Banyai et al. |
| 10,639,609 B2 | 5/2020 | Banyai et al. |
| 10,669,304 B2 | 6/2020 | Indermuhle et al. |
| 10,744,477 B2 | 8/2020 | Banyai et al. |
| 10,754,994 B2 | 8/2020 | Peck |
| 10,773,232 B2 | 9/2020 | Banyai et al. |
| 10,844,373 B2 | 11/2020 | Cox et al. |
| 10,894,242 B2 | 1/2021 | Marsh et al. |
| 10,894,959 B2 | 1/2021 | Cox et al. |
| 10,907,274 B2 | 2/2021 | Cox |
| 10,936,953 B2 | 3/2021 | Bramlett et al. |
| 10,969,965 B2 | 4/2021 | Malina et al. |
| 10,975,372 B2 | 4/2021 | Cox et al. |
| 10,987,648 B2 | 4/2021 | Peck et al. |
| 11,185,837 B2 | 11/2021 | Banyai et al. |
| 11,214,798 B2 | 1/2022 | Brown |
| 11,263,354 B2 | 3/2022 | Peck |
| 11,332,738 B2 | 5/2022 | Nugent et al. |
| 11,332,740 B2 | 5/2022 | Nugent et al. |
| 11,377,676 B2 | 7/2022 | Wu et al. |
| 11,407,837 B2 | 8/2022 | Glanville |
| 11,452,980 B2 | 9/2022 | Banyai et al. |
| 11,492,665 B2 | 11/2022 | Zeitoun et al. |
| 11,492,727 B2 | 11/2022 | Tabibiazar et al. |
| 11,492,728 B2 | 11/2022 | Sato |
| 11,512,347 B2 | 11/2022 | Peck |
| 11,550,939 B2 | 1/2023 | Peck et al. |
| 11,559,778 B2 | 1/2023 | Banyai et al. |
| 11,562,103 B2 | 1/2023 | Peck |
| 2001/0018512 A1 | 8/2001 | Blanchard |
| 2002/0025561 A1 | 2/2002 | Hodgson |
| 2002/0094533 A1 | 7/2002 | Hess et al. |
| 2002/0095073 A1 | 7/2002 | Jacobs et al. |
| 2002/0160536 A1 | 10/2002 | Regnier et al. |
| 2002/0164824 A1 | 11/2002 | Xiao et al. |
| 2003/0120035 A1 | 6/2003 | Gao et al. |
| 2003/0171325 A1 | 9/2003 | Gascoyne et al. |
| 2004/0087008 A1 | 5/2004 | Schembri |
| 2004/0259146 A1 | 12/2004 | Friend et al. |
| 2005/0137805 A1 | 6/2005 | Lewin et al. |
| 2005/0227235 A1 | 10/2005 | Carr et al. |
| 2006/0127920 A1 | 6/2006 | Church et al. |
| 2007/0196834 A1 | 8/2007 | Cerrina et al. |
| 2008/0085511 A1 | 4/2008 | Peck et al. |
| 2008/0085514 A1 | 4/2008 | Peck et al. |
| 2008/0227160 A1 | 9/2008 | Kool |
| 2008/0287320 A1 | 11/2008 | Baynes et al. |
| 2008/0300842 A1 | 12/2008 | Govindarajan et al. |
| 2009/0062129 A1 | 3/2009 | McKernan et al. |
| 2009/0239759 A1 | 9/2009 | Balch |
| 2009/0285825 A1 | 11/2009 | Kini et al. |
| 2010/0004143 A1 | 1/2010 | Shibahara |
| 2010/0099103 A1 | 4/2010 | Hsieh et al. |
| 2010/0111768 A1 | 5/2010 | Banerjee et al. |
| 2010/0216648 A1 | 8/2010 | Staehler et al. |
| 2010/0311960 A1 | 12/2010 | Dellinger |
| 2011/0172127 A1 | 7/2011 | Jacobson et al. |
| 2011/0217738 A1 | 9/2011 | Jacobson |
| 2012/0129704 A1 | 5/2012 | Gunderson et al. |
| 2012/0164691 A1 | 6/2012 | Eshoo et al. |
| 2012/0231968 A1 | 9/2012 | Bruhn et al. |
| 2012/0264653 A1 | 10/2012 | Carr et al. |
| 2013/0017642 A1 | 1/2013 | Milgrew et al. |
| 2013/0017977 A1 | 1/2013 | Oleinikov |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0130321 A1 | 5/2013 | Staehler et al. |
| 2013/0165328 A1 | 6/2013 | Previte et al. |
| 2014/0106394 A1 | 4/2014 | Ko et al. |
| 2014/0178992 A1 | 6/2014 | Nakashima et al. |
| 2015/0038373 A1 | 2/2015 | Banyai et al. |
| 2015/0120265 A1 | 4/2015 | Amirav-Drory et al. |
| 2015/0196917 A1 | 7/2015 | Kay et al. |
| 2016/0089651 A1 | 3/2016 | Banyai |
| 2016/0090592 A1 | 3/2016 | Banyai et al. |
| 2016/0096160 A1 | 4/2016 | Banyai et al. |
| 2016/0251651 A1 | 9/2016 | Banyai et al. |
| 2016/0303535 A1 | 10/2016 | Banyai et al. |
| 2016/0333340 A1 | 11/2016 | Wu |
| 2016/0339409 A1 | 11/2016 | Banyai et al. |
| 2016/0340672 A1 | 11/2016 | Banyai et al. |
| 2016/0354752 A1 | 12/2016 | Banyai et al. |
| 2017/0095785 A1 | 4/2017 | Banyai et al. |
| 2017/0159044 A1 | 6/2017 | Toro et al. |
| 2017/0327819 A1 | 11/2017 | Banyai et al. |
| 2017/0357752 A1 | 12/2017 | Diggans |
| 2017/0362589 A1 | 12/2017 | Banyai et al. |
| 2018/0029001 A1 | 2/2018 | Banyai et al. |
| 2018/0104664 A1 | 4/2018 | Fernandez |
| 2018/0142289 A1 | 5/2018 | Zeitoun et al. |
| 2018/0264428 A1 | 9/2018 | Banyai et al. |
| 2018/0282721 A1 | 10/2018 | Cox et al. |
| 2019/0314783 A1 | 10/2019 | Banyai et al. |
| 2019/0352635 A1 | 11/2019 | Toro et al. |
| 2019/0366293 A1 | 12/2019 | Banyai et al. |
| 2019/0366294 A1 | 12/2019 | Banyai et al. |
| 2020/0102611 A1 | 4/2020 | Zeitoun et al. |
| 2020/0156037 A1 | 5/2020 | Banyai et al. |
| 2020/0181667 A1 | 6/2020 | Wu et al. |
| 2020/0222875 A1 | 7/2020 | Peck et al. |
| 2020/0283760 A1 | 9/2020 | Nugent et al. |
| 2020/0299322 A1 | 9/2020 | Indermuhle et al. |
| 2020/0299684 A1 | 9/2020 | Toro et al. |
| 2020/0330953 A1 | 10/2020 | Banyai et al. |
| 2021/0002710 A1 | 1/2021 | Gantt et al. |
| 2021/0040476 A1 | 2/2021 | Cox et al. |
| 2021/0071168 A1 | 3/2021 | Nugent et al. |
| 2021/0102192 A1 | 4/2021 | Tabibiazar et al. |
| 2021/0102195 A1 | 4/2021 | Sato et al. |
| 2021/0102198 A1 | 4/2021 | Cox et al. |
| 2021/0115594 A1 | 4/2021 | Cox et al. |
| 2021/0129108 A1 | 5/2021 | Marsh et al. |
| 2021/0142182 A1 | 5/2021 | Bramlett et al. |
| 2021/0170356 A1 | 6/2021 | Peck et al. |
| 2021/0179724 A1 | 6/2021 | Sato et al. |
| 2021/0180046 A1 | 6/2021 | Cox et al. |
| 2021/0207197 A1 | 7/2021 | Gantt et al. |
| 2021/0332078 A1 | 10/2021 | Wu |
| 2021/0348220 A1 | 11/2021 | Zeitoun et al. |
| 2021/0355194 A1 | 11/2021 | Sato et al. |
| 2021/0395344 A1 | 12/2021 | Sato et al. |
| 2022/0032256 A1 | 2/2022 | Lackey et al. |
| 2022/0064206 A1 | 3/2022 | Fernandez et al. |
| 2022/0064313 A1 | 3/2022 | Sato et al. |
| 2022/0064628 A1 | 3/2022 | Toro et al. |
| 2022/0106586 A1 | 4/2022 | Nugent et al. |
| 2022/0106590 A1 | 4/2022 | Arbiza et al. |
| 2022/0135690 A1 | 5/2022 | Sato et al. |

(56) References Cited

U.S. PATENT DOCUMENTS

| | | |
|---|---|---|
| 2022/0135965 A1 | 5/2022 | Gantt et al. |
| 2022/0145289 A1 | 5/2022 | Lackey et al. |
| 2022/0206001 A1 | 6/2022 | Sato |
| 2022/0243195 A1 | 8/2022 | Nugent et al. |
| 2022/0246236 A1 | 8/2022 | Amirav-Drory |
| 2022/0259319 A1 | 8/2022 | Sato et al. |
| 2022/0259638 A1 | 8/2022 | Brown |
| 2022/0277808 A1 | 9/2022 | Arbiza et al. |
| 2022/0281989 A1 | 9/2022 | Glanville |
| 2022/0307010 A1 | 9/2022 | Sato et al. |
| 2022/0315971 A1 | 10/2022 | Wu et al. |
| 2022/0323924 A1 | 10/2022 | Lackey et al. |
| 2022/0325276 A2 | 10/2022 | Banyai et al. |
| 2022/0325278 A1 | 10/2022 | Nugent et al. |
| 2022/0348659 A1 | 11/2022 | Sato et al. |
| 2022/0356463 A1 | 11/2022 | Shen et al. |
| 2022/0356468 A1 | 11/2022 | Sato et al. |
| 2022/0411784 A1 | 12/2022 | Sato et al. |
| 2023/0002478 A1 | 1/2023 | Sato et al. |
| 2023/0054232 A1 | 2/2023 | Peck |
| 2023/0086062 A1 | 3/2023 | Banyai et al. |
| 2023/0096464 A1 | 3/2023 | Sato |
| 2023/0115861 A1 | 4/2023 | Nugent et al. |
| 2023/0192818 A1* | 6/2023 | Sato .............. C07K 16/10 424/133.1 |

FOREIGN PATENT DOCUMENTS

| | | |
|---|---|---|
| JP | H07505530 A | 6/1995 |
| JP | 2001518086 A | 10/2001 |
| JP | 2002538790 A | 11/2002 |
| JP | 2004268394 A | 9/2004 |
| JP | 2006503586 A | 2/2006 |
| JP | 2007314746 A | 12/2007 |
| JP | 2008214343 A | 9/2008 |
| JP | 2009294195 A | 12/2009 |
| JP | 2012507513 A | 3/2012 |
| JP | 2016527313 A | 9/2016 |
| WO | WO-9320242 A1 | 10/1993 |
| WO | WO-02072791 A2 | 9/2002 |
| WO | WO-2004039953 A2 | 5/2004 |
| WO | WO-2005059096 A2 | 6/2005 |
| WO | WO-2008054543 A2 | 5/2008 |
| WO | WO-2008063135 A1 | 5/2008 |
| WO | WO-2010053443 A1 | 5/2010 |
| WO | WO-2011109031 A1 | 9/2011 |
| WO | WO-2012078312 A2 | 6/2012 |
| WO | WO-2012154201 A1 | 11/2012 |
| WO | WO-2014021938 A1 | 2/2014 |
| WO | WO-2015021080 A2 | 2/2015 |
| WO | WO-2022010934 A2 | 1/2022 |
| WO | WO-2022076326 A1 | 4/2022 |
| WO | WO-2022086866 A1 | 4/2022 |
| WO | WO-2022087293 A1 | 4/2022 |
| WO | WO-2022098662 A2 | 5/2022 |
| WO | WO-2022159620 A1 | 7/2022 |
| WO | WO-2022178137 A1 | 8/2022 |
| WO | WO-2022204309 A1 | 9/2022 |
| WO | WO-2022204316 A2 | 9/2022 |
| WO | WO-2022217004 A1 | 10/2022 |
| WO | WO-2022235579 A1 | 11/2022 |
| WO | WO-2022235584 A1 | 11/2022 |
| WO | WO-2022271884 A2 | 12/2022 |
| WO | WO-2023023183 A2 | 2/2023 |
| WO | WO-2023023190 A2 | 2/2023 |
| WO | WO-2023023285 A2 | 2/2023 |
| WO | WO-2023069367 A1 | 4/2023 |

OTHER PUBLICATIONS

Seq ID No. 9 aligned with UniProt A0A679G9E9_SARS2 accessed Dec. 28, 2023 (Year: 2023).*
Seq ID No. 8 aligned with UniProt A0A679G9E9_SARS2 accessed Dec. 28, 2023 (Year: 2023).*
Seq ID No 9 aligned with Seq ID No. 7 (Year: 2023).*
Seq ID No 8 aligned with Seq ID No. 7 (Year: 2023).*
Bracken, C.J., Lim, S.A., Solomon, P. et al. Bi-paratopic and multivalent VH domains block ACE2 binding and neutralize SARS-CoV-2. Nat Chem Biol 17, 113-121 (2021). (Year: 2021).*
Agbavwe et al.: Efficiency, Error and Yield in Light-Directed Maskless Synthesis of DNA Microarrays. Journal of Nanobiotechnology. 9(57):1-17 (2011).
Arkles et al.: The Role of Polarity in the Structure of Silanes Employed in Surface Modification. Silanes and Other Coupling Agents. 5:51-64 (2009).
ATDBio. Nucleic Acid Structure, Nucleic Acids Book, 9 pages, published on Jan. 22, 2005. from: http://www.atdbio.com/content/5/Nucleic-acid-structure.
ATDBio. Solid-Phase Oligonucleotide Synthesis, Nucleic Acids Book, 20 pages, Published on Jul. 31, 2011. from: http://www.atdbio.com/content/17/Solid-phase-oligonucleotide-synthesis.
Berg: Biochemistry. 5th ED. New York (2002) 148-149.
Blanchard et al.: High-Density Oligonucleotide Arrays. Biosensors & Bioelectronics, 11(6/7):687-690 (1996).
Buermans et al.: Next Generation sequencing technology: Advances and applications, Biochimica et Biophysica Acta (BBA)—Molecular Basis of Disease, 1842:1931-1941 (2014).
Cheng et al.: High throughput parallel synthesis of oligonucleotides with 1536 channel synthesizer. Nucleic Acids Res. 30(18):e93 (2002).
Cleary et al.: Production of complex nucleic acid libraries using highly parallel in situ oligonucleotide synthesis. Nat Methods. 1(3):241-248 (2004).
Cohen et al.: Human population: The next half century. Science. 302:1172-1175 (2003).
Cruse et al.: Atlas of Immunology. Third Edition. Boca Raton:CRC Press (pp. 282-283) (2010).
Elsik et al.: The Genome sequence of taurine cattle: A window of ruminant biology and evolution. Science. 324:522-528 (2009).
Fodor et al.: Light-directed, spatially addressable parallel chemical synthesis. Science. 251(4995):767-773 (1991).
Gao et al.: A method for the generation of combinatorial antibody libraries using pIX phage display. PNAS 99(20):12612-12616 (2002).
GE Healthcare. AKTA oligopilot plus. Data File 18-114-66 ADC. 8 pages (2006).
GE Healthcare. Robust and cost-efficient oligonucleotide synthesis. Application Note 28-4058-08 AA. 4 pages (2005).
Gibson et al.: Creation of a Bacterial Cell Controlled by a Chemically Synthesized Genome. Science. 329(5989):52-56 (2010).
Hasin-Brumshtein et al.: The Effects of Mismatches on DNA Capture by Hybridization. Twist WhitePaper. 6 pages (May 7, 2019).
Hastie et al.: Defining variant-resistant epitopes targeted by SARS-CoV-2 antibodies: A global consortium study. Science. 374:472-478 (2021).
Hudson: Matrix Assisted Synthetic Transformations: A Mosaic of Diverse Contributions. Journal of Combinatorial Chemistry. 1(6):403-457 (1999).
Kong et al.: Parallel gene synthesis in a microfluidic device. Nucleic Acids Res. 35(8):e61 (2007).
Kosuri and Church. Large-scale de novo DNA synthesis: technologies and applications. Nature Methods. 11:499-507 (2014) Available at: http://www.nature.com/nmeth/journal/v11/n5/full/nmeth.2918.html.
Kosuri et al.: A scalable gene synthesis by selective amplification of DNA pools from high-fidelity microchips. Nature Biotechnology. 28:1295-1299 (2010).
Kosuri et al.: A scalable gene synthesis platform using high-fidelity DNA microchips Nat.Biotechnol. 28(12):1295-1299 (2010).
Krayden, Inc.: A Guide to Silane Solutions. Silane coupling agents. 7 pages. Published on May 31, 2005 at: http://krayden.com/pdf/xia_silane_chemistry.pdf.
Lausted et al.: POSaM: a fast, flexible, open-source, inkjet oligonucleotide synthesizer and microarrayer. Genome Biology. 5:R58, 17 pages (2004) available at https://www.ncbi.nlm.nih.gov/pmc/articles/PMC507883/.

(56) References Cited

OTHER PUBLICATIONS

Lebl et al.: Economical Parallel Oligonucleotide and Peptide Synthesizer—Pet Oligator. Int. J. Peptide Res. Ther. 13(1-2):367-376 (2007).
Leproust et al.: Synthesis of high-quality libraries of long (150mer) oligonucleotides by a novel depurination controlled process. Nucleic Acids Research. 38(8):2522-2540 (2010).
Lewontin and Harti, Population genetics in forensic DNA typing. Science, 254:1745-1750, 1991.
Ma et al.: DNA synthesis, assembly and application in synthetic biology. Current Opinion in Chemical Biology. 16:260-267 (2012).
Ma et al.: Versatile surface functionalization of cyclic olefin copolymer (COC) with sputtered SiO2 thin film for potential BioMEMS applications. Journal of Materials Chemistry. 11 pages (2009).
Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).
McBride & Caruthers. An investigation of several deoxynucleoside phosphoramidites useful for synthesizing deoxyoligonucleotides. Tetrahedron Lett. 24:245-248 (1983).
Mitra et al.: In situ localized amplification and contact replication of many individual DNA molecules. Nucleic Acids Res. 27(24):e34 (1999).
Morin et al.: Profiling the HeLa S3 transcriptome using randomly primed cDNA and massively parallel short-read sequencing. Biotechniques. 45:81-94 (2008).
Opposition to European Patent No. 3030682 filed Mar. 3, 2021.
PCT/US2014/049834 International Preliminary Report on Patentability dated Feb. 18, 2016.
PCT/US2014/049834 International Search Report and Written Opinion mailed Mar. 19, 2015.
PCT/US2014/049834 Invitation to Pay Additional Fees mailed Jan. 5, 2015.
Pirrung. How to make a DNA chip. Angew. Chem. Int. Ed. 41:1276-1289 (2002).
Pray. Discovery of DNA Structure and Function: Watson and Crick. Nature Education.6 pages (2008) available at: http://www.nature.com/scitable/topicpage/discovery-of-dna-structure-and-function-watson-397.
Quan et al.: Parallel on-chip gene synthesis and application to optimization of protein expression. Nature Biotechnology. 29:449-452 (2011).
Rafalski and Morgante. Corn and humans: recombination and linkage disequilibrium in two genomes of similar size. Trends in Genetics. 20(2):103-111 (2004).
Rogozin et al.: Origin and evolution of spliceosomal introns. Biology Direct, 7:11 (2012).
Saaem et al.: In situ synthesis of DNA microarray on functionalized cyclic olefin copolymer substrate ACS Applied Materials & Interfaces. 2(2):491-497 (2010).
Sargolzaei et al.: Extent of linkage disequilibrium in Holstein cattle in North America. J.Dairy Science. 91:2106-2117 (2007).
Srivannavit et al.: Design and fabrication of microwell array chips for a solution-based, photogenerated acid-catalyzed parallel oligonucleotide DNA synthesis. Sensors and Actuators A. 116:150-160 (2004).
STEEL. The Flow-Thru Chip a Three-dimensional biochip platform. In: Schena, Microarray Biochip Technology, Chapter 5, Natick, MA: Eaton Publishing, 2000, 33 pages.
Taylor et al.: Impact of surface chemistry and blocking strategies on DNA microarrays. Nucleic Acids Research, 31(16):e87 19 pages (2003).
Tian et al.: Accurate multiplex gene synthesis from programmable DNA microchips. Nature. 432(7020):1050-1054 (2004).
U.S. Appl. No. 14/452,429 Notice of Allowance dated Jun. 7, 2016.
U.S. Appl. No. 14/452,429 Office Action mailed Apr. 9, 2015.
U.S. Appl. No. 14/452,429 Office Action mailed Oct. 21, 2015.
U.S. Appl. No. 14/452,429 Restriction Requirement mailed Dec. 12, 2014.
U.S. Appl. No. 14/885,962 Notice of Allowance dated Nov. 8, 2017 and Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 28, 2018.
U.S. Appl. No. 14/885,965 Office Action dated Aug. 30, 2017.
U.S. Appl. No. 14/885,965 Office Action dated Feb. 10, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/187,714 Final Office Action dated Sep. 17, 2019.
U.S. Appl. No. 15/187,714 Office Action dated Apr. 4, 2019.
U.S. Appl. No. 15/187,714 Restriction Requirement dated Sep. 17, 2018.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Notice of Allowance dated Dec. 14, 2017.
U.S. Appl. No. 15/245,054 Office Action dated Mar. 21, 2017.
U.S. Appl. No. 15/245,054 Office Action dated Oct. 19, 2016.
U.S. Appl. No. 15/377,547 Final Office Action dated Feb. 8, 2019.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/602,991 Final Office Action dated Dec. 13, 2018.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated May 31, 2019.
U.S. Appl. No. 15/602,991 Office Action dated Sep. 21, 2017.
U.S. Appl. No. 15/603,013 Final Office Action dated Nov. 6, 2019.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Jun. 26, 2019.
U.S. Appl. No. 15/603,013 Office Action dated Oct. 20, 2017.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/991,992 Office Action dated May 21, 2020.
U.S. Appl. No. 15/991,992 Restriction Requirement dated Mar. 10, 2020.
U.S. Appl. No. 16/039,256 Final Office Action dated Mar. 30, 2021.
U.S. Appl. No. 16/039,256 Office Action dated Aug. 20, 2020.
U.S. Appl. No. 16/039,256 Office Action dated May 10, 2022.
U.S. Appl. No. 16/039,256 Restriction Requirement dated May 18, 2020.
U.S. Appl. No. 16/409,608 Office Action dated Sep. 9, 2019.
U.S. Appl. No. 16/535,777 Final Office Action dated Oct. 20, 2020.
U.S. Appl. No. 16/535,777 Office Action dated Feb. 8, 2021.
U.S. Appl. No. 16/535,777 Office Action dated Jan. 23, 2020.
U.S. Appl. No. 16/535,779 First Action Interview dated Feb. 10, 2020.
U.S. Appl. No. 16/737,401 Final Office Action dated Jun. 13, 2022.
U.S. Appl. No. 16/737,401 Office Action dated Jan. 5, 2022.
U.S. Appl. No. 16/737,401 Restriction Requirement dated Nov. 15, 2021.
Van Tassell et al.: SNP discovery and allele frequency estimation by deep sequencing of reduced representation libraries. Nature Methods. 5:247-252 (2008).
Xu et al.: Design of 240,000 orthogonal 25mer DNA barcode probes. PNAS. 106(7):2289-2294 (2009).

(56) References Cited

OTHER PUBLICATIONS

Yuan et al.: Rapid discovery of diverse neutralizing SARS-CoV-2 antibodies from large-scale synthetic phage libraries. MABS 14(1):e2002236 1-17 (2022).

* cited by examiner

Bispecific Antibody 1
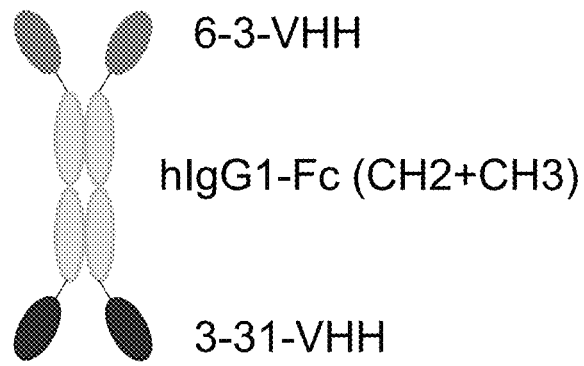
6-3-VHH
hIgG1-Fc (CH2+CH3)
3-31-VHH
VHH-Fc-VHH quadrivalent bispecific
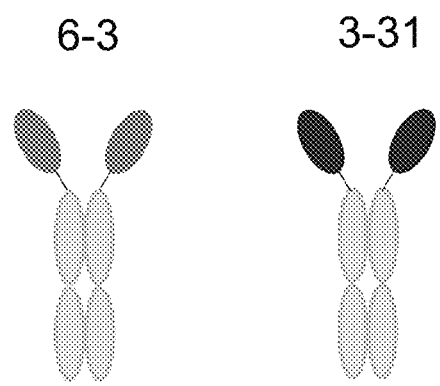
6-3   3-31
VHH-Fc parental bivalent monospecific
*FIG. 10*

|  | $EC_{50}$ | $EC_{80}$ | $EC_{90}$ | Hill Slope |
|---|---|---|---|---|
| Bebtelovimab | 13.42 (11.40-15.77) | 30.72 (24.54-38.81) | 49.86 (37.21-68.34) | 1.675 (1.385-2.051) |
| Bispecific Antibody 1 | 62.83 (50.56-77.63) | 273.2 (204.6-373.8) | 645.6 (430.0-1,008) | 0.9431 (0.7950-1.139) |

| | EC$_{50}$ | EC$_{80}$ | EC$_{90}$ | Hill Slope |
|---|---|---|---|---|
| Bebtelovimab | 13.42 (11.40-15.77) | 30.72 (24.54-38.81) | 49.86 (37.21-68.34) | 1.675 (1.385-2.051) |
| Bispecific Antibody 1 | 5,713 (3,600-13,961) | >6,200 | >6,200 | 0.7022 (.4235-1.107) |
| Sotrovimab | >6,200 | >6,200 | >6,200 | 0.4428 (0.3124-0.6357) |
| Bispecific Antibody 1 and Sotrovimab | 1,625 (1,171-2,346) | >6,200 | >6,200 | 0.7019 (0.5390-0.9150) |

| | EC$_{50}$ | EC$_{80}$ | EC$_{90}$ | Hill Slope |
|---|---|---|---|---|
| Bebtelovimab | 13.42 (11.40-15.77) | 30.72 (24.54-38.81) | 49.86 (37.21-68.34) | 1.675 (1.385-2.051) |
| Bispecific Antibody 1 | 5,713 (3,600-13,961) | >6,200 | >6,200 | 0.7022 (.4235-1.107) |
| Casirivimab Imedivimab | 2,154 (1,630-2,920) | >6,200 | >6,200 | 0.8638 (0.6944-1.080) |
| Bispecific Antibody 1 and Casirivimab and Imedivimab | 3,231 (2,400-4,626) | >6,200 | >6,200 | 0.7052 (0.5581-0.8862) |

| | EC$_{50}$ | EC$_{80}$ | EC$_{90}$ | Hill Slope |
|---|---|---|---|---|
| Bebtelovimab | 13.42 (11.40-15.77) | 30.72 (24.54-38.81) | 49.86 (37.21-68.34) | 1.675 (1.385-2.051) |
| Bispecific Antibody 1 | 5,713 (3,600-13,961) | >6,200 | >6,200 | 0.7022 (.4235-1.107) |
| Bamlanivimab Etesevimab | >6,200 | >6,200 | >6,200 | 0.6010 (0.3354-1.105) |
| Bispecific Antibody 1 and Bamlanivimab and Etesevimab | >6,200 | >6,200 | >6,200 | 0.2087 (0.1341-0.3006) |

| | EC$_{50}$ | EC$_{80}$ | EC$_{90}$ | Hill Slope |
|---|---|---|---|---|
| Bebtelovimab | 13.42 (11.40-15.77) | 30.72 (24.54-38.81) | 49.86 (37.21-68.34) | 1.675 (1.385-2.051) |
| Bispecific Antibody 1 | 5,713 (3,600-13,961) | >6,200 | >6,200 | 0.7022 (.4235-1.107) |
| Tixagevimab Cilgavimab | 248.6 (201.9-306.0) | 1,400 (995.0-2,034) | 3,847 (2,370->6,200) | 0.8021 (0.6811-0.9588) |
| Bispecific Antibody 1 and Tixagevimab and Cilgavimab | 506 (410.5-628.3) | 1,506 (1,057-2,219) | 2,850 (1,760-4,853) | 1.271 (1.011-1.650) |

Binding of Bispecific Antibody 1 to C1q by ELISA

Signal Test for the Binding of ACE2-muFc with Biotinylated SARS-Co Spike RBD in Cross-Titration Matrix

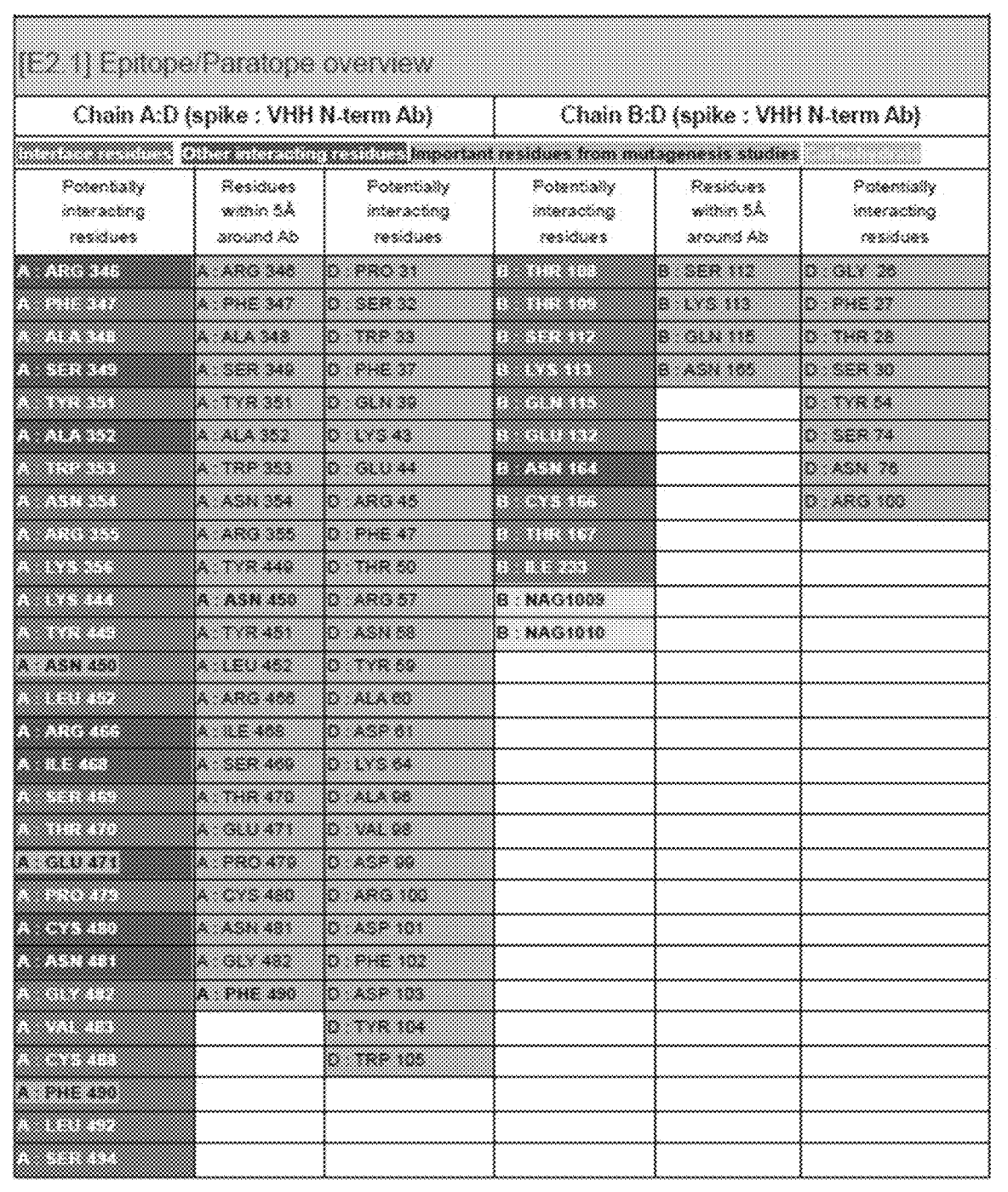

| [E2.1] Epitope/Paratope overview | | | | | |
|---|---|---|---|---|---|
| Chain A:D (spike : VHH N-term Ab) | | | Chain B:D (spike : VHH N-term Ab) | | |
| Interacting residues / Other interaction residues / Important residues from mutagenesis studies | | | | | |
| Potentially interacting residues | Residues within 5Å around Ab | Potentially interacting residues | Potentially interacting residues | Residues within 5Å around Ab | Potentially interacting residues |
| A : ARG 346 | A : ARG 346 | D : PRO 31 | B : THR 109 | B : SER 112 | D : GLY 26 |
| A : PHE 347 | A : PHE 347 | D : SER 32 | B : THR 109 | B : LYS 113 | D : PHE 27 |
| A : ALA 348 | A : ALA 348 | D : TRP 33 | B : SER 112 | B : GLU 115 | D : THR 28 |
| A : SER 349 | A : SER 349 | D : PHE 37 | B : LYS 113 | B : ASN 168 | D : SER 30 |
| A : TYR 351 | A : TYR 351 | D : GLN 39 | B : GLN 115 | | D : TYR 54 |
| A : ALA 352 | A : ALA 352 | D : LYS 43 | B : GLU 157 | | D : SER 74 |
| A : TRP 353 | A : TRP 353 | D : GLU 44 | B : ASN 164 | | D : ASN 76 |
| A : ASN 354 | A : ASN 354 | D : ARG 45 | B : LYS 165 | | D : ARG 160 |
| A : ARG 355 | A : ARG 355 | D : PHE 47 | B : THR 167 | | |
| A : LYS 356 | A : TYR 449 | D : THR 50 | B : GLU 169 | | |
| A : LYS 444 | A : ASN 450 | D : ARG 57 | B : NAG1009 | | |
| A : TYR 445 | A : TYR 451 | D : ASN 58 | B : NAG1010 | | |
| A : ASN 450 | A : LEU 452 | D : TYR 59 | | | |
| A : LEU 452 | A : ARG 466 | D : ALA 60 | | | |
| A : ARG 466 | A : ILE 468 | D : ASP 61 | | | |
| A : ILE 468 | A : SER 469 | D : LYS 64 | | | |
| A : SER 469 | A : THR 470 | D : ALA 66 | | | |
| A : THR 470 | A : GLU 471 | D : VAL 98 | | | |
| A : GLU 471 | A : PRO 479 | D : ASP 99 | | | |
| A : PRO 479 | A : CYS 480 | D : ARG 100 | | | |
| A : CYS 480 | A : ASN 481 | D : ASP 101 | | | |
| A : ASN 481 | A : GLY 482 | D : PHE 102 | | | |
| A : GLY 482 | A : PHE 490 | D : ASP 103 | | | |
| A : VAL 483 | | D : TYR 104 | | | |
| A : CYS 488 | | D : TRP 105 | | | |
| A : PHE 490 | | | | | |
| A : LEU 92 | | | | | |
| A : SER 94 | | | | | |

*FIG. 30*

[E2.2] Explicit bonds list

| Chain A:D (spike : VHH N-term Ab) | | | Chain B:D (spike : VHH N-term Ab) | | |
|---|---|---|---|---|---|
| interface area [Å²] | 913.1 | | interface area [Å²] | 295.9 | |
| Hydrogen bonds | | | | | |
| Chain A | Distance (Å) | Chain D | Chain B | Distance (Å) | Chain D |
| A:THR 470 [OG1] | 3.29 | D:SER 32 [O] | B:ASN 164 [OD1] | 3.19 | D:THR 28 [N] |
| A:THR 470 [N] | 3.90 | D:SER 32 [OG] | B:NAG1309 [O3] | 2.60 | D:TYR 54 [OH] |
| A:THR 470 [OG1] | 2.87 | D:SER 32 [OG] | | | |
| A:ASN 461 [N] | 3.22 | D:TYR 59 [O] | | | |
| A:ARG 466 [NH2] | 3.73 | D:ARG 100 [O] | | | |
| A:ARG 346 [NH1] | 2.91 | D:ASP 103 [O] | | | |
| A:ASN 450 [O] | 2.90 | D:TRP 105 [NE1] | | | |
| A:ASN 450 [OD1] | 2.76 | D:ARG 46 [NH2] | | | |
| A:ILE 468 [O] | 3.45 | D:TRP 33 [N] | | | |
| A:THR 470 [O] | 2.81 | D:ASN 58 [ND2] | | | |
| A:GLU 471 [OE2] | 2.78 | D:ASN 58 [ND2] | | | |
| A:ASN 461 [OD1] | 3.61 | D:ASP 61 [N] | | | |

*FIG. 31*

[E2.3] Comparison to mutagenesis studies

| Residues identified in mutagenesis studies | Confirmed by structural study | Unconfirmed by structural study |
|---|---|---|
| A:ASN 450 | A:ASN 450 | A:ILE 472 |
| A:ILE 472 | A:PHE 490 | |
| A:PHE 490 | | |
| Notes | | |

*FIG. 32*

N-term spike  RBD spike
ACE2 interacting residues  Other interacting residues  Important residues from mutagenesis studies

```
         10         20         30         40         50         60
MFVFLVLLPL VSSQCVNLTT RTQLPPAY T N SFTRGVYYPD KVFRSSVLHS TQDLFLPFFS 70         80         90        100        110        120
NVTWFHAIHV SGTNGTKRFD NPVLPFNDGV YFASTEKSNI IRGWIFGTTL DSKTQSLLIV 130        140        150        160        170        180
NNATNVVIKV CEFQFCNDPF LGVYYHKNNK SWMESEFRVY SSANNCTFEY VSQPFLMDLE 190        200        210        220        230        240
GKQGNFKNLR EFVFKNIDGY FKIYSKHTPI NLVRDLPQGF SALEPLVDLP IGINITRFQT 250        260        270        280        290        300
LLALHRSYLT PGDSSSGWTA GAAAYYVGYL QPRTFLLKYN ENGTITDAVD CALDPLSETK 310        320        330        340        350        360
CTLKSFTVEK GIYQTSNFRV QPTESIVRFP NITNLCPFGE VFNATRFASV YAWNRKRISN 370        380        390        400        410        420
CVADYSVLYN SASFSTFKCY GVSPTKLNDL CFTNVYADSF VIRGDEVRQI APGQTGKIAD 430        440        450        460        470        480
YNYKLPDDFT GCVIAWNSNN LDSKVGGNYN YRLFRKSNLK PFERDISTEI YQAGSTPCNG 490        500        510        520        530        540
VEGFNCYFPL QSYGFQPTNG VGYQPYRVVV LSFELLHAPA TVCGPKKS TNLVKNKCVN 550        560        570        580        590        600
FNFNGLTGTG VLTESNKKFL PFQQFGRDIA DTTDAVRDPQ TLEILDITPC SFGGVSVITP 610        620        630        640        650        660
GTNTSNQVAV LYQDVNCTEV PVAIHADQLT PTWRVYSTGS NVFQTRAGCL IGAEHVNNSY 670        680        690        700        710        720
ECDIPIGAGI CASYQTQTNS PRRARSVASQ SIIAYTMSLG AENSVAYSNN SIAIPTNFTI 730        740        750        760        770        780
SVTTEILPVS MTKTSVDCTM YICGDSTECS NLLLQYGSFC TQLNRALTGI AVEQDKNTQE 790        800        810        820        830        840
VFAQVKQIYK TPPIKDFGGF NFSQILPDPS KPSKRSFIED LLFNKVTLAD AGFIKQYGDC
```

*FIG. 33*

```
          850        860        870        880        890        900
LGDIAARDLI CAQKFNGLTV LPPLLTDEMI AQYTSALLAG TITSGWTFGA GAALQIPFAM 910        920        930        940        950        960
QMAYRFNGIG VTQNVLYENQ KLIANQFNSA IGKIQDSLSS TASALGKLQD VVNQNAQALN 970        980        990       1000       1010       1020
TLVKQLSSNF GAISSVLNDI LSRLDKVEAE VQIDRLITGR LQSLQTYVTQ QLIRAAEIRA 1030       1040       1050       1060       1070       1080
SANLAATKMS ECVLGQSKRV DFCGKGYHLM SFPQSAPHGV VFLHVTYVPA QEKNFTTAPA 1090       1100       1110       1120       1130       1140
ICHDGKAHFP REGVFVSNGT HWFVTQRNFY EPQIITTDNT FVSGNCDVVI GIVNNTVYDP 1150       1160       1170       1180       1190       1200
LQPELDSFKE ELDKYFKNHT SPDVDLGDIS GINASVVNIQ KEIDRLNEVA KNLNESLIDL 1210       1220       1230       1240       1250       1260
QELGKYEQYI KWPWYIWLGF IAGLIAIVMV TIMLCCMTSC CSCLKGCCSC GSCCKFDEDD

1270
SEPVLKGVKL HYT
```

| [E2.6] Comparison to escape studies at VHH1 position | | |
|---|---|---|
| Residues identified in escape studies | Belong to the spike:VHH interface | Do not belong to the spike:VHH interface or not built in the model |
| A: PHE 490 (RBD) | A: PHE 490 (RBD) | |
| A: ASN 354 (RBD) | A: ASN 354 (RBD) | |
| A: PHE 275 (N-term) | | A: PHE 275 (N-term) |
| A: TYR 655 (Elsewhere) | | A: TYR 655 (Elsewhere) |
| A: ARG 685 (Elsewhere) | | A: ARG 685 (Elsewhere) |
| A: PHE 759 (Elsewhere) | | A: PHE 759 (Elsewhere) |

[E3.1] Epitope/Paratope overview

| Chain B : D (spike : VHH N-term Ab) | | | Chain C : D (spike : VHH N-term Ab) | |
|---|---|---|---|---|
| Interface residues | Close interaction residues | Important residues from mutagenesis studies | | |
| Potentially interacting residues | Residues within 5Å around Ab | Potentially interacting residues | Potentially interacting residues | Potentially interacting residues |
| B ALA 344 | B ARG 346 | D SER 32 | | |
| B ARG 346 | B PHE 347 | D TRP 33 | | |
| B PHE 347 | B ALA 348 | D PHE 37 | | |
| B ALA 348 | B SER 349 | D GLN 39 | | |
| B SER 349 | B TYR 351 | D LYS 43 | | |
| B TYR 351 | B ALA 352 | D GLU 44 | | |
| B ALA 352 | B TRP 353 | D ARG 45 | | |
| B ASN 354 | B ASN 354 | D PHE 47 | | |
| B ARG 355 | B ARG 355 | D THR 50 | | |
| B GLY 356 | B LYS 356 | D ILE 51 | | |
| B SER 359 | B SER 359 | D ASN 52 | | |
| B TYR 449 | B TYR 449 | D GLU 53 | | |
| B ASN 450 | B ASN 450 | D GLY 55 | | |
| B LEU 452 | B LEU 452 | D ARG 57 | | |
| B ARG 455 | B ARG 455 | D ASN 58 | | |
| B ILE 468 | B ILE 468 | D TYR 59 | | |
| B SER 469 | B THR 470 | D ALA 60 | | |
| B THR 470 | B GLU 471 | D ASP 61 | | |
| B GLU 471 | B ILE 472 | D SER 62 | | |
| B ILE 472 | B PRO 479 | D TYR 64 | | |
| B PRO 479 | B CYS 480 | D VAL 66 | | |
| B CYS 480 | B ASN 481 | D ASP 99 | | |
| B ASN 481 | B PHE 490 | D ARG 100 | | |
| B PHE 490 | B LEU 492 | D ASP 101 | | |
| B LEU 492 | B SER 494 | D PHE 102 | | |
| B SER 494 | | D ASP 103 | | |
| | | D TYR 104 | | |
| | | D TRP 105 | | |

*FIG. 38*

| [E3.2] Explicit bonds list | | | | | |
|---|---|---|---|---|---|
| Chain B:D (spike : VHH N-term Ab) | | | Chain C:D (spike : VHH N-term Ab) | | |
| interface area [Å²] | 918.9 | | | | |
| Hydrogen bonds | | | Hydrogen bonds | | |
| Chain B | Distance [Å] | Chain D | Chain C | Distance [Å] | Chain D |
| B:ARG 346 [NE] | 2.80 | D:ASP 103 [O] | | | |
| B:ARG 346 [NH1] | 2.86 | D:ASP 103 [OD1] | | | |
| B:SER 349 [N] | 2.80 | D:ASP 103 [OD1] | | | |
| B:ARG 466 [NH1] | 2.90 | D:ASP 99 [O] | | | |
| B:ARG 466 [NH1] | 2.85 | D:ASP 101 [O] | | | |
| B:THR 470 [OG1] | 2.83 | D:ASN 58 [OD1] | | | |
| B:ASN 481 [N] | 2.88 | D:TYR 59 [O] | | | |
| B:ASN 481 [ND2] | 3.06 | D:TYR 59 [O] | | | |
| B:TYR 449 [O] | 2.82 | D:ARG 45 [NH2] | | | |
| B:ASN 450 [O] | 3.74 | D:TRP 106 [NE1] | | | |
| B:ASN 450 [OD1] | 2.81 | D:ARG 45 [NH2] | | | |
| B:PRO 479 [O] | 3.05 | D:TYR 59 [N] | | | |
| B:ASN 481 [O] | 2.86 | D:ASP 61 [N] | | | |
| Salt bridges | | | Salt bridges | | |
| Chain B | distance[Å] | Chain D | | | |
| B:ARG 346 [NH1] | 3.53 | D:ASP 103 [OD2] | | | |
| B:ARG 346 [NH1] | 2.86 | D:ASP 103 [OD1] | | | |

*FIG. 39*

| [E3.3] Comparison to mutagenesis studies |||
|---|---|---|
| Residues identified in mutagenesis studies | Confirmed by structural study | Rejected by structural study |
| A: ASN 450 | A: ASN 450 | |
| A: ILE 472 | A: PHE 490 | |
| A: PHE 490 | A: ILE 472 | |
| Notes |||
| Unlike epitope 1, in epitope 2 residue 472 was found to also interact with the VHH based on manual inspection of the map and strong surrounding densities. |||

FIG. 40

N-term spike   RBD spike
Interface residues  Other interaction residues  Interacting residues from mutagenesis studies

```
        10          20          30          40          50          60
MFVFLVLLPL VSSQCVNLTT RTQLPPAYTN SFTRGVYYPD KVFRSSVLHS TQDLFLPFFS 70          80          90         100         110         120
NVTWFHAIHV SGTNGTKRFD NPVLPFNDGV YFASTEKSNI IRGWIFGTTL DSKTQSLLIV 130         140         150         160         170         180
NNATNVVIKV CEFQFCNDPF LGVYYHKNNK SWMESEFRVY SSANNCTFEY VSQPFLMDLE 190         200         210         220         230         240
GKQGNFKNLR EFVFKNIDGY FKIYSKHTPI NLVRDLPQGF SALEPLVDLP IGINITRFQT 250         260         270         280         290         300
LLALHRSYLT PGDSSSGWTA GAAAYYVGYL QPRTFLLKYN ENGTITDAVD CALDPLSETK 310         320         330         340         350         360
CTLKSFTVEK GIYQTSNFRV QPTESIVRFP NITNLCPFGE VFNATRFASV YAWNRKRISN 370         380         390         400         410         420
CVADYSVLYN SASFSTFKCY GVSPTKLNDL CFTNVYADSF VIRGDEVRQI APGQTGKIAD 430         440         450         460         470         480
YNYKLPDDFT GCVIAWNSNN LDSKVGGNYN YLYRLFRKSN LKPFERDIST EIYQAGSTPC 490         500         510         520         530         540
NGVEGFNCYF PLQSYGFQPT NGVGYQPYRV VVLSFELLHA PATVCGPKKS TNLVKNKCVN 550         560         570         580         590         600
FNFNGLTGTG VLTESNKKFL PFQQFGRDIA DTTDAVRDPQ TLEILDITPC SFGGVSVITP 610         620         630         640         650         660
GTNTSNQVAV LYQDVNCTEV PVAIHADQLT PTWRVYSTGS NVFQTRAGCL IGAEHVNNSY 670         680         690         700         710         720
ECDIPIGAGI CASYQTQTNS PRRARSVASQ SIIAYTMSLG AENSVAYSNN SIAIPTNFTI 730         740         750         760         770         780
SVTTEILPVS MTKTSVDCTM YICGDSTECS NLLLQYGSFC TQLNRALTGI AVEQDKNTQE 790         800         810         820         830         840
VFAQVKQIYK TPPIKDFGGF NFSQILPDPS KPSKRSFIED LLFNKVTLAD AGFIKQYGDC
```

*FIG. 41*

```
         850         860         870         880         890         900
LGDIAARDLI CAQKFNGLTV LPPLLTDEMI AQYTSALLAG TITSGWTFGA GAALQIPFAM 910         920         930         940         950         960
QMAYRFNGIG VTQNVLYENQ KLIANQFNSA IGKIQDSLSS TASALGKLQD VVNQNAQALN 970         980         990        1000        1010        1020
TLVKQLSSNF GAISSVLNDI LSRLDKVEAE VQIDRLITGR LQSLQTYVTQ QLIRAAEIRA 1030        1040        1050        1060        1070        1080
SANLAATKMS ECVLGQSKRV DFCGKGYHLM SFPQSAPHGV VFLHVTYVPA QEKNFTTAPA 1090        1100        1110        1120        1130        1140
ICHDGKAHFP REGVFVSNGT HWFVTQRNFY EPQIITTDNT FVSGNCDVVI GIVNNTVYDP 1150        1160        1170        1180        1190        1200
LQPELDSFKE ELDKYFKNHT SPDVDLGDIS GINASVVNIQ KEIDRLNEVA KNLNESLIDL 1210        1220        1230        1240        1250        1260
QELGKYEQYI KWPWYIWLGF IAGLIAIVMV TIMLCCMTSC CSCLKGCCSC GSCCKFDEDD

1270
SEPVLKGVKL HYT
```

| [E3.6] Comparison to escape studies at VHH 2 position |||
|---|---|---|
| Residues identified in escape studies | Belong to the spike:VHH interface | Do not belong to the spike:VHH interface or not built in the model |
| A: PHE 490 (RBD) | A: PHE 490 (RBD) | |
| A: ASN 354 (RBD) | A: ASN 354 (RBD) | |
| A: PHE 275 (N-term) | | A: PHE 275 (N-term) |
| A: TYR 655 (Elsewhere) | | A: TYR 655 (Elsewhere) |
| A: ARG 685 (Elsewhere) | | A: ARG 685 (Elsewhere) |
| A: PHE 759 (Elsewhere) | | A: PHE 759 (Elsewhere) |

| [E4] Comparison of VHH1 and VHH2 epitopes/paratopes ||||||
| --- | --- | --- | --- | --- | --- |
| Epitope description ||| Paratope description |||
| Chain A epitope 1 : chain B epitope 2 ||| Chain D epitope 1 : chain D epitope 2 |||
| Unique spike residues at epitope 1 | Shared spike residues at epitopes 1 and 2 | Unique spike residues at epitope 2 | Unique VHH residues at epitope 1 | Shared VHH residues at epitopes 1 and 2 | Unique VHH residues at epitope 2 |
| A : TRP 353 | A : ARG 346 | B : ALA 344 | D : PRO 31 | D : SER 32 | D : ILE 51 |
| A : LYS 444 | A : PHE 347 | B : SER 399 | D : LYS 64 | D : TRP 33 | D : ASN 52 |
| A : GLY 482 | A : ALA 348 | B : ILE 472 | D : ALA 98 | D : PHE 37 | D : GLU 53 |
| A : VAL 483 | A : SER 349 | | | D : GLN 39 | D : GLY 56 |
| A : CYS 488 | A : TYR 351 | | | D : LYS 43 | D : SER 62 |
| | A : ALA 352 | | | D : GLU 44 | D : TYR 64 |
| | A : ASN 354 | | | D : ARG 46 | |
| | A : ARG 355 | | | D : PHE 47 | |
| | A : LYS 356 | | | D : THR 50 | |
| | A : LYS 444 | | | D : ARG 57 | |
| | A : TYR 449 | | | D : ASN 58 | |
| | A : ASN 450 | | | D : TYR 59 | |
| | A : LEU 452 | | | D : ALA 60 | |
| | A : ARG 466 | | | D : ASP 61 | |
| | A : ILE 468 | | | D : VAL 98 | |
| | A : SER 469 | | | D : ASP 99 | |
| | A : THR 470 | | | D : ARG 100 | |
| | A : GLU 471 | | | D : ASP 101 | |
| | A : PRO 479 | | | D : PHE 102 | |
| | A : CYS 480 | | | D : ASP 103 | |
| | A : ASN 481 | | | D : TYR 104 | |
| | A : LEU 492 | | | D : TRP 105 | |
| | A : SER 494 | | | | |

*FIG. 46*

```
                         SEQUENCE LISTING

Sequence total quantity: 9
SEQ ID NO: 1            moltype = AA  length = 9
FEATURE                 Location/Qualifiers
source                  1..9
                        mol_type = protein
                        organism = synthetic construct
SEQUENCE: 1
STFSINAMG                                                                  9

SEQ ID NO: 2            moltype = AA  length = 13
FEATURE                 Location/Qualifiers
source                  1..13
                        mol_type = protein
                        organism = synthetic construct
SEQUENCE: 2
AGITSSGGYT NYA                                                            13

SEQ ID NO: 3            moltype = AA  length = 18
FEATURE                 Location/Qualifiers
source                  1..18
                        mol_type = protein
                        organism = synthetic construct
SEQUENCE: 3
CAADGVPEYS DYASGPVW                                                       18

SEQ ID NO: 4            moltype = AA  length = 9
FEATURE                 Location/Qualifiers
source                  1..9
                        mol_type = protein
                        organism = synthetic construct
SEQUENCE: 4
FTFSPSWMG                                                                  9

SEQ ID NO: 5            moltype = AA  length = 13
FEATURE                 Location/Qualifiers
source                  1..13
                        mol_type = protein
                        organism = synthetic construct
SEQUENCE: 5
VATINEYGGR NYA                                                            13

SEQ ID NO: 6            moltype = AA  length = 11
FEATURE                 Location/Qualifiers
source                  1..11
                        mol_type = protein
                        organism = synthetic construct
SEQUENCE: 6
CARVDRDFDY W                                                              11

SEQ ID NO: 7            moltype = AA  length = 123
FEATURE                 Location/Qualifiers
source                  1..123
                        mol_type = protein
                        organism = synthetic construct
SEQUENCE: 7
EVQLVESGGG LVQPGGSLRL SCAASGSTFS INAMGWFRQA PGKEREFVAG ITSSGGYTNY          60
ADSVKGRFTI SADNSKNTAY LQMNSLKPED TAVYYCAADG VPEYSDYASG PVWGQGTLVT         120
VSS                                                                      123

SEQ ID NO: 8            moltype = AA  length = 1271
FEATURE                 Location/Qualifiers
source                  1..1271
                        mol_type = protein
                        organism = synthetic construct
SEQUENCE: 8
MFVFLVLLPL VSSQCVNLTT RTQLPPAYTN SFTRGVYYPD KVFRSSVLHS TQDLFLPFFS          60
NVTWFHAIHV SGTNGTKRFD NPVLPFNDGV YFASTEKSNI IRGWIFGILD SKTQSLLIVN         120
```

-continued

```
NATNVVIKVC EFQFCNDPFL GVYYHKNNKS WMESEFRVYS SANNCTFEYV SQPFLMDLEG  180
KQGNFKNLRE FVFKNIDGYF KIYSKHTPIN LVRDLPQGFS ALEPLVDLPI GINITRFQTL  240
LALHRSYLTP GDSSSGWTAG AAAYYVGYLQ PRTFLLKYNE NGTITDAVDC ALDPLSETKC  300
TLKSFTVEKG IYQTSNFRVQ PTESIVRFPN ITNLCPFGEV FNATRFASVY AWNRKRISNC  360
VADYSVLYNS ASFSTFKCYG VSPTKLNDLC FTNVYADSFV IRGDEVRQIA PGQTGKIADY  420
NYKLPDDFTG CVIAWNSNNL DSKVGGNYYL YRLFRKSNLK PFERDISTEY QAGSTPCNGV  480
EGFNCYFFLO SYGFQPTNGV GYQPYRVVVL SFELLHAPAT VCGPKKSTNL VKNKCVNFNF  540
NGLTGTGVLT ESNKKFLPFQ QFGRDIADTT DAVRDPQTLE ILDITPCSFG GVSVITPGTN  600
TSNQVAVLYQ DVNCTEVPVA IHADQLTPTW RVYSTGSNVF QTRAGCLIGA EHVNNSYECD  660
IPIGAGICAS YQTQTNSPRR ARSVASQSII AYTMSLGAEN SVAYSNNSIA IPTNFTISVT  720
TEILPVSMTK TSVDCTMYIC GDSTECSNLL LQYGSFCTQL NRALTGIAVE QDKNTQEVFA  780
QVKQIYKTPP IKDFGGFNFS QILPDPSKPS KRSFIEDLLF NKVTLADAGF IKQYGDCLGD  840
IAARDLICAQ KFNGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN QNAQALNTLV  960
KQLSSNFGAI SSVLNDILSR LDKVEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVTGIV NNTVYDPLQP  1140
ELDSFKEELD KYFKNHTSPD VDLGDISGIN ASVVNIQKEI DRLNEVAKNL INESLIDLQE  1200
LGKYEQYIKW PWYIWLGFIA GLIAIVMVTI MLCCMTSCCS CLKGCCSCGS CCKFDEDDSE  1260
PVLKGVKLHY T                                                     1271

SEQ ID NO: 9            moltype = AA  length = 1271
FEATURE                 Location/Qualifiers
source                  1..1271
                        mol_type = protein
                        organism = synthetic construct
SEQUENCE: 9
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EYQAGSTPCN  480
GVEGFNCYPL OSYGFQPTNG VGYQPYRVVV LSFELLHAPA TVCGPKKSTN LVKNKCVNFN  540
FNGLTGTGVL TESNKKFLPF QQFGRDIADT TDAVRDPQTL EILDITPCSF GGVSVITPGT  600
NTSNQVAVLY QDVNCTEVPV AIHADQLTPT WRVYSTGSNV FQTRAGCLIG AEHVNNSYEC  660
DIPIGAGICA SYQTQTNSPR RARSVASQSI IAYTMSLGAE NSVAYSNNSI AIPTNFTISV  720
TTEILPVSMT KTSVDCTMYI CGDSTECSNL LLQYGSFCTQ LNRALTGIAV EQDKNTQEVF  780
AQVKQIYKTP PIKDFGGFNF SQILPDPSKP SKRSFIEDLL FNKVTLADAG FIKQYGDCLG  840
DIAARDLICA QKFNGLTVLP PLLTDEMIAQ YTSALLAGTI TSGWTFGAGA ALQIPFAMQM  900
AYRFNGIGVT QNVLYENQKL IANQFNSAIG KIQDSLSSTA SALGKLQDVV NQNAQALNTL  960
VKQLSSNFGA ISSVLNDILS RLDKVEAEVO IDRLITGRLQ SLQTYVTQQL IRAAEIRASA  1020
NLAATKMSEC VLGQSKRVDF CGKGYHLMSF PQSAPHGVVF LHVTYVPAQE KNFTTAPAIC  1080
HDGKAHFPRE GVFVSNGTHW FVTQRNFYEP QIITTONTFV SGNCDVVIGI VNNTVYDPLQ  1140
PELDSFKEEL DKYFKNHTSP DVDLGDISGI NASVVNIQKE IDRLNEVAKN LNESLIDLQE  1200
LGKYEQYIKW PWYIWLGFIA GLIAIVMVTI MLCCMTSCCS CLKGCCSCGS CCKFDEDDSE  1260
PVLKGVKLHY T                                                     1271
```

BISPECIFIC SARS-CoV-2 ANTIBODIES AND METHODS OF USE

CROSS REFERENCE

This application claims the benefit of U.S. Provisional Patent Application No. 63/296,087, filed on Jan. 3, 2022, which is herein incorporated by reference in its entirety.

SEQUENCE LISTING

The instant application contains a Sequence Listing which has been submitted electronically in XML format and is hereby incorporated by reference in its entirety. Said XML copy, created on Feb. 7, 2023, is named 44854-849_201_SL.xml and is 11,550 bytes in size.

BACKGROUND

Since its emergence in December 2019, SARS-CoV-2 continues to evolve substantially, acquiring sets of mutations that enhance the virus's potency, transmissibility, infectivity, and ability to escape natural and acquired immunity. Virtually all of these fitness-enhancing mutations are found in Spike (S), the protein through which SARS-CoV-2 attaches to host cells during infection. The receptor-binding domain (RBD) of S is the primary target of neutralizing antibodies produced after natural infection with or vaccination against SARS-CoV-2; this fact has fueled speculation that SARS-CoV-2 could escape natural and acquired immunity. Several variants of concern have displayed varying degrees of immune escape, including the Alpha (B.1.1.7), Beta (B.1.351), and Delta (B.1.617.2) variants. The Omicron variant, which possesses at least 30 mutations in S alone, is particularly concerning. SARS-CoV-2 escape mutations from current therapeutics endangers ongoing public health responses and underscores the need for new therapeutic approaches, such as multivalent antibodies, which have recently been shown to potentiate SARS-CoV-2 neutralization and reduce immune escape when compared to monovalent antibodies.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF SUMMARY

Provided herein are bispecific antibodies or antibody fragments thereof comprising at least two binding domains to a spike glycoprotein or a receptor of the spike glycoprotein: a) a first binding domain of the at least two binding domains comprising a first variable domain, heavy chain region (VH), wherein the first VH region comprises complementarity determining regions CDRH1, CDRH2, and CDRH3, and wherein (i) an amino acid sequence of CDRH1 is as set forth in SEQ ID NO: 1; (ii) an amino acid sequence of CDRH2 is as set forth in SEQ ID NO: 2; and (iii) an amino acid sequence of CDRH3 as set forth in SEQ ID NO: 3; and b) a second binding domain of the at least two binding domains comprising a first variable domain, heavy chain region (VH), wherein the first VH region comprises complementarity determining regions CDRH1, CDRH2, and CDRH3, and wherein (i) an amino acid sequence of CDRH1 is as set forth in SEQ ID NO: 4; (ii) an amino acid sequence of CDRH2 is as set forth in SEQ ID NO: 5; and (iii) an amino acid sequence of CDRH3 as set forth in SEQ ID NO: 6.

In some embodiments, the bispecific antibody is bivalent, trivalent, or tetravalent. In some embodiments, the bispecific antibody is bivalent. In some embodiments, the bispecific antibody is tetravalent. In some embodiments, the bispecific antibody or antibody fragment thereof comprises a KD of less than 50 nM. In some embodiments, the bispecific antibody or antibody fragment thereof comprises a KD of less than 25 nM. In some embodiments, the bispecific antibody or antibody fragment thereof comprises a KD of less than 10 nM. In some embodiments, the bispecific antibody or antibody fragment thereof comprises a KD of less than 5 nM.

Further provided herein are bispecific antibodies or antibody fragments thereof comprising an amino acid sequence comprising at least 90% identity to SEQ ID NO: 8 or SEQ ID NO: 9. In some embodiments, the bispecific antibody or antibody fragment thereof comprises a KD of less than 50 nM. In some embodiments, the bispecific antibody or antibody fragment thereof comprises a KD of less than 25 nM. In some embodiments, the bispecific antibody or antibody fragment thereof comprises a KD of less than 10 nM. In some embodiments, the bispecific antibody or antibody fragment thereof comprises a KD of less than 5 nM.

Further provided herein are methods of treating a SARS-CoV-2 infection, comprising administering the bispecific antibody or antibody fragment thereof described herein. In some embodiments, the bispecific antibody is administered prior to exposure to SARS-CoV-2. In some embodiments, the bispecific antibody is administered at least about 1 week prior to exposure to SARS-CoV-2. In some embodiments, the bispecific antibody is administered at least about 1 month prior to exposure to SARS-CoV-2. In some embodiments, the bispecific antibody is administered at least about 5 months prior to exposure to SARS-CoV-2. In some embodiments, the bispecific antibody is administered after exposure to SARS-CoV-2. In some embodiments, the bispecific antibody is administered at most about 24 hours after exposure to SARS-CoV-2. In some embodiments, the bispecific antibody is administered at most about 1 week after exposure to SARS-CoV-2. In some embodiments, the bispecific antibody is administered at most about 1 month after exposure to SARS-CoV-2.

Further provided herein are methods of treating an individual with a SARS-CoV-2 infection with the bispecific antibody or antibody fragment thereof described herein, comprising: a) obtaining or having obtained a sample from the individual; b) performing or having performed an expression level assay on the sample to determine expression levels of SARS-CoV-2 antibodies; and c) if the sample has an expression level of the SARS-CoV-2 antibodies then administering to the individual the antibody or antibody fragment described herein, thereby treating the SARS-CoV-2 infection.

Further provided herein are methods for diagnosing an individual with a SARS-CoV-2 infection with the bispecific antibody or antibody fragment thereof described herein, comprising: a) obtaining or having obtained a sample from the individual; and b) performing or having performed an expression level assay on the sample to determine expression levels of SARS-CoV-2 antibodies using the bispecific antibody or antibody fragment thereof described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A are SPR traces of 6-3, 3-31, and Bispecific Antibody 1 binding to the S1 monomers and S trimers of SARS-CoV-2 Delta and Omicron. FIG. 2B depicts binding of Bispecific Antibody 1 to Omicron S1 RBD displayed on the surface of yeast. Binding of Omicron S1 RBD by Bispecific Antibody 1 is confirmed by high fluorescence in both channels.

FIG. 10 depicts Bispecific Antibody 1, formed from parental antibodies 3-31 and 6-3.

FIG. 11A show neutralization curves for rVSV-SARS-CoV2. FIG. 11B shows escape from 6-3 parent. FIG. 11C shows escape from Bispecific Antibody 1.

FIGS. 12A-12F show neutralization curves of SARS-CoV-2 BA.5. FIG. 12A shows neutralization curves for Bispecific Antibody 1 and bebtelovimab. FIG. 12B shows neutralization curves for Bispecific Antibody 1 and Centivax. FIG. 12C shows neutralization curves for Bispecific Antibody 1 and Sotrovimab FIG. 12D shows neutralization curves for Bispecific Antibody 1, Casirivimab, and Imdevimab. FIG. 12E shows neutralization curves for Bispecific Antibody 1, Bamlanivimab, and Etesevimab. FIG. 12F shows neutralization curves for Bispecific Antibody 1, Tixagevimab, and Cilgavimab.

FIG. 13 shows additional neutralization data for Bispecific Antibody 1 against rVSV-SARS-CoV-2, Wuhan and Omicron variants.

FIGS. 14A-14F show the results of antibody characterization by an in vitro antibody-dependent cell mediated cytotoxicity (ADCC) assay. FIG. 14A shows the results of FACS binding assays of the control, Rituxan, to Raji cells. FIG. 14B shows the results of FACS binding assays of bispecific antibody 1 to CHO-K1/Spike cells. FIG. 14C shows results of ADCC E/T optimization using the control, Herceptin. FIG. 14D shows results of ADCC assays at different E/T ratios for both bispecific antibody 1 and human IgG1. FIG. 14E shows results of an ADCC dose-response study using the control, Herceptin. FIG. 14F shows the results of ADCC dose-response studies using bispecific antibody 1 and human IgG1.

FIGS. 15A-15D show the results of complement-dependent cytotoxicity (CDC) assays. FIG. 15A shows results of CDC % NHSC optimization using the control, Rituxan. FIG. 15B shows target cell lysis results of CDC assays at different % NHSC for bispecific antibody 1 and human IgG1, the negative control. FIG. 15C shows results of an CDC dose-response study using the control, Rituxan. FIG. 15D the results of CDC dose-response studies using bispecific antibody 1 and human IgG1.

FIGS. 16A-16B show the results of in vitro antibody-dependent cellular phagocytosis (ADCP) assays. FIG. 16A shows results of an ADCP dose-response study using the control, Rituxan. FIG. 16B the results of ADCP dose-response studies using bispecific antibody 1 and human IgG1.

FIGS. 17A-17B show the results of in vitro antibody-dependent enhancement (ADE) experiments. FIG. 17A shows the results of pseudovirus entry assays. FIG. 17B shows the results of antibody-dependent enhancement (ADE) assays using human IgG1.

FIG. 18 shows binding of bispecific antibody 1 (Panel A) and an isotype control (Panel B) to FcγR1.

FIG. 19 shows binding of bispecific antibody 1 to FcγR2a, allelic variant R167, via a kinetic model (Panel A) and via a steady-state binding isotherm (Panel B).

FIG. 20 shows binding of bispecific antibody 1 to FcγR2a, allelic variant H167, via a kinetic model (Panel A) and via a steady-state binding isotherm (Panel B).

FIG. 21 shows binding of bispecific antibody 1 to FcγR2b/c via a kinetic model (Panel A) and via a steady-state binding isotherm (Panel B).

FIG. 22 shows binding of bispecific antibody 1 to FcγR3a, allelic variant 176F, via a kinetic model (Panel A) and via a steady-state binding isotherm (Panel B).

FIG. 23 shows binding of bispecific antibody 1 to FcγR3a, allelic variant 176V, via a kinetic model (Panel A) and via a steady-state binding isotherm (Panel B).

FIG. 24 shows binding of bispecific antibody 1 to FcRn at pH 6.0 via a kinetic model (Panel A) and via a steady-state binding isotherm (Panel B).

FIG. 25 shows a direct comparison of C1q binding to ELISA plates adsorbed with bispecific antibody 1 and control antibodies of various isotypes.

FIG. 26 shows the results of a signal test for the binding of ACE2-muFc with biotinylated SARS-CoV2 spike RBD in a cross-titration matrix.

FIG. 27 shows dose dependent inhibition of ACE2-muFc/SARS-CoV-2 spike protein interactions. The SARS-CoV-2 spike proteins used in these assays were RBD, ancestral variant (Panel A); trimer, D614 variant (Panel B); trimer, delta variant (Panel C); and trimer, omicron variant (Panel D).

FIGS. 28A-28D shows reconstructed consensus maps from CryoEM studies. FIG. 28A shows a global consensus map. FIG. 28B masked refinement map around VHH position 1 and 2. FIG. 28C shows a multi-body refinement map around VHH position 1 and spike chain B N-terminal domain. FIG. 28D shows a masked refinement map around VHH position 2.

FIGS. 29A-29D show reconstructed densities of bispecific antibody 1 together with modeled coordinates from the side (FIG. 29A), the front (FIG. 29B), the back (FIG. 29C), and the top (FIG. 29D). Magenta, red, and green represent monomers of the spike trimer, further denoted as chain A, chain B, and chain C, respectively. Grey density represents the bispecific antibody constant fragment, while the VHH1 is depicted in gold, the VHH2 is depicted in blue, and the VHH3 is depicted in orange.

FIG. 30 shows an overview of epitope and paratope interactions.

FIG. 31 shows an overview of explicit bonds.

FIG. 32 shows a comparison to mutagenesis studies.

FIG. 33 shows an annotated sequence of bispecific antibody 1 (SEQ ID NO: 8).

Figure 34A:
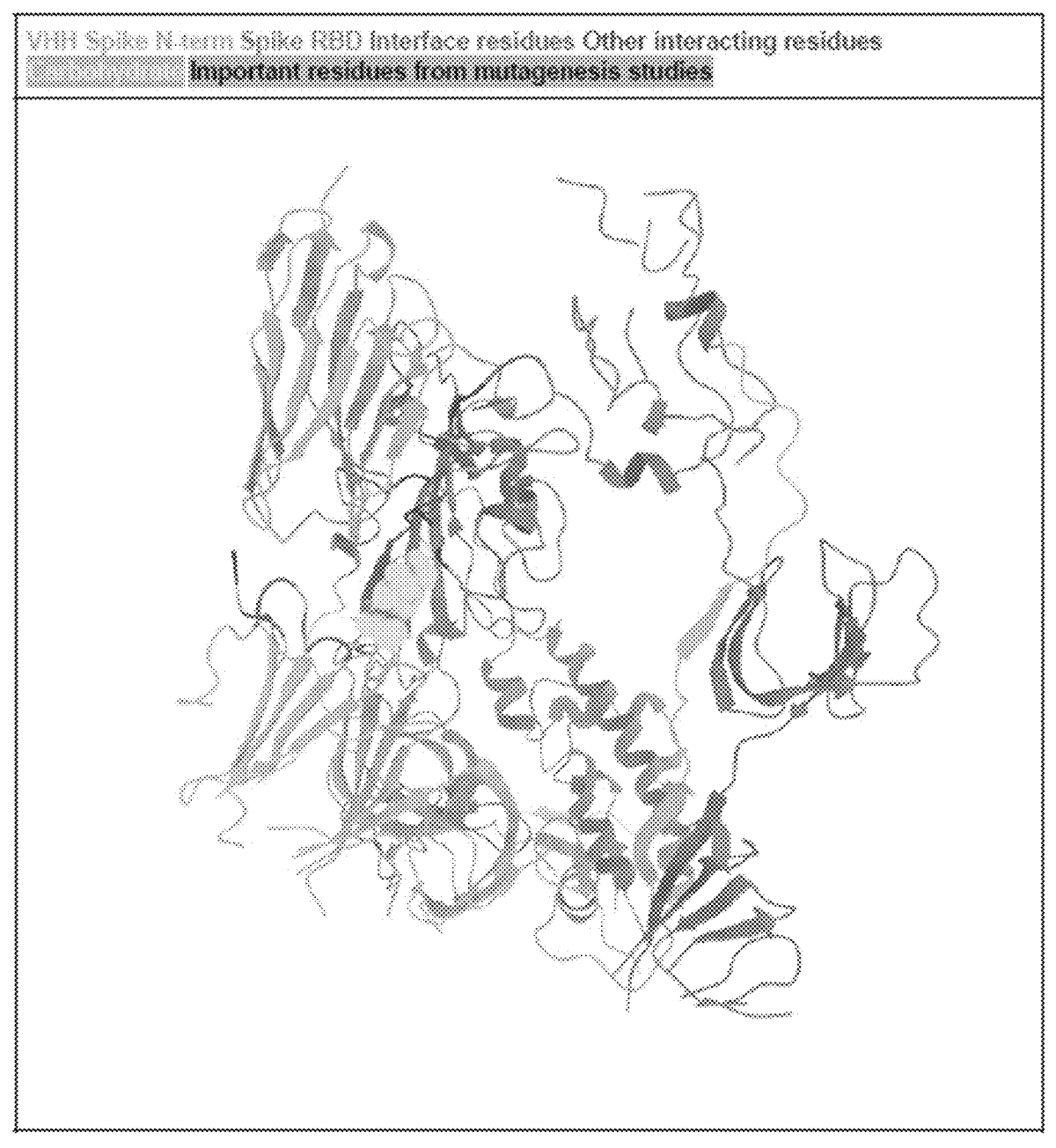
Figure 34B:
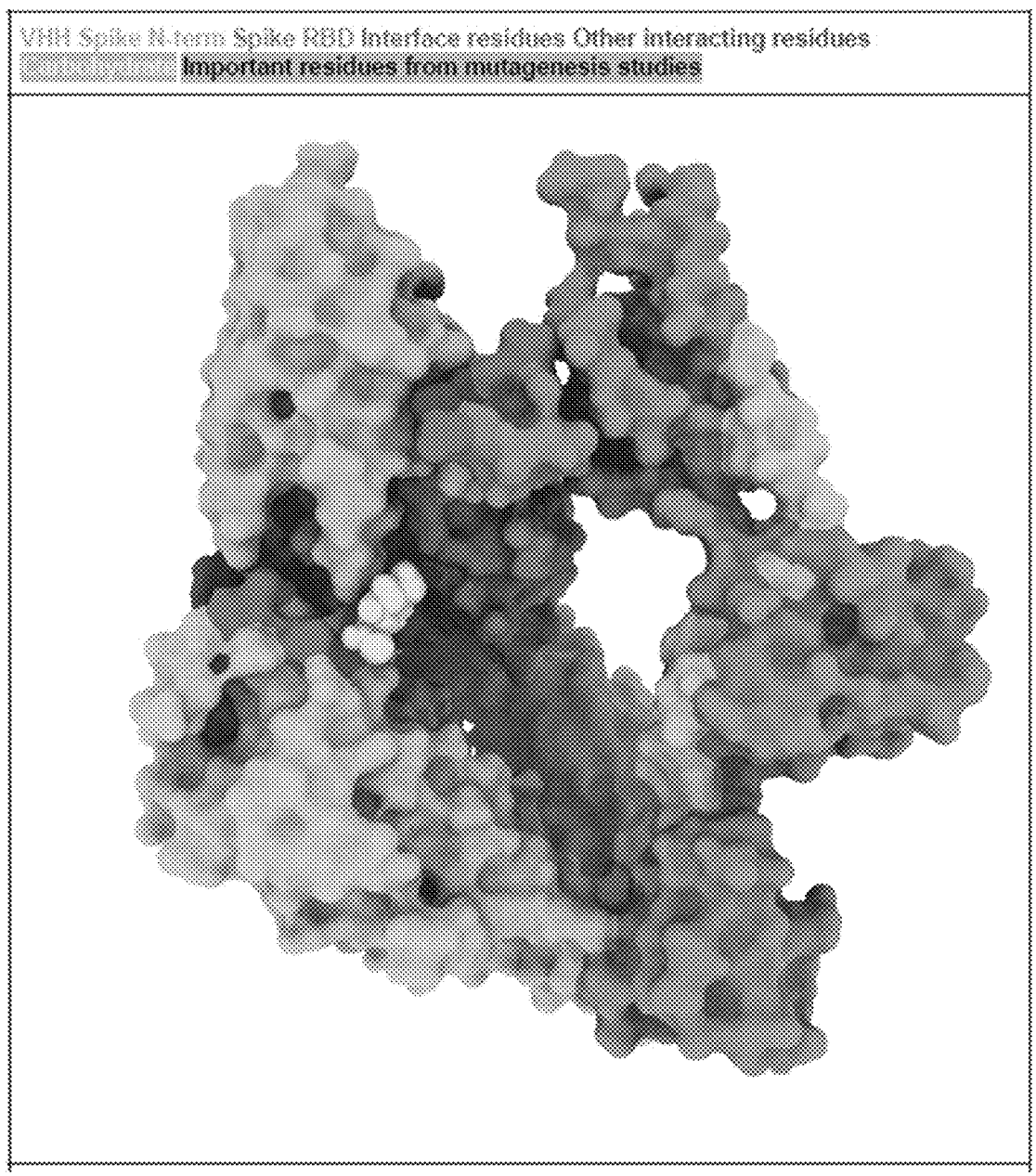

FIGS. 34A-34B show an atomic model of SARS-CoV-2 spike protein with the N-terminal VHH at epitope 1 (orange) on RBD down (red) domain in a cartoon representation (FIG. 34A) and a surface representation (FIG. 34B).

Figure 35A:
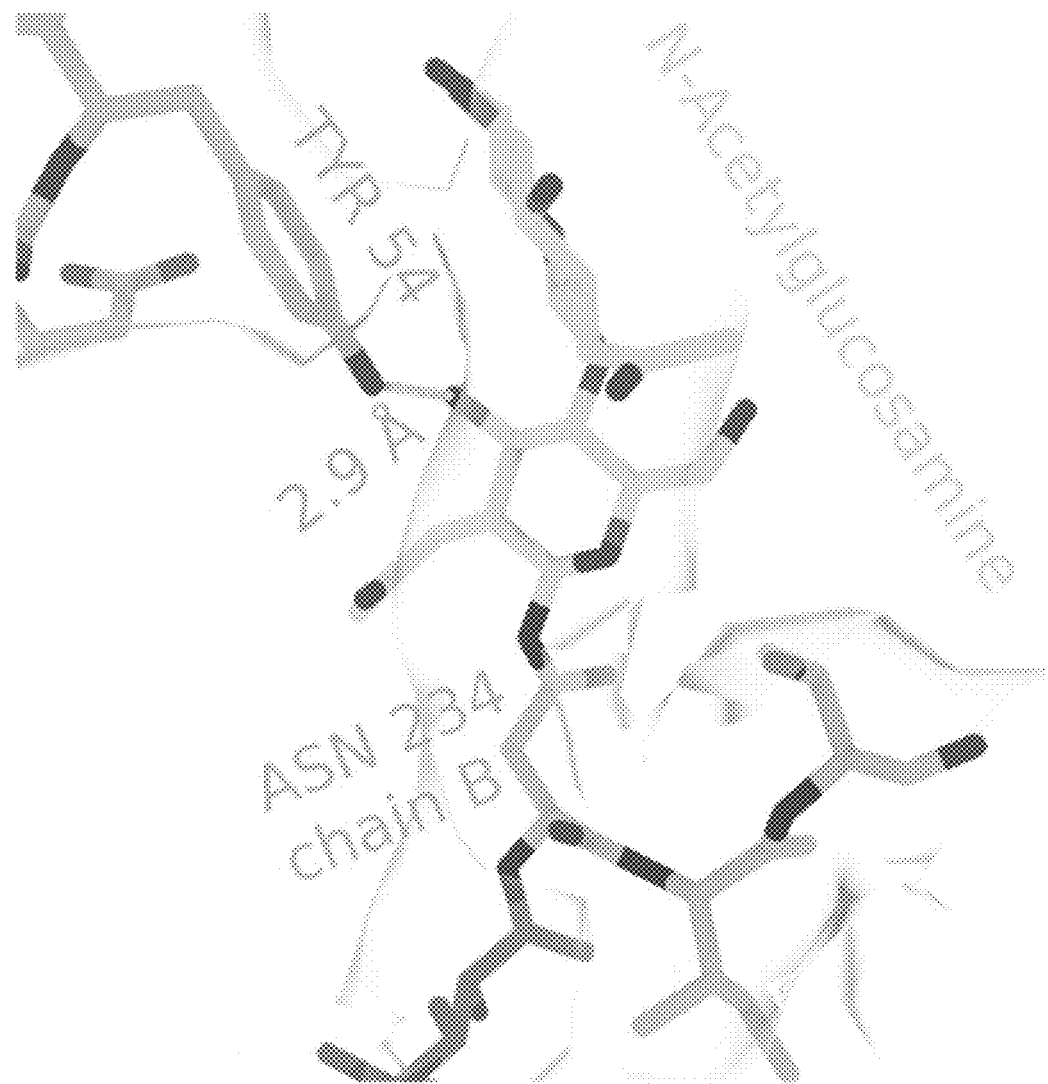
Figure 35B:
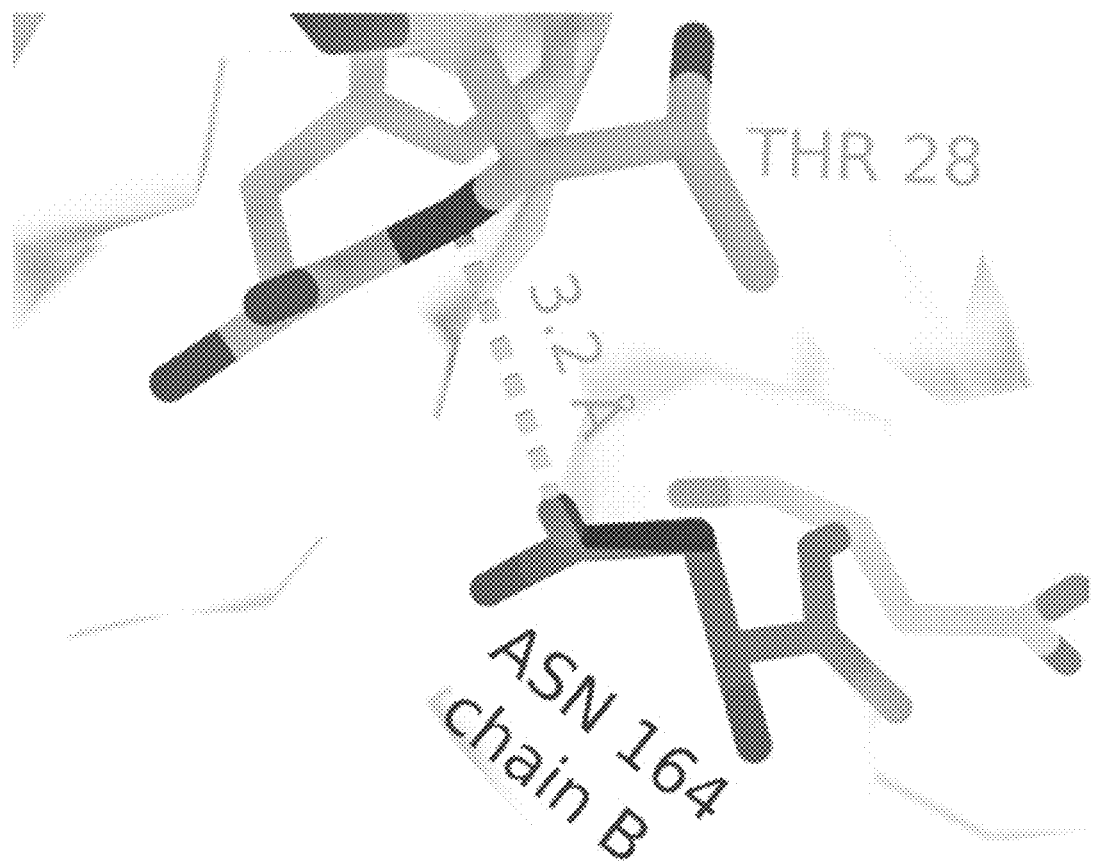
Figure 35C:
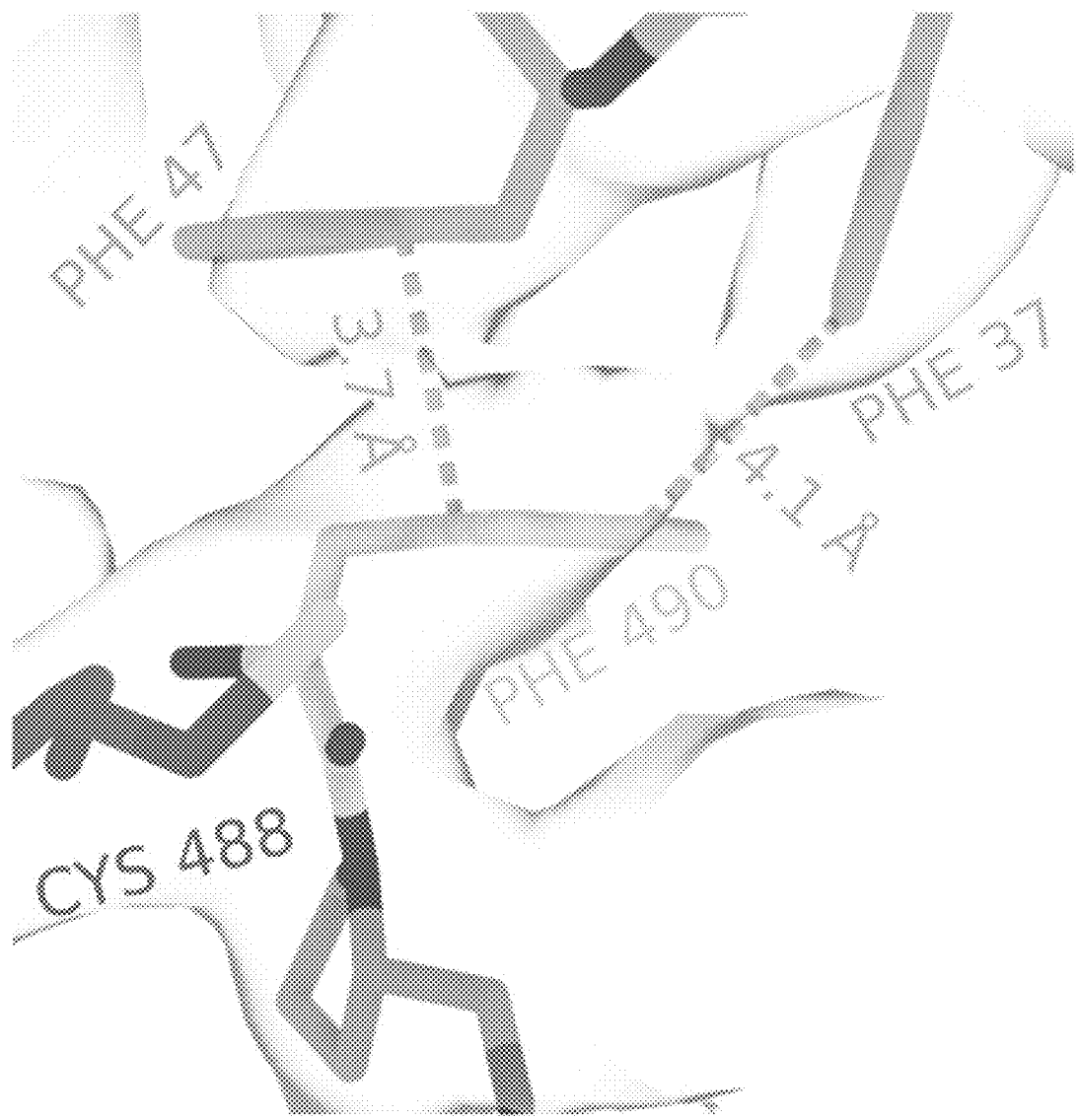
Figure 35D:
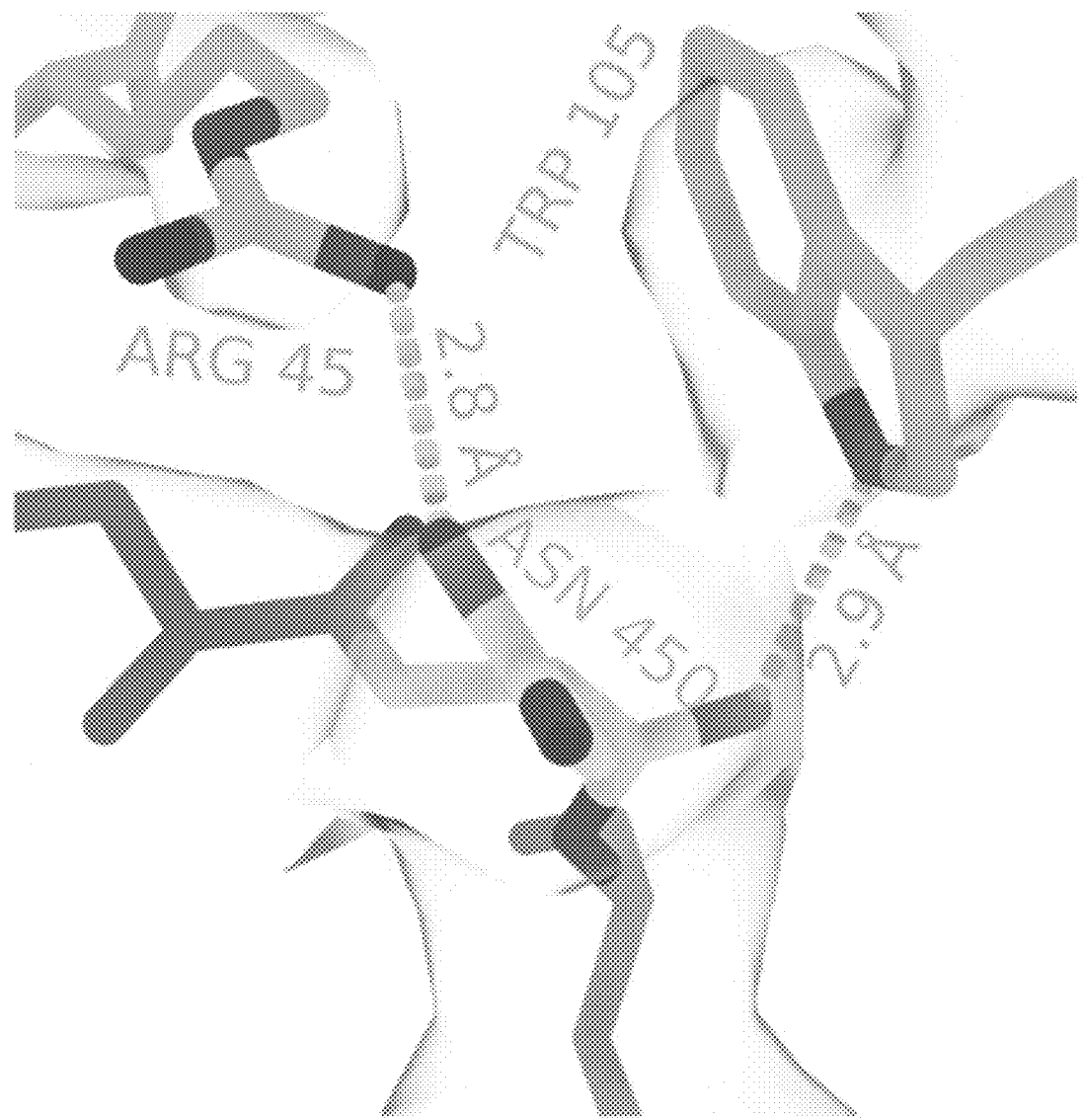
Figure 35E:
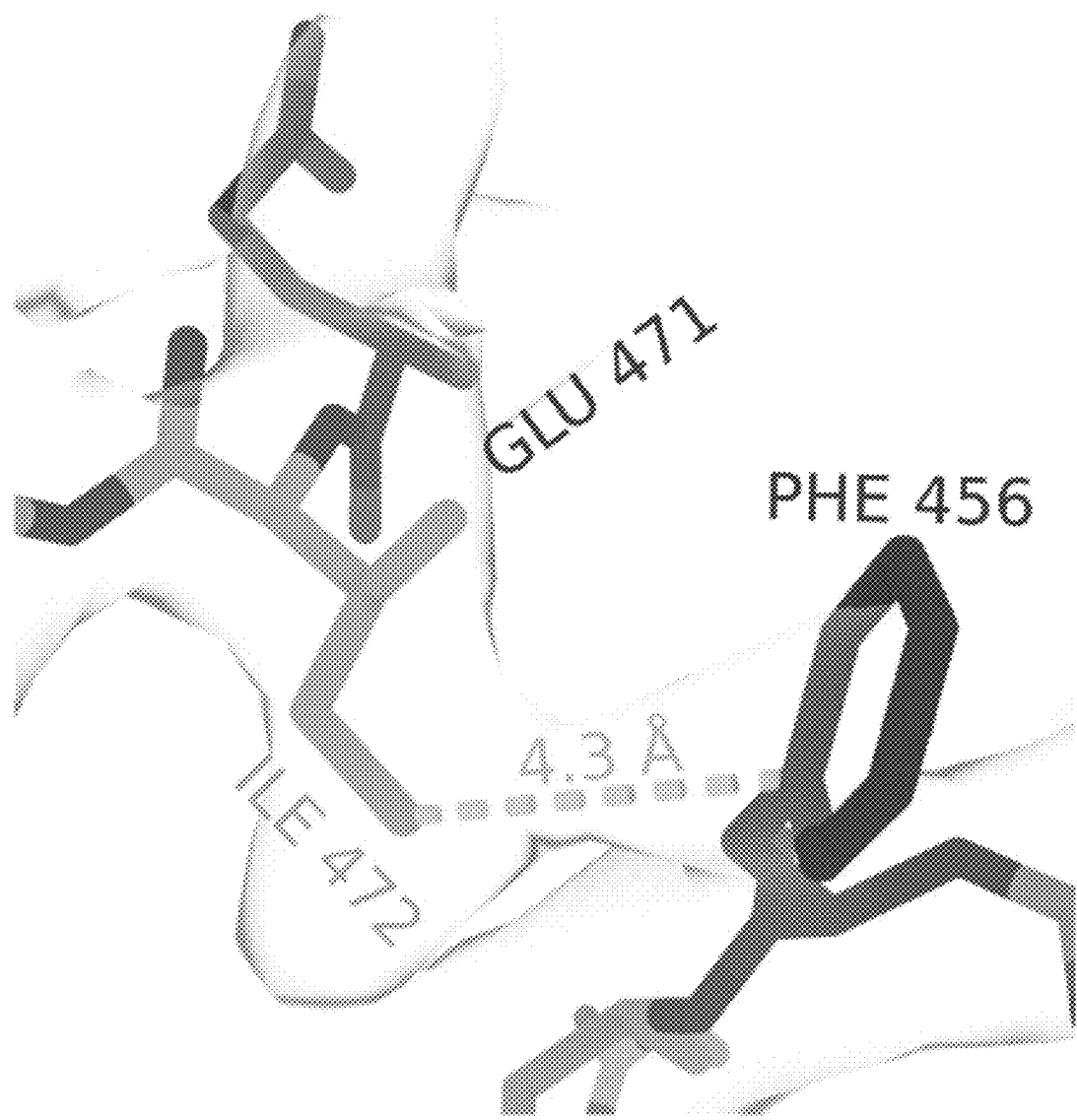
Figure 35F:
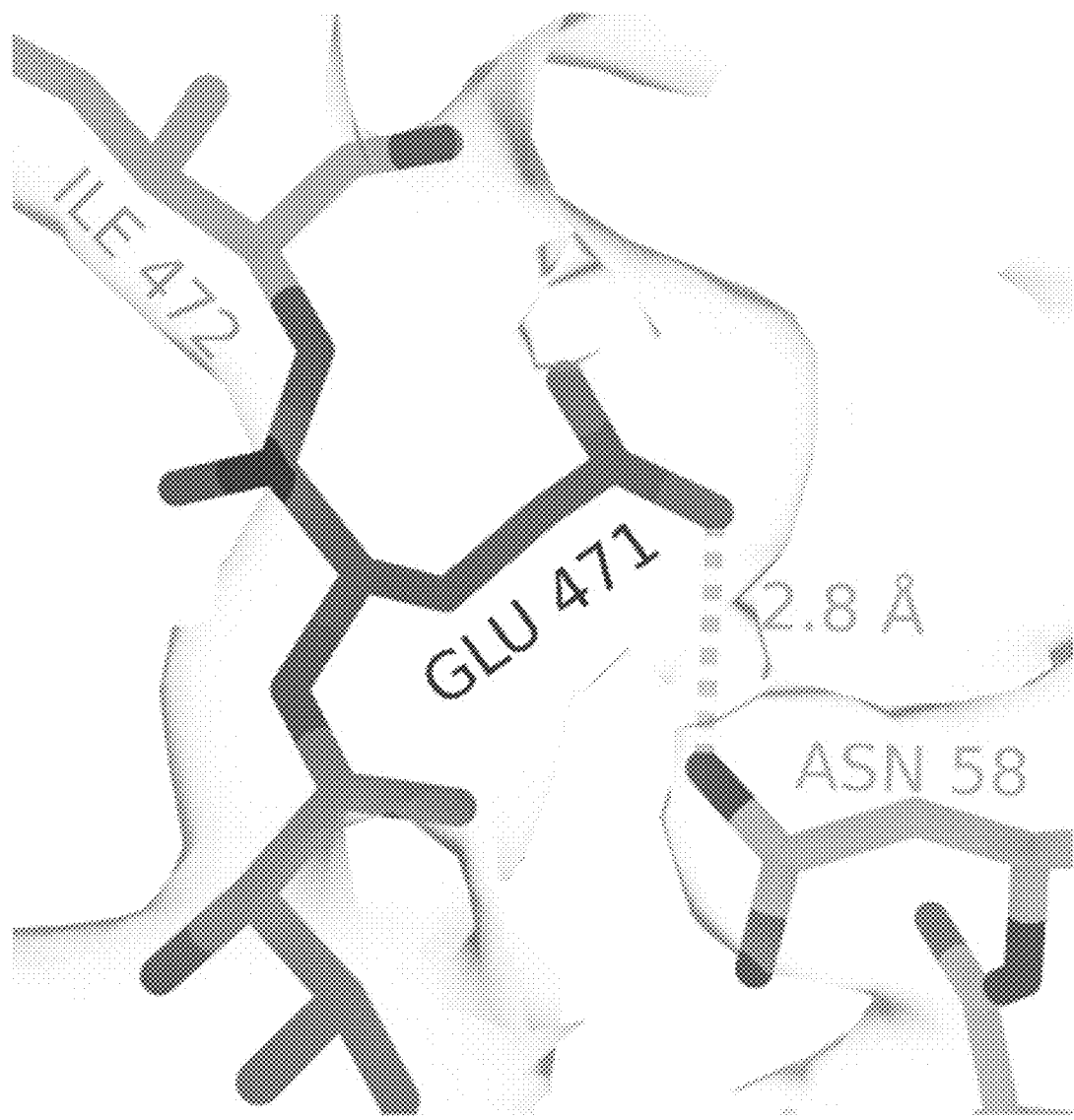

FIGS. 35A-35F show specific interactions between the VHH and the spike protein. FIG. 35A shows the importance of the glycosylated ASN 234 in the spike protein in VHH binding. FIG. 35B shows the interaction between ASN 164 (spike) sidechain and backbone of THR 28 (VHH). FIG. 35C shows stacking interaction between PHE 490 (spike) and PHE 37, and 47 (both from VHH). FIG. 35D shows the interaction between ARG 45 and TRP 105 (both from VHH) and ASN 450 (spike). FIG. 35E shows that ILE 472 (spike) in epitope 1 interacts with PHE 456 (spike). FIG. 35F shows the interaction between GLU 471 sidechain (spike) and ASN 58 sidechain.

FIG. 36 shows a comparison between escape studies and studies at VHH1 positions.

Figure 37A:
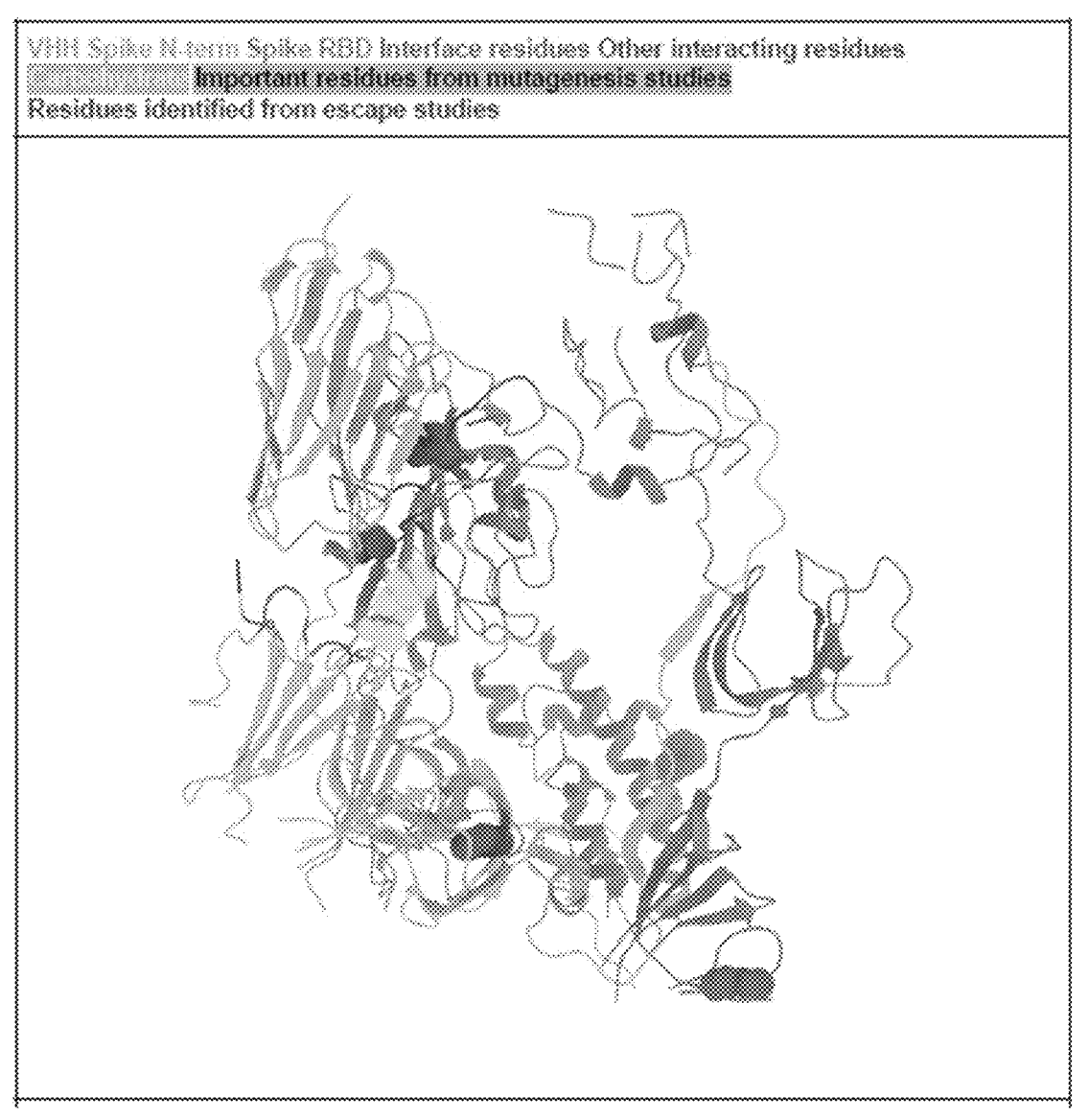
Figure 37B:
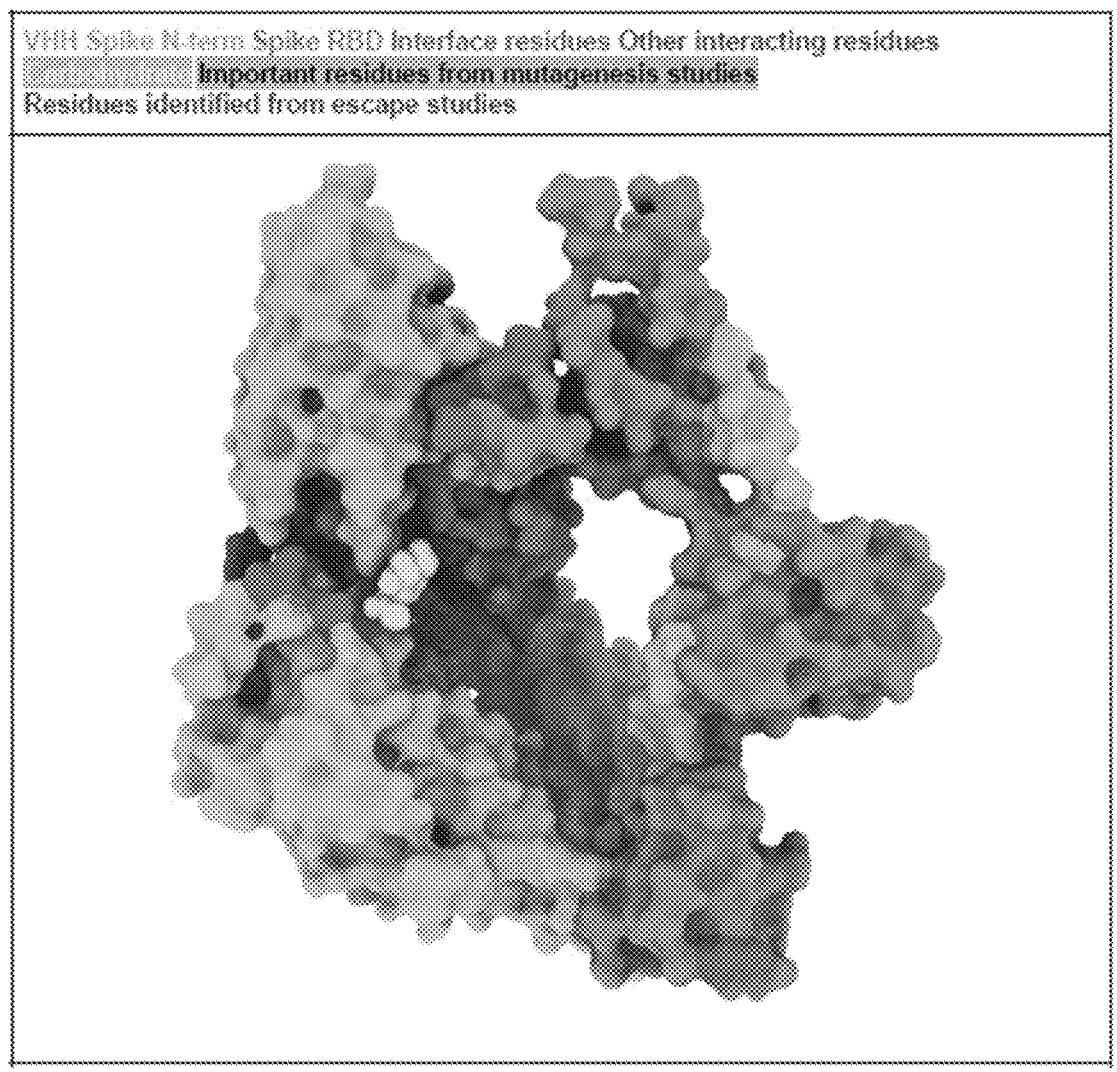
Figure 37C:
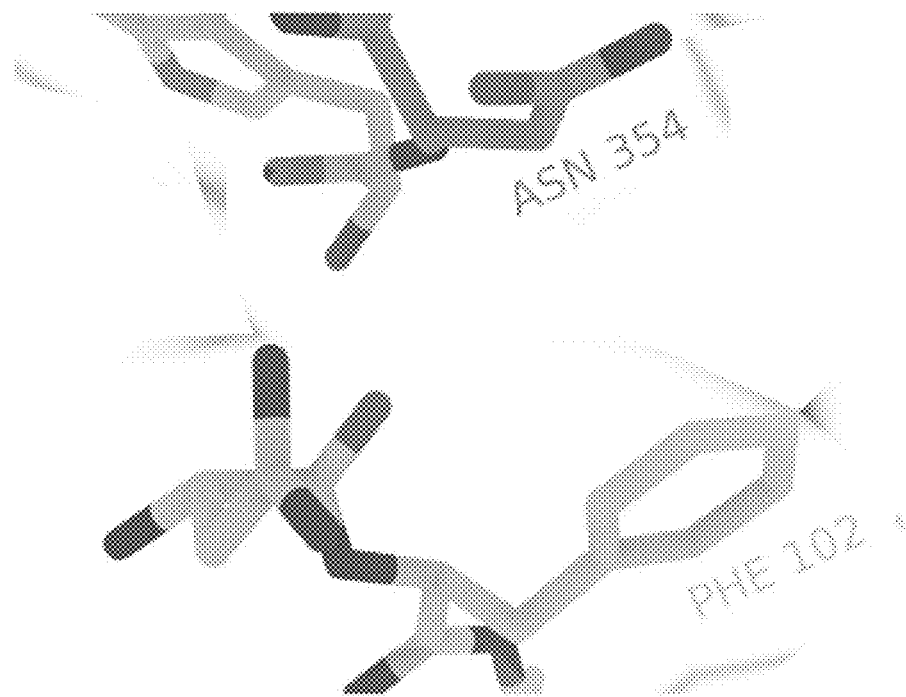

FIGS. 37A-37B show atomic models of SARS-CoV-2 spike proteins with N-terminal VHH at epitope 1 (orange) on RBD down (red) domain in a cartoon representation (FIG. 37A) and a surface representation (FIG. 37B). Residues identified in the escape studies are depicted as brown spheres. FIG. 37C shows that residue ASN 354 (spike) is interacting with PHE 102 (VHH) in the VHH1 position.

FIG. 38 shows an overview of epitope and paratope interactions.

FIG. 39 shows an overview of explicit bonds.

FIG. 40 shows a comparison to mutagenesis studies

FIG. 41 shows an annotated sequence of bispecific antibody 1 (SEQ ID NO: 9).

Figure 42A:
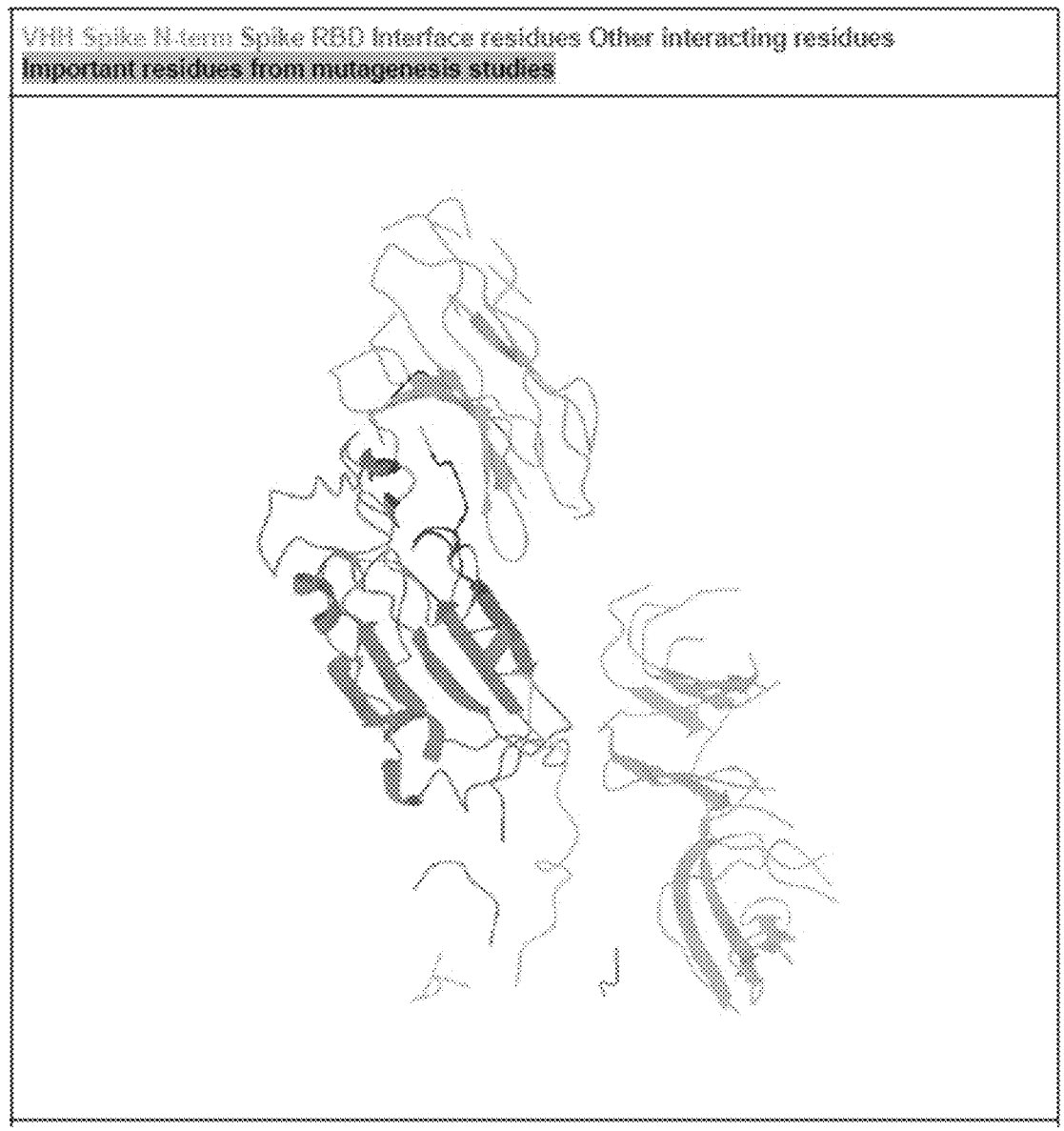
Figure 42B:
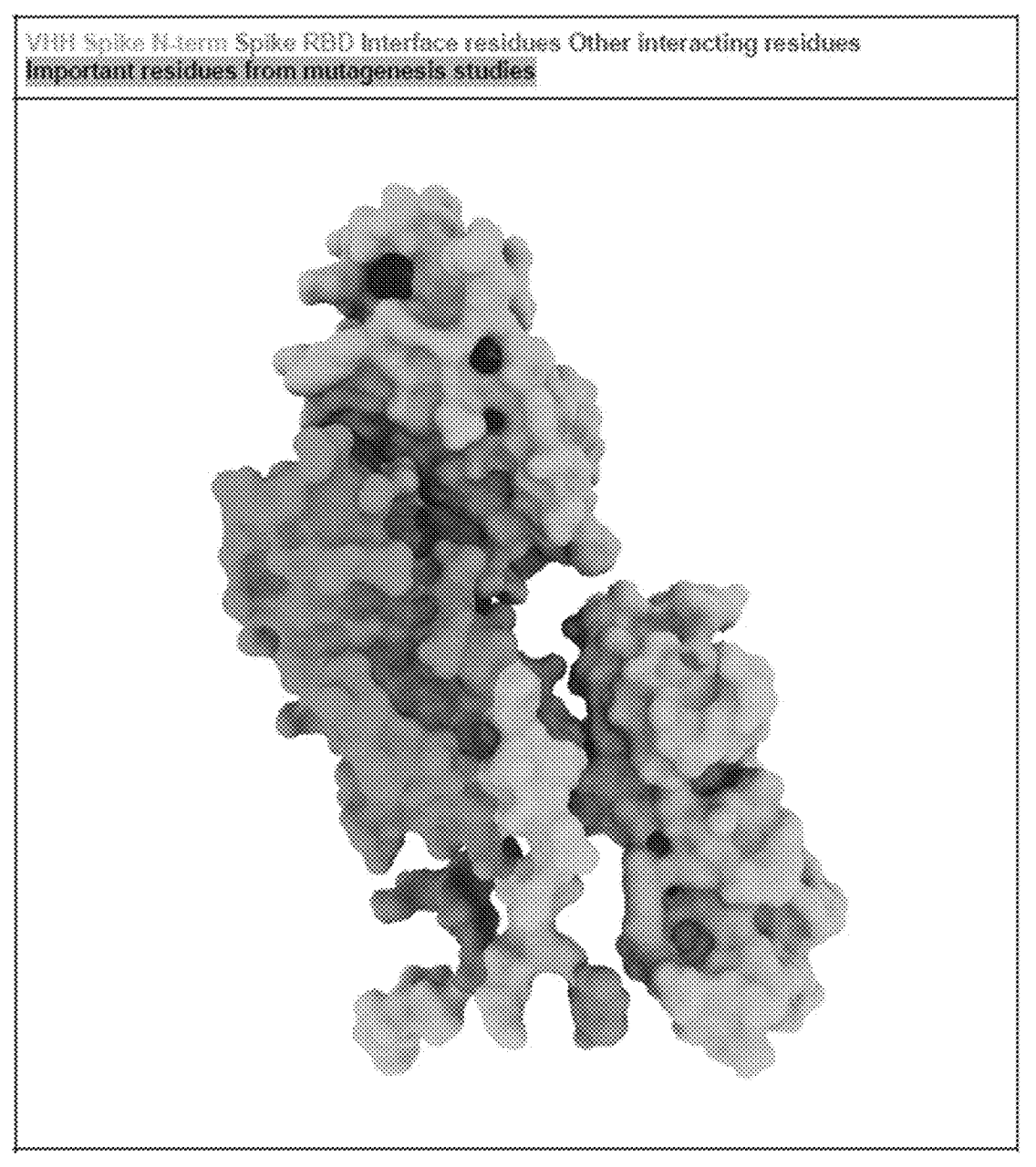

FIGS. 42A-42B show atomic models of SARS-CoV-2 spike proteins with N-terminal VHH at epitope 2 (orange) on RBD up (red) domain in a cartoon representation (FIG. 42A) and a surface representation (FIG. 42B).

Figure 43A:
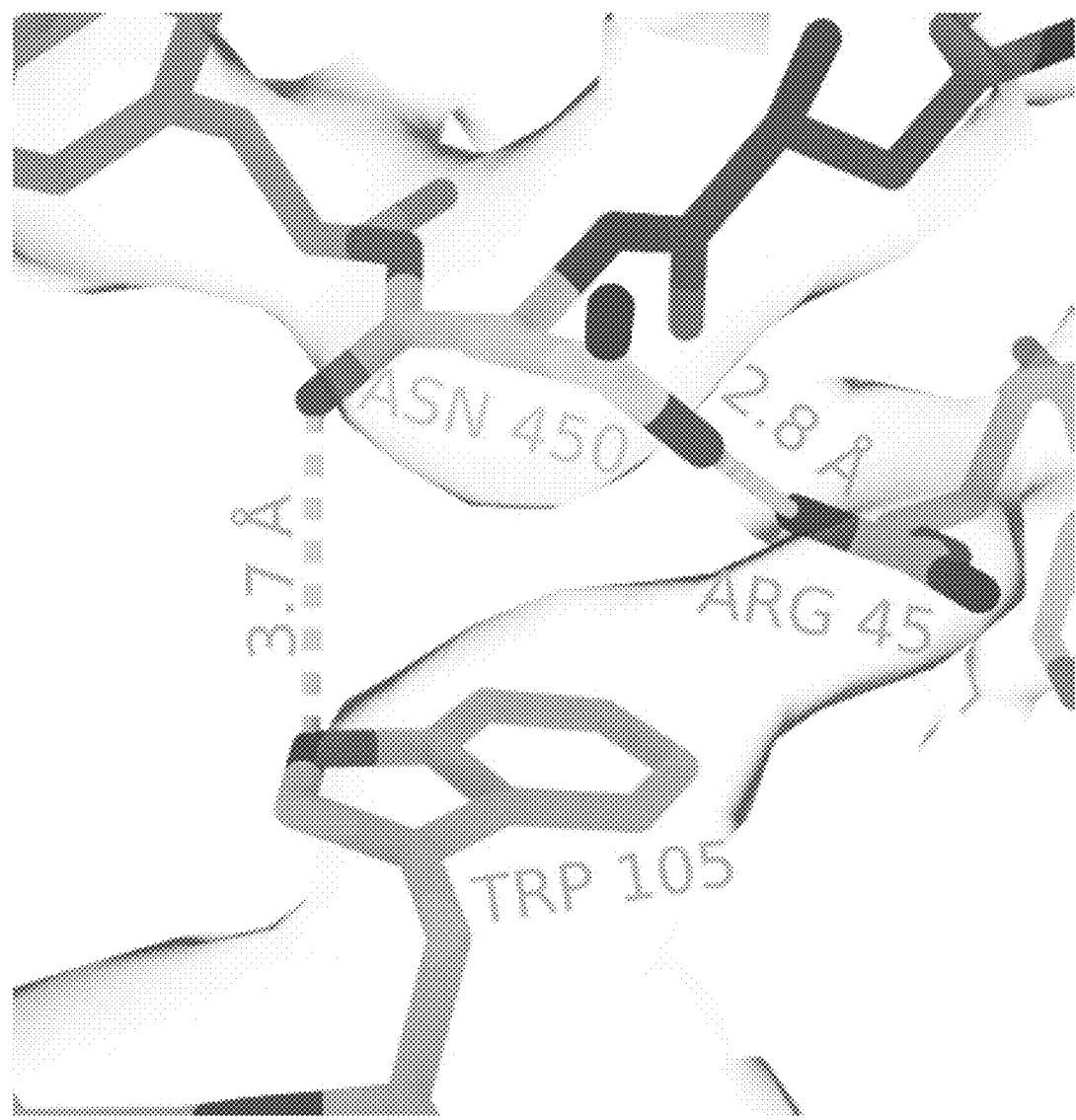
Figure 43B:
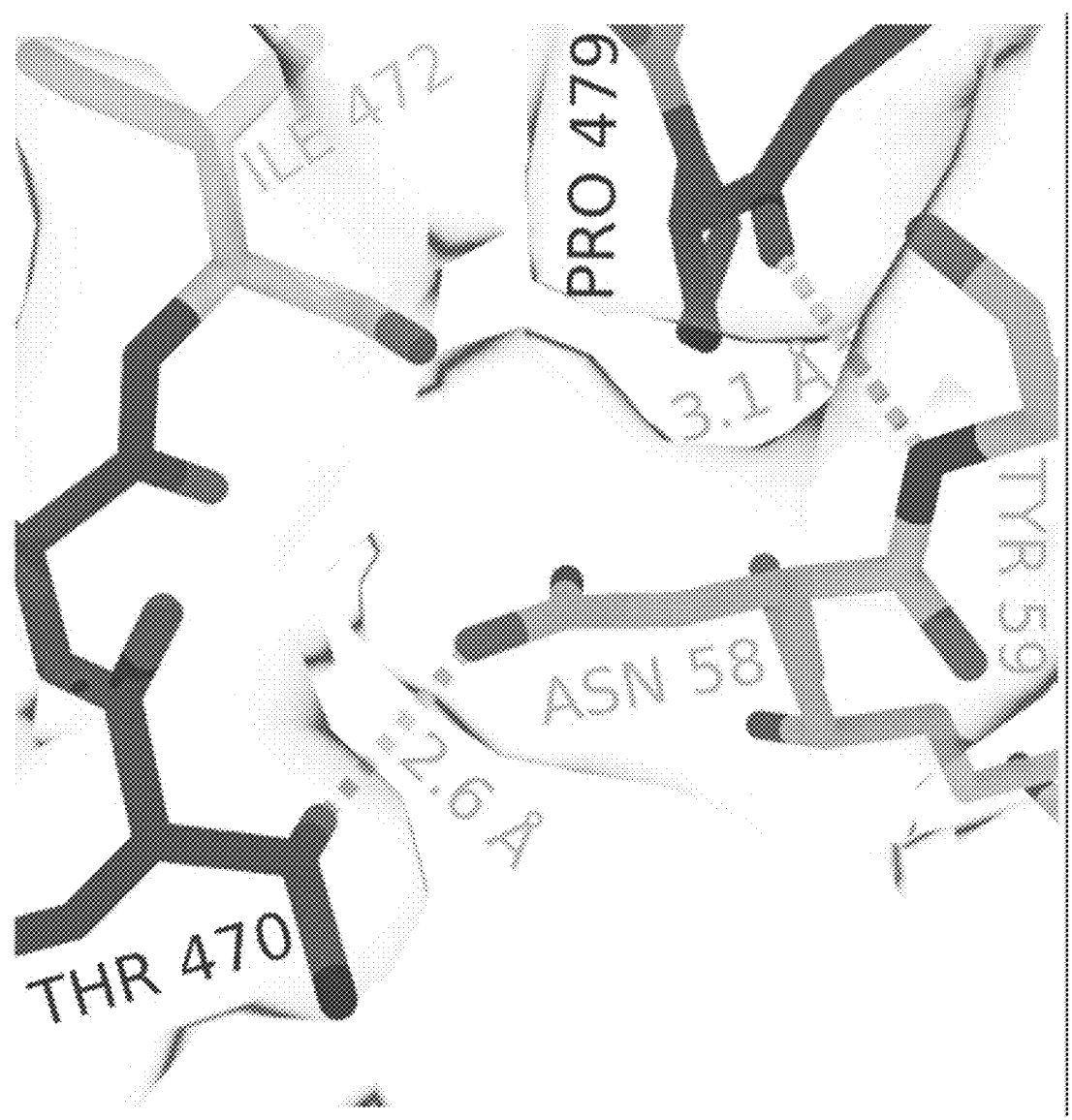
Figure 43C:
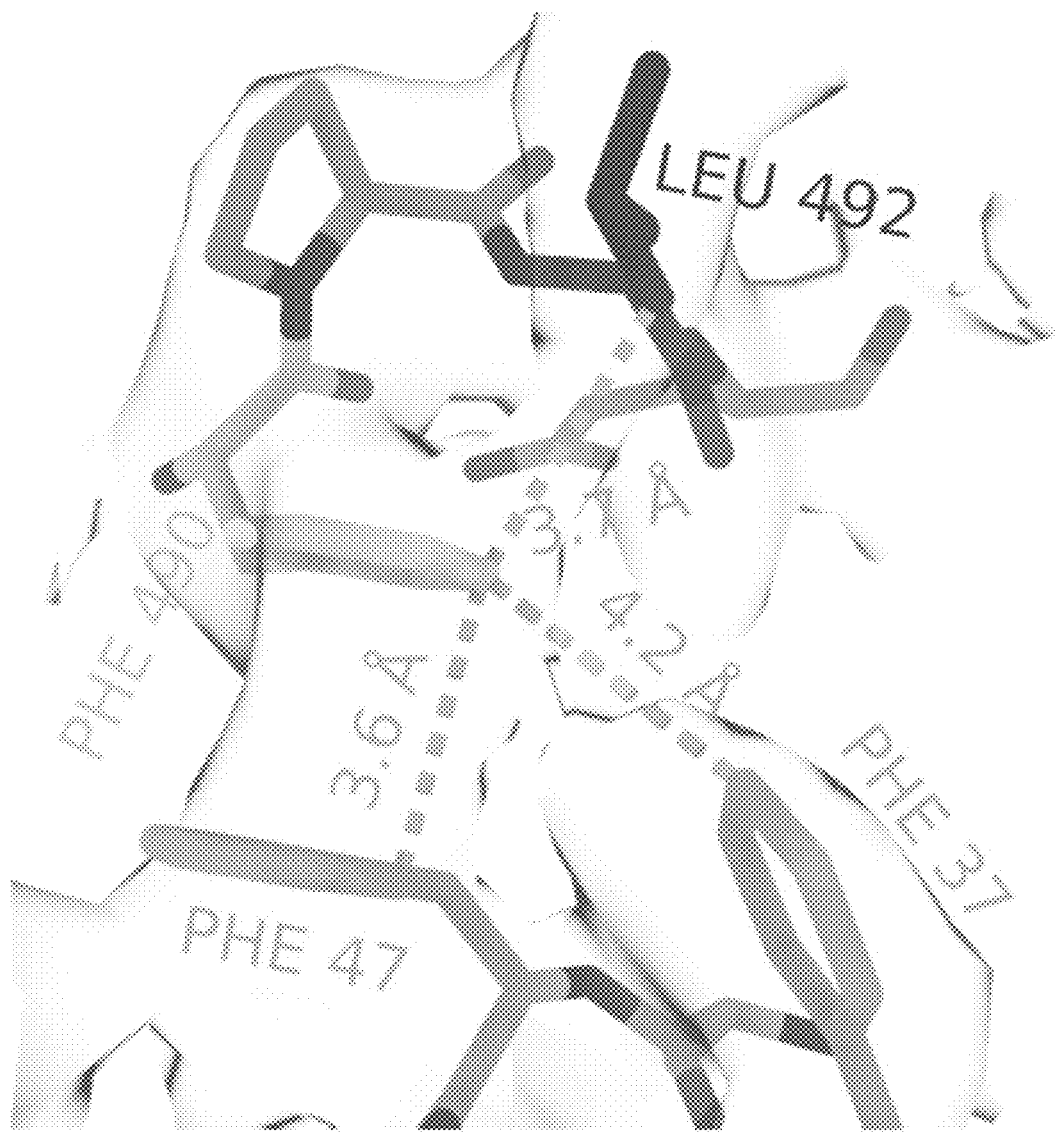
Figure 43D:
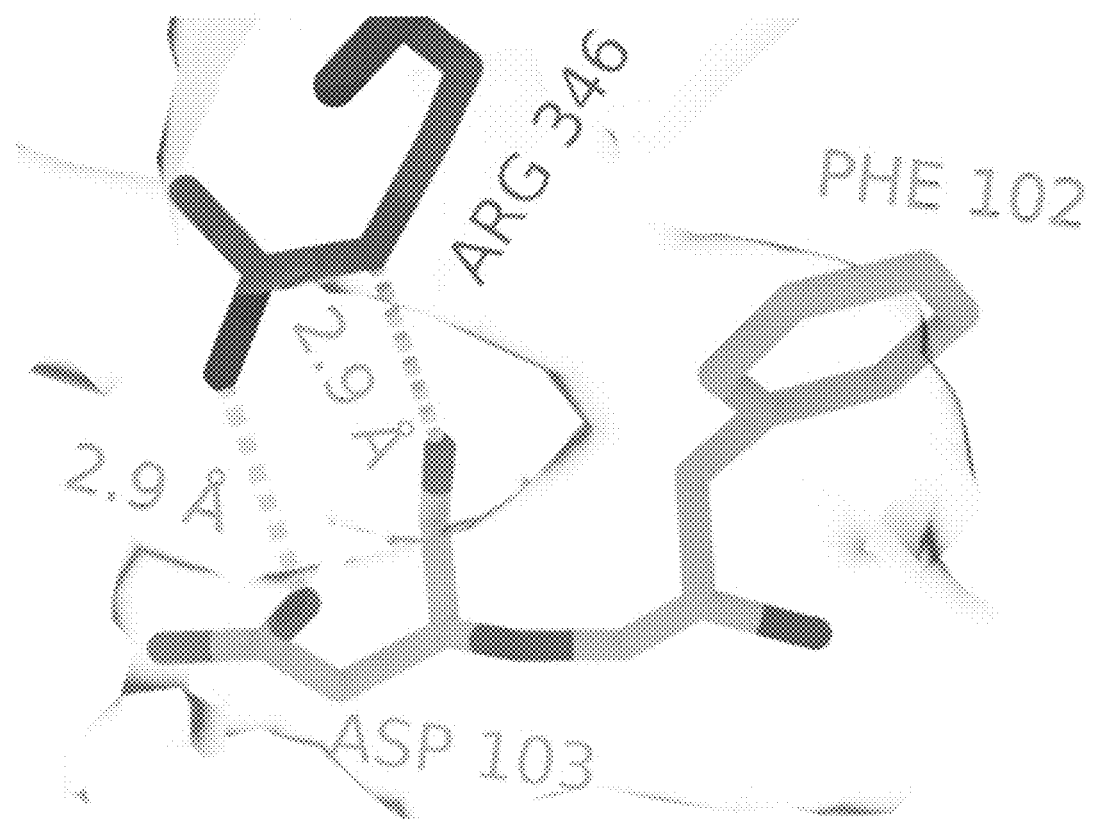

FIGS. 43A-43D show specific interactions between the VHH and the spike protein. FIG. 43A shows residue ASN 450 (spike) is interacting with ARG 45 and TRP 105 (both from VHH). FIG. 43B shows the interaction between THR 470 (spike) and ASN 58 (VHH) as well as the interaction between PRO 479 (spike) with the backbone of TYR 59. FIG. 43C shows that PHE 490 appears to interact with PHE 37 and 47 (VHH) through a stacking interaction. FIG. 43D shows the hydrogen bonds between ARG 346 (spike) and ASP 103 (VHH).

FIG. 44 shows a comparison between escape studies and studies at VHH2 positions.

Figure 45A:
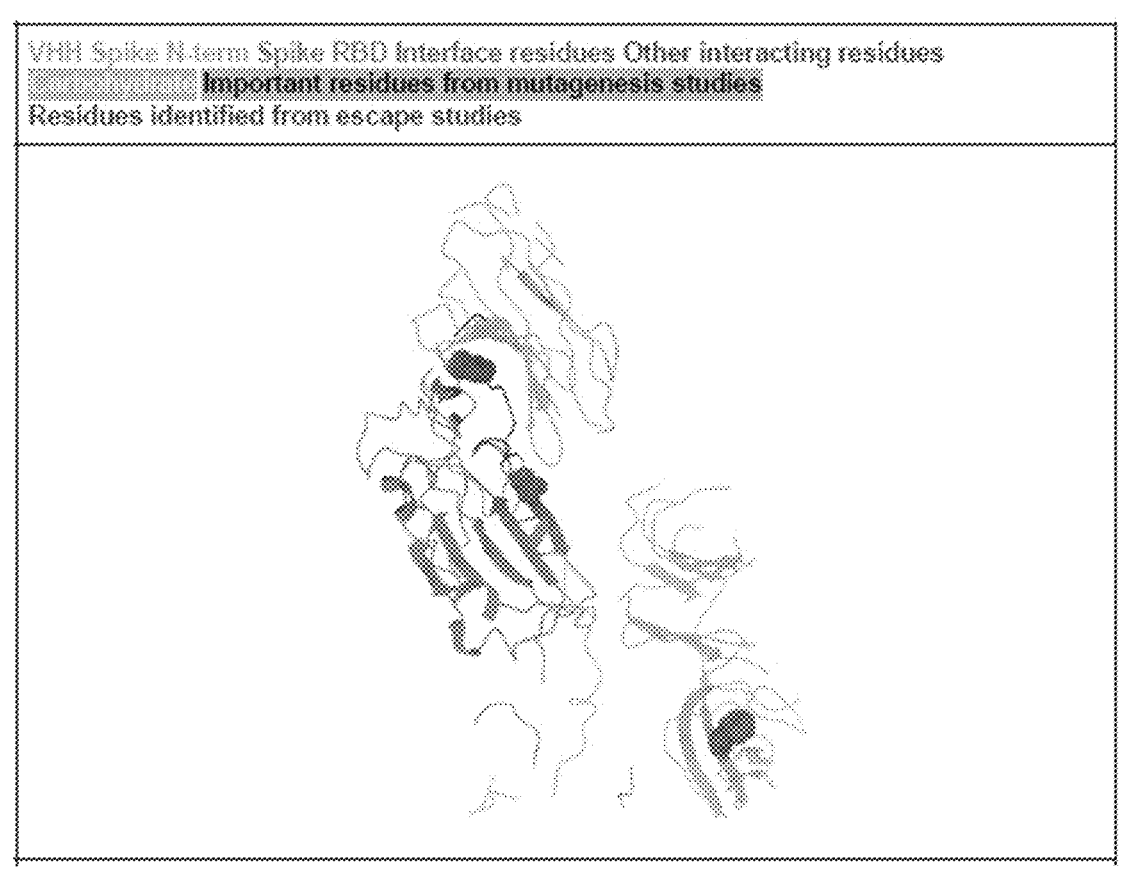
Figure 45B:
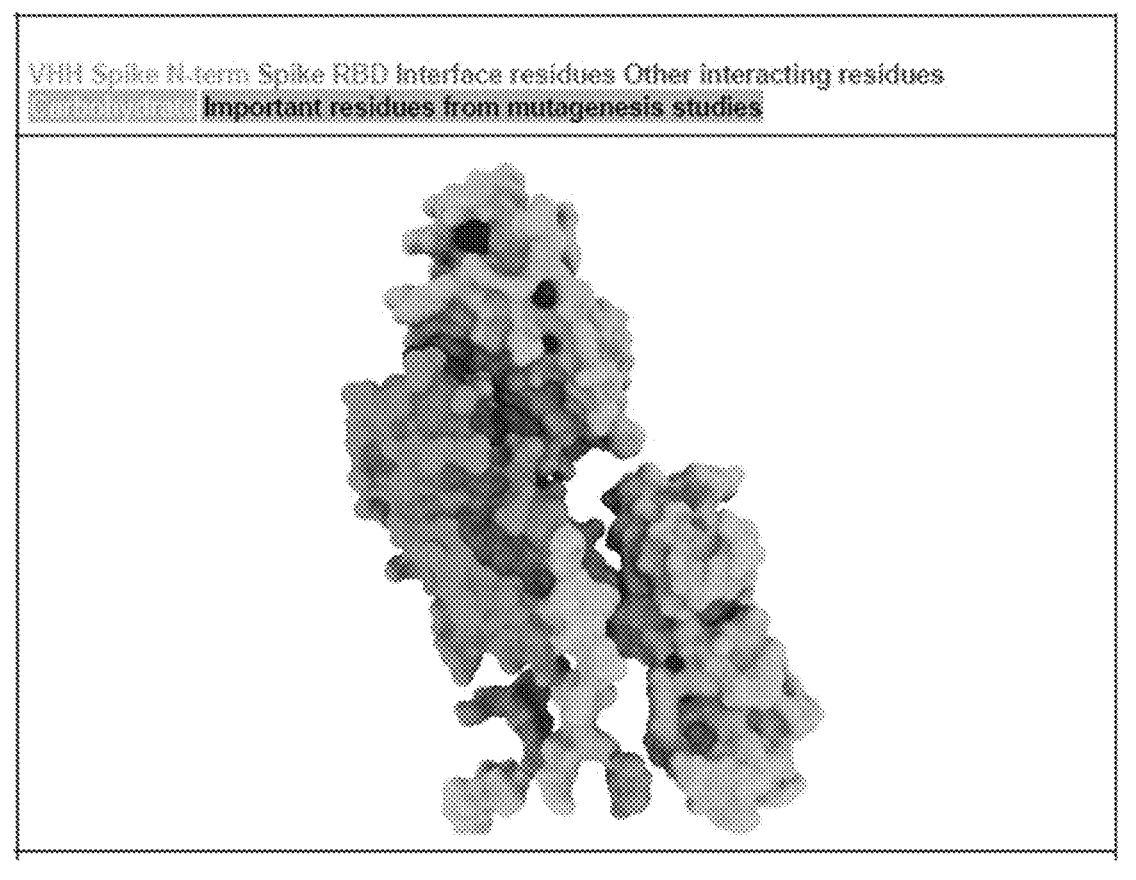
Figure 45C:
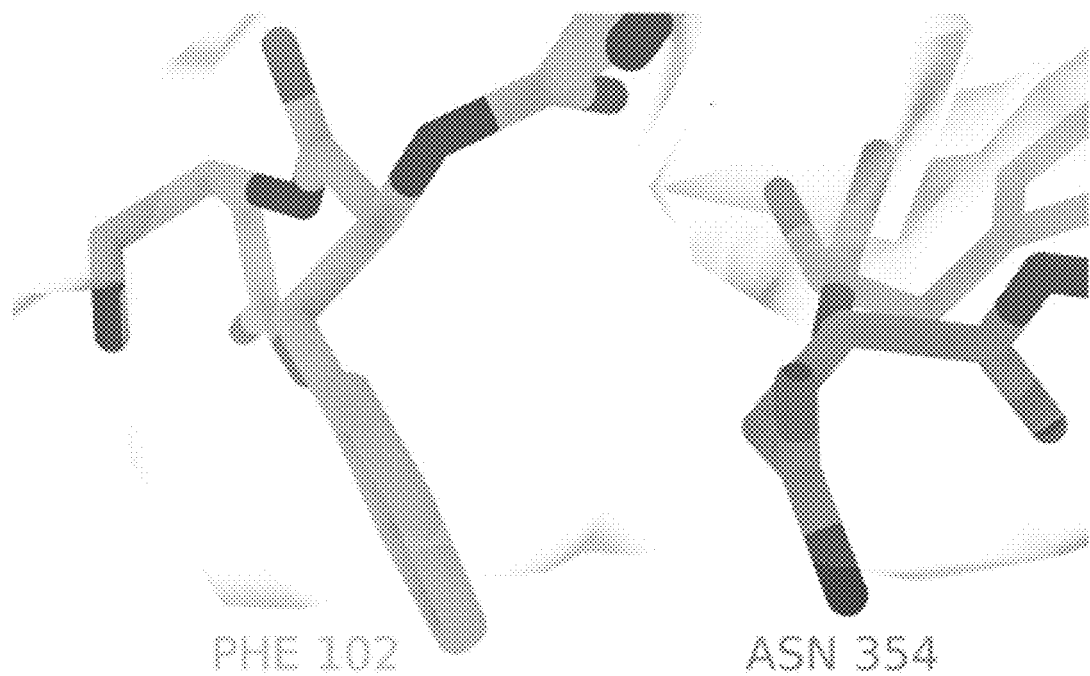

FIGS. 45A-45B show atomic models of SARS-CoV-2 spike proteins with N-terminal VHH at epitope 2 (orange) on RBD up (red) domain in a cartoon representation (FIG. 45A) and a surface representation (FIG. 45B). Residues identified in the escape studies are depicted as brown spheres. FIG. 45C shows residue ASN 354 (spike) interacting with PHE 102 (VHH).

Figure 45D:
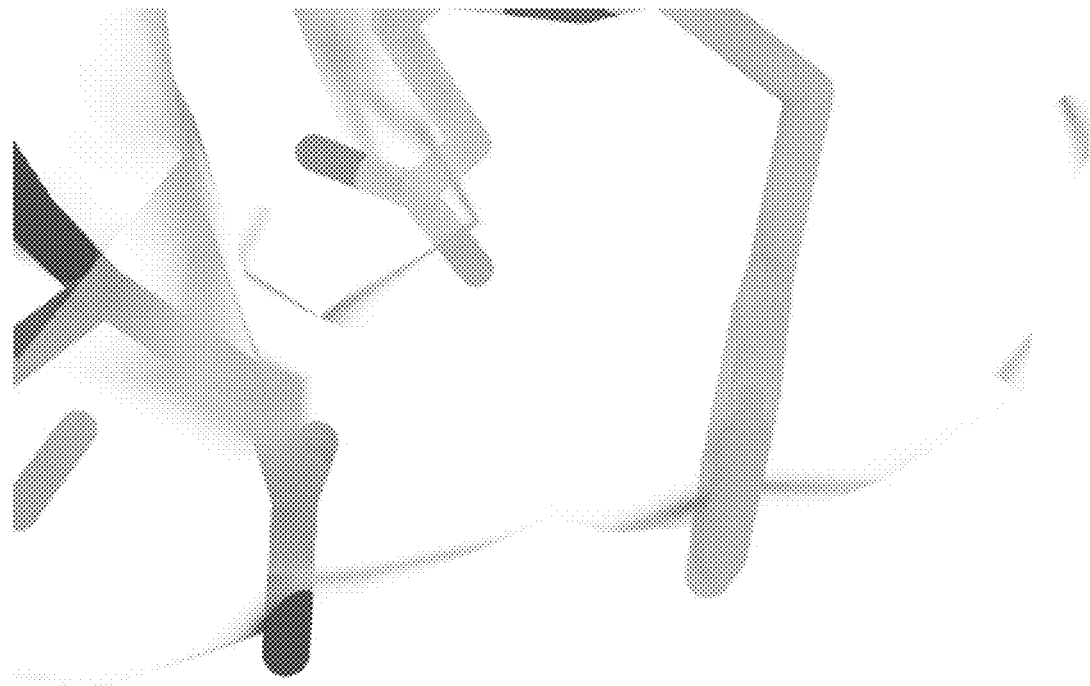

FIG. 45D is a closer view of the interaction described in FIG. 45C.

FIG. 46 shows a comparison of the VHH1 and VHH2 epitopes and paratopes.

Figure 47A:
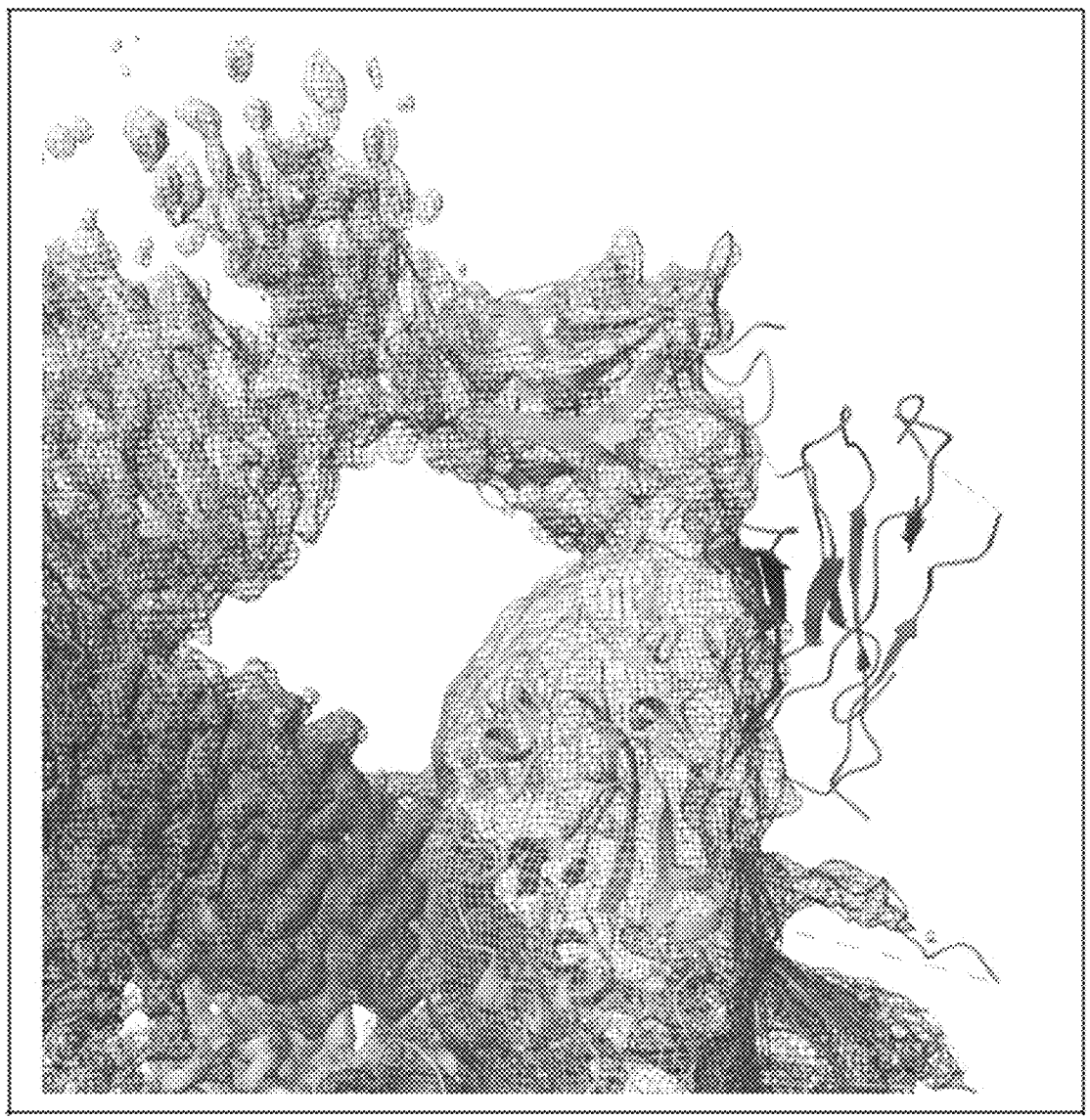
Figure 47B:
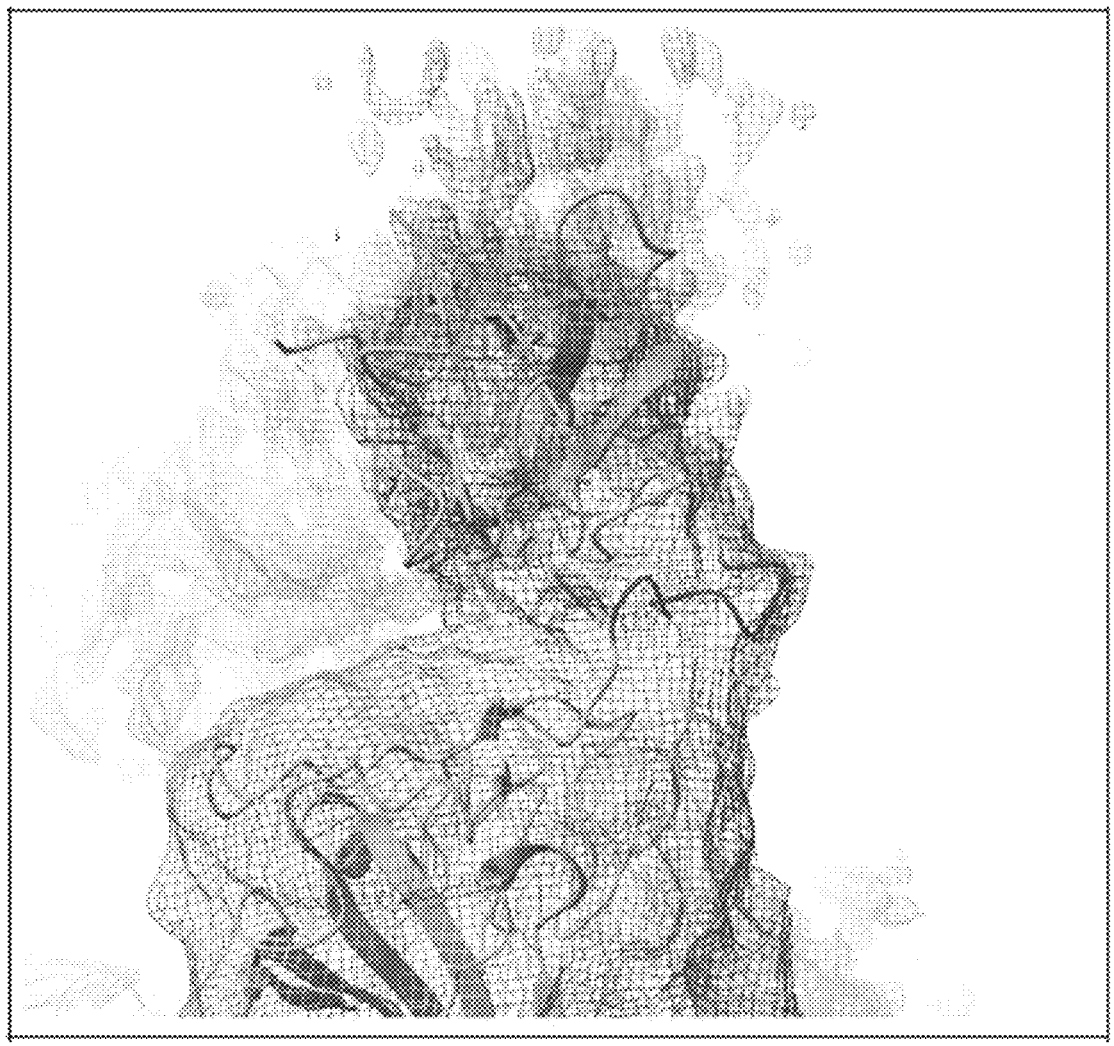

FIGS. 47A-47B show low-resolution density images of VHH3. FIG. 47A shows VHH3 positioned on top of the RBD up domain in a distinctly different position from the VHH1 and VHH2. FIG. 47B shows the VHH3 from a side view with interactions marked in red.

DETAILED DESCRIPTION

The present disclosure employs, unless otherwise indicated, conventional molecular biology techniques, which are within the skill of the art. Unless defined otherwise, all technical and scientific terms used herein have the same meaning as is commonly understood by one of ordinary skill in the art.

Definitions

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

Unless specifically stated, as used herein, the term "nucleic acid" encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands). Nucleic acid sequences, when provided, are listed in the 5' to 3' direction, unless stated otherwise. Methods described herein provide for the generation of isolated nucleic acids. Methods described herein additionally provide for the generation of isolated and purified nucleic acids. A "nucleic acid" as referred to herein can comprise at least 5, 10, 20, 30, 40, 50, 60, 70, 80, 90, 100, 125, 150, 175, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, 2000, or more bases in length. Moreover, provided herein are methods for the synthesis of any number of polypeptide-segments encoding nucleotide sequences, including sequences encoding non-ribosomal peptides (NRPs), sequences encoding non-ribosomal peptide-synthetase (NRPS) modules and synthetic variants, polypeptide segments of other modular proteins, such as antibodies, polypeptide segments from other protein families, including non-coding DNA or RNA, such as regulatory sequences e.g. promoters, transcription factors, enhancers, siRNA, shRNA, RNAi, miRNA, small nucleolar RNA derived from microRNA, or any functional or structural DNA or RNA unit of interest. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. cDNA encoding for a gene or gene fragment referred herein may comprise at least one region encoding for exon sequences without an intervening intron sequence in the genomic equivalent sequence. cDNA described herein may be generated by de novo synthesis.

Antibody Optimization Library for Coronavirus

Provided herein are methods, compositions, and systems for the optimization of antibodies for coronavirus. In some embodiments, the antibodies are optimized for SARS-CoV, MERS-CoV, CoV-229E, HCoV-NL63, HCoV-OC43, or HCoV-HKU1. In some embodiments, the antibodies are optimized for SARS-CoV-2. In some embodiments, the antibodies are optimized for a receptor that binds to the coronavirus. In some embodiments, the receptor of the coronavirus is ACE2 or dipeptidyl peptidase 4 (DPP4). In some embodiments, the antibodies are optimized based on interactions between the coronavirus and the receptor that binds the coronavirus. In some embodiments, the antibodies are optimized for angiotensin-converting enzyme 2 (ACE2). In some embodiments, the antibodies are optimized based on interactions between SARS-CoV-2 and ACE2.

Figure 4:
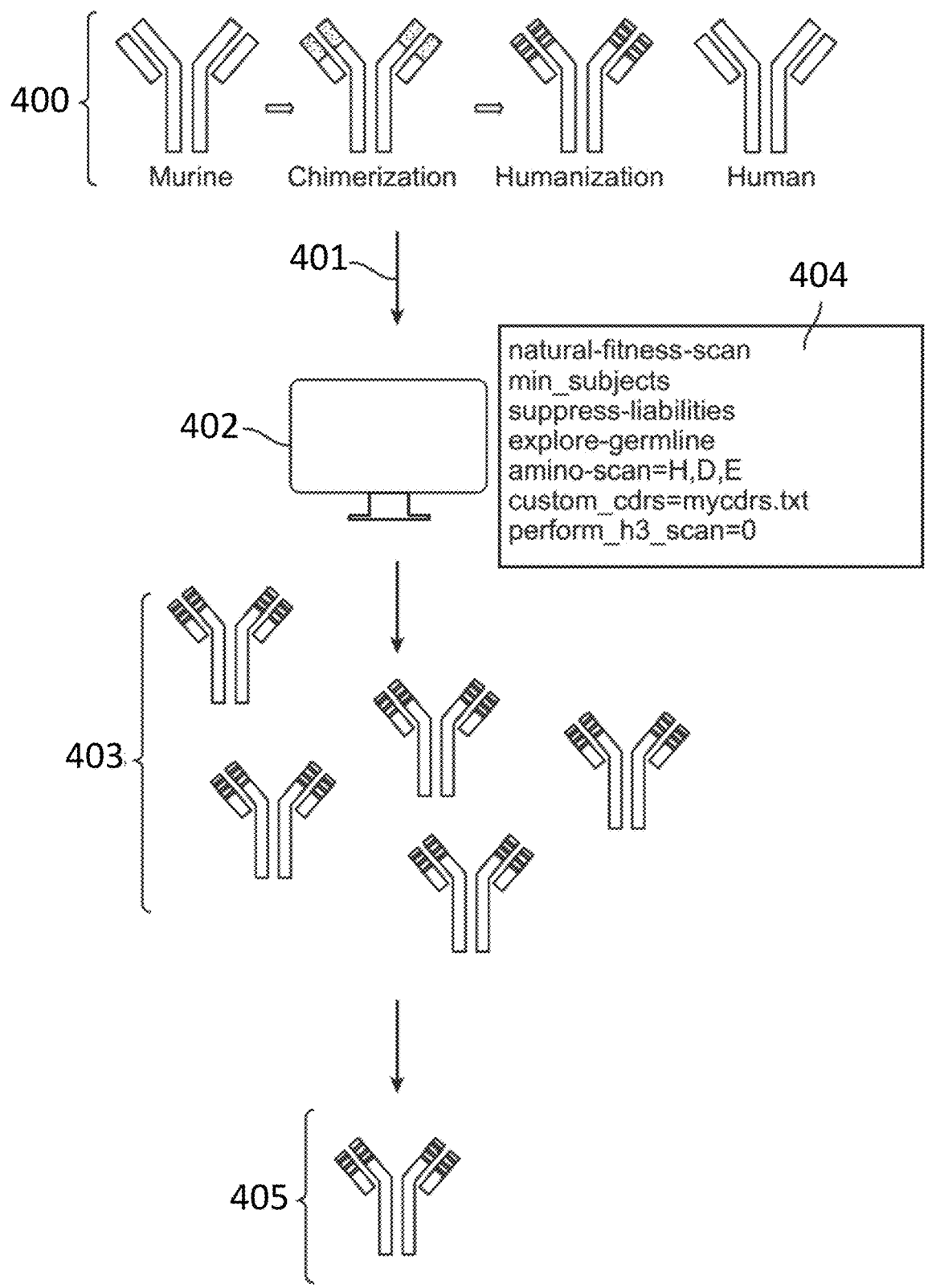
FIG. 4 depicts a workflow for antibody optimization.

Antibodies are in some instances optimized by the design of in-silico libraries comprising variant sequences of an input antibody sequence (FIG. 4). Input sequences 400 are in some instances modified in-silico 402 with one or more mutations or variants to generate libraries of optimized sequences 403. In some instances, such libraries are synthesized, cloned into expression vectors, and translation products (antibodies) evaluated for activity. In some instances, fragments of sequences are synthesized and subsequently assembled. In some instances, expression vectors are used to display and enrich desired antibodies, such as phage display. Selection pressures used during enrichment in some instances includes, but is not limited to, binding affinity, toxicity, immunological tolerance, stability, receptor-ligand competition, or developability. Such expression vectors allow antibodies with specific properties to be selected ("panning"), and subsequent propagation or amplification of such sequences enriches the library with these sequences. Panning rounds can be repeated any number of times, such as 1, 2, 3, 4, 5, 6, 7, or more than 7 rounds. Sequencing at one or more rounds is in some instances used to identify which sequences 405 have been enriched in the library.

Described herein are methods and systems of in-silico library design. For example, an antibody or antibody fragment sequence is used as input. In some instances, the antibody sequence used as input is an antibody or antibody fragment sequence that binds SARS-CoV-2. In some instances, the input is an antibody or antibody fragment sequence that binds a protein of SARS-CoV-2. In some instances, the protein is a spike glycoprotein, a membrane protein, an envelope protein, a nucleocapsid protein, or combinations thereof. In some instances, the protein is a spike glycoprotein of SARS-CoV-2. In some instances, the protein is a receptor binding domain of SARS-CoV-2. In some instances, the input sequence is an antibody or antibody fragment sequence that binds angiotensin-converting enzyme 2 (ACE2). In some instances, the input sequence is an antibody or antibody fragment sequence that binds an extracellular domain of the angiotensin-converting enzyme 2 (ACE2).

A database 402 comprising known mutations or variants of one or more viruses is queried 401, and a library 403 of sequences comprising combinations of these mutations or variants are generated. In some instances, the database comprises known mutations or variants of SARS-CoV-like coronaviruses, SARS-CoV-2, SARS-CoV, or combinations thereof. In some instances, the database comprises known mutations or variants of the spike protein of SARS-CoV-like coronaviruses, SARS-CoV-2, SARS-CoV, or combinations thereof. In some instances, the database comprises known mutations or variants of the receptor binding domain of SARS-CoV-like coronaviruses, SARS-CoV-2, SARS-CoV, or combinations thereof. In some instances, the database comprises mutations or variants of a protein of SARS-CoV-like coronaviruses, SARS-CoV-2, SARS-CoV, or combinations thereof that binds to ACE2.

In some instances, the input sequence is a heavy chain sequence of an antibody or antibody fragment that binds SARS-CoV-like coronaviruses, SARS-CoV-2, SARS-CoV, or combinations thereof. In some instances, the input sequence is a light chain sequence of an antibody or antibody fragment that binds SARS-CoV-like coronaviruses, SARS-CoV-2, SARS-CoV, or combinations thereof. In some instances, the heavy chain sequence comprises varied CDR regions. In some instances, the light chain sequence comprises varied CDR regions. In some instances, known mutations or variants from CDRs are used to build the sequence library. Filters 404, or exclusion criteria, are in some instances used to select specific types of variants for members of the sequence library. For example, sequences having a mutation or variant are added if a minimum number of organisms in the database have the mutation or variant. In some instances, additional CDRs are specified for inclusion in the database. In some instances, specific mutations or variants or combinations of mutations or variants are excluded from the library (e.g., known immunogenic sites, structure sites, etc.). In some instances, specific sites in the input sequence are systematically replaced with histidine, aspartic acid, glutamic acid, or combinations thereof. In some instances, the maximum or minimum number of mutations or variants allowed for each region of an antibody are specified. Mutations or variants in some instances are described relative to the input sequence or the input sequence's corresponding germline sequence. For example, sequences generated by the optimization comprise at least 1, 2, 3, 4, 5, 6, 7, 8, 9, 10, 11, 12, 13, 14, 15, 16, or more than 16 mutations or variants from the input sequence. In some instances, sequences generated by the optimization comprise no more than 1, 2, 3, 4, 5, 6, 7, 8, 9, 10, 11, 12, 13, 14, 15, 16, or no more than 18 mutations or variants from the input sequence. In some instances, sequences generated by the optimization comprise about 1, 2, 3, 4, 5, 6, 7, 8, 9, 10, 11, 12, 13, 14, 15, 16, or about 18 mutations or variants relative to the input sequence. In some instances, sequences generated by the optimization comprise about 1, 2, 3, 4, 5, 6, or 7 mutations or variants from the input sequence in a first CDR region. In some instances, sequences generated by the optimization comprise about 1, 2, 3, 4, 5, 6, or 7 mutations or variants from the input sequence in a second CDR region. In some instances, sequences generated by the optimization comprise about 1, 2, 3, 4, 5, 6, or 7 mutations or variants from the input sequence in a third CDR region. In some instances, sequences generated by the optimization comprise about 1, 2, 3, 4, 5, 6, or 7 mutations or variants from the input sequence in a first CDR region of a heavy chain. In some instances, sequences generated by the optimization comprise about 1, 2, 3, 4, 5, 6, or 7 mutations or variants from the input sequence in a second CDR region of a heavy chain. In some instances, sequences generated by the optimization comprise about 1, 2, 3, 4, 5, 6, or 7 mutations or variants from the input sequence in a third CDR region of a heavy chain. In some instances, sequences generated by the optimization comprise about 1, 2, 3, 4, 5, 6, or 7 mutations or variants from the input sequence in a first CDR region of a light chain. In some instances, sequences generated by the optimization comprise about 1, 2, 3, 4, 5, 6, or 7 mutations or variants from the input sequence in a second CDR region of a light chain. In some instances, sequences generated by the optimization comprise about 1, 2, 3, 4, 5, 6, or 7 mutations or variants from the input sequence in a third CDR region of a light chain. In some instances, a first CDR region is CDR1. In some instances, a second CDR region is CDR2. In some instances, a third CDR region is CDR3. In-silico antibodies libraries are in some instances synthesized, assembled, and enriched for desired sequences.

The germline sequences corresponding to an input sequence may also be modified to generate sequences in a library. For example, sequences generated by the optimization methods described herein comprise at least 1, 2, 3, 4, 5, 6, 7, 8, 9, 10, 11, 12, 13, 14, 15, 16, or more than 16 mutations or variants from the germline sequence. In some instances, sequences generated by the optimization comprise no more than 1, 2, 3, 4, 5, 6, 7, 8, 9, 10, 11, 12, 13, 14, 15, 16, or no more than 18 mutations or variants from the germline sequence. In some instances, sequences generated by the optimization comprise about 1, 2, 3, 4, 5, 6, 7, 8, 9, 10, 11, 12, 13, 14, 15, 16, or about 18 mutations or variants relative to the germline sequence.

Provided herein are methods, systems, and compositions for antibody optimization, wherein the input sequence comprises mutations or variants in an antibody region. Exemplary regions of the antibody include, but are not limited to, a complementarity-determining region (CDR), a variable domain, or a constant domain. In some instances, the CDR is CDR1, CDR2, or CDR3. In some instances, the CDR is a heavy domain including, but not limited to, CDRH1, CDRH2, and CDRH3. In some instances, the CDR is a light domain including, but not limited to, CDRL1, CDRL2, and CDRL3. In some instances, the variable domain is variable domain, light chain (VL) or variable domain, heavy chain (VH). In some instances, the VL domain comprises kappa or lambda chains. In some instances, the constant domain is constant domain, light chain (CL) or constant domain, heavy chain (CH). In some instances, sequences generated by the optimization comprise about 1, 2, 3, 4, 5, 6, or 7 mutations or variants from the germline sequence in a first CDR region. In some instances, sequences generated by the optimization comprise about 1, 2, 3, 4, 5, 6, or 7 mutations or variants from the germline sequence in a second CDR region. In some instances, sequences generated by the optimization comprise about 1, 2, 3, 4, 5, 6, or 7 mutations or variants from the germline sequence in a third CDR region. In some instances, sequences generated by the optimization comprise about 1, 2, 3, 4, 5, 6, or 7 mutations or variants from the germline sequence in a first CDR region of a heavy chain. In some instances, sequences generated by the optimization comprise about 1, 2, 3, 4, 5, 6, or 7 mutations or variants from the germline sequence in a second CDR region of a heavy chain. In some instances, sequences generated by the optimization comprise about 1, 2, 3, 4, 5, 6, or 7 mutations or variants from the germline sequence in a third CDR region of a heavy chain. In some instances, sequences generated by the optimization comprise about 1, 2, 3, 4, 5, 6, or 7 mutations or variants from the germline sequence in a first CDR region of a light chain. In some instances, sequences generated by the optimization comprise about 1, 2, 3, 4, 5, 6, or 7 mutations or variants from the germline sequence in a second CDR region of a light chain. In some instances, sequences generated by the optimization comprise about 1, 2, 3, 4, 5, 6, or 7 mutations or variants from the germline sequence in a third CDR region of a light chain. In some instances, a first CDR region is CDR1. In some instances, a second CDR region is CDR2. In some instances, a third CDR region is CDR3.

VHH Libraries

Provided herein are methods, compositions, and systems for generation of antibodies or antibody fragments. In some instances, the antibodies or antibody fragments are single domain antibodies. Methods, compositions, and systems described herein for the optimization of antibodies comprise a ratio-variant approach that mirror the natural diversity of antibody sequences. In some instances, libraries of optimized antibodies comprise variant antibody sequences. In some instances, the variant antibody sequences are designed comprising variant CDR regions. In some instances, the variant antibody sequences comprising variant CDR regions are generated by shuffling the natural CDR sequences in a llama, humanized, or chimeric framework. In some instances, such libraries are synthesized, cloned into expression vectors, and translation products (antibodies) evaluated for activity. In some instances, fragments of sequences are synthesized and subsequently assembled. In some instances, expression vectors are used to display and enrich desired antibodies, such as phage display. In some instances, the phage vector is a Fab phagemid vector. Selection pressures used during enrichment in some instances includes, but is not limited to, binding affinity, toxicity, immunological tolerance, stability, receptor-ligand competition, or developability. Such expression vectors allow antibodies with specific properties to be selected ("panning"), and subsequent propagation or amplification of such sequences enriches the library with these sequences. Panning rounds can be repeated any number of times, such as 1, 2, 3, 4, 5, 6, 7, or more than 7 rounds. In some instances, each round of panning involves a number of washes. In some instances, each round of panning involves at least or about 1, 2, 3, 4, 5, 6, 7, 8, 9, 10, 11, 12, 13, 14, 15, 16, or more than 16 washes.

Described herein are methods and systems of in-silico library design. Libraries as described herein, in some instances, are designed based on a database comprising a variety of antibody sequences. In some instances, the database comprises a plurality of variant antibody sequences against various targets. In some instances, the database comprises at least 100, 500, 1000, 1500, 2000, 2500, 3000, 3500, 4000, 4500, 5000, or more than 5000 antibody sequences. An exemplary database is an iCAN database. In some instances, the database comprises naïve and memory B-cell receptor sequences. In some instances, the naïve and memory B-cell receptor sequences are human, mouse, or primate sequences. In some instances, the naïve and memory B-cell receptor sequences are human sequences. In some instances, the database is analyzed for position specific variation. In some instances, antibodies described herein comprise position specific variations in CDR regions. In some instances, the CDR regions comprise multiple sites for variation.

Described herein are libraries comprising variation in a CDR region. In some instances, the CDR is CDR1, CDR2, or CDR3 of a variable heavy chain. In some instances, the CDR is CDR1, CDR2, or CDR3 of a variable light chain. In some instances, the libraries comprise multiple variants encoding for CDR1, CDR2, or CDR3. In some instances, the libraries as described herein encode for at least 50, 100, 200, 300, 400, 500, 1000, 1200, 1500, 1700, 2000, 2500, 3000, 3500, 4000, 4500, 5000, or more than 5000 CDR1 sequences. In some instances, the libraries as described herein encode for at least 50, 100, 200, 300, 400, 500, 1000, 1200, 1500, 1700, 2000, 2500, 3000, 3500, 4000, 4500, 5000, or more than 5000 CDR2 sequences. In some instances, the libraries as described herein encode for at least 50, 100, 200, 300, 400, 500, 1000, 1200, 1500, 1700, 2000, 2500, 3000, 3500, 4000, 4500, 5000, or more than 5000 CDR3 sequences. In-silico antibodies libraries are in some instances synthesized, assembled, and enriched for desired sequences.

Following synthesis of CDR1 variants, CDR2 variants, and CDR3 variants, in some instances, the CDR1 variants, the CDR2 variants, and the CDR3 variants are shuffled to generate a diverse library. In some instances, the diversity of the libraries generated by methods described herein have a theoretical diversity of at least or about $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, or more than $10^{18}$ sequences. In some instances, the library has a final library diversity of at least or about $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, or more than $10^{18}$ sequences.

The germline sequences corresponding to a variant sequence may also be modified to generate sequences in a library. For example, sequences generated by methods described herein comprise at least 1, 2, 3, 4, 5, 6, 7, 8, 9, 10, 11, 12, 13, 14, 15, 16, or more than 16 mutations or variants from the germline sequence. In some instances, sequences generated comprise no more than 1, 2, 3, 4, 5, 6, 7, 8, 9, 10, 11, 12, 13, 14, 15, 16, or no more than 18 mutations or variants from the germline sequence. In some instances, sequences generated comprise about 1, 2, 3, 4, 5, 6, 7, 8, 9, 10, 11, 12, 13, 14, 15, 16, or about 18 mutations or variants relative to the germline sequence.

Coronavirus Antibody Libraries

Provided herein are libraries generated from antibody optimization methods described herein. Antibodies described herein result in improved functional activity, structural stability, expression, specificity, or a combination thereof.

Provided herein are methods and compositions relating to SARS-CoV-2 binding libraries comprising nucleic acids encoding for a SARS-CoV-2 antibody. Further provided herein are methods and compositions relating to ACE2 binding libraries comprising nucleic acids encoding for an ACE2 antibody. Such methods and compositions in some instances are generated by the antibody optimization methods and systems described herein. Libraries as described herein may be further variegated to provide for variant libraries comprising nucleic acids each encoding for a predetermined variant of at least one predetermined reference nucleic acid sequence. Further described herein are protein libraries that may be generated when the nucleic acid libraries are translated. In some instances, nucleic acid libraries as described herein are transferred into cells to generate a cell library. Also provided herein are downstream applications for the libraries synthesized using methods described herein. Downstream applications include identification of variant nucleic acids or protein sequences with enhanced biologically relevant functions, e.g., improved stability, affinity, binding, functional activity, and for the treatment or prevention of an infection caused by a coronavirus such as SARS-CoV-2.

Provided herein are methods and compositions relating to SARS-CoV-2 binding libraries comprising nucleic acids encoding for a SARS-CoV-2 antibody. Further provided herein are methods and compositions comprising antibodies (e.g., bispecific antibodies) for binding and neutralizing the SARS-CoV-2. In some embodiments, the antibodies described herein are capable of binding and neutralizing SARS-CoV-2 variants (e.g., Delta and Omicron).

In some instances, an antibody or antibody fragment (e.g., bispecific antibody) described herein comprises a sequence of any one as provided in Tables 1-2. In some instances, an antibody or antibody fragment described herein comprises a sequence that is at least 80% identical to a sequence of any one as provided in Tables 1-2. In some instances, an antibody or antibody fragment described herein comprises a sequence that is at least 85% identical to a sequence of any one as provided in Tables 1-2. In some instances, an antibody or antibody fragment described herein comprises a sequence that is at least 90% identical to a sequence of any one as provided in Tables 1-2. In some instances, an antibody or antibody fragment described herein comprises a sequence that is at least 95% identical to a sequence of any one as provided in Tables 1-2.

TABLE 1

Variable Domain Heavy Chain CDR Sequences

| Variant | SEQ ID NO | CDRH1 | SEQ ID NO | CDRH2 | SEQ ID NO | CDRH3 |
|---|---|---|---|---|---|---|
| 3-31 | 1 | STFSINAMG | 2 | AGITSSGGYTNYA | 3 | CAADGVPEYSDYASGPVW |
| 6-3 | 4 | FTFSPSWMG | 5 | VATINEYGGRNYA | 6 | CARVDRDFDYW |

TABLE 2

Variable Domain Heavy Chain Sequences

| Variant | SEQ ID NO | Sequence |
|---|---|---|
| 3-31 | 7 | EVQLVESGGGLVQPGGSLRLSCAASGSTFSINAMGWFRQAPGKEREFVAGITSSGGYTNYADSVKGRFTISADNSKNTAYLQMNSLKPEDTAVYYCAADGVPEYSDYASGPVWGQGTLVTVSS |

In some instances, an antibody or antibody fragment (e.g., bispecific antibody) described herein comprises a sequence of any one of SEQ ID NOs: 1-7. In some instances, an antibody or antibody fragment described herein comprises a sequence that is at least 80% identical to a sequence of any one of SEQ ID NOs: 1-7. In some instances, an antibody or antibody fragment described herein comprises a sequence that is at least 85% identical to a sequence of any one of SEQ ID NOs: 1-7. In some instances, an antibody or antibody fragment described herein comprises a sequence that is at least 90% identical to a sequence of any one of SEQ ID NOs: 1-7. In some instances, an antibody or antibody fragment described herein comprises a sequence that is at least 95% identical to a sequence of any one of SEQ ID NOs: 1-7.

In some instances, an antibody or antibody fragment described herein comprises a CDRH1 sequence of any one of SEQ ID NOs: 1 or 4. In some instances, an antibody or antibody fragment described herein comprises a sequence that is at least 80% identical to a CDRH1 sequence of any one of SEQ ID NOs: 1 or 4. In some instances, an antibody or antibody fragment described herein comprises a sequence that is at least 85% identical to a CDRH1 sequence of any one of SEQ ID NOs: 1 or 4. In some instances, an antibody or antibody fragment described herein comprises a sequence that is at least 90% identical to a CDRH1 sequence of any one of SEQ ID NOs: 1 or 4. In some instances, an antibody or antibody fragment described herein comprises a sequence that is at least 95% identical to a CDRH1 sequence of any one of SEQ ID NOs: 1 or 4.

In some instances, an antibody or antibody fragment described herein comprises a CDRH2 sequence of any one of SEQ ID NOs: 2 or 5. In some instances, an antibody or antibody fragment described herein comprises a sequence that is at least 80% identical to a CDRH2 sequence of any one of SEQ ID NOs: 2 or 5. In some instances, an antibody or antibody fragment described herein comprises a sequence that is at least 85% identical to a CDRH2 sequence of any one of SEQ ID NOs: 2 or 5. In some instances, an antibody or antibody fragment described herein comprises a sequence that is at least 90% identical to a CDRH2 sequence of any one of SEQ ID NOs: 2 or 5. In some instances, an antibody or antibody fragment described herein comprises a sequence that is at least 95% identical to a CDRH2 sequence of any one of SEQ ID NOs: 2 or 5.

In some instances, an antibody or antibody fragment described herein comprises a CDRH3 sequence of any one of SEQ ID NOs: 3 or 6. In some instances, an antibody or antibody fragment described herein comprises a sequence that is at least 80% identical to a CDRH3 sequence of any one of SEQ ID NOs: 3 or 6. In some instances, an antibody or antibody fragment described herein comprises a sequence that is at least 85% identical to a CDRH3 sequence of any one of SEQ ID NOs: 3 or 6. In some instances, an antibody or antibody fragment described herein comprises a sequence that is at least 90% identical to a CDRH3 sequence of any one of SEQ ID NOs: 3 or 6. In some instances, an antibody or antibody fragment described herein comprises a sequence that is at least 95% identical to a CDRH3 sequence of any one of SEQ ID NOs: 3 or 6.

In some instances, an antibody or antibody fragment described herein comprises a CDRH1 sequence of SEQ ID NO: 1; a CDRH2 sequence of SEQ ID NO: 2; and a CDRH3 sequence of SEQ ID NO: 3. In some instances, an antibody or antibody fragment described herein comprises a sequence that is at least 80% identical to a CDRH1 sequence of SEQ ID NO: 1; a CDRH2 sequence of SEQ ID NO: 2; and a CDRH3 sequence of SEQ ID NO: 3. In some instances, an antibody or antibody fragment described herein comprises a sequence that is at least 85% identical to a CDRH1 sequence of SEQ ID NO: 1; a CDRH2 sequence of SEQ ID NO: 2; and a CDRH3 sequence of SEQ ID NO: 3. In some instances, an antibody or antibody fragment described herein comprises a sequence that is at least 90% identical to a CDRH1 sequence of SEQ ID NO: 1; a CDRH2 sequence of SEQ ID NO: 2; and a CDRH3 sequence of SEQ ID NO: 3. In some instances, an antibody or antibody fragment described herein comprises a sequence that is at least 95% identical to a CDRH1 sequence of SEQ ID NO: 1; a CDRH2 sequence of SEQ ID NO: 2; and a CDRH3 sequence of SEQ ID NO: 3.

In some instances, an antibody or antibody fragment described herein comprises a CDRH1 sequence of SEQ ID NO: 4; a CDRH2 sequence of SEQ ID NO: 5; and a CDRH3 sequence of SEQ ID NO: 6. In some instances, an antibody or antibody fragment described herein comprises a sequence that is at least 80% identical to a CDRH1 sequence of SEQ ID NO: 4; a CDRH2 sequence of SEQ ID NO: 5; and a CDRH3 sequence of SEQ ID NO: 6. In some instances, an antibody or antibody fragment described herein comprises a sequence that is at least 85% identical to a CDRH1 sequence of SEQ ID NO: 4; a CDRH2 sequence of SEQ ID NO: 5; and a CDRH3 sequence of SEQ ID NO: 6. In some instances, an antibody or antibody fragment described herein comprises a sequence that is at least 90% identical to a CDRH1 sequence of SEQ ID NO: 4; a CDRH2 sequence of SEQ ID NO: 5; and a CDRH3 sequence of SEQ ID NO: 6. In some instances, an antibody or antibody fragment described herein comprises a sequence that is at least 95% identical to a CDRH1 sequence of SEQ ID NO: 4; a CDRH2 sequence of SEQ ID NO: 5; and a CDRH3 sequence of SEQ ID NO: 6.

Described herein, in some embodiments, are bispecific antibodies. In some instances, the bispecific antibody described herein comprises a first CDRH1 sequence of SEQ ID NO: 1 and a second CDRH1 sequence of SEQ ID NO: 4. In some instances, the bispecific antibody described herein comprises a sequence that is at least 80% identical to a first CDRH1 sequence of SEQ ID NO: 1 and a second CDRH1 sequence of SEQ ID NO: 4. In some instances, the bispecific antibody described herein comprises a sequence that is at least 85% identical to a first CDRH1 sequence of SEQ ID NO: 1 and a second CDRH1 sequence of SEQ ID NO: 4. In some instances, the bispecific antibody described herein comprises a sequence that is at least 90% identical to a first CDRH1 sequence of SEQ ID NO: 1 and a second CDRH1 sequence of SEQ ID NO: 4. In some instances, the bispecific antibody described herein comprises a sequence that is at least 95% identical to a first CDRH1 sequence of SEQ ID NO: 1 and a second CDRH1 sequence of SEQ ID NO: 4.

In some instances, the bispecific antibody described herein comprises a first CDRH2 sequence of SEQ ID NO: 2 and a second CDRH2 sequence of SEQ ID NO: 5. In some instances, the bispecific antibody described herein comprises a sequence that is at least 80% identical to a first CDRH2 sequence of SEQ ID NO: 2 and a second CDRH2 sequence of SEQ ID NO: 5. In some instances, the bispecific antibody described herein comprises a sequence that is at least 85% identical to a first CDRH2 sequence of SEQ ID NO: 2 and a second CDRH2 sequence of SEQ ID NO: 5. In some instances, the bispecific antibody described herein comprises a sequence that is at least 90% identical to a first CDRH2 sequence of SEQ ID NO: 2 and a second CDRH2 sequence of SEQ ID NO: 5. In some instances, the bispecific antibody described herein comprises a sequence that is at least 95% identical to a first CDRH2 sequence of SEQ ID NO: 2 and a second CDRH2 sequence of SEQ ID NO: 5.

In some instances, the bispecific antibody described herein comprises a first CDRH3 sequence of SEQ ID NO: 3 and a second CDRH3 sequence of SEQ ID NO: 6. In some instances, the bispecific antibody described herein comprises a sequence that is at least 80% identical to a first CDRH3 sequence of SEQ ID NO: 3 and a second CDRH3 sequence of SEQ ID NO: 6. In some instances, the bispecific antibody described herein comprises a sequence that is at least 85% identical to a first CDRH3 sequence of SEQ ID NO: 3 and a second CDRH3 sequence of SEQ ID NO: 6. In some instances, the bispecific antibody described herein comprises a sequence that is at least 90% identical to a first CDRH3 sequence of SEQ ID NO: 3 and a second CDRH3 sequence of SEQ ID NO: 6. In some instances, the bispecific antibody described herein comprises a sequence that is at least 95% identical to a first CDRH3 sequence of SEQ ID NO: 3 and a second CDRH3 sequence of SEQ ID NO: 6.

Described herein, in some embodiments, are antibodies or antibody fragments (e.g., bispecific antibodies) comprising a first variable domain, heavy chain region (VH) comprising an amino acid sequence at least about 90% identical to a sequence as set forth in SEQ ID NO: 7. In some instances, the antibodies or antibody fragments comprise a VH comprising at least or about 70%, 80%, 85%, 90%, 91%, 92%, 93%, 94%, 95%, 96%, 97%, 98%, 99%, or 100% sequence identity to in SEQ ID NO: 7.

Described herein, in some embodiments, are antibodies or antibody fragments (e.g., bispecific antibodies) comprising an amino acid sequence at least about 90% identical to a sequence as set forth in SEQ ID NO: 8. In some instances, the antibodies or antibody fragments comprise an antibody comprising at least or about 70%, 80%, 85%, 90%, 91%, 92%, 93%, 94%, 95%, 96%, 97%, 98%, 99%, or 100% sequence identity to in SEQ ID NO: 8.

Described herein, in some embodiments, are antibodies or antibody fragments (e.g., bispecific antibodies) comprising an amino acid sequence at least about 90% identical to a sequence as set forth in SEQ ID NO: 9. In some instances, the antibodies or antibody fragments comprise an antibody comprising at least or about 70%, 80%, 85%, 90%, 91%, 92%, 93%, 94%, 95%, 96%, 97%, 98%, 99%, or 100% sequence identity to in SEQ ID NO: 9.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

The term "homology" or "similarity" between two proteins is determined by comparing the amino acid sequence and its conserved amino acid substitutes of one protein sequence to the second protein sequence. Similarity may be determined by procedures which are well-known in the art, for example, a BLAST program (Basic Local Alignment Search Tool at the National Center for Biological Information).

Provided herein are libraries comprising nucleic acids encoding for SARS-CoV-2 antibodies. Antibodies described herein allow for improved stability for a range of SARS-CoV-2 or ACE2 binding domain encoding sequences. In some instances, the binding domain encoding sequences are determined by interactions between SARS-CoV-2 and ACE2.

Sequences of binding domains based on surface interactions between SARS-CoV-2 and ACE2 are analyzed using various methods. For example, multispecies computational analysis is performed. In some instances, a structure analysis is performed. In some instances, a sequence analysis is performed. Sequence analysis can be performed using a database known in the art. Non-limiting examples of databases include, but are not limited to, NCBI BLAST (blast.ncbi.nlm.nih.gov/Blast.cgi), UCSC Genome Browser (genome.ucsc.edu/), UniProt (www.uniprot.org/), and IUPHAR/BPS Guide to PHARMACOLOGY (guidetopharmacology.org/).

Described herein are SARS-CoV-2 or ACE2 binding domains designed based on sequence analysis among various organisms. For example, sequence analysis is performed to identify homologous sequences in different organisms. Exemplary organisms include, but are not limited to, mouse, rat, equine, sheep, cow, primate (e.g., chimpanzee, baboon, gorilla, orangutan, monkey), dog, cat, pig, donkey, rabbit, fish, fly, and human. In some instances, homologous sequences are identified in the same organism, across individuals.

Following identification of SARS-CoV-2 or ACE2 binding domains, libraries comprising nucleic acids encoding for the SARS-CoV-2 or ACE2 binding domains may be generated. In some instances, libraries of SARS-CoV-2 or ACE2 binding domains comprise sequences of SARS-CoV-2 or ACE2 binding domains designed based on conformational ligand interactions, peptide ligand interactions, small molecule ligand interactions, extracellular domains of SARS-CoV-2 or ACE2, or antibodies that target SARS-CoV-2 or ACE2. Libraries of SARS-CoV-2 or ACE2 binding domains may be translated to generate protein libraries. In some instances, libraries of SARS-CoV-2 or ACE2 binding domains are translated to generate peptide libraries, immunoglobulin libraries, derivatives thereof, or combinations thereof. In some instances, libraries of SARS-CoV-2 or ACE2 binding domains are translated to generate protein libraries that are further modified to generate peptidomimetic libraries. In some instances, libraries of SARS-CoV-2 or ACE2 binding domains are translated to generate protein libraries that are used to generate small molecules.

Methods described herein provide for synthesis of libraries of SARS-CoV-2 or ACE2 binding domains comprising nucleic acids each encoding for a predetermined variant of at least one predetermined reference nucleic acid sequence. In some cases, the predetermined reference sequence is a nucleic acid sequence encoding for a protein, and the variant library comprises sequences encoding for variation of at least a single codon such that a plurality of different variants of a single residue in the subsequent protein encoded by the synthesized nucleic acid are generated by standard translation processes. In some instances, the libraries of SARS-CoV-2 or ACE2 binding domains comprise varied nucleic acids collectively encoding variations at multiple positions. In some instances, the variant library comprises sequences encoding for variation of at least a single codon in a SARS-CoV-2 or ACE2 binding domain. In some instances, the variant library comprises sequences encoding for variation of multiple codons in a SARS-CoV-2 or ACE2 binding domain. An exemplary number of codons for variation include, but are not limited to, at least or about 1, 5, 10, 15, 20, 25, 30, 35, 40, 45, 50, 55, 60, 65, 70, 75, 80, 85, 90, 95, 100, 125, 150, 175, 225, 250, 275, 300, or more than 300 codons.

Methods described herein provide for synthesis of libraries comprising nucleic acids encoding for the SARS-CoV-2 or ACE2 binding domains, wherein the libraries comprise sequences encoding for variation of length of the SARS-CoV-2 or ACE2 binding domains. In some instances, the library comprises sequences encoding for variation of length of at least or about 1, 5, 10, 15, 20, 25, 30, 35, 40, 45, 50, 55, 60, 65, 70, 75, 80, 85, 90, 95, 100, 125, 150, 175, 225, 250, 275, 300, or more than 300 codons less as compared to a predetermined reference sequence. In some instances, the library comprises sequences encoding for variation of length of at least or about 1, 5, 10, 15, 20, 25, 30, 35, 40, 45, 50, 55, 60, 65, 70, 75, 80, 85, 90, 95, 100, 125, 150, 175, 200, 225, 250, 275, 300, or more than 300 codons more as compared to a predetermined reference sequence.

In some instances, the SARS-CoV-2 antibody comprises a binding affinity (e.g., $K_D$) to SARS-CoV-2 of less than 1 nM, less than 1.2 nM, less than 2 nM, less than 5 nM, less than 10 nM, less than 11 nm, less than 13.5 nM, less than 15 nM, less than 20 nM, less than 25 nM, or less than 30 nM. In some instances, the SARS-CoV-2 antibody comprises a $K_D$ of less than 1 nM. In some instances, the SARS-CoV-2 antibody comprises a $K_D$ of less than 1.2 nM. In some instances, the SARS-CoV-2 antibody comprises a $K_D$ of less than 2 nM. In some instances, the SARS-CoV-2 antibody comprises a $K_D$ of less than 5 nM. In some instances, the SARS-CoV-2 antibody comprises a $K_D$ of less than 10 nM. In some instances, the SARS-CoV-2 antibody comprises a $K_D$ of less than 13.5 nM. In some instances, the SARS-CoV-2 antibody comprises a $K_D$ of less than 15 nM. In some instances, the SARS-CoV-2 antibody comprises a $K_D$ of less than 20 nM. In some instances, the SARS-CoV-2 antibody comprises a $K_D$ of less than 25 nM. In some instances, the SARS-CoV-2 antibody comprises a $K_D$ of less than 30 nM.

In some instances, the SARS-CoV-2 immunoglobulin is an agonist. In some instances, the SARS-CoV-2 immunoglobulin is an antagonist. In some instances, the SARS-CoV-2 immunoglobulin is an allosteric modulator. In some instances, the allosteric modulator is a negative allosteric modulator. In some instances, the allosteric modulator is a positive allosteric modulator. In some instances, the SARS-CoV-2 immunoglobulin results in agonistic, antagonistic, or allosteric effects at a concentration of at least or about 1 nM, 2 nM, 4 nM, 6 nM, 8 nM, 10 nM, 20 nM, 30 nM, 40 nM, 50 nM, 60 nM, 70 nM, 80 nM, 90 nM, 100 nM, 120 nM, 140 nM, 160 nM, 180 nM, 200 nM, 300 nM, 400 nM, 500 nM, 600 nM, 700 nM, 800 nM, 900 nM, 1000 nM, or more than 1000 nM. In some instances, the SARS-CoV-2 immunoglobulin is a negative allosteric modulator. In some instances, the SARS-CoV-2 immunoglobulin is a negative allosteric modulator at a concentration of at least or about 0.001, 0.005, 0.01, 0.05, 0.1, 0.5, 1 nM, 2 nM, 4 nM, 6 nM, 8 nM, 10 nM, 20 nM, 30 nM, 40 nM, 50 nM, 60 nM, 70 nM, 80 nM, 90 nM, 100 nM, or more than 100 nM. In some instances, the SARS-CoV-2 immunoglobulin is a negative allosteric modulator at a concentration in a range of about 0.001 to about 100, 0.01 to about 90, about 0.1 to about 80, 1 to about 50, about 10 to about 40 nM, or about 1 to about 10 nM. In some instances, the SARS-CoV-2 immunoglobulin comprises an EC50 or IC50 of at least or about 0.001, 0.0025, 0.005, 0.01, 0.025, 0.05, 0.06, 0.07, 0.08, 0.9, 0.1, 0.5, 1, 2, 3, 4, 5, 6, or more than 6 nM. In some instances, the SARS-CoV-2 immunoglobulin comprises an EC50 or IC50 of at least or about 1 nM, 2 nM, 4 nM, 6 nM, 8 nM, 10 nM, 20 nM, 30 nM, 40 nM, 50 nM, 60 nM, 70 nM, 80 nM, 90 nM, 100 nM, or more than 100 nM.

In some instances, the affinity of the SARS-CoV-2 antibody generated by methods as described herein is at least or about 1.5×, 2.0×, 5×, 10×, 20×, 30×, 40×, 50×, 60×, 70×, 80×, 90×, 100×, 200×, or more than 200× improved binding affinity as compared to a comparator antibody. In some instances, the SARS-CoV-2 antibody generated by methods as described herein is at least or about 1.5×, 2.0×, 5×, 10×, 20×, 30×, 40×, 50×, 60×, 70×, 80×, 90×, 100×, 200×, or more than 200× improved function as compared to a comparator antibody. In some instances, the comparator antibody is an antibody with similar structure, sequence, or antigen target.

Provided herein are SARS-CoV-2 or ACE2 binding libraries comprising nucleic acids encoding for antibodies comprising SARS-CoV-2 or ACE2 binding domains comprise variation in domain type, domain length, or residue variation. In some instances, the domain is a region in the antibody comprising the SARS-CoV-2 or ACE2 binding domains. For example, the region is the VH, CDRH3, or VL domain. In some instances, the domain is the SARS-CoV-2 or ACE2 binding domain.

Methods described herein provide for synthesis of a SARS-CoV-2 or ACE21 binding library of nucleic acids each encoding for a predetermined variant of at least one predetermined reference nucleic acid sequence. In some cases, the predetermined reference sequence is a nucleic acid sequence encoding for a protein, and the variant library comprises sequences encoding for variation of at least a single codon such that a plurality of different variants of a single residue in the subsequent protein encoded by the synthesized nucleic acid are generated by standard translation processes. In some instances, the SARS-CoV-2 or ACE2 binding library comprises varied nucleic acids collectively encoding variations at multiple positions. In some instances, the variant library comprises sequences encoding for variation of at least a single codon of a VH or VL domain. In some instances, the variant library comprises sequences encoding for variation of at least a single codon in a SARS-CoV-2 or ACE2 binding domain. For example, at least one single codon of a SARS-CoV-2 or ACE2 binding domain is varied. In some instances, the variant library comprises sequences encoding for variation of multiple codons of a VH or VL domain. In some instances, the variant library comprises sequences encoding for variation of multiple codons in a SARS-CoV-2 or ACE2 binding domain. An exemplary number of codons for variation include, but are not limited to, at least or about 1, 5, 10, 15, 20, 25, 30, 35, 40, 45, 50, 55, 60, 65, 70, 75, 80, 85, 90, 95, 100, 125, 150, 175, 225, 250, 275, 300, or more than 300 codons.

Methods described herein provide for synthesis of a SARS-CoV-2 or ACE2 binding library of nucleic acids each encoding for a predetermined variant of at least one predetermined reference nucleic acid sequence, wherein the SARS-CoV-2 or ACE2 binding library comprises sequences encoding for variation of length of a domain. In some instances, the domain is VH or VL domain. In some instances, the domain is the SARS-CoV-2 or ACE2binding domain. In some instances, the library comprises sequences encoding for variation of length of at least or about 1, 5, 10, 15, 20, 25, 30, 35, 40, 45, 50, 55, 60, 65, 70, 75, 80, 85, 90, 95, 100, 125, 150, 175, 225, 250, 275, 300, or more than 300 codons less as compared to a predetermined reference sequence. In some instances, the library comprises sequences encoding for variation of length of at least or about 1, 5, 10, 15, 20, 25, 30, 35, 40, 45, 50, 55, 60, 65, 70, 75, 80, 85, 90, 95, 100, 125, 150, 175, 200, 225, 250, 275, 300, or more than 300 codons more as compared to a predetermined reference sequence.

Provided herein are SARS-CoV-2 or ACE2 binding libraries comprising nucleic acids encoding for antibodies comprising SARS-CoV-2 or ACE2 binding domains, wherein the SARS-CoV-2 or ACE2 binding libraries are synthesized with various numbers of fragments. In some instances, the fragments comprise the VH or VL domain. In some instances, the SARS-CoV-2 or ACE2 binding libraries are synthesized with at least or about 2 fragments, 3 fragments, 4 fragments, 5 fragments, or more than 5 fragments. The length of each of the nucleic acid fragments or average length of the nucleic acids synthesized may be at least or about 50, 75, 100, 125, 150, 175, 200, 225, 250, 275, 300, 325, 350, 375, 400, 425, 450, 475, 500, 525, 550, 575, 600, or more than 600 base pairs. In some instances, the length is about 50 to 600, 75 to 575, 100 to 550, 125 to 525, 150 to 500, 175 to 475, 200 to 450, 225 to 425, 250 to 400, 275 to 375, or 300 to 350 base pairs.

SARS-CoV-2 or ACE2 binding libraries comprising nucleic acids encoding for antibodies comprising SARS-CoV-2 or ACE2 binding domains as described herein comprise various lengths of amino acids when translated. In some instances, the length of each of the amino acid fragments or average length of the amino acid synthesized may be at least or about 15, 20, 25, 30, 35, 40, 45, 50, 55, 60, 65, 70, 75, 80, 85, 90, 95, 100, 105, 110, 115, 120, 125, 130, 135, 140, 145, 150, or more than 150 amino acids. In some instances, the length of the amino acid is about 15 to 150, 20 to 145, 25 to 140, 30 to 135, 35 to 130, 40 to 125, 45 to 120, 50 to 115, 55 to 110, 60 to 110, 65 to 105, 70 to 100, or 75 to 95 amino acids. In some instances, the length of the amino acid is about 22 to about 75 amino acids.

SARS-CoV-2 or ACE2 binding libraries comprising de novo synthesized variant sequences encoding for antibodies comprising SARS-CoV-2 or ACE2 binding domains comprise a number of variant sequences. In some instances, a number of variant sequences is de novo synthesized for a CDRH1, CDRH2, CDRH3, CDRL1, CDRL2, CDRL3, VL, VH, or a combination thereof. In some instances, a number of variant sequences is de novo synthesized for framework element 1 (FW1), framework element 2 (FW2), framework element 3 (FW3), or framework element 4 (FW4). In some instances, a number of variant sequences are de novo synthesized for a SARS-CoV-2 or ACE2 binding domain. The number of variant sequences may be at least or about 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, or more than 500 sequences. In some instances, the number of variant sequences is about 10 to 300, 25 to 275, 50 to 250, 75 to 225, 100 to 200, or 125 to 150 sequences.

SARS-CoV-2 or ACE2 binding libraries comprising de novo synthesized variant sequences encoding for antibodies comprising SARS-CoV-2 or ACE2 binding domains comprise improved diversity. In some instances, variants include affinity maturation variants. Alternatively or in combination, variants include variants in other regions of the antibody including, but not limited to, CDRH1, CDRH2, CDRL1, CDRL2, and CDRL3. In some instances, the number of variants of the SARS-CoV-2 or ACE2 binding libraries is least or about $10^4$, $10^5$, $10^6$, $10^7$, $10^8$, $10^9$, $10^{10}$, $10^{11}$, $10^{12}$, $10^{13}$, $10^{14}$ or more than $10^{14}$ non-identical sequences.

Following synthesis of SARS-CoV-2 antibody libraries, libraries may be used for screening and analysis. For example, libraries are assayed for library displayability and panning. In some instances, displayability is assayed using a selectable tag. Exemplary tags include, but are not limited to, a radioactive label, a fluorescent label, an enzyme, a chemiluminescent tag, a colorimetric tag, an affinity tag or other labels or tags that are known in the art. In some instances, the tag is histidine, polyhistidine, myc, hemagglutinin (HA), or FLAG. For example, SARS-CoV-2 binding libraries comprise nucleic acids encoding antibodies comprising SARS-CoV-2 binding domains with multiple tags such as GFP, FLAG, and Lucy as well as a DNA barcode. In some instances, libraries are assayed by sequencing using various methods including, but not limited to, single-molecule real-time (SMRT) sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis.

As used herein, the term antibody will be understood to include proteins having the characteristic two-armed, Y-shape of a typical antibody molecule as well as one or more fragments of an antibody that retain the ability to specifically bind to an antigen. Exemplary antibodies include, but are not limited to, a monoclonal antibody, a polyclonal antibody, a bi-specific antibody, a bispecific antibody, a grafted antibody, a human antibody, a humanized antibody, a synthetic antibody, a chimeric antibody, a camelized antibody, a single-chain Fvs (scFv) (including fragments in which the VL and VH are joined using recombinant methods by a synthetic or natural linker that enables them to be made as a single protein chain in which the VL and VH regions pair to form monovalent molecules, including single chain Fab and scFab), a single chain antibody, a Fab fragment (including monovalent fragments comprising the VL, VH, CL, and CH1 domains), a F(ab')2 fragment (including bivalent fragments comprising two Fab fragments linked by a disulfide bridge at the hinge region), a Fd fragment (including fragments comprising the VH and CH1 fragment), a Fv fragment (including fragments comprising the VL and VH domains of a single arm of an antibody), a single-domain antibody (dAb or sdAb) (including fragments comprising a VH domain), an isolated complementarity determining region (CDR), a diabody (including fragments comprising bivalent dimers such as two VL and VH domains bound to each other and recognizing two different antigens), a fragment comprised of only a single monomeric variable domain, disulfide-linked Fvs (sdFv), an intrabody, an anti-idiotypic (anti-Id) antibody, or ab antigen-binding fragments thereof. In some instances, the libraries disclosed herein comprise nucleic acids encoding for an antibody, wherein the antibody is a Fv antibody, including Fv antibodies comprised of the minimum antibody fragment which contains a complete antigen-recognition and antigen-binding site. In some embodiments, the Fv antibody consists of a dimer of one heavy chain and one light chain variable domain in tight, non-covalent association, and the three hypervariable regions of each variable domain interact to define an antigen-binding site on the surface of the VH-VL dimer. In some embodiments, the six hypervariable regions confer antigen-binding specificity to the antibody. In some embodiments, a single variable domain (or half of an Fv comprising only three hypervariable regions specific for an antigen, including single domain antibodies isolated from camelid animals comprising one heavy chain variable domain such as VHH antibodies or nanobodies) has the ability to recognize and bind antigen. In some instances, the libraries disclosed herein comprise nucleic acids encoding for an antibody, wherein the antibody is a single-chain Fv or scFv, including antibody fragments comprising a VH, a VL, or both a VH and VL domain, wherein both domains are present in a single polypeptide chain. In some embodiments, the Fv polypeptide further comprises a polypeptide linker between the VH and VL domains allowing the scFv to form the desired structure for antigen binding. In some instances, a scFv is linked to the Fc fragment or a VHH is linked to the Fc fragment (including minibodies). In some instances, the antibody comprises immunoglobulin molecules and immunologically active fragments of immunoglobulin molecules, e.g., molecules that contain an antigen binding site. Immunoglobulin molecules are of any type (e.g., IgG, IgE, IgM, IgD, IgA and IgY), class (e.g., IgG 1, IgG 2, IgG 3, IgG 4, IgA 1 and IgA 2) or subclass.

In some embodiments, the antibody is a multivalent antibody. In some embodiments, the antibody is a monovalent, bivalent, or multivalent antibody. In some instances, the antibody is monospecific, bispecific, or multispecific. In some embodiments, the antibody is monovalent monospecific, monovalent bispecific, monovalent multispecific, bivalent monospecific, bivalent bispecific, bivalent multispecific, multivalent monospecific, multivalent bispecific, multivalent multispecific. In some instances, the antibody is homodimeric, heterodimeric, or heterotrimeric.

In some embodiments, libraries comprise immunoglobulins that are adapted to the species of an intended therapeutic target. Generally, these methods include "mammalization" and comprises methods for transferring donor antigen-binding information to a less immunogenic mammal antibody acceptor to generate useful therapeutic treatments. In some instances, the mammal is mouse, rat, equine, sheep, cow, primate (e.g., chimpanzee, baboon, gorilla, orangutan, monkey), dog, cat, pig, donkey, rabbit, and human. In some instances, provided herein are libraries and methods for felinization and caninization of antibodies.

"Humanized" forms of non-human antibodies can be chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. In some instances, these modifications are made to further refine antibody performance.

"Caninization" can comprise a method for transferring non-canine antigen-binding information from a donor antibody to a less immunogenic canine antibody acceptor to generate treatments useful as therapeutics in dogs. In some instances, caninized forms of non-canine antibodies provided herein are chimeric antibodies that contain minimal sequence derived from non-canine antibodies. In some instances, caninized antibodies are canine antibody sequences ("acceptor" or "recipient" antibody) in which hypervariable region residues of the recipient are replaced by hypervariable region residues from a non-canine species ("donor" antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the canine antibody are replaced by corresponding non-canine FR residues. In some instances, caninized antibodies include residues that are not found in the recipient antibody or in the donor antibody. In some instances, these modifications are made to further refine antibody performance. The caninized antibody may also comprise at least a portion of an immunoglobulin constant region (Fc) of a canine antibody.

"Felinization" can comprise a method for transferring non-feline antigen-binding information from a donor antibody to a less immunogenic feline antibody acceptor to generate treatments useful as therapeutics in cats. In some instances, felinized forms of non-feline antibodies provided herein are chimeric antibodies that contain minimal sequence derived from non-feline antibodies. In some instances, felinized antibodies are feline antibody sequences ("acceptor" or "recipient" antibody) in which hypervariable region residues of the recipient are replaced by hypervariable region residues from a non-feline species ("donor" antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the feline antibody are replaced by corresponding non-feline FR residues. In some instances, felinized antibodies include residues that are not found in the recipient antibody or in the donor antibody. In some instances, these modifications are made to further refine antibody performance. The felinized antibody may also comprise at least a portion of an immunoglobulin constant region (Fc) of a felinize antibody.

Methods as described herein may be used for optimization of libraries encoding a non-immunoglobulin. In some instances, the libraries comprise antibody mimetics. Exemplary antibody mimetics include, but are not limited to, anticalins, affilins, affibody molecules, affimers, affitins, alphabodies, avimers, atrimers, DARPins, fynomers, Kunitz domain-based proteins, monobodies, anticalins, knottins, armadillo repeat protein-based proteins, and bicyclic peptides.

Libraries described herein comprising nucleic acids encoding for an antibody comprise variations in at least one region of the antibody. Exemplary regions of the antibody for variation include, but are not limited to, a complementarity-determining region (CDR), a variable domain, or a constant domain. In some instances, the CDR is CDR1, CDR2, or CDR3. In some instances, the CDR is a heavy domain including, but not limited to, CDRH1, CDRH2, and CDRH3. In some instances, the CDR is a light domain including, but not limited to, CDRL1, CDRL2, and CDRL3. In some instances, the variable domain is variable domain, light chain (VL) or variable domain, heavy chain (VH). In some instances, the VL domain comprises kappa or lambda chains. In some instances, the constant domain is constant domain, light chain (CL) or constant domain, heavy chain (CH).

Methods described herein provide for synthesis of libraries comprising nucleic acids encoding an antibody, wherein each nucleic acid encodes for a predetermined variant of at least one predetermined reference nucleic acid sequence. In some cases, the predetermined reference sequence is a nucleic acid sequence encoding for a protein, and the variant library comprises sequences encoding for variation of at least a single codon such that a plurality of different variants of a single residue in the subsequent protein encoded by the synthesized nucleic acid are generated by standard translation processes. In some instances, the antibody library comprises varied nucleic acids collectively encoding variations at multiple positions. In some instances, the variant library comprises sequences encoding for variation of at least a single codon of a CDRH1, CDRH2, CDRH3, CDRL1, CDRL2, CDRL3, VL, or VH domain. In some instances, the variant library comprises sequences encoding for variation of multiple codons of a CDRH1, CDRH2, CDRH3, CDRL1, CDRL2, CDRL3, VL, or VH domain. In some instances, the variant library comprises sequences encoding for variation of multiple codons of framework element 1 (FW1), framework element 2 (FW2), framework element 3 (FW3), or framework element 4 (FW4). An exemplary number of codons for variation include, but are not limited to, at least or about 1, 5, 10, 15, 20, 25, 30, 35, 40, 45, 50, 55, 60, 65, 70, 75, 80, 85, 90, 95, 100, 125, 150, 175, 225, 250, 275, 300, or more than 300 codons.

In some instances, the at least one region of the antibody for variation is from heavy chain V-gene family, heavy chain D-gene family, heavy chain J-gene family, light chain V-gene family, or light chain J-gene family. In some instances, the light chain V-gene family comprises immunoglobulin kappa (IGK) gene or immunoglobulin lambda (IGL). Exemplary regions of the antibody for variation include, but are not limited to, IGHV1-18, IGHV1-69, IGHV1-8, IGHV3-21, IGHV3-23, IGHV3-30/33m, IGHV3-28, IGHV1-69, IGHV3-74, IGHV4-39, IGHV4-59/61, IGKV1-39, IGKV1-9, IGKV2-28, IGKV3-11, IGKV3-15, IGKV3-20, IGKV4-1, IGLV1-51, IGLV2-14, IGLV1-40, and IGLV3-1. In some instances, the gene is IGHV1-69, IGHV3-30, IGHV3-23, IGHV3, IGHV1-46, IGHV3-7, IGHV1, or IGHV1-8. In some instances, the gene is IGHV1-69 and IGHV3-30. In some instances, the region of the antibody for variation is IGHJ3, IGHJ6, IGHJ, IGHJ4, IGHJ5, IGHJ2, or IGH1. In some instances, the region of the antibody for variation is IGHJ3, IGHJ6, IGHJ, or IGHJ4. In some instances, the at least one region of the antibody for variation is IGHV1-69, IGHV3-23, IGKV3-20, IGKV1-39, or combinations thereof. In some instances, the at least one region of the antibody for variation is IGHV1-69 and IGKV3-20, In some instances, the at least one region of the antibody for variation is IGHV1-69 and IGKV1-39. In some instances, the at least one region of the antibody for variation is IGHV3-23 and IGKV3-20. In some instances, the at least one region of the antibody for variation is IGHV3-23 and IGKV1-39.

Provided herein are libraries comprising nucleic acids encoding for antibodies, wherein the libraries are synthesized with various numbers of fragments. In some instances, the fragments comprise the CDRH1, CDRH2, CDRH3, CDRL1, CDRL2, CDRL3, VL, or VH domain. In some instances, the fragments comprise framework element 1 (FW1), framework element 2 (FW2), framework element 3 (FW3), or framework element 4 (FW4). In some instances, the antibody libraries are synthesized with at least or about 2 fragments, 3 fragments, 4 fragments, 5 fragments, or more than 5 fragments. The length of each of the nucleic acid fragments or average length of the nucleic acids synthesized may be at least or about 50, 75, 100, 125, 150, 175, 200, 225, 250, 275, 300, 325, 350, 375, 400, 425, 450, 475, 500, 525, 550, 575, 600, or more than 600 base pairs. In some instances, the length is about 50 to 600, 75 to 575, 100 to 550, 125 to 525, 150 to 500, 175 to 475, 200 to 450, 225 to 425, 250 to 400, 275 to 375, or 300 to 350 base pairs.

Libraries comprising nucleic acids encoding for antibodies as described herein comprise various lengths of amino acids when translated. In some instances, the length of each of the amino acid fragments or average length of the amino acid synthesized may be at least or about 15, 20, 25, 30, 35, 40, 45, 50, 55, 60, 65, 70, 75, 80, 85, 90, 95, 100, 105, 110, 115, 120, 125, 130, 135, 140, 145, 150, or more than 150 amino acids. In some instances, the length of the amino acid is about 15 to 150, 20 to 145, 25 to 140, 30 to 135, 35 to 130, 40 to 125, 45 to 120, 50 to 115, 55 to 110, 60 to 110, 65 to 105, 70 to 100, or 75 to 95 amino acids. In some instances, the length of the amino acid is about 22 amino acids to about 75 amino acids. In some instances, the antibodies comprise at least or about 100, 200, 300, 400, 500, 600, 700, 800, 900, 1000, 2000, 3000, 4000, 5000, or more than 5000 amino acids.

A number of variant sequences for the at least one region of the antibody for variation are de novo synthesized using methods as described herein. In some instances, a number of variant sequences is de novo synthesized for CDRH1, CDRH2, CDRH3, CDRL1, CDRL2, CDRL3, VL, VH, or combinations thereof. In some instances, a number of variant sequences is de novo synthesized for framework element 1 (FW1), framework element 2 (FW2), framework element 3 (FW3), or framework element 4 (FW4). The number of variant sequences may be at least or about 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, or more than 500 sequences. In some instances, the number of variant sequences is at least or about 500, 600, 700, 800, 900, 1000, 2000, 3000, 4000, 5000, 6000, 7000, 8000, or more than 8000 sequences. In some instances, the number of variant sequences is about 10 to 500, 25 to 475, 50 to 450, 75 to 425, 100 to 400, 125 to 375, 150 to 350, 175 to 325, 200 to 300, 225 to 375, 250 to 350, or 275 to 325 sequences.

Variant sequences for the at least one region of the antibody, in some instances, vary in length or sequence. In some instances, the at least one region that is de novo synthesized is for CDRH1, CDRH2, CDRH3, CDRL1, CDRL2, CDRL3, VL, VH, or combinations thereof. In some instances, the at least one region that is de novo synthesized is for framework element 1 (FW1), framework element 2 (FW2), framework element 3 (FW3), or framework element 4 (FW4). In some instances, the variant sequence comprises at least or about 1, 2, 3, 4, 5, 6, 7, 8, 9, 10, 15, 20, 25, 30, 35, 40, 45, 50, or more than 50 variant nucleotides or amino acids as compared to wild-type. In some instances, the variant sequence comprises at least or about 1, 2, 3, 4, 5, 6, 7, 8, 9, 10, 15, 20, 25, 30, 35, 40, 45, or 50 additional nucleotides or amino acids as compared to wild-type. In some instances, the variant sequence comprises at least or about 1, 2, 3, 4, 5, 6, 7, 8, 9, 10, 15, 20, 25, 30, 35, 40, 45, or 50 less nucleotides or amino acids as compared to wild-type. In some instances, the libraries comprise at least or about $10^1$, $10^2$, $10^3$, $10^4$, $10^5$, $10^6$, $10^7$, $10^8$, $10^9$, $10^{10}$, or more than $10^{10}$ variants.

Following synthesis of antibody libraries, antibody libraries may be used for screening and analysis. For example, antibody libraries are assayed for library displayability and panning. In some instances, displayability is assayed using a selectable tag. Exemplary tags include, but are not limited to, a radioactive label, a fluorescent label, an enzyme, a chemiluminescent tag, a colorimetric tag, an affinity tag or other labels or tags that are known in the art. In some instances, the tag is histidine, polyhistidine, myc, hemagglutinin (HA), or FLAG. In some instances, antibody libraries are assayed by sequencing using various methods including, but not limited to, single-molecule real-time (SMRT) sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis. In some instances, antibody libraries are displayed on the surface of a cell or phage. In some instances, antibody libraries are enriched for sequences with a desired activity using phage display.

In some instances, the antibody libraries are assayed for functional activity, structural stability (e.g., thermal stable or pH stable), expression, specificity, or a combination thereof. In some instances, the antibody libraries are assayed for antibody capable of folding. In some instances, a region of the antibody is assayed for functional activity, structural stability, expression, specificity, folding, or a combination thereof. For example, a VH region or VL region is assayed for functional activity, structural stability, expression, specificity, folding, or a combination thereof.

In some instances, the affinity of antibodies or IgGs generated by methods as described herein is at least or about 1.5×, 2.0×, 5×, 10×, 20×, 30×, 40×, 50×, 60×, 70×, 80×, 90×, 100×, 200×, or more than 200× improved binding affinity as compared to a comparator antibody. In some instances, the affinity of antibodies or IgGs generated by methods as described herein is at least or about 1.5×, 2.0×, 5×, 10×, 20×, 30×, 40×, 50×, 60×, 70×, 80×, 90×, 100×, 200×, or more than 200× improved function as compared to a comparator antibody. In some instances, the comparator antibody is an antibody with similar structure, sequence, or antigen target.

Expression Systems

Provided herein are libraries comprising nucleic acids encoding for antibody comprising binding domains, wherein the libraries have improved specificity, stability, expression, folding, or downstream activity. In some instances, libraries described herein are used for screening and analysis.

Provided herein are libraries comprising nucleic acids encoding for antibody comprising binding domains, wherein the nucleic acid libraries are used for screening and analysis. In some instances, screening and analysis comprises in vitro, in vivo, or ex vivo assays. Cells for screening include primary cells taken from living subjects or cell lines. Cells may be from prokaryotes (e.g., bacteria and fungi) or eukaryotes (e.g., animals and plants). Exemplary animal cells include, without limitation, those from a mouse, rabbit, primate, and insect. In some instances, cells for screening include a cell line including, but not limited to, Chinese Hamster Ovary (CHO) cell line, human embryonic kidney (HEK) cell line, or baby hamster kidney (BHK) cell line. In some instances, nucleic acid libraries described herein may also be delivered to a multicellular organism. Exemplary multicellular organisms include, without limitation, a plant, a mouse, rabbit, primate, and insect.

Nucleic acid libraries described herein may be screened for various pharmacological or pharmacokinetic properties. In some instances, the libraries are screened using in vitro assays, in vivo assays, or ex vivo assays. For example, in vitro pharmacological or pharmacokinetic properties that are screened include, but are not limited to, binding affinity, binding specificity, and binding avidity. Exemplary in vivo pharmacological or pharmacokinetic properties of libraries described herein that are screened include, but are not limited to, therapeutic efficacy, activity, preclinical toxicity properties, clinical efficacy properties, clinical toxicity properties, immunogenicity, potency, and clinical safety properties.

Provided herein are nucleic acid libraries, wherein the nucleic acid libraries may be expressed in a vector. Expression vectors for inserting nucleic acid libraries disclosed herein may comprise eukaryotic or prokaryotic expression vectors. Exemplary expression vectors include, without limitation, mammalian expression vectors: pSF-CMV-NEO-NH2-PPT-3XFLAG, pSF-CMV-NEO-COOH-3XFLAG, pSF-CMV-PURO-NH2-GST-TEV, pSF-OXB20-COOH-TEV-FLAG(R)-6His, pCEP4 pDEST27, pSF-CMV-Ub-KrYFP, pSF-CMV-FMDV-daGFP, pEF1a-mCherry-N1 Vector, pEF1a-tdTomato Vector, pSF-CMV-FMDV-Hygro, pSF-CMV-PGK-Puro, pMCP-tag(m), and pSF-CMV-PURO-NH2-CMYC; bacterial expression vectors: pSF-OXB20-BetaGal, pSF-OXB20-Fluc, pSF-OXB20, and pSF-Tac; plant expression vectors: pRI 101-AN DNA and pCambia2301; and yeast expression vectors: pTYB21 and pKLAC2, and insect vectors: pAc5.1/V5-His A and pDEST8. In some instances, the vector is pcDNA3 or pcDNA3.1.

Described herein are nucleic acid libraries that are expressed in a vector to generate a construct comprising an antibody. In some instances, a size of the construct varies. In some instances, the construct comprises at least or about 500, 600, 700, 800, 900, 1000, 1100, 1300, 1400, 1500, 1600, 1700, 1800, 2000, 2400, 2600, 2800, 3000, 3200, 3400, 3600, 3800, 4000, 4200, 4400, 4600, 4800, 5000, 6000, 7000, 8000, 9000, 10000, or more than 10000 bases. In some instances, a the construct comprises a range of about 300 to 1,000, 300 to 2,000, 300 to 3,000, 300 to 4,000, 300 to 5,000, 300 to 6,000, 300 to 7,000, 300 to 8,000, 300 to 9,000, 300 to 10,000, 1,000 to 2,000, 1,000 to 3,000, 1,000 to 4,000, 1,000 to 5,000, 1,000 to 6,000, 1,000 to 7,000, 1,000 to 8,000, 1,000 to 9,000, 1,000 to 10,000, 2,000 to 3,000, 2,000 to 4,000, 2,000 to 5,000, 2,000 to 6,000, 2,000 to 7,000, 2,000 to 8,000, 2,000 to 9,000, 2,000 to 10,000, 3,000 to 4,000, 3,000 to 5,000, 3,000 to 6,000, 3,000 to 7,000, 3,000 to 8,000, 3,000 to 9,000, 3,000 to 10,000, 4,000 to 5,000, 4,000 to 6,000, 4,000 to 7,000, 4,000 to 8,000, 4,000 to 9,000, 4,000 to 10,000, 5,000 to 6,000, 5,000 to 7,000, 5,000 to 8,000, 5,000 to 9,000, 5,000 to 10,000, 6,000 to 7,000, 6,000 to 8,000, 6,000 to 9,000, 6,000 to 10,000, 7,000 to 8,000, 7,000 to 9,000, 7,000 to 10,000, 8,000 to 9,000, 8,000 to 10,000, or 9,000 to 10,000 bases.

Provided herein are libraries comprising nucleic acids encoding for antibodies, wherein the nucleic acid libraries are expressed in a cell. In some instances, the libraries are synthesized to express a reporter gene. Exemplary reporter genes include, but are not limited to, acetohydroxyacid synthase (AHAS), alkaline phosphatase (AP), beta galactosidase (LacZ), beta glucuronidase (GUS), chloramphenicol acetyltransferase (CAT), green fluorescent protein (GFP), red fluorescent protein (RFP), yellow fluorescent protein (YFP), cyan fluorescent protein (CFP), cerulean fluorescent protein, citrine fluorescent protein, orange fluorescent protein, cherry fluorescent protein, turquoise fluorescent protein, blue fluorescent protein, horseradish peroxidase (HRP), luciferase (Luc), nopaline synthase (NOS), octopine synthase (OCS), luciferase, and derivatives thereof. Methods to determine modulation of a reporter gene are well known in the art, and include, but are not limited to, fluorometric methods (e.g. fluorescence spectroscopy, Fluorescence Activated Cell Sorting (FACS), fluorescence microscopy), and antibiotic resistance determination.

Diseases and Disorders

Provided herein are SARS-CoV-2 binding libraries comprising nucleic acids encoding for antibodies comprising SARS-CoV-2 binding domains may have therapeutic effects. In some instances, the SARS-CoV-2 binding libraries result in protein when translated that is used to treat a disease or disorder. In some instances, the protein is an immunoglobulin. In some instances, the protein is a peptidomimetic. In some instances, the disease or disorder is a viral infection caused by SARS-CoV-2. In some instances, the disease or disorder is a respiratory disease or disorder caused by SARS-CoV-2.

SARS-CoV-2 variant antibody libraries as described herein may be used to treat SARS-CoV-2. In some embodiments, the SARS-CoV-2 variant antibody libraries are used to treat or prevent symptoms of SARS-CoV-2. These symptoms include, but are not limited to, fever, chills, cough, fatigue, headaches, loss of taste, loss of smell, nausea, vomiting, muscle weakness, sleep difficulties, anxiety, and depression. In some embodiments, the SARS-CoV-2 variant antibody libraries are used to treat a subject who has symptoms for an extended period of time. In some embodiments, the subject has symptoms for an extended period of time after testing negative for SARS-CoV-2. In some embodiments, the subject has symptoms for an extended period of time including at least 1 week, 2 weeks, 3 weeks, 1 month, 2 months, 3 months, 4 months, 5 months, 6 months, 7 months, 8 months, 9 months, 10 months, 11 months, 1 year, or more than 1 year.

In some instances, the subject is a mammal. In some instances, the subject is a mouse, rabbit, dog, or human. Subjects treated by methods described herein may be infants, adults, or children. Pharmaceutical compositions comprising antibodies or antibody fragments as described herein may be administered intravenously or subcutaneously. In some instances, a pharmaceutical composition comprises an antibody or antibody fragment (e.g., bispecific antibody) comprising a sequence of any one as provided in Tables 1-2. In some instances, an antibody or antibody fragment described herein comprises a sequence that is at least 80% identical to a sequence of any one as provided in Tables 1-2. In some instances, an antibody or antibody fragment described herein comprises a sequence that is at least 85% identical to a sequence of any one as provided in Tables 1-2. In some instances, an antibody or antibody fragment described herein comprises a sequence that is at least 90% identical to a sequence of any one as provided in Tables 1-2. In some instances, an antibody or antibody fragment described herein comprises a sequence that is at least 95% identical to a sequence of any one as provided in Tables 1-2.

In some instances, a pharmaceutical composition comprises an antibody or antibody fragment (e.g., bispecific antibody) comprising a sequence of any one of SEQ ID NOs: 1-7. In some instances, an antibody or antibody fragment described herein comprises a sequence that is at least 80% identical to a sequence of any one of SEQ ID NOs: 1-7. In some instances, an antibody or antibody fragment described herein comprises a sequence that is at least 85% identical to a sequence of any one of SEQ ID NOs: 1-7. In some instances, an antibody or antibody fragment described herein comprises a sequence that is at least 90% identical to a sequence of any one of SEQ ID NOs: 1-7. In some instances, an antibody or antibody fragment described herein comprises a sequence that is at least 95% identical to a sequence of any one of SEQ ID NOs: 1-7.

In some embodiments, the immunity occurs at least about 30 minutes, 1 hour, 5 hours, 10 hours, 16 hours, 20 hours, 24 hours, 2 days, 3 days, 4 days, 5 days, 6 days, 1 week, 2 weeks, or more than 2 weeks after exposure to SARS-CoV-2 antibodies. In some instances, the immunity lasts for at least about 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, or more than 5 years after exposure to SARS-CoV-2 antibodies.

In some embodiments, the subject receives the SARS-CoV-2 antibodies prior to exposure to SARS-CoV-2. In some embodiments, the subject receives the SARS-CoV-2 antibodies at least about 30 minutes, 1 hour, 4 hours, 8 hours, 12 hours, 16 hours, 20 hours, 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, or more than 5 years prior to exposure to SARS-CoV-2. In some embodiments, the subject receives the SARS-CoV-2 antibodies after exposure to SARS-CoV-2. In some embodiments, the subject receives the SARS-CoV-2 antibodies at least about 30 minutes, 1 hour, 4 hours, 8 hours, 12 hours, 16 hours, 20 hours, 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, or more than 5 years after exposure to SARS-CoV-2.

SARS-CoV-2 antibodies described herein may be administered through various routes. The administration may, depending on the composition being administered, for example, be oral, pulmonary, intravenous, intraperitoneal, intramuscular, intracavity, subcutaneous, or transdermal.

Described herein are compositions or pharmaceutical compositions comprising SARS-CoV-2 antibodies or antibody fragment thereof that comprise various dosages of the antibodies or antibody fragment. In some instances, the dosage is ranging from about 1 to 25 mg/kg, from about 1 to 50 mg/kg, from about 1 to 80 mg/kg, from about 1 to about 100 mg/kg, from about 5 to about 100 mg/kg, from about 5 to about 80 mg/kg, from about 5 to about 60 mg/kg, from about 5 to about 50 mg/kg or from about 5 to about 500 mg/kg which can be administered in single or multiple doses. In some instances, the dosage is administered in an amount of about 0.01 mg/kg, about 0.05 mg/kg, about 0.10 mg/kg, about 0.25 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, about 105 mg/kg, about 110 mg/kg, about 115 mg/kg, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 240, about 250, about 260, about 270, about 275, about 280, about 290, about 300, about 310, about 320, about 330, about 340, about 350, about 360 mg/kg, about 370 mg/kg, about 380 mg/kg, about 390 mg/kg, about 400 mg/kg, 410 mg/kg, about 420 mg/kg, about 430 mg/kg, about 440 mg/kg, about 450 mg/kg, about 460 mg/kg, about 470 mg/kg, about 480 mg/kg, about 490 mg/kg, or about 500 mg/kg.

SARS-CoV-2 antibodies or antibody fragment thereof described herein, in some embodiments, improve disease severity. In some embodiments, the SARS-CoV-2 antibodies or antibody fragment thereof improve disease severity at a dose level of about 0.01 mg/kg, about 0.05 mg/kg, about 0.10 mg/kg, about 0.25 mg/kg, about 0.5 mg/kg, about 1 mg/kg, about 5 mg/kg, about 10 mg/kg, about 15 mg/kg, or about 20 mg/kg. In some embodiments, the SARS-CoV-2 antibodies or antibody fragment thereof improve disease severity at a dose level of about 1 mg/kg, about 5 mg/kg, or about 10 mg/kg. In some embodiments, disease severity is determined by percent weight loss. In some embodiments, the SARS-CoV-2 antibodies or antibody fragment thereof protects against weight loss at a dose level of about 0.01 mg/kg, about 0.05 mg/kg, about 0.10 mg/kg, about 0.25 mg/kg, about 0.5 mg/kg, about 1 mg/kg, about 5 mg/kg, about 10 mg/kg, about 15 mg/kg, or about 20 mg/kg. In some embodiments, the SARS-CoV-2 antibodies or antibody fragment thereof protects against weight loss at a dose level of about 1 mg/kg, about 5 mg/kg, or about 10 mg/kg. In some embodiments, SARS-CoV-2 antibodies or antibody fragment thereof.

Variant Libraries

Codon Variation

Variant nucleic acid libraries described herein may comprise a plurality of nucleic acids, wherein each nucleic acid encodes for a variant codon sequence compared to a reference nucleic acid sequence. In some instances, each nucleic acid of a first nucleic acid population contains a variant at a single variant site. In some instances, the first nucleic acid population contains a plurality of variants at a single variant site such that the first nucleic acid population contains more than one variant at the same variant site. The first nucleic acid population may comprise nucleic acids collectively encoding multiple codon variants at the same variant site. The first nucleic acid population may comprise nucleic acids collectively encoding up to 19 or more codons at the same position. The first nucleic acid population may comprise nucleic acids collectively encoding up to 60 variant triplets at the same position, or the first nucleic acid population may comprise nucleic acids collectively encoding up to 61 different triplets of codons at the same position. Each variant may encode for a codon that results in a different amino acid during translation. Table 3 provides a listing of each codon possible (and the representative amino acid) for a variant site.

TABLE 3

List of codons and amino acids

| Amino Acids | One letter code | Three letter code | Codons | | | | | |
|---|---|---|---|---|---|---|---|---|
| Alanine | A | Ala | GCA | GCC | GCG | | GCT | |
| Cysteine | C | Cys | TGC | | | | TGT | |
| Aspartic acid | D | Asp | GAC | | | | GAT | |
| Glutamic acid | E | Glu | GAA | | | | GAG | |
| Phenylalanine | F | Phe | TTC | | | | TTT | |
| Glycine | G | Gly | GGA | GGC | GGG | | GGT | |
| Histidine | H | His | CAC | | | | CAT | |
| Isoleucine | I | Iso | ATA | ATC | | | ATT | |
| Lysine | K | Lys | AAA | | | | AAG | |
| Leucine | L | Leu | TTA | TTG | CTA | CTC | CTG | CTT |
| Methionine | M | Met | | | | ATG | | |
| Asparagine | N | Asn | AAC | | | | AAT | |
| Proline | P | Pro | CCA | CCC | CCG | | CCT | |
| Glutamine | Q | Gln | CAA | | | | CAG | |
| Arginine | R | Arg | AGA | AGG | CGA | CGC | CGG | CGT |
| Serine | S | Ser | AGC | AGT | TCA | TCC | TCG | TCT |
| Threonine | T | Thr | ACA | ACC | ACG | | ACT | |
| Valine | V | Val | GTA | GTC | GTG | | GTT | |
| Tryptophan | W | Trp | | | | TGG | | |
| Tyrosine | Y | Tyr | TAC | | | | TAT | |

A nucleic acid population may comprise varied nucleic acids collectively encoding up to 20 codon variations at multiple positions. In such cases, each nucleic acid in the population comprises variation for codons at more than one position in the same nucleic acid. In some instances, each nucleic acid in the population comprises variation for codons at 1, 2, 3, 4, 5, 6, 7, 8, 9, 10, 11, 12, 13, 14, 15, 16, 17, 18, 19, 20 or more codons in a single nucleic acid. In some instances, each variant long nucleic acid comprises variation for codons at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more codons in a single long nucleic acid. In some instances, the variant nucleic acid population comprises variation for codons at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more codons in a single nucleic acid. In some instances, the variant nucleic acid population comprises variation for codons in at least about 10, 20, 30, 40, 50, 60, 70, 80, 90, 100 or more codons in a single long nucleic acid.

Highly Parallel Nucleic Acid Synthesis

Provided herein is a platform approach utilizing miniaturization, parallelization, and vertical integration of the end-to-end process from polynucleotide synthesis to gene assembly within nanowells on silicon to create a revolutionary synthesis platform. Devices described herein provide, with the same footprint as a 96-well plate, a silicon synthesis platform is capable of increasing throughput by a factor of up to 1,000 or more compared to traditional synthesis methods, with production of up to approximately 1,000,000 or more polynucleotides, or 10,000 or more genes in a single highly-parallelized run.

With the advent of next-generation sequencing, high resolution genomic data has become an important factor for studies that delve into the biological roles of various genes in both normal biology and disease pathogenesis. At the core of this research is the central dogma of molecular biology and the concept of "residue-by-residue transfer of sequential information." Genomic information encoded in the DNA is transcribed into a message that is then translated into the protein that is the active product within a given biological pathway.

Another exciting area of study is on the discovery, development and manufacturing of therapeutic molecules focused on a highly-specific cellular target. High diversity DNA sequence libraries are at the core of development pipelines for targeted therapeutics. Gene variants are used to express proteins in a design, build, and test protein engineering cycle that ideally culminates in an optimized gene for high expression of a protein with high affinity for its therapeutic target. As an example, consider the binding pocket of a receptor. The ability to test all sequence permutations of all residues within the binding pocket simultaneously will allow for a thorough exploration, increasing chances of success. Saturation mutagenesis, in which a researcher attempts to generate all possible mutations or variants at a specific site within the receptor, represents one approach to this development challenge. Though costly and time and labor-intensive, it enables each variant to be introduced into each position. In contrast, combinatorial mutagenesis, where a few selected positions or short stretch of DNA may be modified extensively, generates an incomplete repertoire of variants with biased representation.

To accelerate the drug development pipeline, a library with the desired variants available at the intended frequency in the right position available for testing—in other words, a precision library, enables reduced costs as well as turnaround time for screening. Provided herein are methods for synthesizing nucleic acid synthetic variant libraries which provide for precise introduction of each intended variant at the desired frequency. To the end user, this translates to the ability to not only thoroughly sample sequence space but also be able to query these hypotheses in an efficient manner, reducing cost and screening time. Genome-wide editing can elucidate important pathways, libraries where each variant and sequence permutation can be tested for optimal functionality, and thousands of genes can be used to reconstruct entire pathways and genomes to re-engineer biological systems for drug discovery.

In a first example, a drug itself can be optimized using methods described herein. For example, to improve a specified function of an antibody, a variant polynucleotide library encoding for a portion of the antibody is designed and synthesized. A variant nucleic acid library for the antibody can then be generated by processes described herein (e.g., PCR mutagenesis followed by insertion into a vector). The antibody is then expressed in a production cell line and screened for enhanced activity. Example screens include examining modulation in binding affinity to an antigen, stability, or effector function (e.g., ADCC, complement, or apoptosis). Exemplary regions to optimize the antibody include, without limitation, the Fc region, Fab region, variable region of the Fab region, constant region of the Fab region, variable domain of the heavy chain or light chain ($V_H$ or $V_L$), and specific complementarity-determining regions (CDRs) of $V_H$ or $V_L$.

Nucleic acid libraries synthesized by methods described herein may be expressed in various cells associated with a disease state. Cells associated with a disease state include cell lines, tissue samples, primary cells from a subject, cultured cells expanded from a subject, or cells in a model system. Exemplary model systems include, without limitation, plant and animal models of a disease state.

To identify a variant molecule associated with prevention, reduction or treatment of a disease state, a variant nucleic acid library described herein is expressed in a cell associated with a disease state, or one in which a cell a disease state can be induced. In some instances, an agent is used to induce a disease state in cells. Exemplary tools for disease state induction include, without limitation, a Cre/Lox recombination system, LPS inflammation induction, and streptozotocin to induce hypoglycemia. The cells associated with a disease state may be cells from a model system or cultured cells, as well as cells from a subject having a particular disease condition. Exemplary disease conditions include a bacterial, fungal, viral, autoimmune, or proliferative disorder (e.g., cancer). In some instances, the variant nucleic acid library is expressed in the model system, cell line, or primary cells derived from a subject, and screened for changes in at least one cellular activity. Exemplary cellular activities include, without limitation, proliferation, cycle progression, cell death, adhesion, migration, reproduction, cell signaling, energy production, oxygen utilization, metabolic activity, and aging, response to free radical damage, or any combination thereof

Substrates

Devices used as a surface for polynucleotide synthesis may be in the form of substrates which include, without limitation, homogenous array surfaces, patterned array surfaces, channels, beads, gels, and the like. Provided herein are substrates comprising a plurality of clusters, wherein each cluster comprises a plurality of loci that support the attachment and synthesis of polynucleotides. In some instances, substrates comprise a homogenous array surface. For example, the homogenous array surface is a homogenous plate. The term "locus" as used herein refers to a discrete region on a structure which provides support for polynucleotides encoding for a single predetermined sequence to extend from the surface. In some instances, a locus is on a two dimensional surface, e.g., a substantially planar surface. In some instances, a locus is on a three-dimensional surface, e.g., a well, microwell, channel, or post. In some instances, a surface of a locus comprises a material that is actively functionalized to attach to at least one nucleotide for polynucleotide synthesis, or preferably, a population of identical nucleotides for synthesis of a population of polynucleotides. In some instances, polynucleotide refers to a population of polynucleotides encoding for the same nucleic acid sequence. In some cases, a surface of a substrate is inclusive of one or a plurality of surfaces of a substrate. The average error rates for polynucleotides synthesized within a library described here using the systems and methods provided are often less than 1 in 1000, less than about 1 in 2000, less than about 1 in 3000 or less often without error correction.

Provided herein are surfaces that support the parallel synthesis of a plurality of polynucleotides having different predetermined sequences at addressable locations on a common support. In some instances, a substrate provides support for the synthesis of more than 50, 100, 200, 400, 600, 800, 1000, 1200, 1400, 1600, 1800, 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical polynucleotides. In some cases, the surfaces provide support for the synthesis of more than 50, 100, 200, 400, 600, 800, 1000, 1200, 1400, 1600, 1800, 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more polynucleotides encoding for distinct sequences. In some instances, at least a portion of the polynucleotides have an identical sequence or are configured to be synthesized with an identical sequence. In some instances, the substrate provides a surface environment for the growth of polynucleotides having at least 80, 90, 100, 120, 150, 175, 200, 225, 250, 275, 300, 325, 350, 375, 400, 425, 450, 475, 500 bases or more.

Provided herein are methods for polynucleotide synthesis on distinct loci of a substrate, wherein each locus supports the synthesis of a population of polynucleotides. In some cases, each locus supports the synthesis of a population of polynucleotides having a different sequence than a population of polynucleotides grown on another locus. In some instances, each polynucleotide sequence is synthesized with 1, 2, 3, 4, 5, 6, 7, 8, 9 or more redundancy across different loci within the same cluster of loci on a surface for polynucleotide synthesis. In some instances, the loci of a substrate are located within a plurality of clusters. In some instances, a substrate comprises at least 10, 500, 1000, 2000, 3000, 4000, 5000, 6000, 7000, 8000, 9000, 10000, 11000, 12000, 13000, 14000, 15000, 20000, 30000, 40000, 50000 or more clusters. In some instances, a substrate comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct loci. In some instances, a substrate comprises about 10,000 distinct loci. The amount of loci within a single cluster is varied in different instances. In some cases, each cluster includes 1, 2, 3, 4, 5, 6, 7, 8, 9, 10, 20, 30, 40, 50, 60, 70, 80, 90, 100, 120, 130, 150, 200, 300, 400, 500 or more loci. In some instances, each cluster includes about 50-500 loci. In some instances, each cluster includes about 100-200 loci. In some instances, each cluster includes about 100-150 loci. In some instances, each cluster includes about 109, 121, 130 or 137 loci. In some instances, each cluster includes about 19, 20, 61, 64 or more loci. Alternatively or in combination, polynucleotide synthesis occurs on a homogenous array surface.

In some instances, the number of distinct polynucleotides synthesized on a substrate is dependent on the number of distinct loci available in the substrate. In some instances, the density of loci within a cluster or surface of a substrate is at least or about 1, 10, 25, 50, 65, 75, 100, 130, 150, 175, 200, 300, 400, 500, 1,000 or more loci per $mm^2$. In some cases, a substrate comprises 10-500, 25-400, 50-500, 100-500, 150-500, 10-250, 50-250, 10-200, or 50-200 $mm^2$. In some instances, the distance between the centers of two adjacent loci within a cluster or surface is from about 10-500, from about 10-200, or from about 10-100 um. In some instances, the distance between two centers of adjacent loci is greater than about 10, 20, 30, 40, 50, 60, 70, 80, 90 or 100 um. In some instances, the distance between the centers of two adjacent loci is less than about 200, 150, 100, 80, 70, 60, 50, 40, 30, 20 or 10 um. In some instances, each locus has a width of about 0.5, 1, 2, 3, 4, 5, 6, 7, 8, 9, 10, 20, 30, 40, 50, 60, 70, 80, 90 or 100 um. In some cases, each locus has a width of about 0.5-100, 0.5-50, 10-75, or 0.5-50 um.

In some instances, the density of clusters within a substrate is at least or about 1 cluster per 100 $mm^2$, 1 cluster per 10 $mm^2$, 1 cluster per 5 $mm^2$, 1 cluster per 4 $mm^2$, 1 cluster per 3 $mm^2$, 1 cluster per 2 $mm^2$, 1 cluster per 1 $mm^2$, 2 clusters per 1 $mm^2$, 3 clusters per 1 $mm^2$, 4 clusters per 1 $mm^2$, 5 clusters per 1 $mm^2$, 10 clusters per 1 $mm^2$, 50 clusters per 1 $mm^2$ or more. In some instances, a substrate comprises from about 1 cluster per 10 $mm^2$ to about 10 clusters per 1 $mm^2$. In some instances, the distance between the centers of two adjacent clusters is at least or about 50, 100, 200, 500, 1000, 2000, or 5000 um. In some cases, the distance between the centers of two adjacent clusters is between about 50-100, 50-200, 50-300, 50-500, and 100-2000 um. In some cases, the distance between the centers of two adjacent clusters is between about 0.05-50, 0.05-10, 0.05-5, 0.05-4, 0.05-3, 0.05-2, 0.1-10, 0.2-10, 0.3-10, 0.4-10, 0.5-10, 0.5-5, or 0.5-2 mm. In some cases, each cluster has a cross section of about 0.5 to about 2, about 0.5 to about 1, or about 1 to about 2 mm. In some cases, each cluster has a cross section of about 0.5, 0.6, 0.7, 0.8, 0.9, 1, 1.1, 1.2, 1.3, 1.4, 1.5, 1.6, 1.7, 1.8, 1.9 or 2 mm. In some cases, each cluster has an interior cross section of about 0.5, 0.6, 0.7, 0.8, 0.9, 1, 1.1, 1.15, 1.2, 1.3, 1.4, 1.5, 1.6, 1.7, 1.8, 1.9 or 2 mm.

In some instances, a substrate is about the size of a standard 96 well plate, for example between about 100 and about 200 mm by between about 50 and about 150 mm. In some instances, a substrate has a diameter less than or equal to about 1000, 500, 450, 400, 300, 250, 200, 150, 100 or 50 mm. In some instances, the diameter of a substrate is between about 25-1000, 25-800, 25-600, 25-500, 25-400, 25-300, or 25-200 mm. In some instances, a substrate has a planar surface area of at least about 100; 200; 500; 1,000; 2,000; 5,000; 10,000; 12,000; 15,000; 20,000; 30,000; 40,000; 50,000 $mm^2$ or more. In some instances, the thickness of a substrate is between about 50-2000, 50-1000, 100-1000, 200-1000, or 250-1000 mm.

Surface Materials

Substrates, devices, and reactors provided herein are fabricated from any variety of materials suitable for the methods, compositions, and systems described herein. In certain instances, substrate materials are fabricated to exhibit a low level of nucleotide binding. In some instances, substrate materials are modified to generate distinct surfaces that exhibit a high level of nucleotide binding. In some instances, substrate materials are transparent to visible and/or UV light. In some instances, substrate materials are sufficiently conductive, e.g., are able to form uniform electric fields across all or a portion of a substrate. In some instances, conductive materials are connected to an electric ground. In some instances, the substrate is heat conductive or insulated. In some instances, the materials are chemical resistant and heat resistant to support chemical or biochemical reactions, for example polynucleotide synthesis reaction processes. In some instances, a substrate comprises flexible materials. For flexible materials, materials can include, without limitation: nylon, both modified and unmodified, nitrocellulose, polypropylene, and the like. In some instances, a substrate comprises rigid materials. For rigid materials, materials can include, without limitation: glass; fuse silica; silicon, plastics (for example polytetrafluoroethylene, polypropylene, polystyrene, polycarbonate, and blends thereof, and the like); metals (for example, gold, platinum, and the like). The substrate, solid support or reactors can be fabricated from a material selected from the group consisting of silicon, polystyrene, agarose, dextran, cellulosic polymers, polyacrylamides, polydimethylsiloxane (PDMS), and glass. The substrates/solid supports or the microstructures, reactors therein may be manufactured with a combination of materials listed herein or any other suitable material known in the art.

Surface Architecture

Provided herein are substrates for the methods, compositions, and systems described herein, wherein the substrates have a surface architecture suitable for the methods, compositions, and systems described herein. In some instances, a substrate comprises raised and/or lowered features. One benefit of having such features is an increase in surface area to support polynucleotide synthesis. In some instances, a substrate having raised and/or lowered features is referred to as a three-dimensional substrate. In some cases, a three-dimensional substrate comprises one or more channels. In some cases, one or more loci comprise a channel. In some cases, the channels are accessible to reagent deposition via a deposition device such as a material deposition device. In some cases, reagents and/or fluids collect in a larger well in fluid communication one or more channels. For example, a substrate comprises a plurality of channels corresponding to a plurality of loci with a cluster, and the plurality of channels are in fluid communication with one well of the cluster. In some methods, a library of polynucleotides is synthesized in a plurality of loci of a cluster.

Provided herein are substrates for the methods, compositions, and systems described herein, wherein the substrates are configured for polynucleotide synthesis. In some instances, the structure is configured to allow for controlled flow and mass transfer paths for polynucleotide synthesis on a surface. In some instances, the configuration of a substrate allows for the controlled and even distribution of mass transfer paths, chemical exposure times, and/or wash efficacy during polynucleotide synthesis. In some instances, the configuration of a substrate allows for increased sweep efficiency, for example by providing sufficient volume for a growing polynucleotide such that the excluded volume by the growing polynucleotide does not take up more than 50, 45, 40, 35, 30, 25, 20, 15, 14, 13, 12, 11, 10, 9, 8, 7, 6, 5, 4, 3, 2, 1%, or less of the initially available volume that is available or suitable for growing the polynucleotide. In some instances, a three-dimensional structure allows for managed flow of fluid to allow for the rapid exchange of chemical exposure.

Provided herein are substrates for the methods, compositions, and systems described herein, wherein the substrates comprise structures suitable for the methods, compositions, and systems described herein. In some instances, segregation is achieved by physical structure. In some instances, segregation is achieved by differential functionalization of the surface generating active and passive regions for polynucleotide synthesis. In some instances, differential functionalization is achieved by alternating the hydrophobicity across the substrate surface, thereby creating water contact angle effects that cause beading or wetting of the deposited reagents. Employing larger structures can decrease splashing and cross-contamination of distinct polynucleotide synthesis locations with reagents of the neighboring spots. In some cases, a device, such as a material deposition device, is used to deposit reagents to distinct polynucleotide synthesis locations. Substrates having three-dimensional features are configured in a manner that allows for the synthesis of a large number of polynucleotides (e.g., more than about 10,000) with a low error rate (e.g., less than about 1:500, 1:1000, 1:1500, 1:2,000, 1:3,000, 1:5,000, or 1:10,000). In some cases, a substrate comprises features with a density of about or greater than about 1, 5, 10, 20, 30, 40, 50, 60, 70, 80, 100, 110, 120, 130, 140, 150, 160, 170, 180, 190, 200, 300, 400 or 500 features per $mm^2$.

A well of a substrate may have the same or different width, height, and/or volume as another well of the substrate. A channel of a substrate may have the same or different width, height, and/or volume as another channel of the substrate. In some instances, the diameter of a cluster or the diameter of a well comprising a cluster, or both, is between about 0.05-50, 0.05-10, 0.05-5, 0.05-4, 0.05-3, 0.05-2, 0.05-1, 0.05-0.5, 0.05-0.1, 0.1-10, 0.2-10, 0.3-10, 0.4-10, 0.5-10, 0.5-5, or 0.5-2 mm. In some instances, the diameter of a cluster or well or both is less than or about 5, 4, 3, 2, 1, 0.5, 0.1, 0.09, 0.08, 0.07, 0.06, or 0.05 mm. In some instances, the diameter of a cluster or well or both is between about 1.0 and 1.3 mm. In some instances, the diameter of a cluster or well, or both is about 1.150 mm. In some instances, the diameter of a cluster or well, or both is about 0.08 mm. The diameter of a cluster refers to clusters within a two-dimensional or three-dimensional substrate.

In some instances, the height of a well is from about 20-1000, 50-1000, 100-1000, 200-1000, 300-1000, 400-1000, or 500-1000 um. In some cases, the height of a well is less than about 1000, 900, 800, 700, or 600 um.

In some instances, a substrate comprises a plurality of channels corresponding to a plurality of loci within a cluster, wherein the height or depth of a channel is 5-500, 5-400, 5-300, 5-200, 5-100, 5-50, or 10-50 um. In some cases, the height of a channel is less than 100, 80, 60, 40, or 20 um.

In some instances, the diameter of a channel, locus (e.g., in a substantially planar substrate) or both channel and locus (e.g., in a three-dimensional substrate wherein a locus corresponds to a channel) is from about 1-1000, 1-500, 1-200, 1-100, 5-100, or 10-100 um, for example, about 90, 80, 70, 60, 50, 40, 30, 20 or 10 um. In some instances, the diameter of a channel, locus, or both channel and locus is less than about 100, 90, 80, 70, 60, 50, 40, 30, 20 or 10 um. In some instances, the distance between the center of two adjacent channels, loci, or channels and loci is from about 1-500, 1-200, 1-100, 5-200, 5-100, 5-50, or 5-30, for example, about 20 um.

Surface Modifications

Provided herein are methods for polynucleotide synthesis on a surface, wherein the surface comprises various surface modifications. In some instances, the surface modifications are employed for the chemical and/or physical alteration of a surface by an additive or subtractive process to change one or more chemical and/or physical properties of a substrate surface or a selected site or region of a substrate surface. For example, surface modifications include, without limitation, (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

In some cases, the addition of a chemical layer on top of a surface (referred to as adhesion promoter) facilitates structured patterning of loci on a surface of a substrate. Exemplary surfaces for application of adhesion promotion include, without limitation, glass, silicon, silicon dioxide and silicon nitride. In some cases, the adhesion promoter is a chemical with a high surface energy. In some instances, a second chemical layer is deposited on a surface of a substrate. In some cases, the second chemical layer has a low surface energy. In some cases, surface energy of a chemical layer coated on a surface supports localization of droplets on the surface. Depending on the patterning arrangement selected, the proximity of loci and/or area of fluid contact at the loci are alterable.

In some instances, a substrate surface, or resolved loci, onto which nucleic acids or other moieties are deposited, e.g., for polynucleotide synthesis, are smooth or substantially planar (e.g., two-dimensional) or have irregularities, such as raised or lowered features (e.g., three-dimensional features). In some instances, a substrate surface is modified with one or more different layers of compounds. Such modification layers of interest include, without limitation, inorganic and organic layers such as metals, metal oxides, polymers, small organic molecules and the like.

In some instances, resolved loci of a substrate are functionalized with one or more moieties that increase and/or decrease surface energy. In some cases, a moiety is chemically inert. In some cases, a moiety is configured to support a desired chemical reaction, for example, one or more processes in a polynucleotide synthesis reaction. The surface energy, or hydrophobicity, of a surface is a factor for determining the affinity of a nucleotide to attach onto the surface. In some instances, a method for substrate functionalization comprises: (a) providing a substrate having a surface that comprises silicon dioxide; and (b) silanizing the surface using, a suitable silanizing agent described herein or otherwise known in the art, for example, an organofunctional alkoxysilane molecule. Methods and functionalizing agents are described in U.S. Pat. No. 5,474,796, which is herein incorporated by reference in its entirety.

In some instances, a substrate surface is functionalized by contact with a derivatizing composition that contains a mixture of silanes, under reaction conditions effective to couple the silanes to the substrate surface, typically via reactive hydrophilic moieties present on the substrate surface. Silanization generally covers a surface through self-assembly with organofunctional alkoxysilane molecules. A variety of siloxane functionalizing reagents can further be used as currently known in the art, e.g., for lowering or increasing surface energy. The organofunctional alkoxysilanes are classified according to their organic functions.

Polynucleotide Synthesis

Methods of the current disclosure for polynucleotide synthesis may include processes involving phosphoramidite chemistry. In some instances, polynucleotide synthesis comprises coupling a base with phosphoramidite. Polynucleotide synthesis may comprise coupling a base by deposition of phosphoramidite under coupling conditions, wherein the same base is optionally deposited with phosphoramidite more than once, i.e., double coupling. Polynucleotide synthesis may comprise capping of unreacted sites. In some instances, capping is optional. Polynucleotide synthesis may also comprise oxidation or an oxidation step or oxidation steps. Polynucleotide synthesis may comprise deblocking, detritylation, and sulfurization. In some instances, polynucleotide synthesis comprises either oxidation or sulfurization. In some instances, between one or each step during a polynucleotide synthesis reaction, the device is washed, for example, using tetrazole or acetonitrile. Time frames for any one step in a phosphoramidite synthesis method may be less than about 2 min, 1 min, 50 sec, 40 sec, 30 sec, 20 sec and 10 sec.

Polynucleotide synthesis using a phosphoramidite method may comprise a subsequent addition of a phosphoramidite building block (e.g., nucleoside phosphoramidite) to a growing polynucleotide chain for the formation of a phosphite triester linkage. Phosphoramidite polynucleotide synthesis proceeds in the 3' to 5' direction. Phosphoramidite polynucleotide synthesis allows for the controlled addition of one nucleotide to a growing nucleic acid chain per synthesis cycle. In some instances, each synthesis cycle comprises a coupling step. Phosphoramidite coupling involves the formation of a phosphite triester linkage between an activated nucleoside phosphoramidite and a nucleoside bound to the substrate, for example, via a linker. In some instances, the nucleoside phosphoramidite is provided to the device activated. In some instances, the nucleoside phosphoramidite is provided to the device with an activator. In some instances, nucleoside phosphoramidites are provided to the device in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition of a nucleoside phosphoramidite, the device is optionally washed. In some instances, the coupling step is repeated one or more additional times, optionally with a wash step between nucleoside phosphoramidite additions to the substrate. In some instances, a polynucleotide synthesis method used herein comprises 1, 2, 3 or more sequential coupling steps. Prior to coupling, in many cases, the nucleoside bound to the device is de-protected by removal of a protecting group, where the protecting group functions to prevent polymerization. A common protecting group is 4,4'-dimethoxytrityl (DMT).

Following coupling, phosphoramidite polynucleotide synthesis methods optionally comprise a capping step. In a capping step, the growing polynucleotide is treated with a capping agent. A capping step is useful to block unreacted substrate-bound 5'—OH groups after coupling from further chain elongation, preventing the formation of polynucleotides with internal base deletions. Further, phosphoramidites activated with 1H-tetrazole may react, to a small extent, with the O6 position of guanosine. Without being bound by theory, upon oxidation with $I_2$/water, this side product, possibly via O6-N7 migration, may undergo depurination. The apurinic sites may end up being cleaved in the course of the final deprotection of the polynucleotide thus reducing the yield of the full-length product. The O6 modifications may be removed by treatment with the capping reagent prior to oxidation with $I_2$/water. In some instances, inclusion of a capping step during polynucleotide synthesis decreases the error rate as compared to synthesis without capping. As an example, the capping step comprises treating the substrate-bound polynucleotide with a mixture of acetic anhydride and 1-methylimidazole. Following a capping step, the device is optionally washed.

In some instances, following addition of a nucleoside phosphoramidite, and optionally after capping and one or more wash steps, the device bound growing nucleic acid is oxidized. The oxidation step comprises the phosphite triester is oxidized into a tetracoordinated phosphate triester, a protected precursor of the naturally occurring phosphate diester internucleoside linkage. In some instances, oxidation of the growing polynucleotide is achieved by treatment with iodine and water, optionally in the presence of a weak base (e.g., pyridine, lutidine, collidine). Oxidation may be carried out under anhydrous conditions using, e.g. tert-Butyl hydroperoxide or (1S)-(+)-(10-camphorsulfonyl)-oxaziridine (CSO). In some methods, a capping step is performed following oxidation. A second capping step allows for device drying, as residual water from oxidation that may persist can inhibit subsequent coupling. Following oxidation, the device and growing polynucleotide is optionally washed. In some instances, the step of oxidation is substituted with a sulfurization step to obtain polynucleotide phosphorothioates, wherein any capping steps can be performed after the sulfurization. Many reagents are capable of the efficient sulfur transfer, including but not limited to 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

In order for a subsequent cycle of nucleoside incorporation to occur through coupling, the protected 5' end of the device bound growing polynucleotide is removed so that the primary hydroxyl group is reactive with a next nucleoside phosphoramidite. In some instances, the protecting group is DMT and deblocking occurs with trichloroacetic acid in dichloromethane. Conducting detritylation for an extended time or with stronger than recommended solutions of acids may lead to increased depurination of solid support-bound polynucleotide and thus reduces the yield of the desired full-length product. Methods and compositions of the disclosure described herein provide for controlled deblocking conditions limiting undesired depurination reactions. In some instances, the device bound polynucleotide is washed after deblocking. In some instances, efficient washing after deblocking contributes to synthesized polynucleotides having a low error rate.

Methods for the synthesis of polynucleotides typically involve an iterating sequence of the following steps: application of a protected monomer to an actively functionalized surface (e.g., locus) to link with either the activated surface, a linker or with a previously deprotected monomer; deprotection of the applied monomer so that it is reactive with a subsequently applied protected monomer; and application of another protected monomer for linking. One or more intermediate steps include oxidation or sulfurization. In some instances, one or more wash steps precede or follow one or all of the steps.

Methods for phosphoramidite-based polynucleotide synthesis comprise a series of chemical steps. In some instances, one or more steps of a synthesis method involve reagent cycling, where one or more steps of the method comprise application to the device of a reagent useful for the step. For example, reagents are cycled by a series of liquid deposition and vacuum drying steps. For substrates comprising three-dimensional features such as wells, microwells, channels and the like, reagents are optionally passed through one or more regions of the device via the wells and/or channels.

Methods and systems described herein relate to polynucleotide synthesis devices for the synthesis of polynucleotides. The synthesis may be in parallel. For example, at least or about at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 100, 150, 200, 250, 300, 350, 400, 450, 500, 550, 600, 650, 700, 750, 800, 850, 900, 1000, 10000, 50000, 75000, 100000 or more polynucleotides can be synthesized in parallel. The total number polynucleotides that may be synthesized in parallel may be from 2-100000, 3-50000, 4-10000, 5-1000, 6-900, 7-850, 8-800, 9-750, 10-700, 11-650, 12-600, 13-550, 14-500, 15-450, 16-400, 17-350, 18-300, 19-250, 20-200, 21-150, 22-100, 23-50, 24-45, 25-40, 30-35. Those of skill in the art appreciate that the total number of polynucleotides synthesized in parallel may fall within any range bound by any of these values, for example 25-100. The total number of polynucleotides synthesized in parallel may fall within any range defined by any of the values serving as endpoints of the range. Total molar mass of polynucleotides synthesized within the device or the molar mass of each of the polynucleotides may be at least or at least about 10, 20, 30, 40, 50, 100, 250, 500, 750, 1000, 2000, 3000, 4000, 5000, 6000, 7000, 8000, 9000, 10000, 25000, 50000, 75000, 100000 picomoles, or more. The length of each of the polynucleotides or average length of the polynucleotides within the device may be at least or about at least 10, 15, 20, 25, 30, 35, 40, 45, 50, 100, 150, 200, 300, 400, 500 nucleotides, or more. The length of each of the polynucleotides or average length of the polynucleotides within the device may be at most or about at most 500, 400, 300, 200, 150, 100, 50, 45, 35, 30, 25, 20, 19, 18, 17, 16, 15, 14, 13, 12, 11, 10 nucleotides, or less. The length of each of the polynucleotides or average length of the polynucleotides within the device may fall from 10-500, 9-400, 11-300, 12-200, 13-150, 14-100, 15-50, 16-45, 17-40, 18-35, 19-25. Those of skill in the art appreciate that the length of each of the polynucleotides or average length of the polynucleotides within the device may fall within any range bound by any of these values, for example 100-300. The length of each of the polynucleotides or average length of the polynucleotides within the device may fall within any range defined by any of the values serving as endpoints of the range.

Methods for polynucleotide synthesis on a surface provided herein allow for synthesis at a fast rate. As an example, at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 100, 125, 150, 175, 200 nucleotides per hour, or more are synthesized. Nucleotides include adenine, guanine, thymine, cytosine, uridine building blocks, or analogs/modified versions thereof. In some instances, libraries of polynucleotides are synthesized in parallel on substrate. For example, a device comprising about or at least about 100; 1,000; 10,000; 30,000; 75,000; 100,000; 1,000,000; 2,000,000; 3,000,000; 4,000,000; or 5,000,000 resolved loci is able to support the synthesis of at least the same number of distinct polynucleotides, wherein polynucleotide encoding a distinct sequence is synthesized on a resolved locus. In some instances, a library of polynucleotides is synthesized on a device with low error rates described herein in less than about three months, two months, one month, three weeks, 15, 14, 13, 12, 11, 10, 9, 8, 7, 6, 5, 4, 3, 2 days, 24 hours or less. In some instances, larger nucleic acids assembled from a polynucleotide library synthesized with low error rate using the substrates and methods described herein are prepared in less than about three months, two months, one month, three weeks, 15, 14, 13, 12, 11, 10, 9, 8, 7, 6, 5, 4, 3, 2 days, 24 hours or less.

In some instances, methods described herein provide for generation of a library of nucleic acids comprising variant nucleic acids differing at a plurality of codon sites. In some instances, a nucleic acid may have 1 site, 2 sites, 3 sites, 4 sites, 5 sites, 6 sites, 7 sites, 8 sites, 9 sites, 10 sites, 11 sites, 12 sites, 13 sites, 14 sites, 15 sites, 16 sites, 17 sites 18 sites, 19 sites, 20 sites, 30 sites, 40 sites, 50 sites, or more of variant codon sites.

In some instances, the one or more sites of variant codon sites may be adjacent. In some instances, the one or more sites of variant codon sites may not be adjacent and separated by 1, 2, 3, 4, 5, 6, 7, 8, 9, 10, or more codons.

In some instances, a nucleic acid may comprise multiple sites of variant codon sites, wherein all the variant codon sites are adjacent to one another, forming a stretch of variant codon sites. In some instances, a nucleic acid may comprise multiple sites of variant codon sites, wherein none the variant codon sites are adjacent to one another. In some instances, a nucleic acid may comprise multiple sites of variant codon sites, wherein some the variant codon sites are adjacent to one another, forming a stretch of variant codon sites, and some of the variant codon sites are not adjacent to one another.

Figure 5:
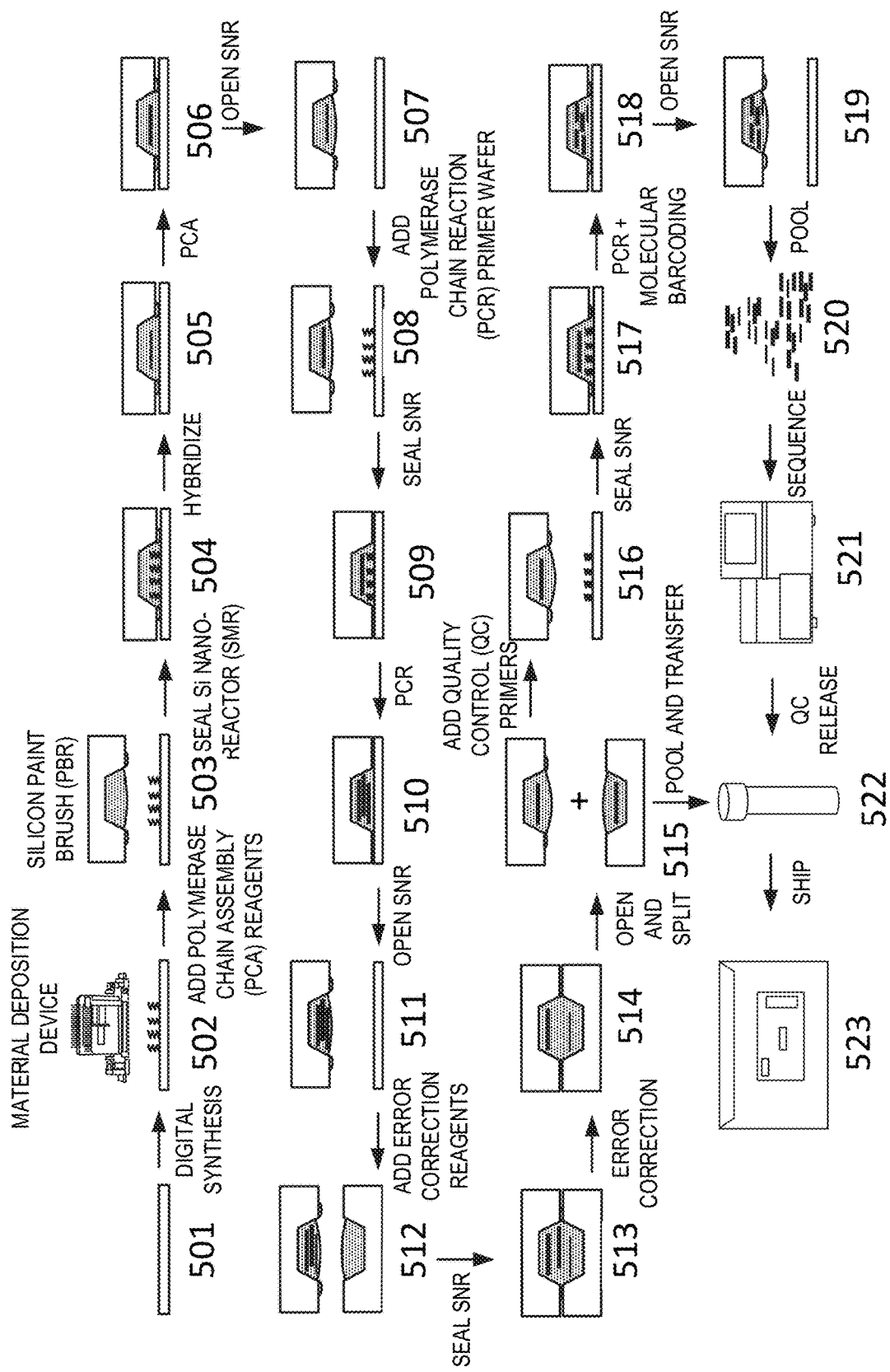
FIG. 5 presents a diagram of steps demonstrating an exemplary process workflow for gene synthesis as disclosed herein.

Referring to the Figures, FIG. 5 illustrates an exemplary process workflow for synthesis of nucleic acids (e.g., genes) from shorter nucleic acids. The workflow is divided generally into phases: (1) de novo synthesis of a single stranded nucleic acid library, (2) joining nucleic acids to form larger fragments, (3) error correction, (4) quality control, and (5) shipment. Prior to de novo synthesis, an intended nucleic acid sequence or group of nucleic acid sequences is preselected. For example, a group of genes is preselected for generation.

Once large nucleic acids for generation are selected, a predetermined library of nucleic acids is designed for de novo synthesis. Various suitable methods are known for generating high density polynucleotide arrays. In the workflow example, a device surface layer is provided. In the example, chemistry of the surface is altered in order to improve the polynucleotide synthesis process. Areas of low surface energy are generated to repel liquid while areas of high surface energy are generated to attract liquids. The surface itself may be in the form of a planar surface or contain variations in shape, such as protrusions or microwells which increase surface area. In the workflow example, high surface energy molecules selected serve a dual function of supporting DNA chemistry, as disclosed in International Patent Application Publication WO/2015/021080, which is herein incorporated by reference in its entirety.

In situ preparation of polynucleotide arrays is generated on a solid support and utilizes single nucleotide extension process to extend multiple oligomers in parallel. A deposition device, such as a material deposition device 501, is designed to release reagents in a step wise fashion such that multiple polynucleotides extend, in parallel, one residue at a time to generate oligomers with a predetermined nucleic acid sequence 502. In some instances, polynucleotides are cleaved from the surface at this stage. Cleavage includes gas cleavage, e.g., with ammonia or methylamine.

The generated polynucleotide libraries are placed in a reaction chamber. In this exemplary workflow, the reaction chamber (also referred to as "nanoreactor") is a silicon coated well, containing PCR reagents and lowered onto the polynucleotide library 503. Prior to or after the sealing 504 of the polynucleotides, a reagent is added to release the polynucleotides from the substrate. In the exemplary workflow, the polynucleotides are released subsequent to sealing of the nanoreactor 504. Once released, fragments of single stranded polynucleotides hybridize in order to span an entire long range sequence of DNA. Partial hybridization 505 is possible because each synthesized polynucleotide is designed to have a small portion overlapping with at least one other polynucleotide in the pool.

After hybridization, a PCA reaction is commenced. During the polymerase cycles, the polynucleotides anneal to complementary fragments and gaps are filled in by a polymerase. Each cycle increases the length of various fragments randomly depending on which polynucleotides find each other. Complementarity amongst the fragments allows for forming a complete large span of double stranded DNA 506.

After PCA is complete, the nanoreactor is separated from the device 507 and positioned for interaction with a device having primers for PCR 508. After sealing, the nanoreactor is subject to PCR 509 and the larger nucleic acids are amplified. After PCR 510, the nanochamber is opened 511, error correction reagents are added 512, the chamber is sealed 513 and an error correction reaction occurs to remove mismatched base pairs and/or strands with poor complementarity from the double stranded PCR amplification products 514. The nanoreactor is opened and separated 515. Error corrected product is next subject to additional processing steps, such as PCR and molecular bar coding, and then packaged 522 for shipment 523.

In some instances, quality control measures are taken. After error correction, quality control steps include for example interaction with a wafer having sequencing primers for amplification of the error corrected product 516, sealing the wafer to a chamber containing error corrected amplification product 517, and performing an additional round of amplification 518. The nanoreactor is opened 519 and the products are pooled 520 and sequenced 521. After an acceptable quality control determination is made, the packaged product 522 is approved for shipment 523.

In some instances, a nucleic acid generate by a workflow such as that in FIG. 5 is subject to mutagenesis using overlapping primers disclosed herein. In some instances, a library of primers are generated by in situ preparation on a solid support and utilize single nucleotide extension process to extend multiple oligomers in parallel. A deposition device, such as a material deposition device, is designed to release reagents in a step wise fashion such that multiple polynucleotides extend, in parallel, one residue at a time to generate oligomers with a predetermined nucleic acid sequence 502.

Computer Systems

Any of the systems described herein, may be operably linked to a computer and may be automated through a computer either locally or remotely. In various instances, the methods and systems of the disclosure may further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the disclosure. The computer systems may be programmed to interface between the user specified base sequence and the position of a material deposition device to deliver the correct reagents to specified regions of the substrate.

Figure 6:
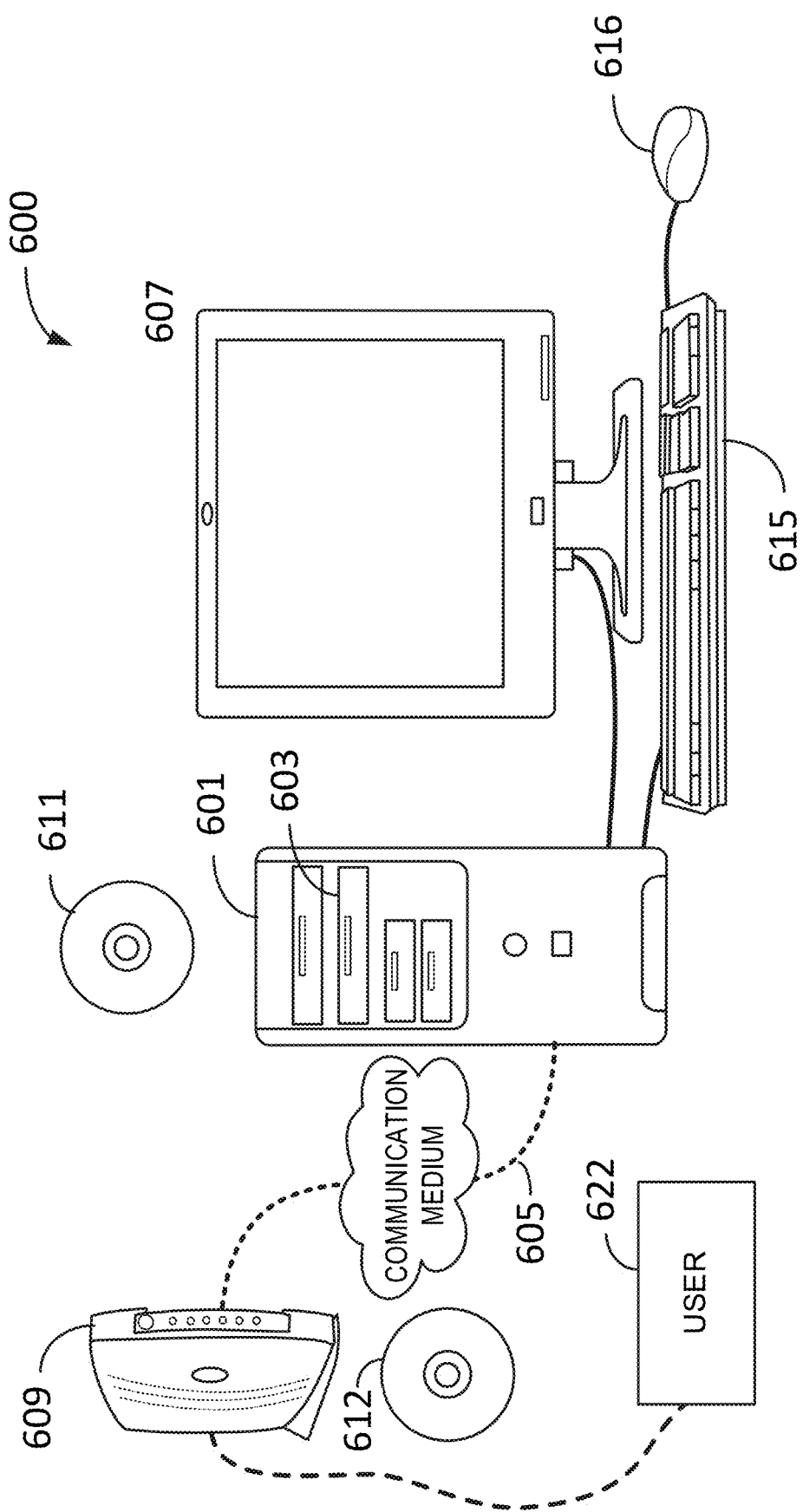
FIG. 6 illustrates an example of a computer system.

The computer system 600 illustrated in FIG. 6 may be understood as a logical apparatus that can read instructions from media 611 and/or a network port 605, which can optionally be connected to server 609 having fixed media 612. The system, such as shown in FIG. 6 can include a CPU 601, disk drives 603, optional input devices such as keyboard 615 and/or mouse 616 and optional monitor 607. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 622 as illustrated in FIG. 6.

Figure 7:
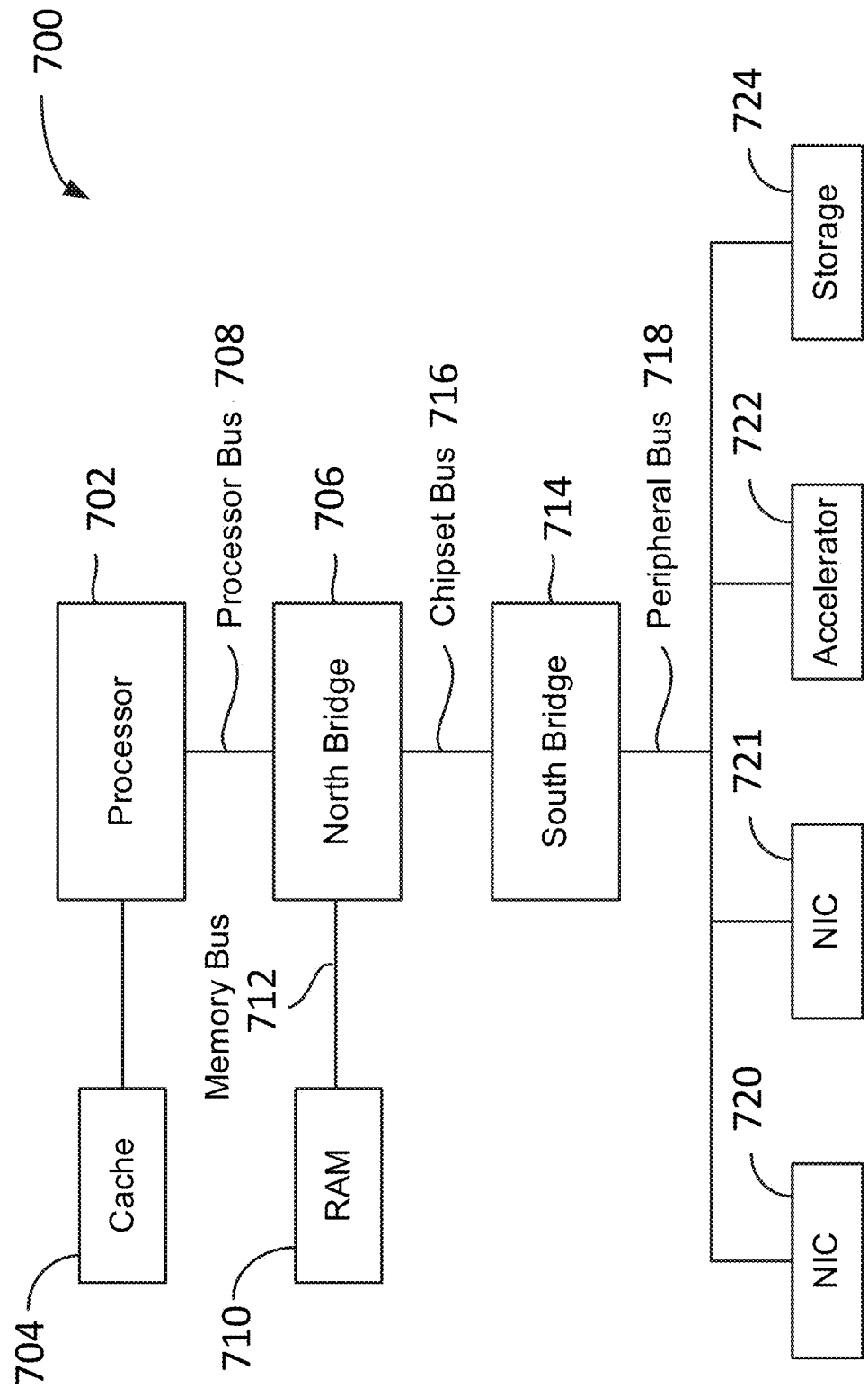
FIG. 7 is a block diagram illustrating an architecture of a computer system.

FIG. 7 is a block diagram illustrating a first example architecture of a computer system 700 that can be used in connection with example instances of the present disclosure. As depicted in FIG. 7, the example computer system can include a processor 702 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4 ™ processor, Marvell PXA 930 ™ processor, or a functionally-equivalent processor. Multiple threads of execution can be used for parallel processing. In some instances, multiple processors or processors with multiple cores can also be used, whether in a single computer system, in a cluster, or distributed across systems over a network comprising a plurality of computers, cell phones, and/or personal data assistant devices.

As illustrated in FIG. 7, a high speed cache 704 can be connected to, or incorporated in, the processor 702 to provide a high speed memory for instructions or data that have been recently, or are frequently, used by processor 702. The processor 702 is connected to a north bridge 706 by a processor bus 708. The north bridge 706 is connected to random access memory (RAM) 710 by a memory bus 712 and manages access to the RAM 710 by the processor 702. The north bridge 706 is also connected to a south bridge 714 by a chipset bus 716. The south bridge 714 is, in turn, connected to a peripheral bus 718. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 718. In some alternative architectures, the functionality of the north bridge can be incorporated into the processor instead of using a separate north bridge chip. In some instances, system 700 can include an accelerator card 722 attached to the peripheral bus 718. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 724 and can be loaded into RAM 710 and/or cache 704 for use by the processor. The system 700 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example instances of the present disclosure. In this example, system 700 also includes network interface cards (NICs) 720 and 721 connected to the peripheral bus for providing network interfaces to external storage, such as Network Attached Storage (NAS) and other computer systems that can be used for distributed parallel processing.

Figure 8:
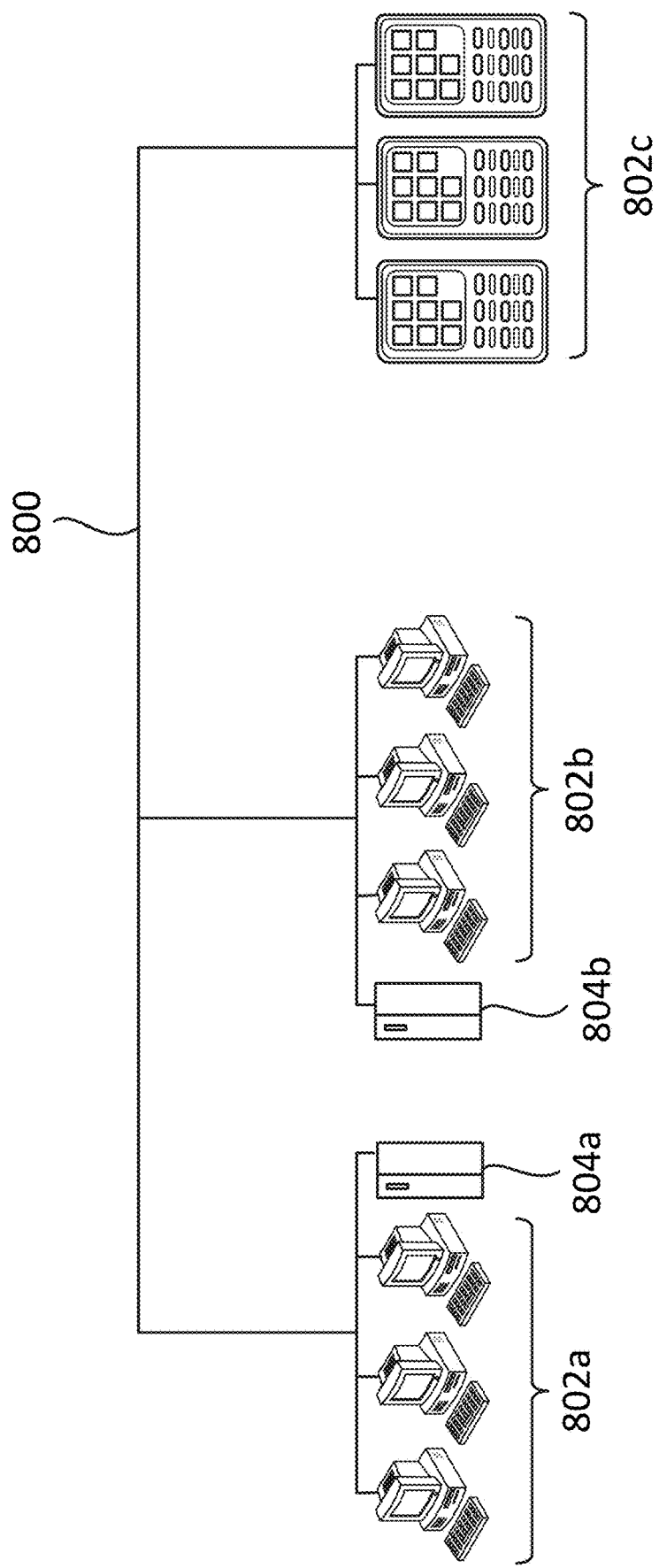
FIG. 8 is a diagram demonstrating a network configured to incorporate a plurality of computer systems, a plurality of cell phones and personal data assistants, and Network Attached Storage (NAS).

FIG. 8 is a diagram showing a network 800 with a plurality of computer systems 802*a*, and 802*b*, a plurality of cell phones and personal data assistants 802*c*, and Network Attached Storage (NAS) 804*a*, and 804*b*. In example instances, systems 802*a*, 802*b*, and 802*c* can manage data storage and optimize data access for data stored in Network Attached Storage (NAS) 804*a* and 804*b*. A mathematical model can be used for the data and be evaluated using distributed parallel processing across computer systems 802*a*, and 802*b*, and cell phone and personal data assistant systems 802*c*. Computer systems 802*a*, and 802*b*, and cell phone and personal data assistant systems 802*c* can also provide parallel processing for adaptive data restructuring of the data stored in Network Attached Storage (NAS) 804*a* and 804*b*. FIG. 8 illustrates an example only, and a wide variety of other computer architectures and systems can be used in conjunction with the various instances of the present disclosure. For example, a blade server can be used to provide parallel processing. Processor blades can be connected through a back plane to provide parallel processing. Storage can also be connected to the back plane or as Network Attached Storage (NAS) through a separate network interface. In some example instances, processors can maintain separate memory spaces and transmit data through network interfaces, back plane or other connectors for parallel processing by other processors. In other instances, some or all of the processors can use a shared virtual address memory space.

Figure 9:
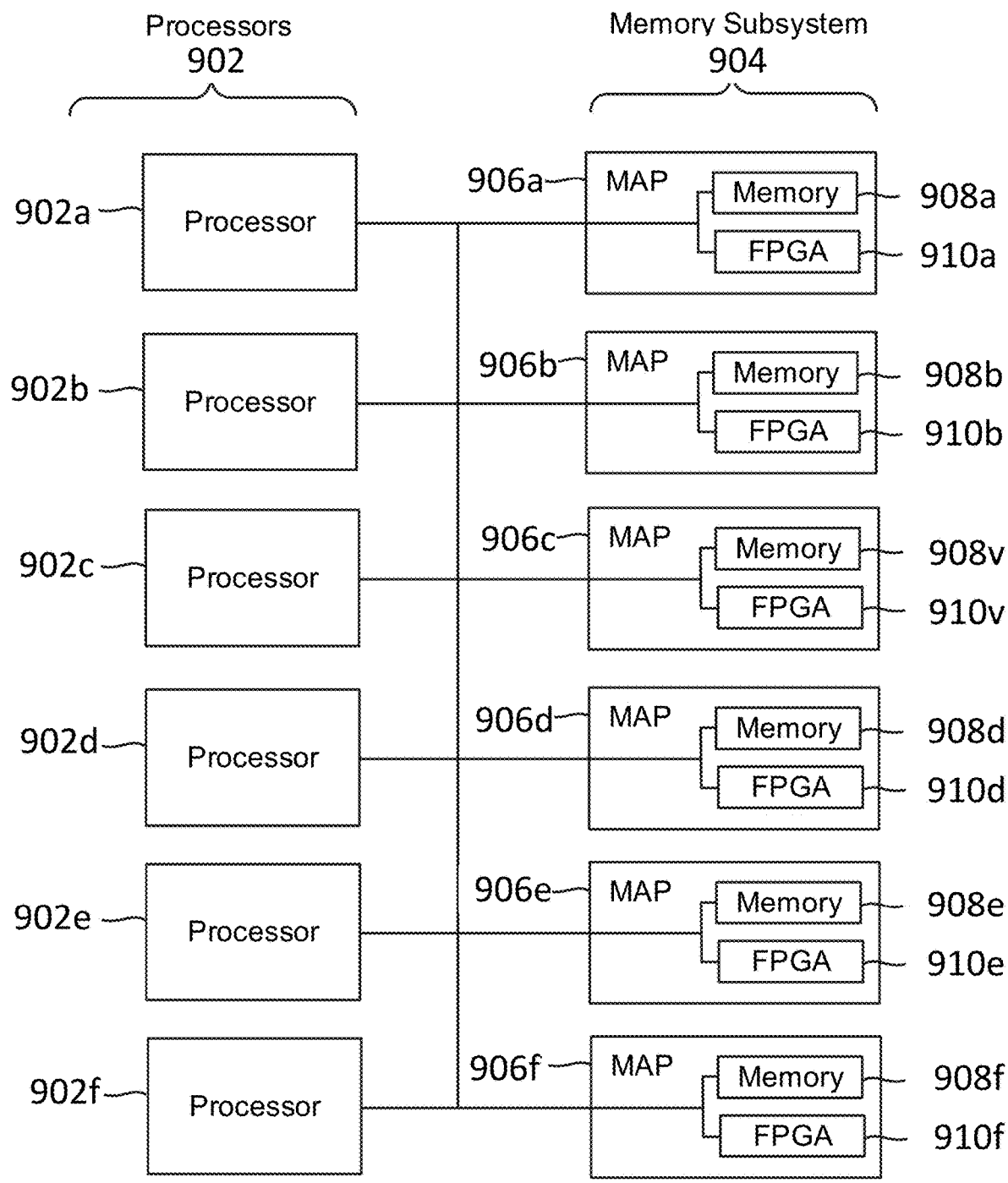
FIG. 9 is a block diagram of a multiprocessor computer system using a shared virtual address memory space.

FIG. 9 is a block diagram of a multiprocessor computer system using a shared virtual address memory space in accordance with an example instance. The system includes a plurality of processors 902*a-f* that can access a shared memory subsystem 904. The system incorporates a plurality of programmable hardware memory algorithm processors (MAPs) 906*a-f* in the memory subsystem 904. Each MAP 906*a-f* can comprise a memory 908*a-f* and one or more field programmable gate arrays (FPGAs) 910*a-f* The MAP provides a configurable functional unit and particular algorithms or portions of algorithms can be provided to the FPGAs 910*a-f* for processing in close coordination with a respective processor. For example, the MAPs can be used to evaluate algebraic expressions regarding the data model and to perform adaptive data restructuring in example instances. In this example, each MAP is globally accessible by all of the processors for these purposes. In one configuration, each MAP can use Direct Memory Access (DMA) to access an associated memory 908*a-f,* allowing it to execute tasks independently of, and asynchronously from the respective microprocessor 902a-f In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example instances, including systems using any combination of general processors, co-processors, FPGAs and other programmable logic devices, system on chips (SOCs), application specific integrated circuits (ASICs), and other processing and logic elements. In some instances, all or part of the computer system can be implemented in software or hardware. Any variety of data storage media can be used in connection with example instances, including random access memory, hard drives, flash memory, tape drives, disk arrays, Network Attached Storage (NAS) and other local or distributed data storage devices and systems.

In example instances, the computer system can be implemented using software modules executing on any of the above or other computer architectures and systems. In other instances, the functions of the system can be implemented partially or completely in firmware, programmable logic devices such as field programmable gate arrays (FPGAs) as referenced in FIG. 7, system on chips (SOCs), application specific integrated circuits (ASICs), or other processing and logic elements. For example, the Set Processor and Optimizer can be implemented with hardware acceleration through the use of a hardware accelerator card, such as accelerator card 722 illustrated in FIG. 7.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Figure 1:
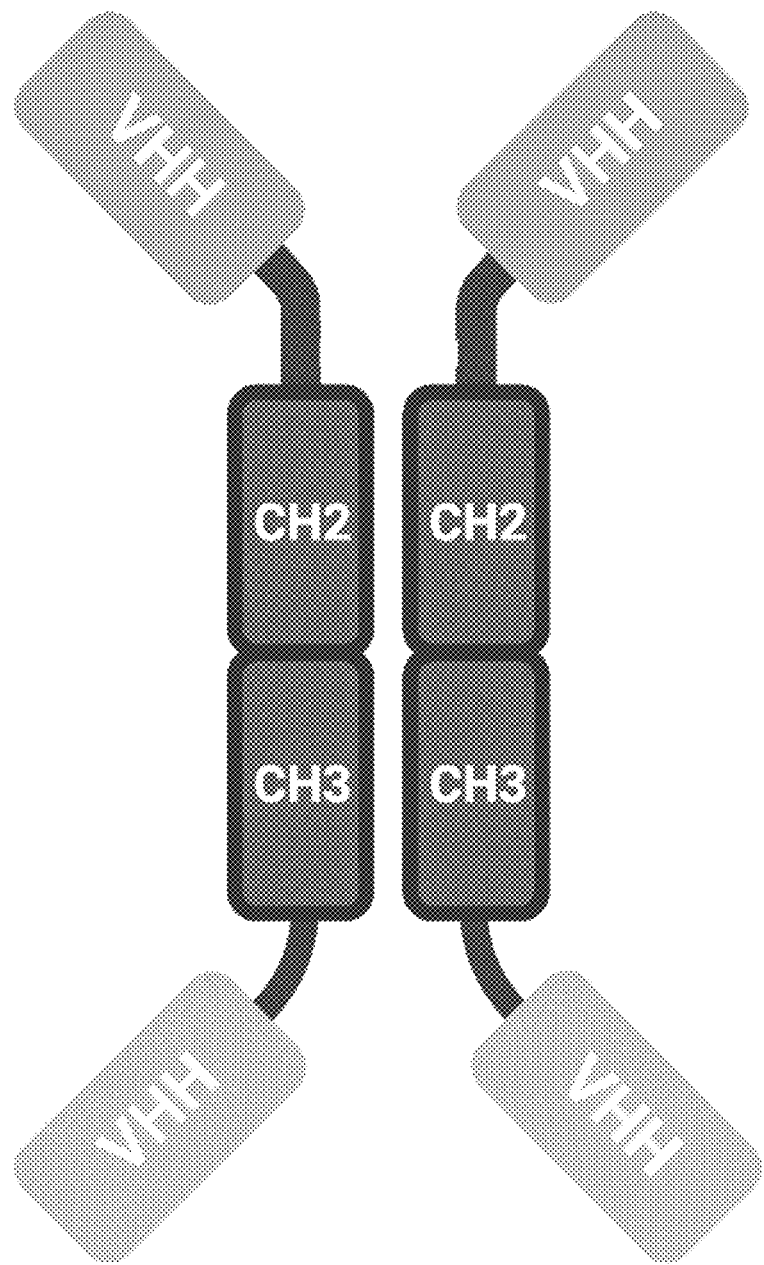
FIG. 1 depicts a schematic of Bispecific Antibody 1, a synthetic bispecific antibody.

Example 1: A Synthetic Bispecific Antibody Capable of Neutralizing SARS-CoV-2 Delta and Omicron A synthetic VHH bispecific antibody ("Bispecific Antibody 1") was generated that is capable of binding and neutralizing the SARS-CoV-2 Delta and Omicron variants. This bispecific antibody links together two humanized VHH antibodies—6-3 and 3-31 with constant heavy chain 2 (CH2) and 3 (CH3) Fc domains (FIG. 1 and FIG. 10). Antibody 6-3, which was discovered by panning a VHH library against the S1 monomer of the SARS-CoV-2 WA1 strain, has been shown to effectively neutralize pseudoviruses encoding the Alpha (B.1.1.7), Beta (B.1.351), and Gamma (P.1) S proteins, but not those encoding L452R-bearing S protein variants such as Delta (B.1.617.2) and Epsilon (B.1.429). Antibody 3-31 was discovered by panning a VHH library against the Beta S1 and was found to bind and neutralize L452R-bearing S protein variants. This Example describes the biophysical and functional characterization of the Bispecific Antibody 1, focusing on its binding and neutralizing of Delta and Omicron.

Materials and Methods

SPR Affinity Measurements

SPR experiments were performed on a Carterra LSA SPR biosensor equipped with a HC30M chip at 25° C. in HBS-TE. Antibodies were diluted to 10 μg/mL and amine-coupled to the sensor chip by EDC/NHS activation, followed by ethanolamine HCl quenching. Increasing concentrations of analyte were flowed over the sensor chip in HBS-TE with 0.5 mg/mL BSA with 5 minute association and 15 minute dissociation. SARS-CoV-2 protein reagents were sourced commercially S1 B.1.1.529 Omicron (Source: Acro S1N-052Ha) and S Trimer B.1.1.529 Omicron (Source: Acro SPN-052 Hz). Following each injection cycle, the surface was regenerated with 2×30-second injections of IgG elution buffer (Thermo). Data were analyzed in Carterra's Kinetics Tool software with 1:1 binding model.

Flow Binding Assay

Growth/induction: EBY100 yeast cells transformed with either pYD1-Wuhan RBD (WT) or pYD1-Omicron RBD were picked from a selective plate and inoculated in 1 mL SD-UT medium (yeast nitrogen base-casamino acids (YNB-CAA) (BD Biosciences 223120)+2% D-(+)-Glucose (Sigma G5767-500G) growth medium including phosphate buffer (5.4 g/l $Na_2HPO_4$, 8.6 g/l $NaH_2PO_4·H_2O$) and ix Penicillin-Streptomycin). The cultures were incubated for approximately 12 h at 30° C. and 250 RPM. 1 OD600 unit of cells was centrifuged for 30 s at 8,000 g. The pellets were resuspended in 1 mL SG-UT [(YNB-CAA) (BD Biosciences 223120)+2% D-(+)-Galactose (Sigma G0625-500G) induction medium including phosphate buffer (5.4 g/l $Na_2HPO_4$, 8.6 g/l NaH2PO4·H2O) and 1×Penicillin-Streptomycin)]. The induced cultures were incubated for approximately 36 h at 23° C. and 250 RPM.

Staining: $6 \times 10^5$ cells were added into the wells of a 96 well filter plate (MSHVS4510 Millipore MultiScreenHTS HV Filter Plate, 0.45 μm, clear, sterile). Each of the 4 monoclonal antibodies (mAbs) were diluted to 1.6, 4, 20 and 100 nM concentrations with DPBS+0.5% BSA+2 mM EDTA+0.1% Tween20. 20 μL of mAb solution was added to the cells in the filter wells and the cells were incubated for 1 h at 4° C. and 750 RPM on a thermomixer (Eppendorf, ThermoMixer C). After the incubation, the liquid in the plate was removed using a vacuum manifold. The pressure was kept at <5 bar. To wash the cells, 200 μL DPBS+0.5% BSA+2 mM EDTA+0.1% Tween20 was added to each well and subsequently removed using the vacuum manifold.

20 μL anti-IgG AlexaFluorophore 647 mAb (5 μg/mL) (Jackson Immunoresearch 109-605-098) was added to the cells and they were incubated for 45 min at 4° C. and 750 RPM on a thermomixer (Eppendorf, ThermoMixer C). The liquid in the plate was removed using a vacuum manifold, and the wash step was repeated.

For the expression staining, 20 μL anti-FLAG PE mAb (1 μg/mL) was added to the cells and they were incubated for 30 min at 4° C. and 750 RPM on a thermomixer (Eppendorf, ThermoMixer C). The liquid in the plate was removed using a vacuum manifold. No wash step was performed. 200 μL DPBS+0.5% BSA+2 mM EDTA+0.1% Tween20 was added to each well and the cells were resuspended by repeated pipetting. 20 μL of resuspended cells were mixed with 180 μL DPBS+0.5% BSA+2 mM EDTA+0.1% Tween20.

Scanning: The cells were scanned using a BD Fortessa analyzer equipped with an HTS system. The following lasers and bandpass (BP) filters were used: 561 nm with a BP filter of 586/15 and 640 nm with a BP filter of 670/14. For each sample, $1*10^4$ events were measured. The data was analyzed using FlowJo V10.4.2.

SARS-CoV-2 Viral Culture

TMPRSS2-VeroE6 kidney epithelial cells were cultured in Dulbecco's Modified Eagle Medium (DMEM) supplemented with 1% sodium pyruvate (NEAA) and 10% fetal bovine serum (FBS) at 37° C. and 5% CO2. The cell line has been tested negative for contamination with mycoplasma. SARS-CoV-2 ancestral strain, lineage A(USA-WA1/2020), was obtained from BEI Resources (#NR-52281). Delta and Omicron variants were isolated from nasopharyngeal specimens. SARS-CoV-2 samples were sequenced as part of the Yale Genomic Surveillance Initiative's weekly surveillance program in Connecticut, United States and lineages were sequenced as described previously (Kalinich et al, 2020). After sequencing of nasopharyngeal specimens, samples selected for virus isolation were isolated as previously described (Lucas et al, 2021).

Briefly, samples were filtered through a 45 μM filter and serially diluted from 1:50 to 1:19,531,250. The dilution was subsequently incubated with TMPRSS2-Vero E6 in a 96 well plate and adsorbed for 1 hour at 37° C. After adsorption, replacement medium was added, and cells were incubated at 37° C. for up to 5 days. Supernatants from cell cultures with cytopathic effect (CPE) were collected, frozen, thawed and subjected to RT-qPCR. Fresh cultures were inoculated with the lysates as described above for viral expansion. Viral infection was subsequently confirmed through reduction of Ct values in the cell cultures with the multiplex variant qPCR assay. Expanded viruses were re-sequenced following the same method as described above and genome sequences were uploaded to GenBank and the aligned consensus genomes are available on GitHub (https://github.com/grubaughlab/paper_2021_Nab-variants). The pelleted virus was then resuspended in PBS and aliquoted for storage at −80° C. Viral titers were measured by standard plaque assay using TMPRSS2-VeroE6. Briefly, 300 μl of serial fold virus dilutions were used to infect Vero E6 cells in MEM supplemented NaHCO$_3$, 4% FBS, 0.6% Avicel RC-581. Plaques were resolved at 48 h post-infection by fixing in 10% formaldehyde for 1 h followed by crystal violet (0.5% in 20% ethanol) staining. Plates were rinsed in water for plaque enumeration. All experiments were performed in a biosafety level 3 laboratory with approval from the Yale Environmental Health and Safety office.

Authentic Virus Neutralization Assay

Serial dilutions of Bispecific Antibody 1 (500 μg/ml to 2.89 ng/ml) were individually incubated with the ancestral SARS-CoV-2 strain (USA-WA1/2020), the Delta variant, or Omicron variant, for 1 h at 37° C. (Viral concentrations were optimized to generate 60-120 plaques per well.) The resulting mixtures were then applied to TMPRSS2-VeroE6 cells, plated in a 12-well plate, for 1 hr, after which MEM supplemented with NaHCO$_3$, 4% FBS, and 0.6% Avicel, was added to each well. At 40 h post-infection, cells were fixed with 10% formaldehyde for 1 h and then stained with 0.5% crystal violet to resolve plaques. All experiments were performed in parallel with baseline controls. Analyses of plaque counts were done using GraphPad Prism software, version 8.4.

Results

Figure 2A:
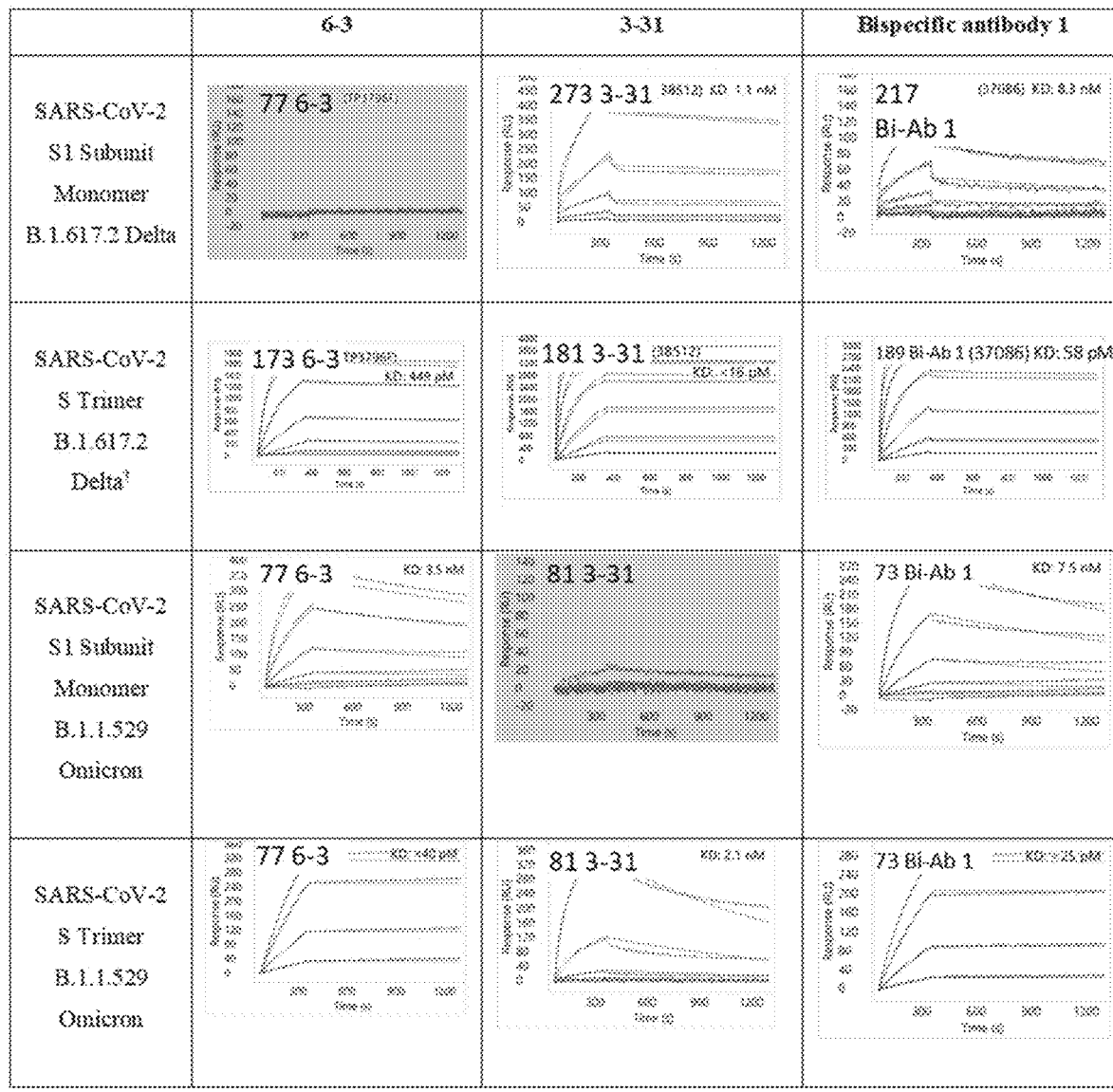
FIGS. 2A-2B depict biophysical characterization of Bispecific Antibody 1 and its parental constructs 6-3 and 3-31.

Bispecific Antibody 1 Binds SARS-CoV-2 Delta and Omicron with Picomolar Affinity Bispecific Antibody 1 was constructed from VHH antibodies discovered in biopanning campaigns against the ancestral (6-3) and Beta (3-31) S proteins. To create a broadly neutralizing antibody, we combined leads 6-3 and 3-31 into a single bispecific construct. Screening by surface plasmon resonance (SPR) revealed picomolar apparent binding affinities between Bispecific Antibody 1 and the prefusion-stabilized S trimers of the Alpha, Beta, Delta, Gamma (P.1), Kappa (B.1.617.1), and Omicron (B.1.529) variants (FIG. 2A; traces for Alpha, Beta, Gamma, and Kappa variants not shown). SPR traces obtained with 6-3 and 3-31 showed which of the two contributed to Bispecific Antibody 1's binding to each S trimer. Although 6-3 bound to the Alpha, Beta, Gamma, Kappa with the same affinity as the ancestral S trimer, it displayed reduced (yet still picomolar) affinities with the Kappa and Delta variants (FIG. 2A; data for Kappa variant not shown). By contrast, 3-31 bound every S trimer variant with low picomolar affinities except the Omicron variant (FIG. 2A). 6-3 displayed low picomolar affinity to the S trimer of Omicron, as did Bispecific Antibody 1. SPR experiments performed using variant S1 monomers showed the same patterns, although apparent binding affinities were in the nanomolar range (FIG. 2A). These data agree with previous biophysical and functional characterizations of 6-3 (Yuan T Z, Garg P, Wang L, Willis J R, Kwan E, Hernandez A G L, Tuscano E, Sever E N, Keane E, Soto C, et al. Rapid discovery of diverse neutralizing SARS-CoV-2 antibodies from large-scale synthetic phage libraries. MAbs 2022; 14:2002236 and Hastie K M, Li H, Bedinger D, Schendel S L, Dennison S M, Li K, Rayaprolu V, Yu X, Mann C, Zandonatti M, et al. Defining variant-resistant epitopes targeted by SARS-CoV-2 antibodies: A global consortium study. Science 2021; 374:472-8.) that showed reduced activity of 6-3 against S proteins bearing the L452R mutation (namely, Delta and Epsilon).

Figure 2B:
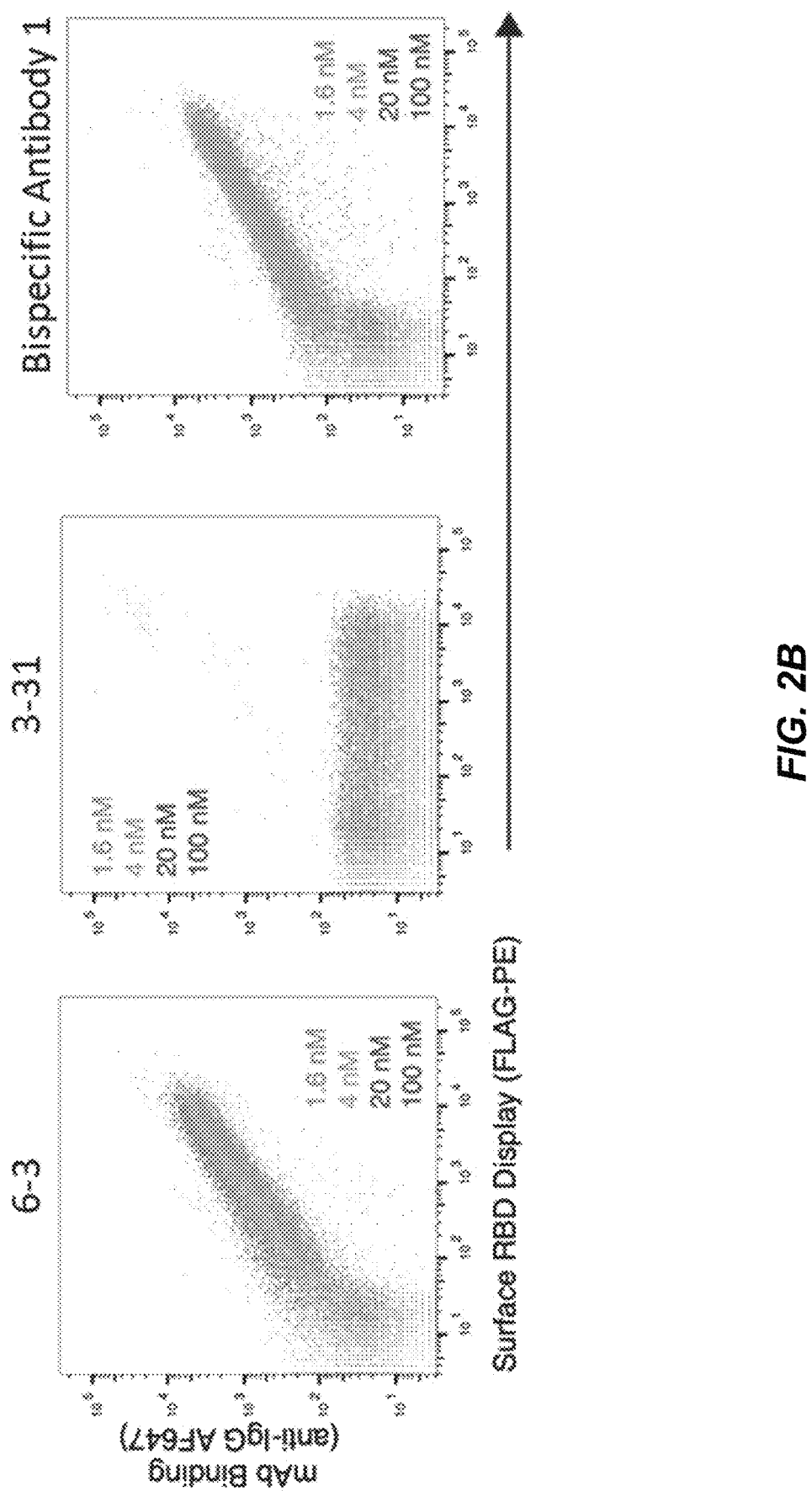

Consistent with the SPR data described above, 6-3 and Bispecific Antibody 1, but not 3-31, bound the Omicron S1 RBD displayed on the surface of yeast, as measured by flow cytometry (FIG. 2B); thus providing independent confirmation that 6-3 mediates the Omicron binding of Bispecific Antibody 1.

Bispecific Antibody 1 Potently Neutralizes SARS-CoV-2 Delta and Omicron

Figure 3:
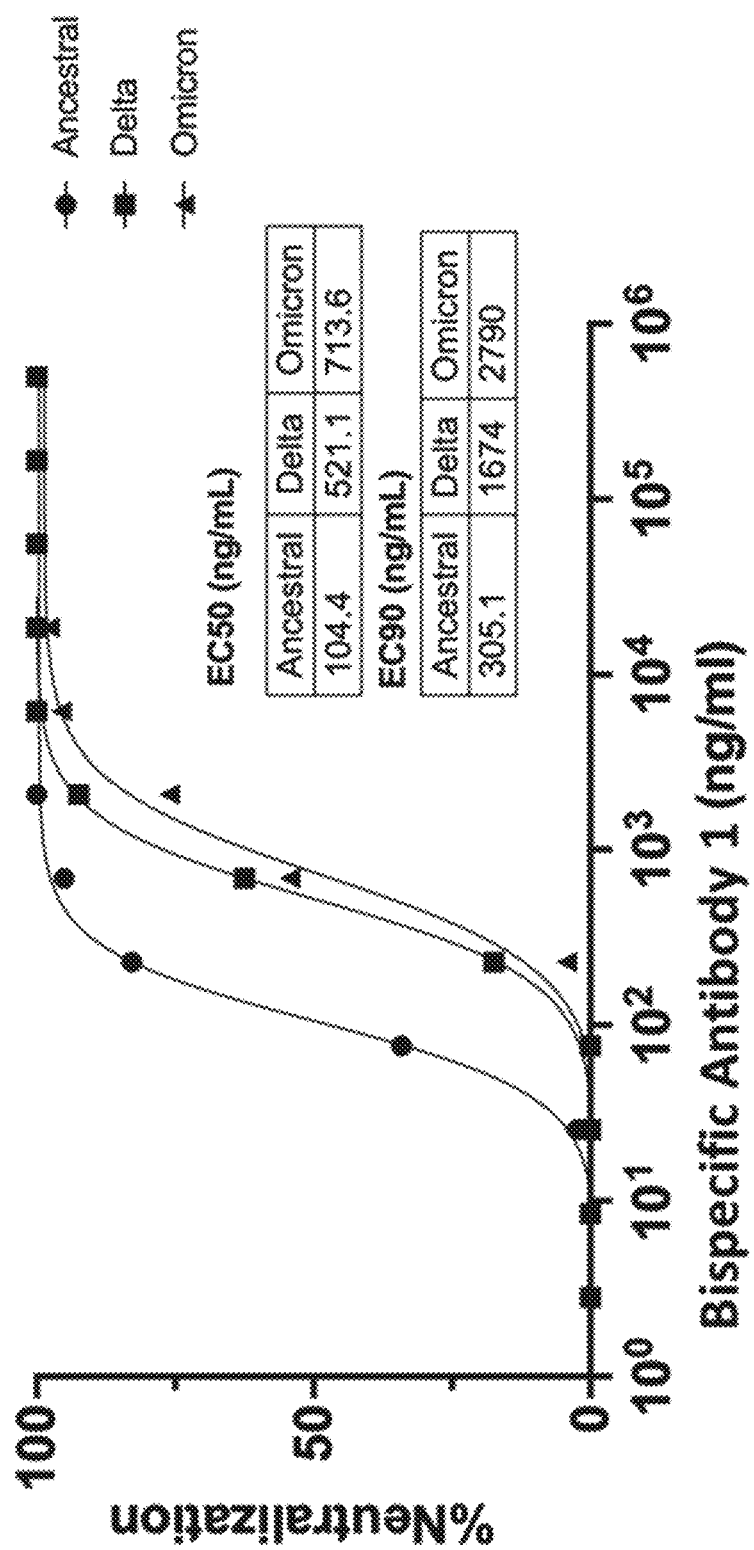
FIG. 3 is a graph illustrating neutralization of authentic SARS-CoV-2 Delta and Omicron by Bispecific Antibody 1. EC50 and EC90 represent the concentrations required to reduce the number of plaques by 50% and 90%, respectively.

To assess the neutralization potential of Bispecific Antibody 1, we utilized authentic viruses isolated from nasopharyngeal specimens of patients in plaque reduction neutralization tests to determine whether Bispecific Antibody 1 can neutralize SARS-CoV-2 Delta and Omicron. As shown in FIG. 3, Bispecific Antibody 1 neutralizes authentic Delta and Omicron at half maximal effective concentrations (EC50) of 521.1 and 713.6 ng/ml, respectively. These values are comparable to those obtained with sotrovimab (VIR-7831), another mAb that neutralizes Delta and Omicron at 325 and 917 ng/ml, respectively.

First detected in November 2021, the Omicron variant has quickly spread worldwide, causing infections in at least 89 countries. Omicron's rapid transmission and sheer number of S mutations, especially in the RBD, quickly sparked concerns about the variant and its ability to escape current therapeutics. Moreover, despite Omicron's meteoric rise, Delta remains a threat to public health, especially because early animal studies indicate that Delta causes more severe disease than Omicron. This Example shows that Bispecific Antibody 1 binds not only Delta, but Omicron as well.

Example 2: Bispecific Antibody 1 Assay Results

Bispecific Antibody 1 was tested against SARS-CoV-2 using multiple assays.

Figure 11A:
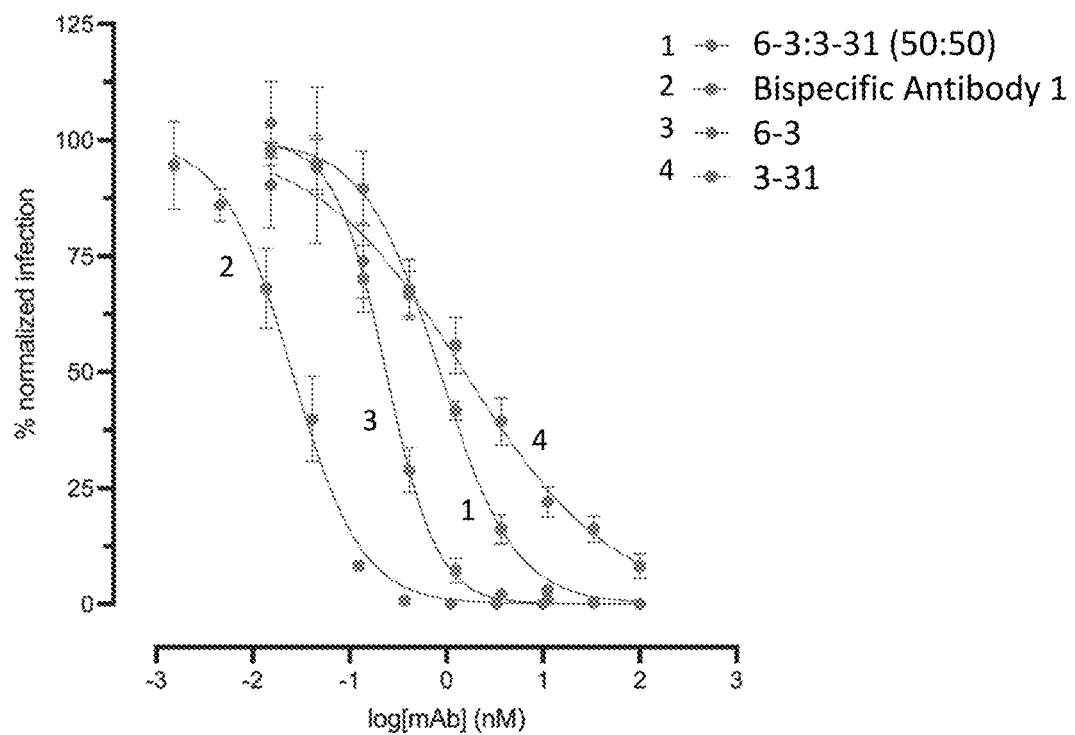
FIGS. 11A-11C show escape assay results for Bispecific Antibody 1.
Figure 11B:
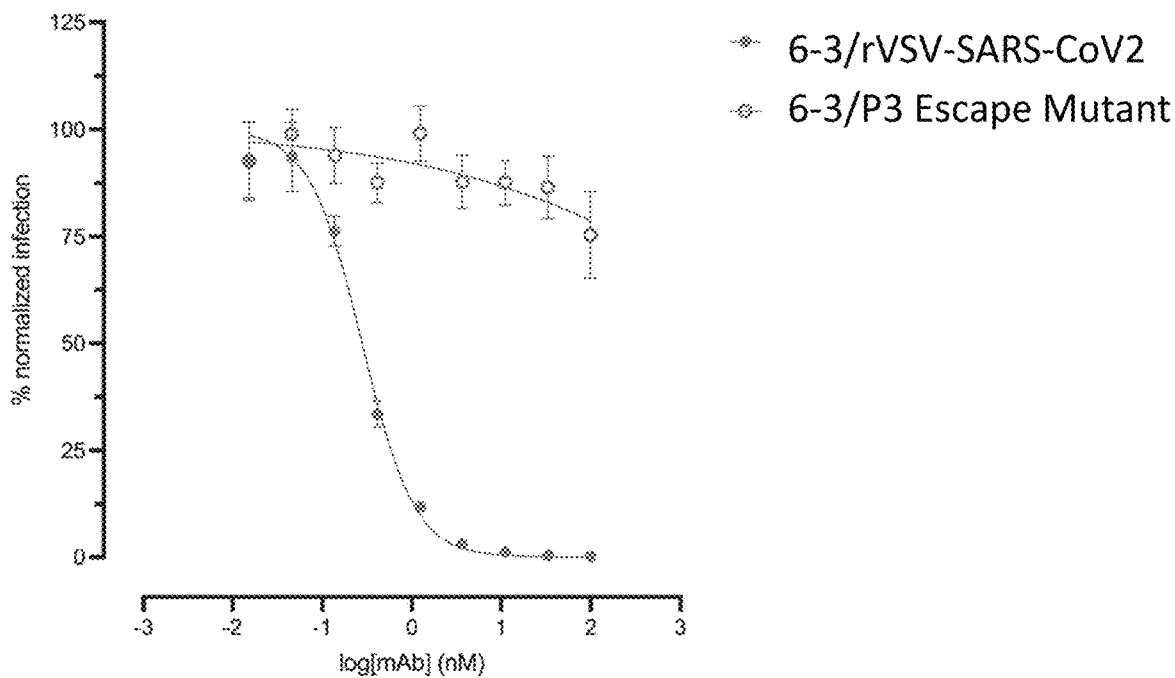
Figure 11C:
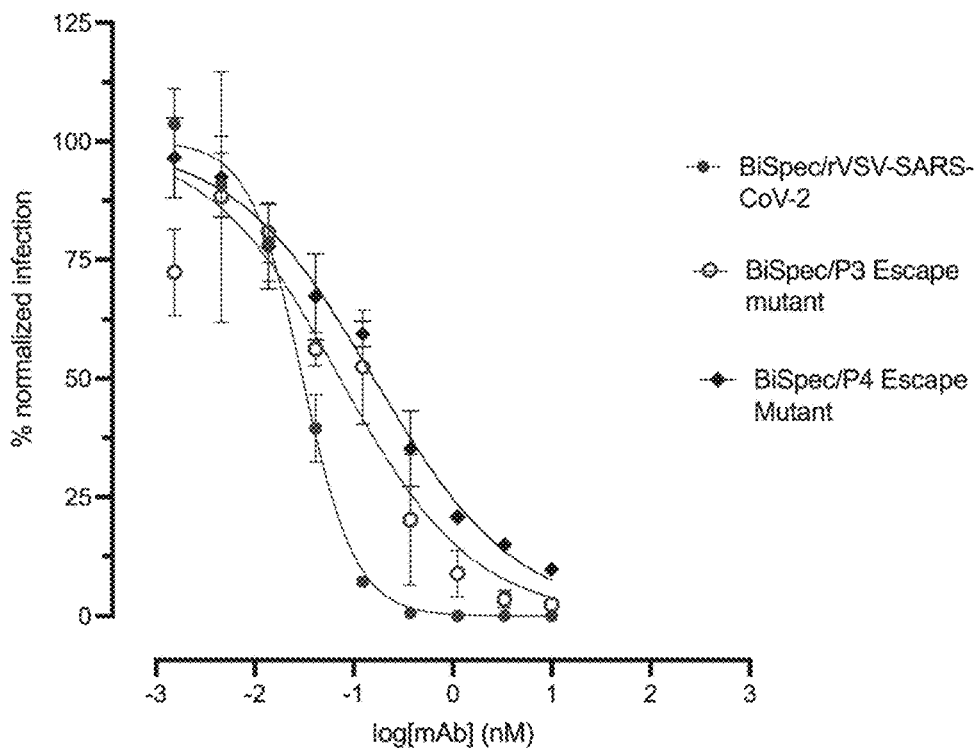
Figure 12A:
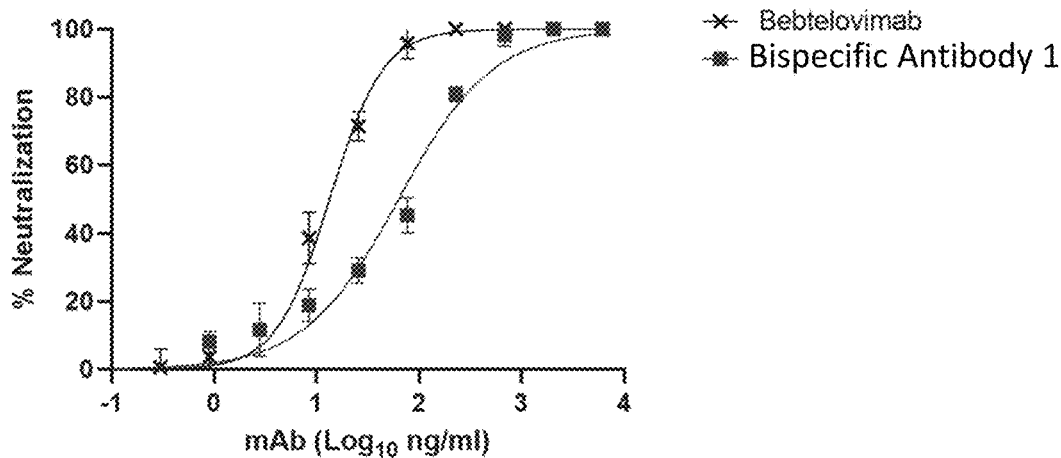
Figure 12B:
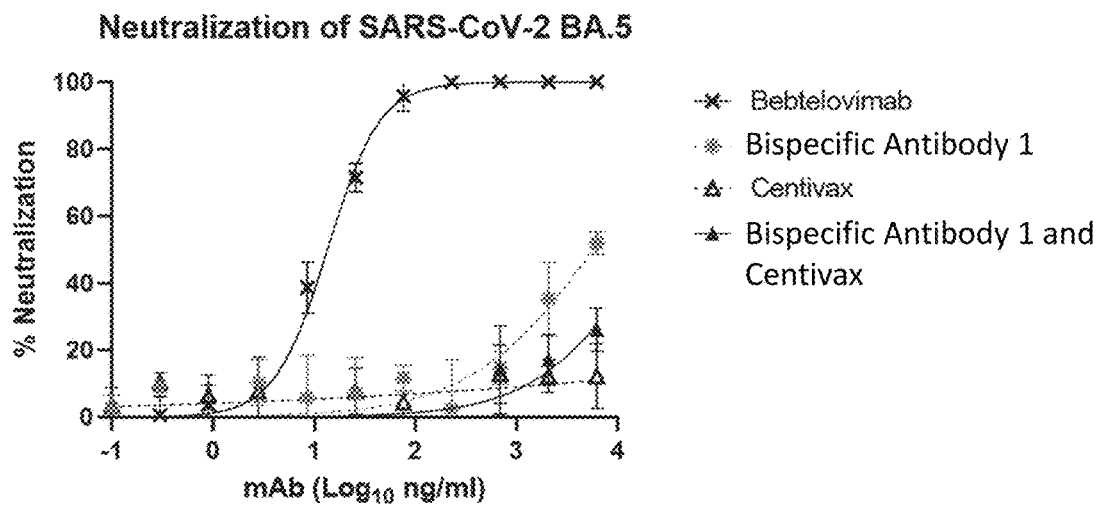
Figure 12C:
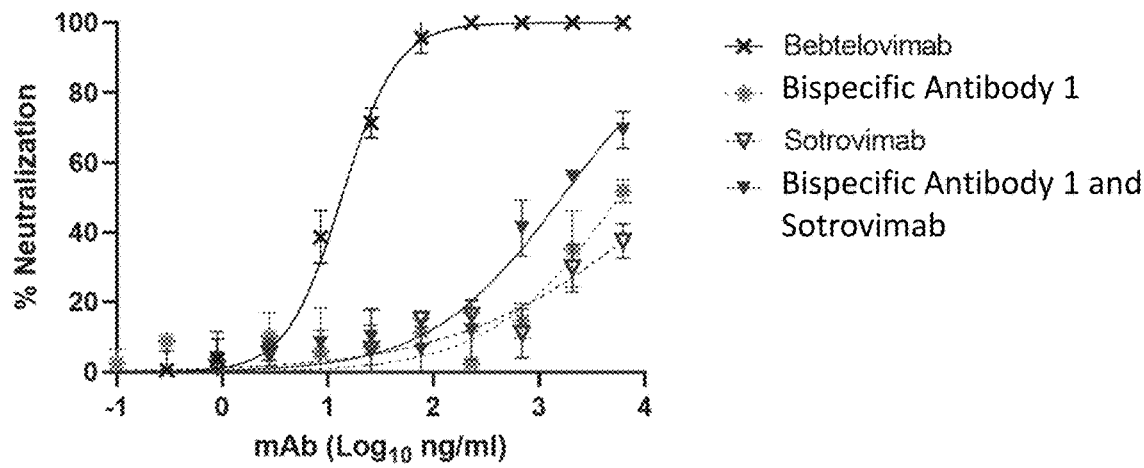
Figure 12D:
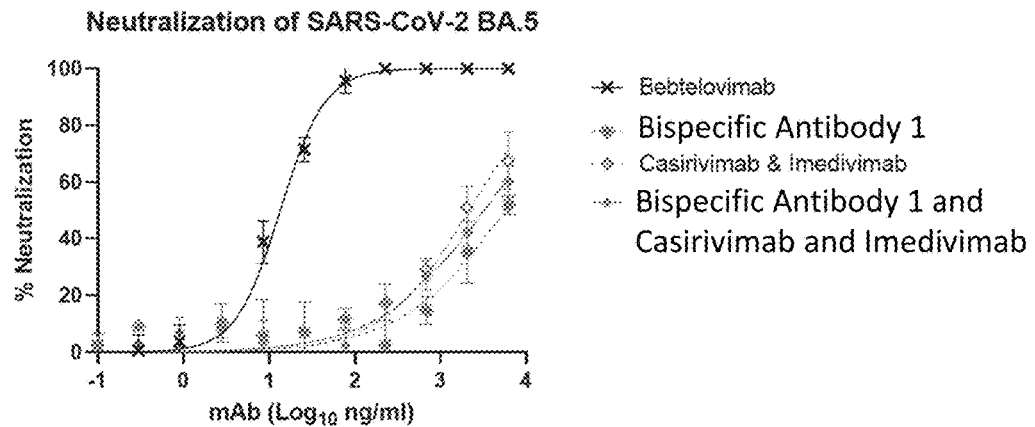
Figure 12E:
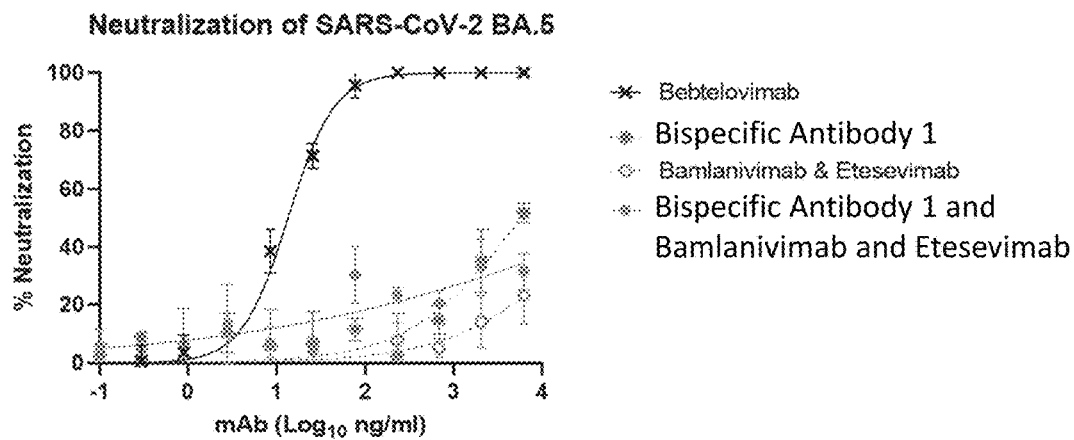
Figure 12F:
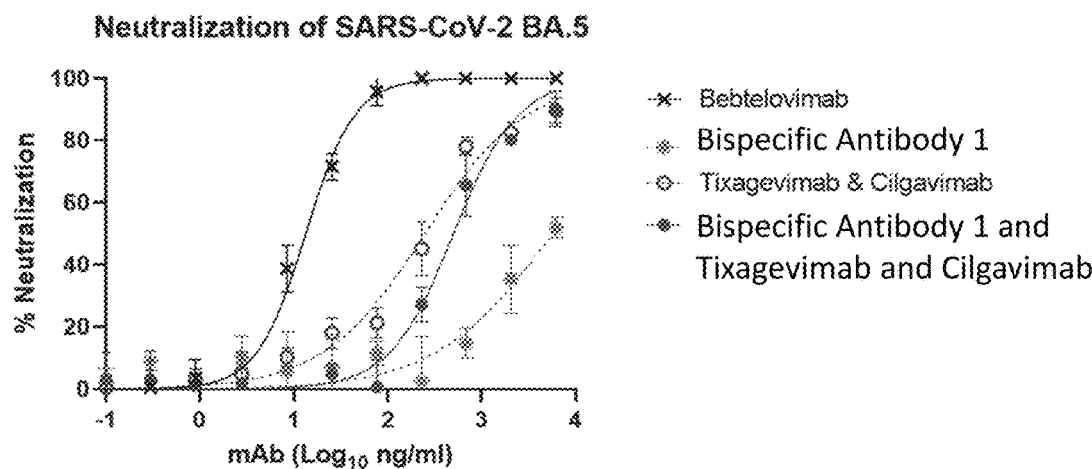

Escape assays were performed to see if SARS-CoV2 is able to evade plaque-purified escape mutants for Bispecific Antibody 1 and parental variant 6-3. The starting virus used was VSV-SARS-CoV-2 c10, containing mutations W64R, A372T (RBD), and H655Y. R685G (S1/S2 junction, furin cleavage site, nonRBD) was observed in plaques during the initial rescue of the virus, but was not supposed to be incorporated in the starting virus (the starting virus was sequence verified to check whether this mutation was pre-existing or acquired upon escape). FIG. 11A shows neutralization curves wherein Bispecific Antibody 1 is more potent than either parent alone or as a cocktail. FIG. 11B and FIG. 11C show escape assay results for parental variant 6-3 and Bispecific Antibody 1, respectively.

Figure 13:
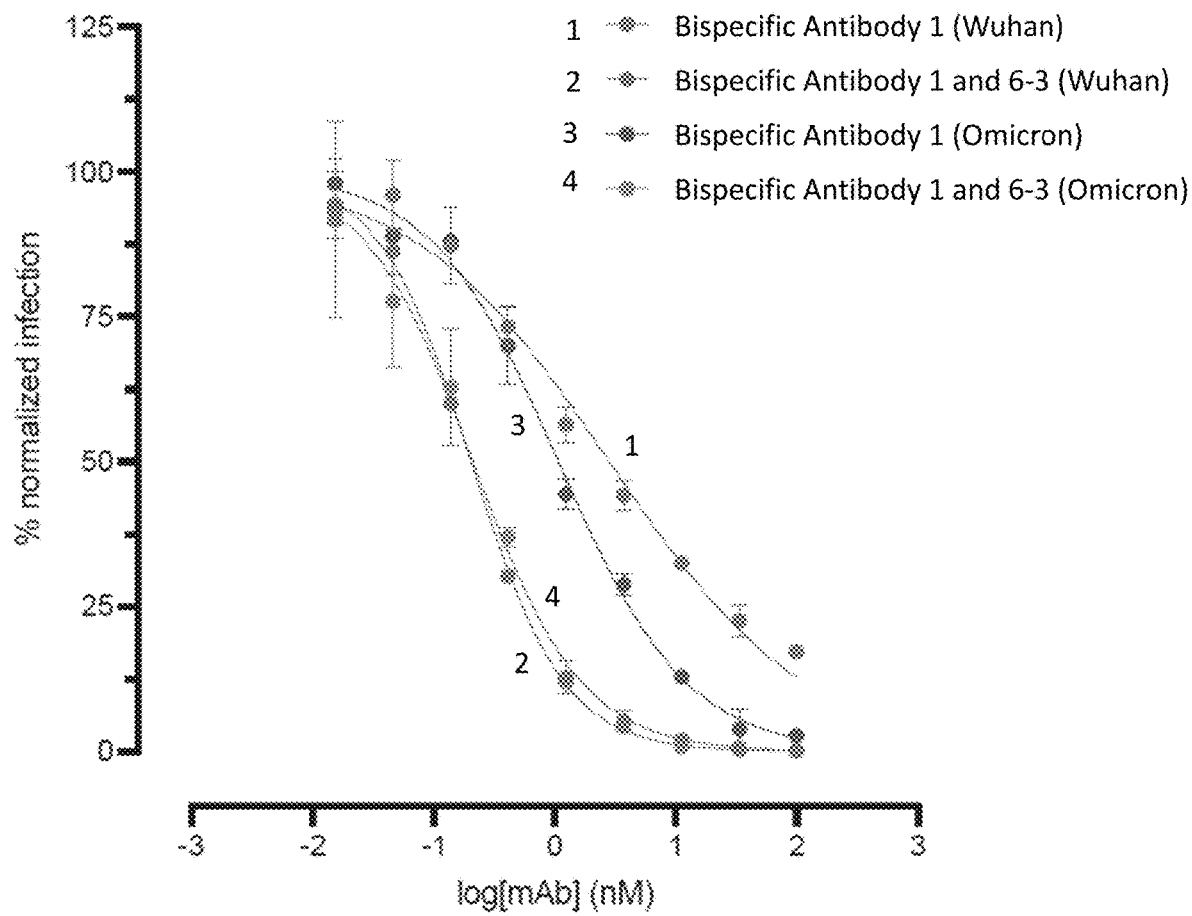

Neutralization assays were performed using Bispecific Antibody 1 with various combinations of therapeutics including Bebtelovimab, Centivax, Sotrovimab, Casirivimab, Imedivimab, Bamlanivimab, Etesevimab, Tixagevimab, and Cilgavimab (FIGS. 12A-12F). Additional neutralization assays were performed using Bispecific Antibody 1 against rVSV-SARS-CoV-2, Wuhan and Omicron variants (FIG. 13).

Figure 14A:
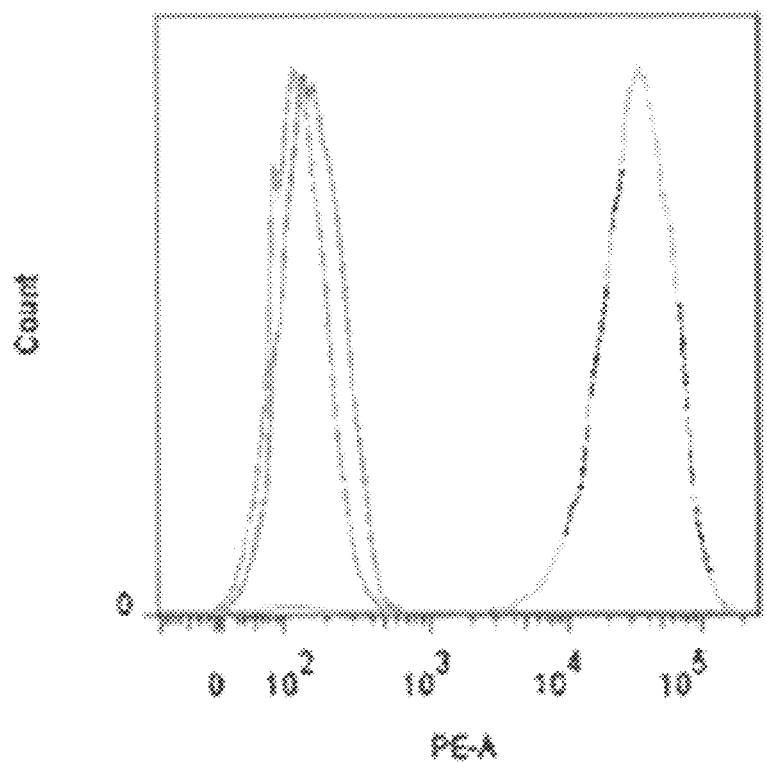
Figure 14B:
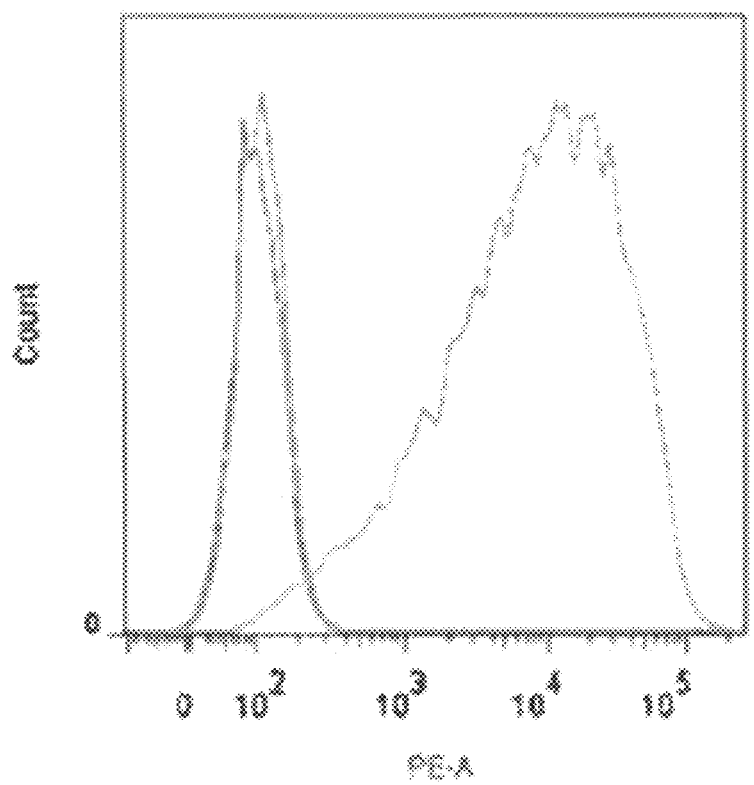

Antibody-dependent cell mediated cytotoxicity (ADCC) assays were performed in order to further characterize Bispecific Antibody 1. FACS binding assays were performed to show that the system control, Rittman, could bind to Raji cells with high affinity (S/N=256.20) (FIG. 14A). The test sample (bispecific antibody 1) could bind to CHO-K1/Spike cells with high affinity (S/N=77.37) (FIG. 14B).

Figure 14C:
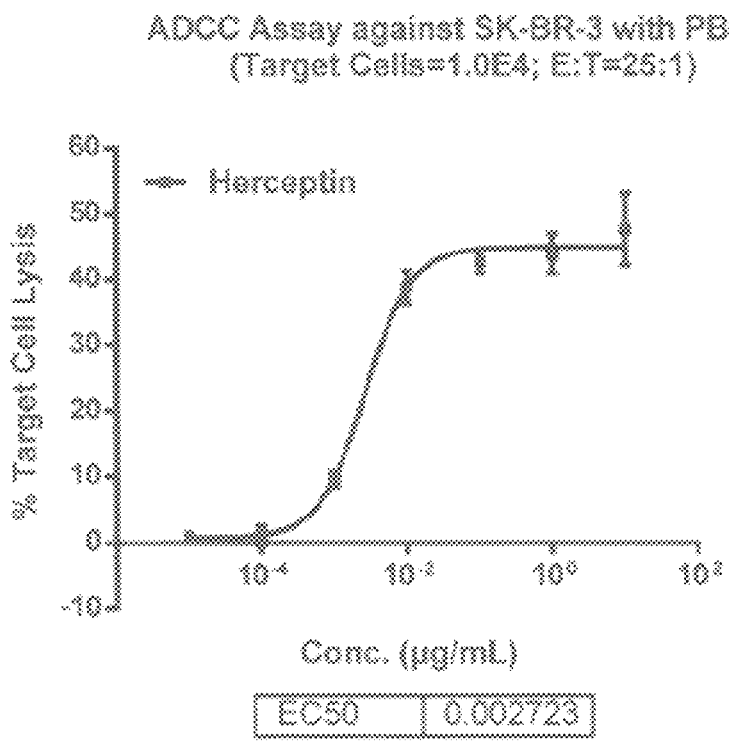
Figure 14D:
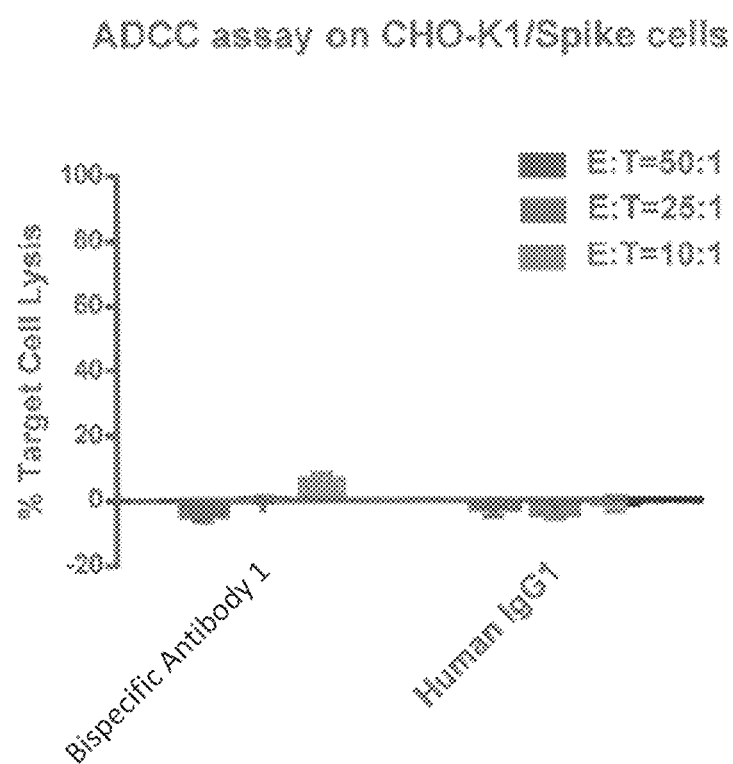
Figure 14E:
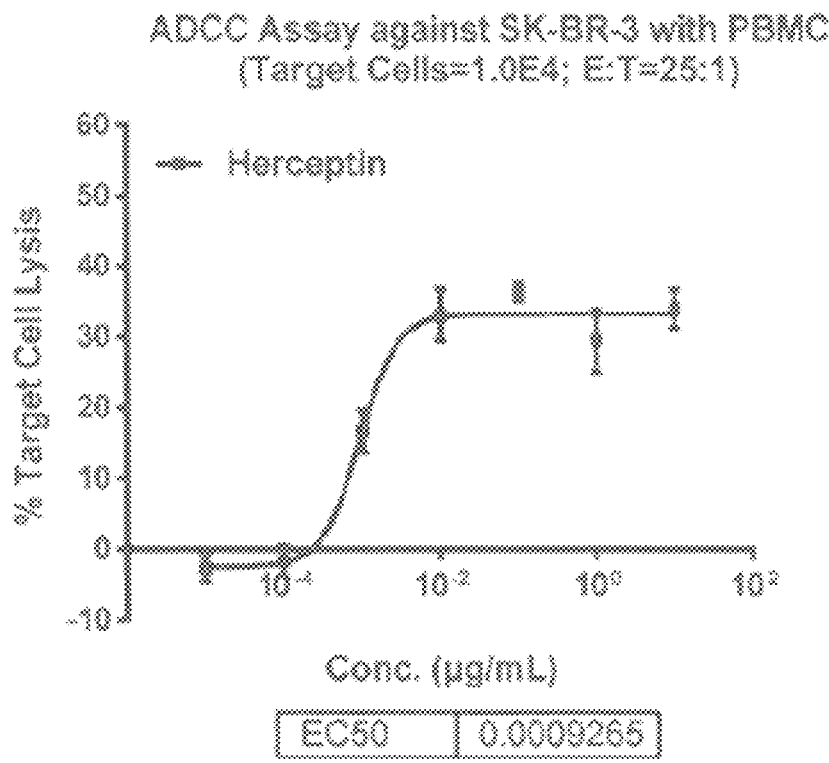
Figure 14F:
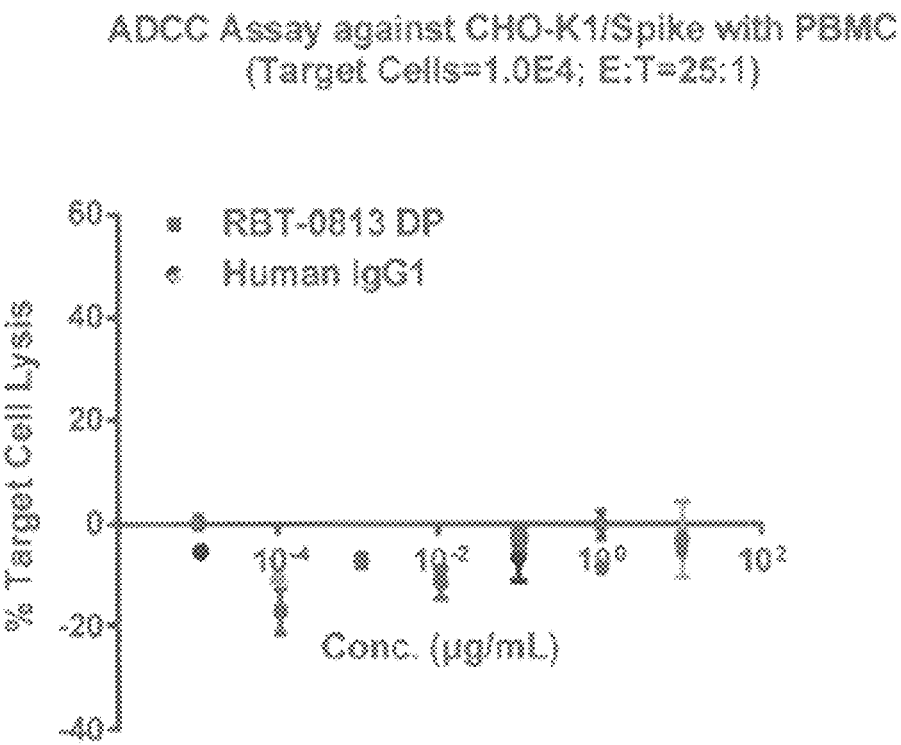

SK-BR-3 cells were treated with serial dilutions of Herceptin under the condition of E/T ratio of 25:1. Results of the ACDD E/T optimization study showed that when E/T ration was 25:1, the $EC_{50}$ value of the system control, Herceptin, was 0.002723 µg/mL (FIG. 14C). When the E/T ratio was 50:1, 25:1, and 10:1, bispecific antibody 1 and human IgG1 were not observed to induce ADCC against CHO-K1/Spike cells (FIG. 14D). With E:T at 25:1, SK-BR-3 cells were treated with serial dilutions of Herceptin and the $EC_{50}$ value of Herceptin was 0.0009265 µg/mL (FIG. 14E). When CHO-K1/Spike cells were treated with serial dilutions of bispecific antibody 1 and Human IgG1, the negative control, neither bispecific antibody 1 nor human IgG1 were observed to induce ADCC against CHO-K1/Spike cells (FIG. 14F).

Figure 15A:
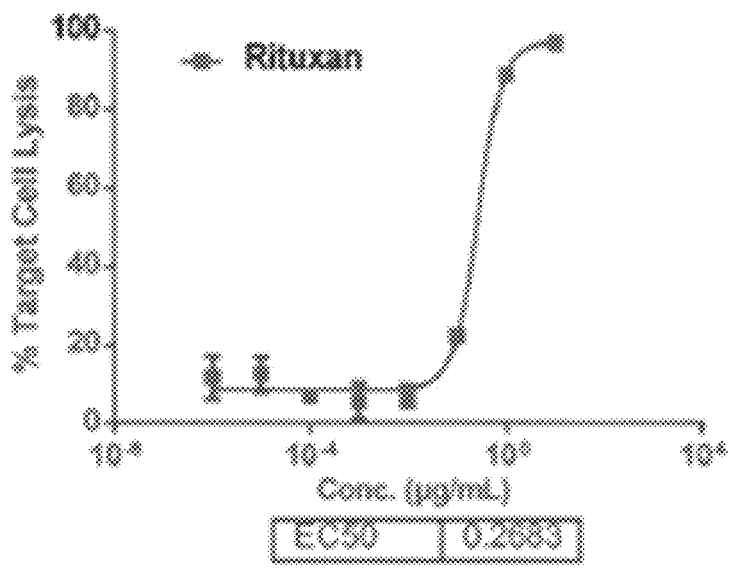
Figure 15B:
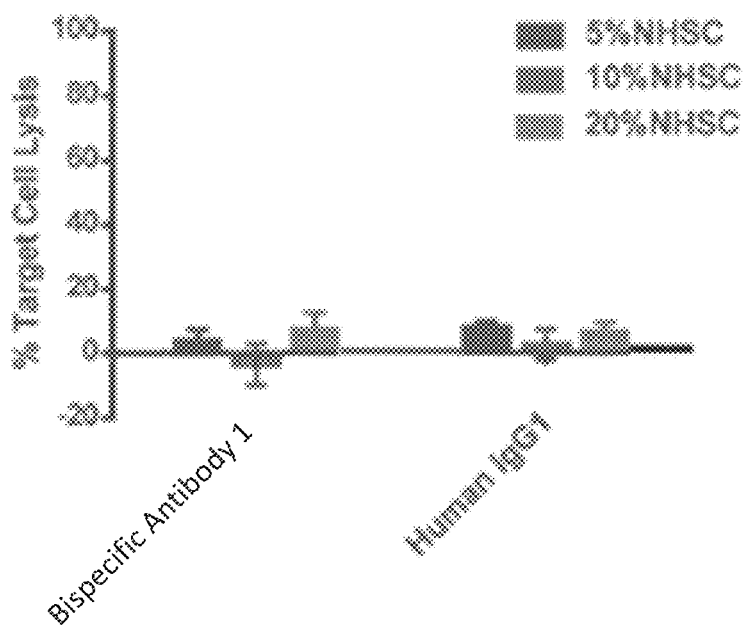

Complement-dependent cytotoxicity (CDC) assays where performed to further characterize bispecific antibody 1 in vitro. Results of the CDC % NHSC optimization study showed that the $EC_{50}$ value of the control, Rituxan with 5% NHSC, was 0.2683 µg/mL (FIG. 15A). With 5% NHSC, 10% NHSC, or 20% NHSC, bispecific antibody 1 and human IgG1 were not observed to induce CDC against CHO-K1/Spike cells (FIG. 15B).

Figure 15C:
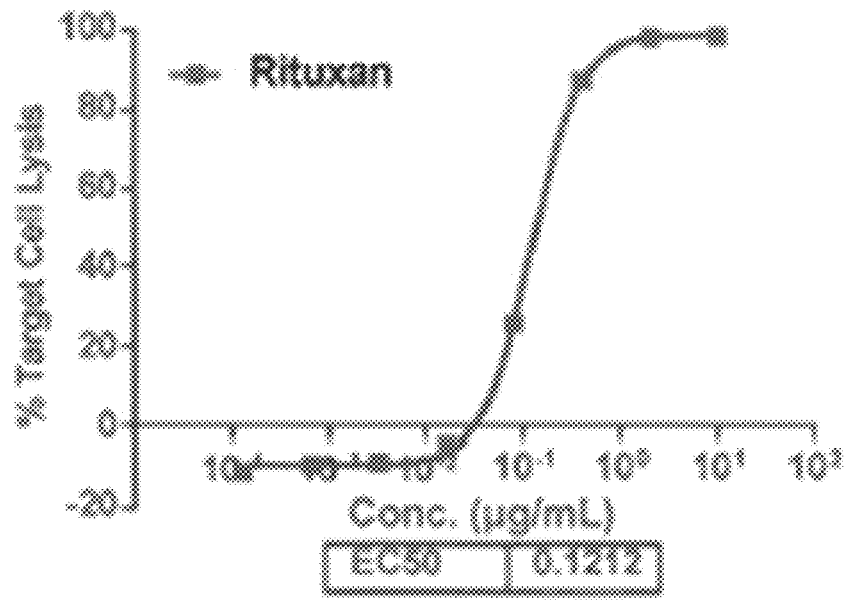
Figure 15D:
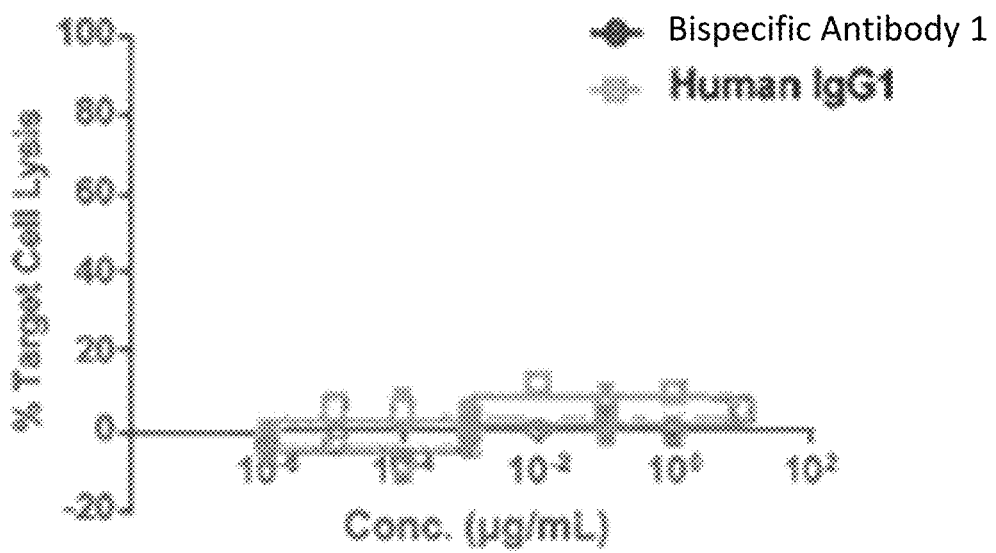

Results of the CDC dose response study showed that the $EC_{50}$ value of the control, Rituxan, with 5% NHSC, was 0.1212 µg/mL (FIG. 15C). With 5% NHSC, bispecific antibody 1 and human IgG1 were not observed to induce CDC against CHO-K1/Spike cells (FIG. 15D).

Figure 16A:
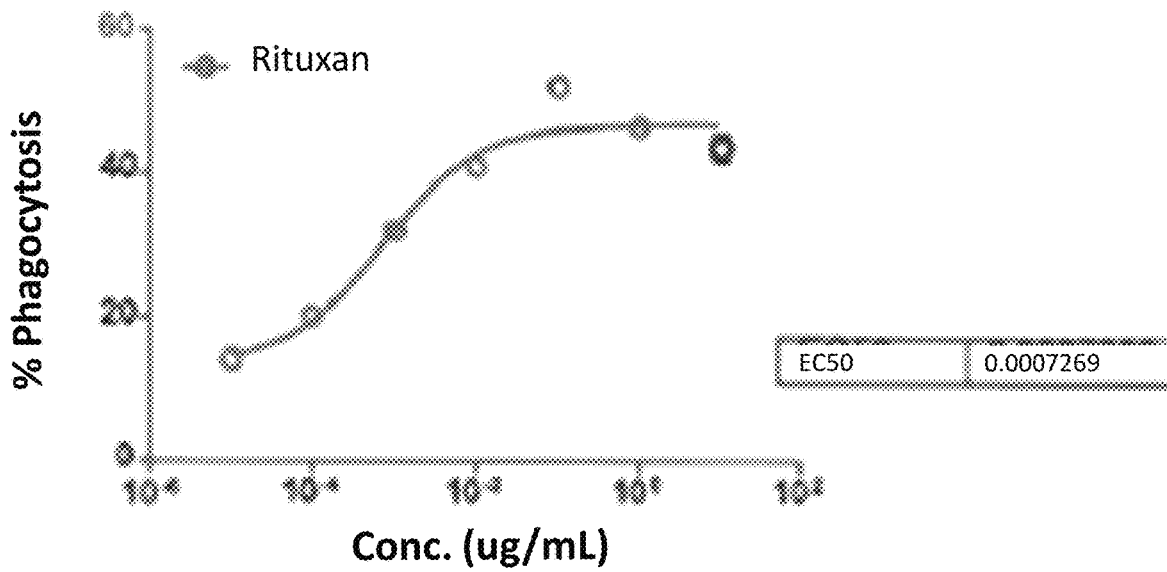
Figure 16B:
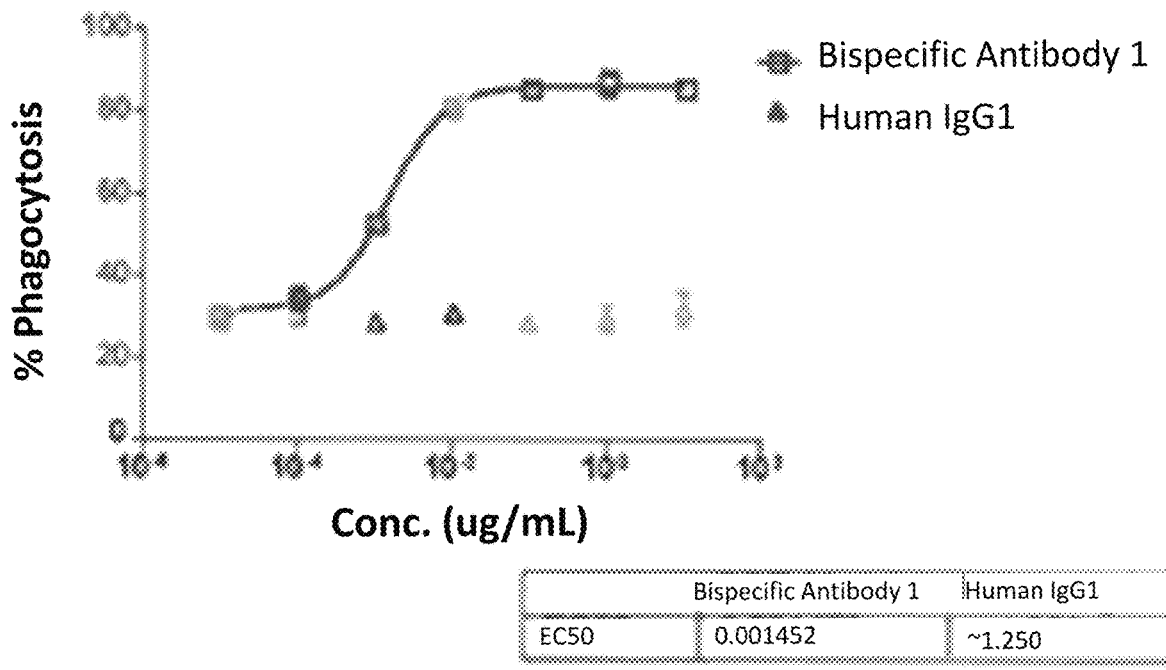

Antibody-dependent cellular phagocytosis (ADCP) assays where performed to further characterize bispecific antibody 1 in vitro. Results of the ADCP dose response study showed that the $EC_{50}$ value of the control, Rituxan, was 0.0007269 µg/mL (FIG. 16A). Results of the ADCP dose response study found that the $EC_{50}$ value of bispecific antibody 1 was 0.001452 µg/mL. Human IgG1 was not observed to induce ADCP against CHO-K1/Spike cells (FIG. 16B).

Antibody-dependent enhancement (ADE) experiments were performed to further characterize bispecific antibody 1. To measure the ADE resulting from anti-spike antibodies, a human monocyte-derived macrophages (hMDMs)-based in vitro assay demonstrated FcγRIIA-mediated enhancement of injection in phagocytes. In this assay, a pseudotyped lentiviral vector with SARS-CoV-2 S protein was constructed to mimic SARS-CooV-2 virus, which can infect target cells expressing hACE2 or phagocytes via interaction with FcγR receptors. The extent of ADE is then determined by detecting the expression levels of a luciferase reporter gene packaged into the lentiviral vector.

Figure 17A:
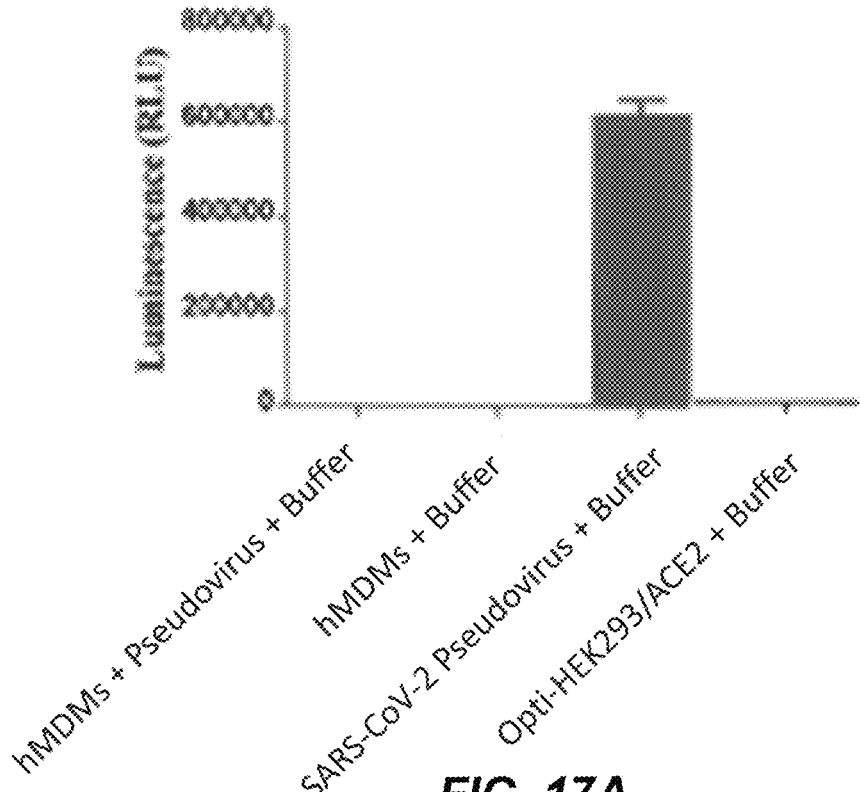
Figure 17B:
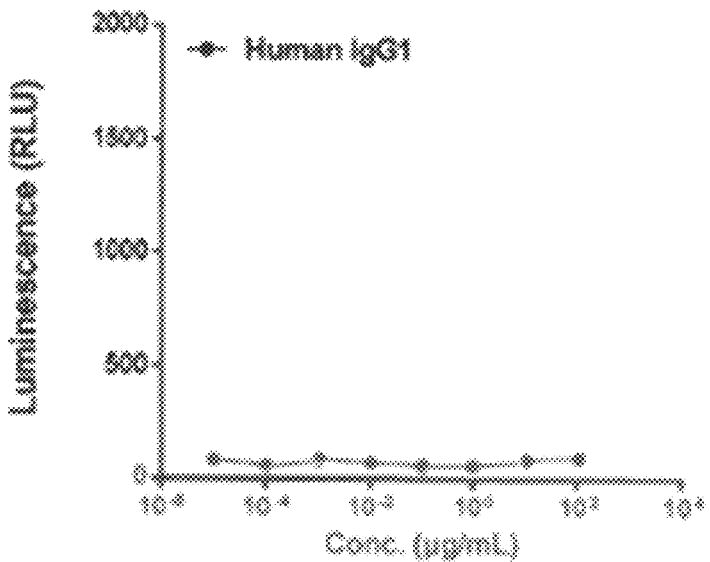
Figure 18:
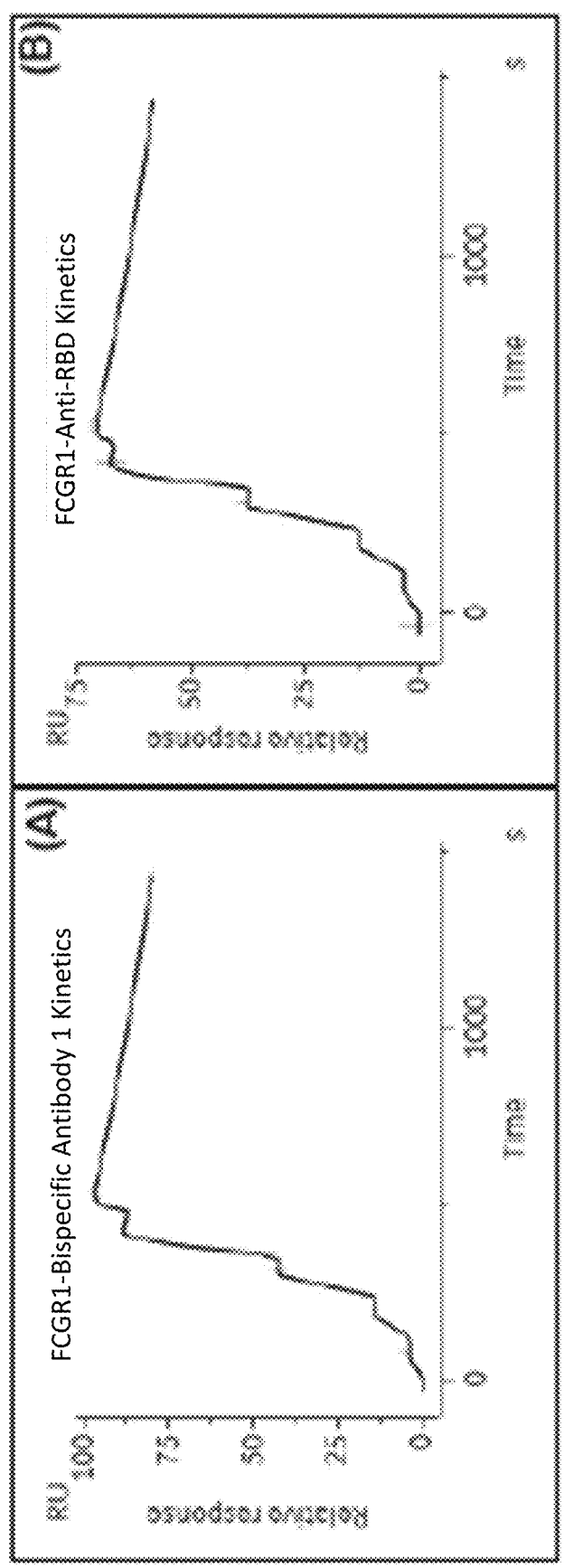
Figure 19:
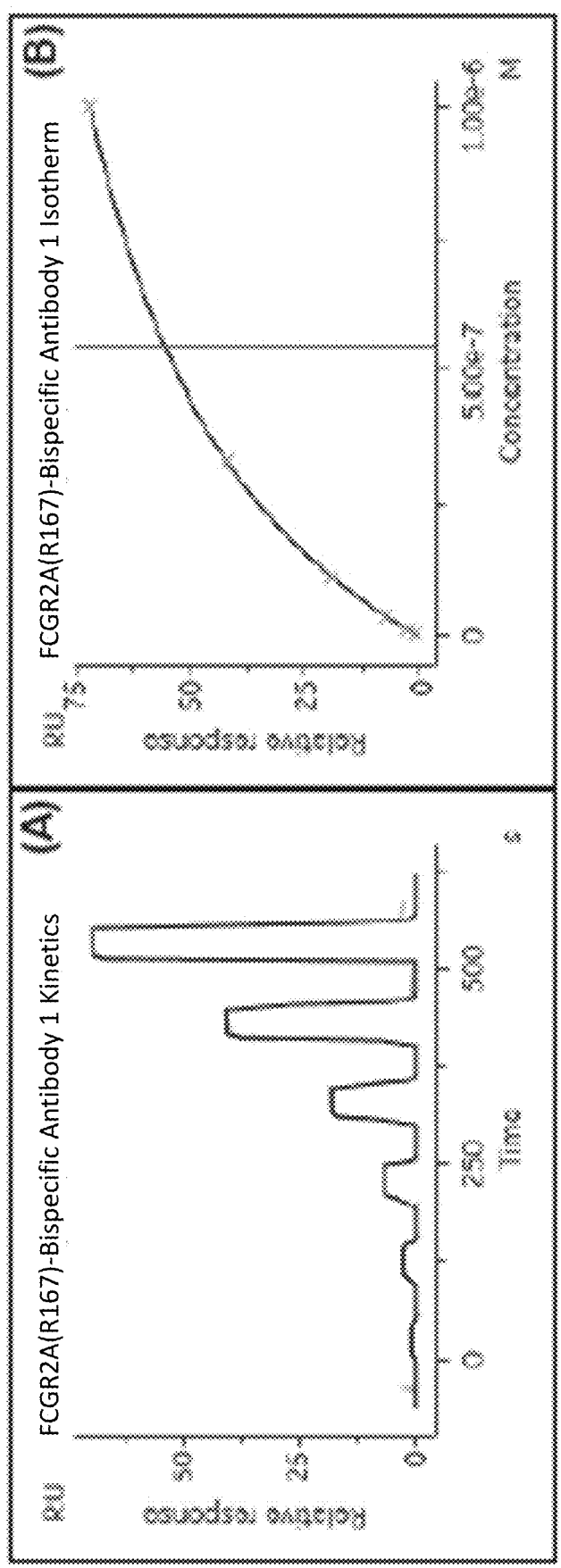
Figure 20:
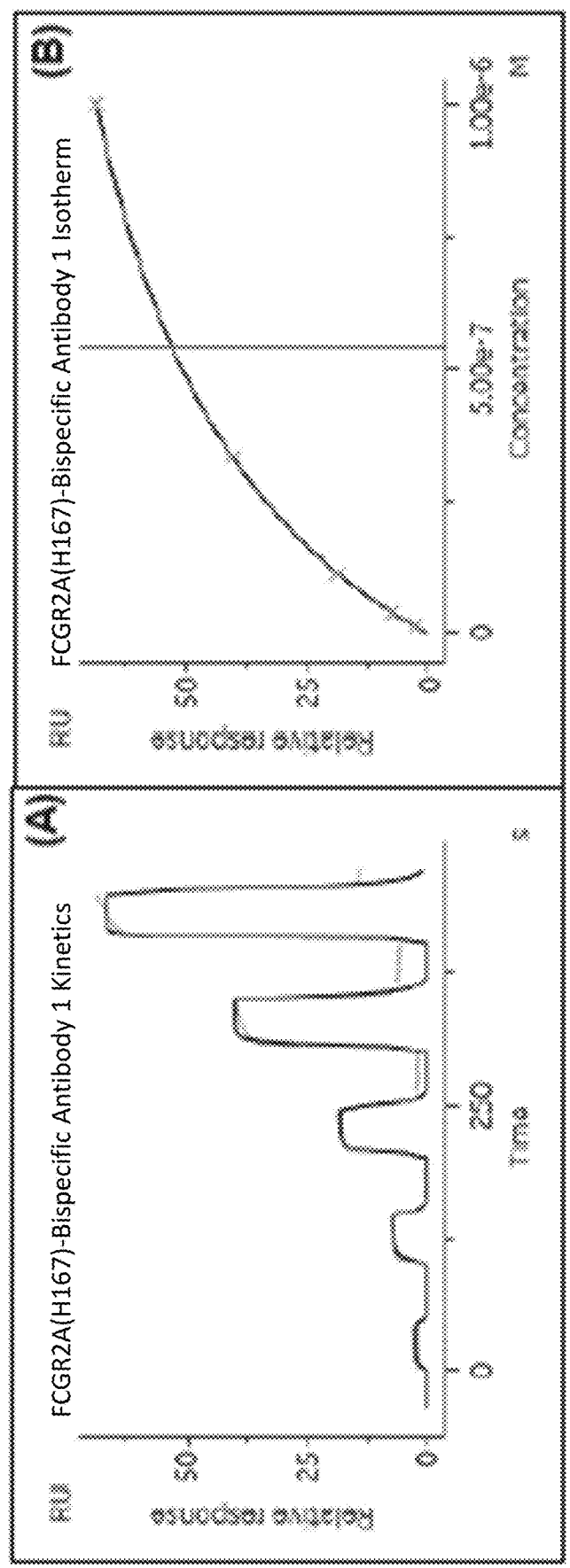
Figure 21:
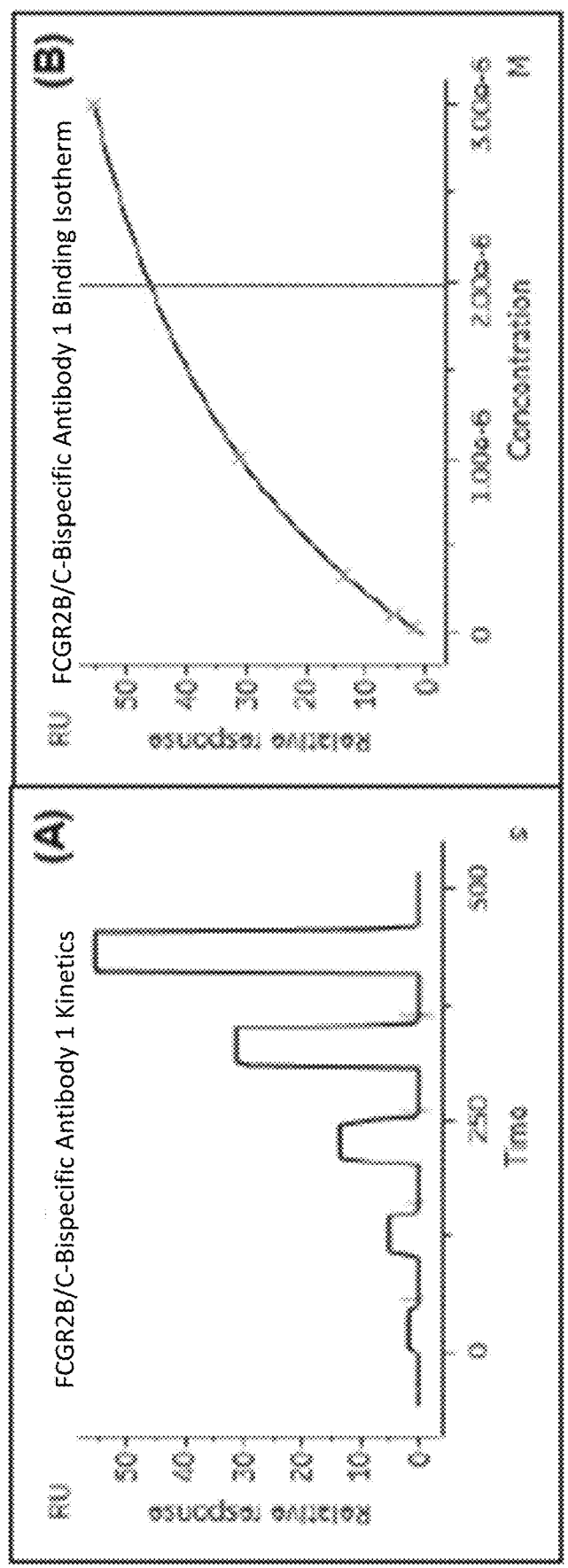
Figure 22:
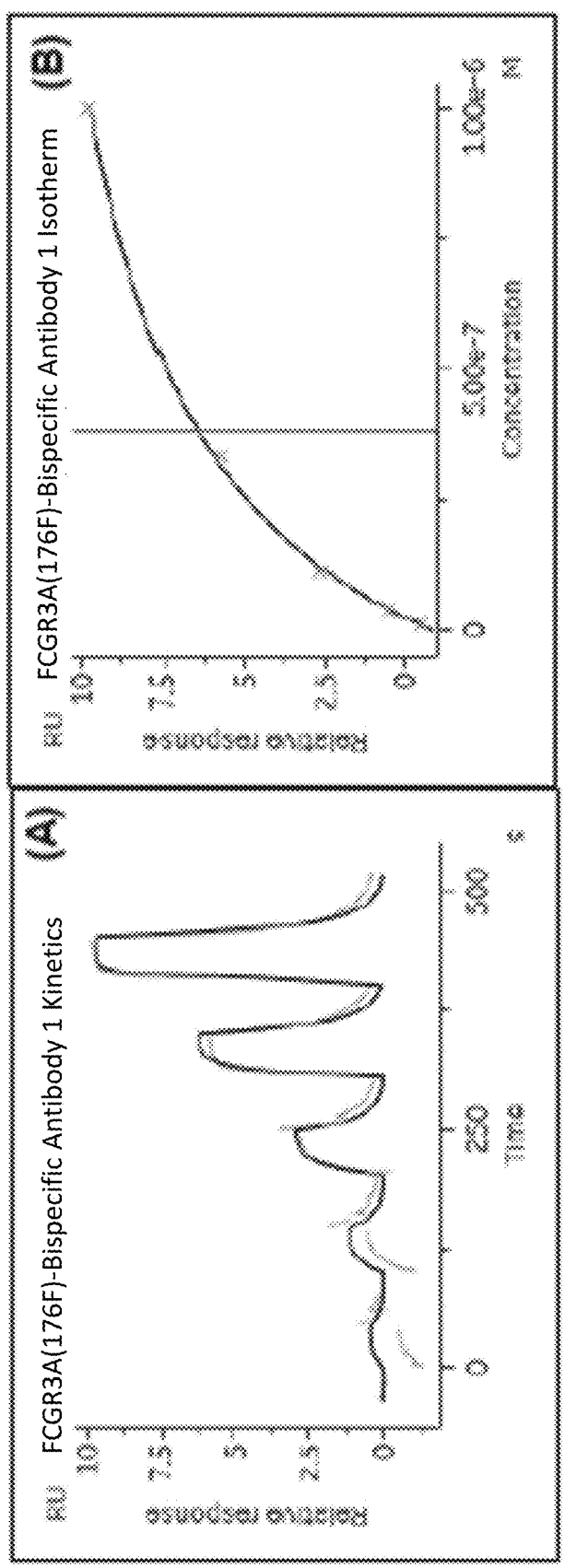
Figure 23:
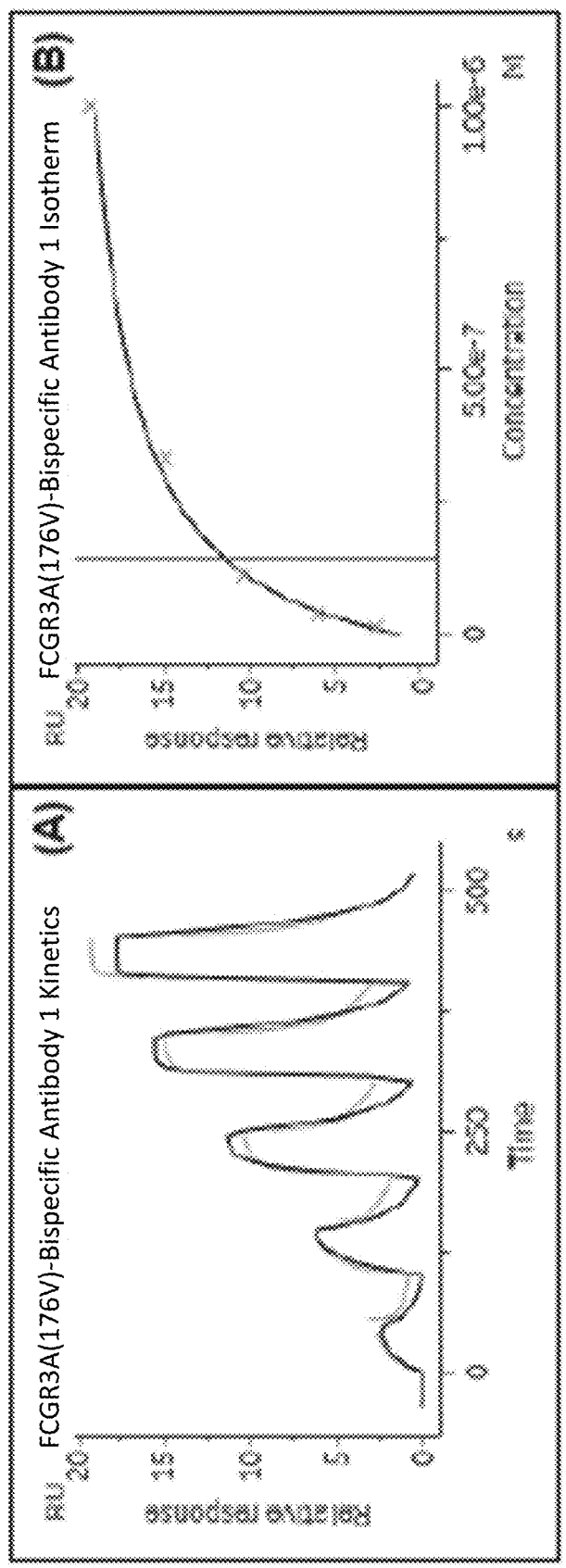
Figure 24:
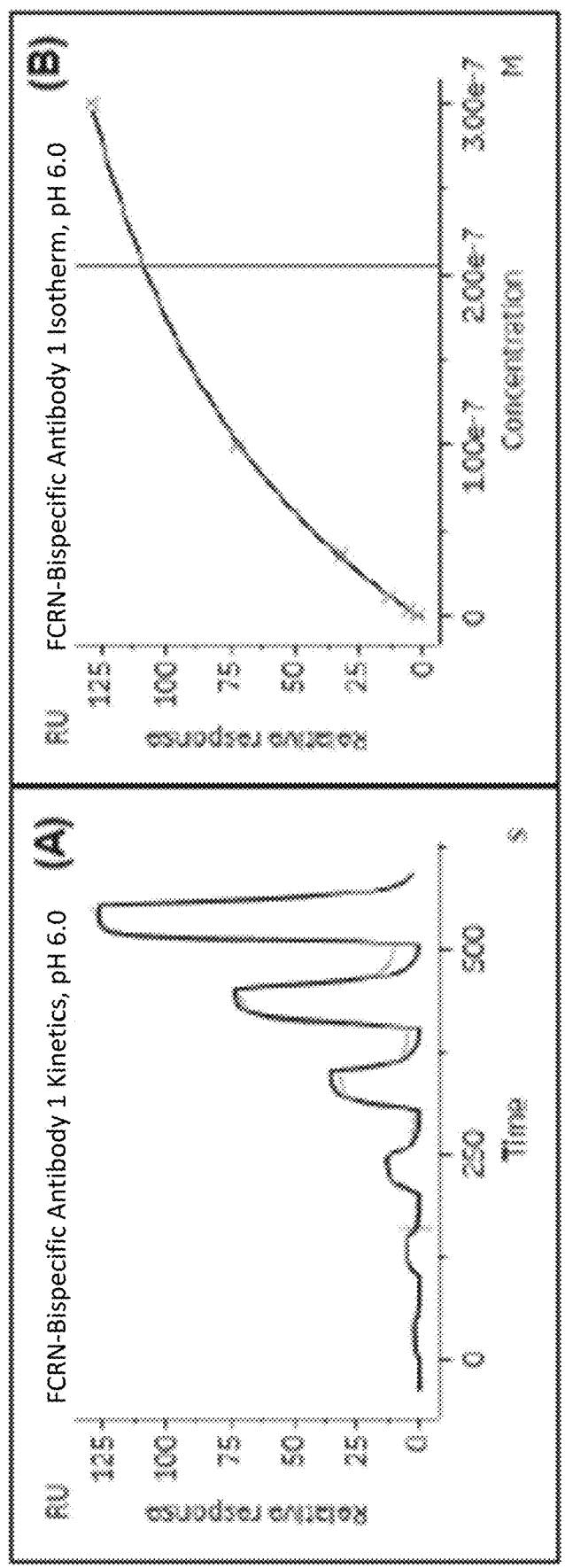

The experimental result of ADE showed that the signal value of the system control (Opti-HEK293/ACE2+SARS-CoV-2 pseudovirus+buffer) was about 6E5, which was significantly higher than that of the blank group (Opti-HEK293/ACE2+buffer), indicating that the virus could infect and enter cells normally (FIG. 17A). In the experimental group, the signal value of pseudovirus infected hMDMs group and the hMDMs blank group was about 100. The maximum signal values of bispecific antibody 1 and human IgG1 did not exceed 100, indicative of no ADE effect (FIG. 17B).

In vitro studies were performed to assess the potential for effector function of bispecific antibody 1 using a panel of Fc receptor binding assays. Bispecific antibody 1 showed binding to the neonatal Fc receptor (FcRn), Fcγ receptors, and C1q, similar to those of an isotype-matched positive control IgG1 antibody. These studies also assessed the ability of bispecific antibody 1 to inhibit the ACE2/SARS-CoV-2 spike binding protein interaction. Bispecific antibody 1 showed inhibition of ancestral spike RBD and SARS-CoV-2 spike trimers of Ancestral, Delta, and Omicron variants.

For the Fc Receptor binding assay, interaction analysis was conducted on a Biacore 8K biosensor equipped with CMS sensor chip at 25° C. in the standard run buffer of HBS-P, pH 7.4 with 0.2 g/L BSA (for FcγR panel) or PBS-P, pH 6.0 with 0.2 g/L of BSA (Dulbecco phosphate buffer saline with 0.01% Tween-20 adjusted to pH6.0 using dilute phosphoric acid) for analysis of FcRn interaction, respectively. Neutravidin (ThermoFisher Scientific, MA, US, Cat #31000) was coated onto all flow cells of the chip at high levels (8000 RUs) using a standard amine-coupling procedure and then coated with high levels of biotinylated SARS-CoV2 Spike RBD (~6000 RUs). The RBD-coated chip was utilized as a 'capture surface' to capture (tether) appropriate amounts of RBT-0813 (~80-500 RUs) on flow cell 2 (the active surface) with flow cell 1 left empty, representing the naked RBD-coated surface, to serve as a reference surface. Binding of Fc receptors (as analytes) to bispecific antibody 1 (as ligand) was evaluated by injecting Fc receptors in increasing concentrations over flow cells 1 and 2 at 30 µL/min using the 'single cycle kinetics' module. Analyte titrations used were 5-(or 6-) membered, 3-fold serial dilutions with top concentration of 30 nM (FcγR1), 300 nM (FcRn), 1000 nM (FcγR2a and 3a) or 3000 nM (FcγR2b/c). Within the same experiment, the binding of Fc receptors (as analytes) to flow cells tethered with a commercially sourced isotype-matched anti-RBD neutralizing antibody (as ligand), served as a positive control. Blank cycles using buffer (instead of Fc receptors) as analyte were used for double-referencing the binding data. After each binding cycle, the ligands (bispecific antibody 1 or the control antibody) were stripped from the RBD-coated surface by regenerating it with 10 mM glycine, pH2.0 for 30 s (for the FcγR interactions) or with PBS-P pH7.4 for 1 min (for the FcRn interactions).

For the SPR data analysis, Biacore data were processed and analyzed in the BiaEvaluation™ software. Biacore data for bispecfic antibody 1 or the isotype-matched (human IgG1) control anti-RBD neutralizing antibody binding to the Fc receptors were fit globally to a simple 1:1 Langmuir binding model to calculate the kinetics parameters, including the association and dissociation kinetic rate constants (ka and kd) and the affinity constant (also known as the equilibrium dissociation constant, or KD) from their ratio, where KD=kd/ka. The binding data were also fitted, where appropriate, to a steady state affinity model to generate binding isotherms to obtain KD using this alternate equilibrium-based model. All interactions except those of the 'high affinity' FcγR1 met the criteria for steady state fitting, which requires that all sensorgrams attain equilibrium binding responses during the allowed association phase per analyte injection.

Figure 25:
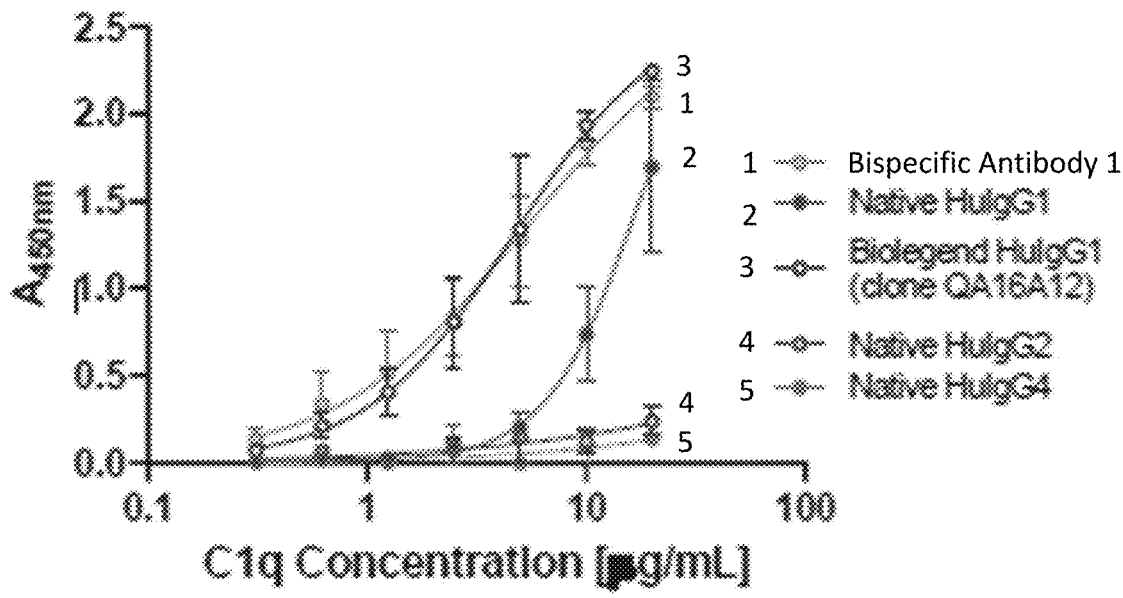

For the complement C1q binding assay (FIG. 25), a Nunc Maxisorp flat bottom ELISA plate was absorption-coated overnight with bispecific antibody 1 and control antibodies (native human IgG1, native human IgG2, native human IgG4 and Biolegend human IgG1 clone QA16A12) at a concentration of 2 μg/ml (15 nM molecules) in PBS at 4° C. Subsequently, the wells were washed and blocked using START-Block buffer for 1 h at room temperature. Dose titrated C1q (20 μg/mL, 2fold dilution in START-Block buffer) was added to the appropriate wells and incubated at room temperature for 1 h with gentle shaking. This was followed by addition of polyclonal sheep anti-human C1q antibody conjugated to horseradish peroxidase (0.5 μg/mL, 1 h incubation) to detect C1q bound to the coated antibodies. The plate was developed by addition of TMB substrate. The reaction was stopped by the addition of ELISA stop solution and the OD was measured at 492 nm using Envision 2105 multimode plate reader.

The SPR based binding interactions of bispecific antibody 1 and anti-RBD neutralizing antibody (isotype control) with 'low affinity' Fc receptors is shown in FIG. 19-FIG. 23 and the deduced KD values derived from the Langmuir 1:1 binding model (kinetic fit) and steady state affinity model (steady state fit). Both binding models estimate comparable KD values for each studied Fc receptor interaction. The only discrepancy observed was for FcγR3a (176V) binding and is likely due to the heterogeneous quality of the commercial protein as judged by the markedly heterogeneous sensorgrams (FIG. 23), resulting in a poor KD estimate from the kinetic fit. When comparing bispecific antibody 1 to the isotype control, the affinities of all 'low affinity' Fc receptors studied were within 2fold or better. Taken together, the results show that bispecific antibody 1 retains the Fc receptor engagement properties that are characteristic of a human IgG1 and would be expected to function similarly in vivo.

Figure 26:
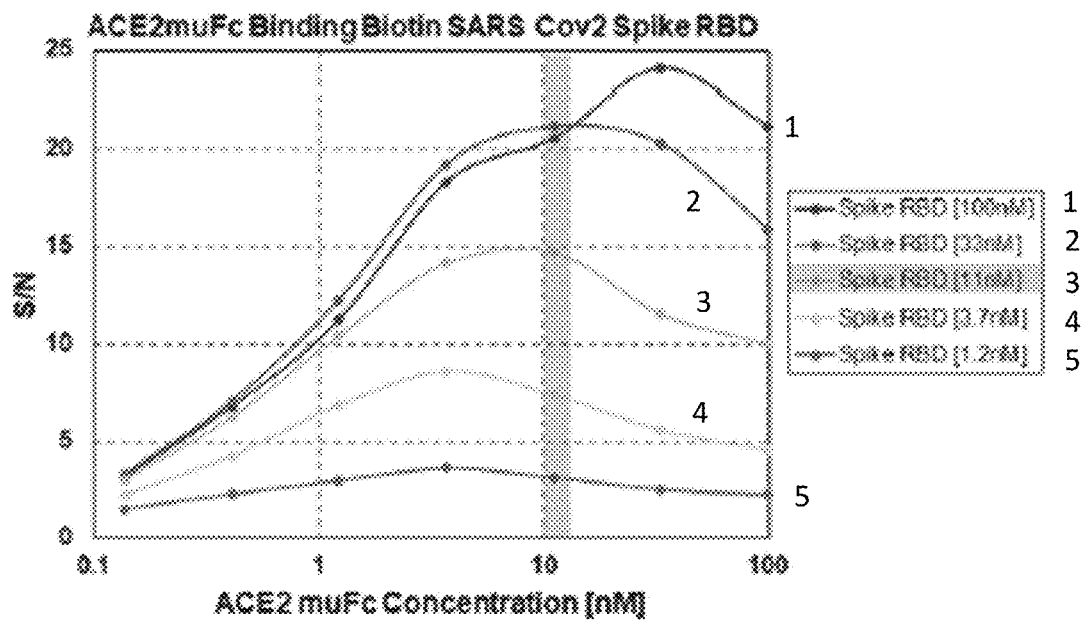
Figure 27:
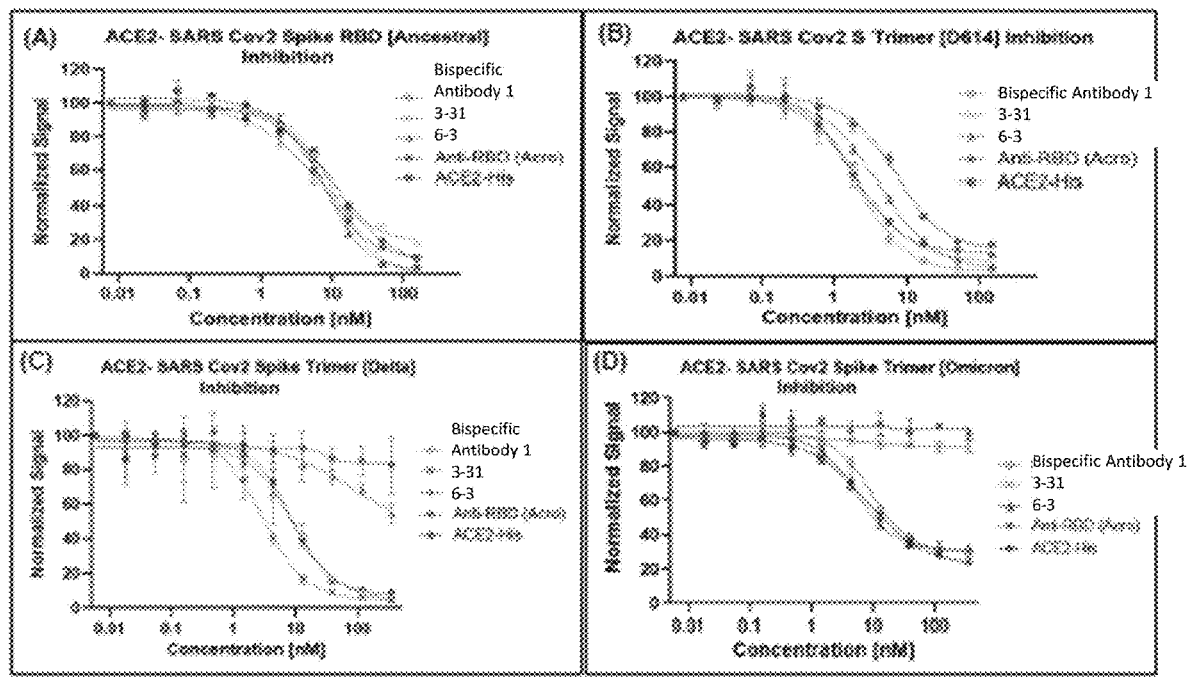
Figure 28A:
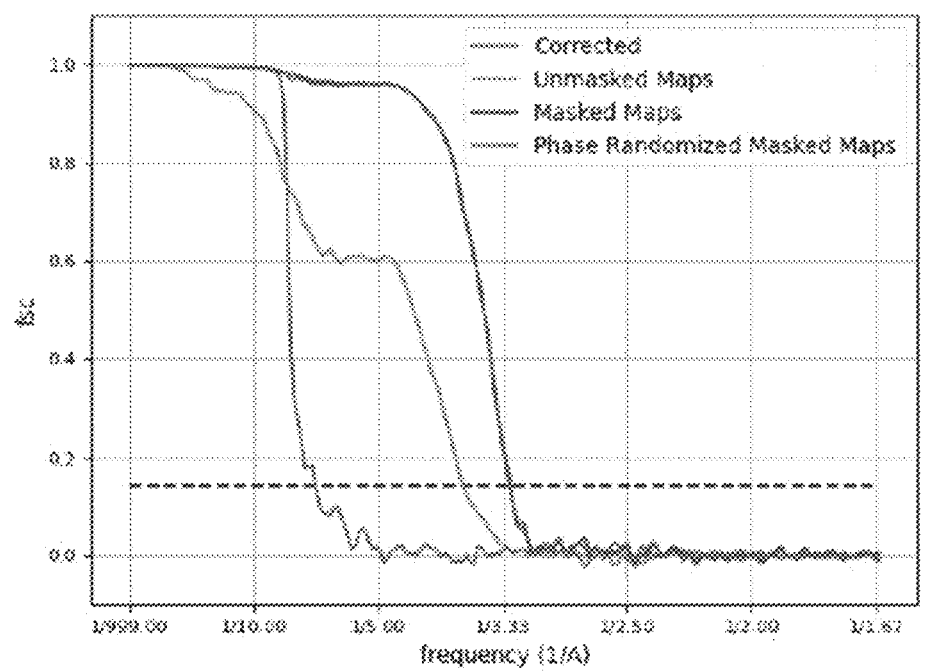
Figure 28B:
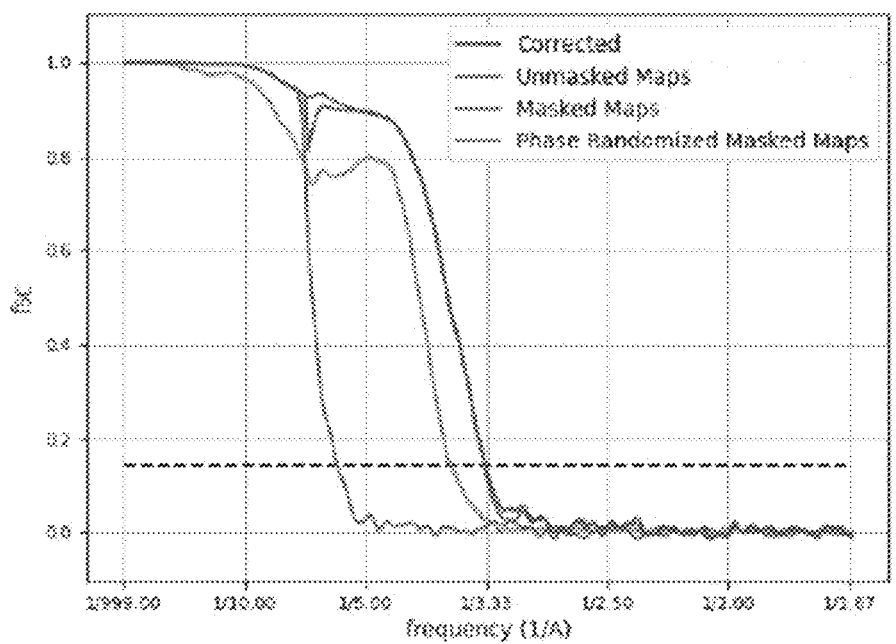
Figure 28C:
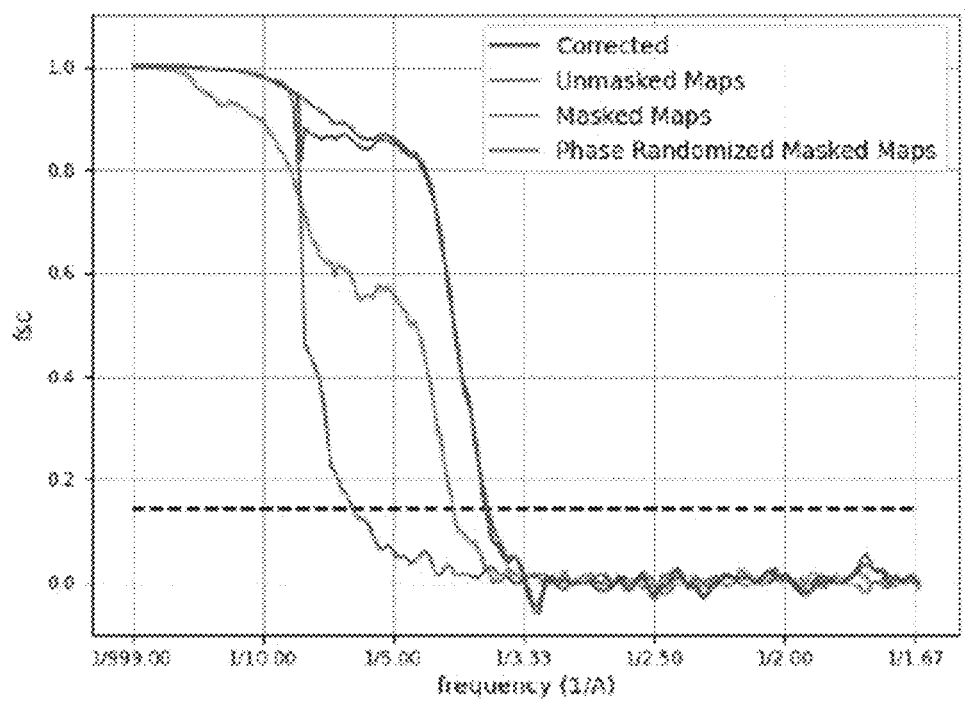
Figure 28D:
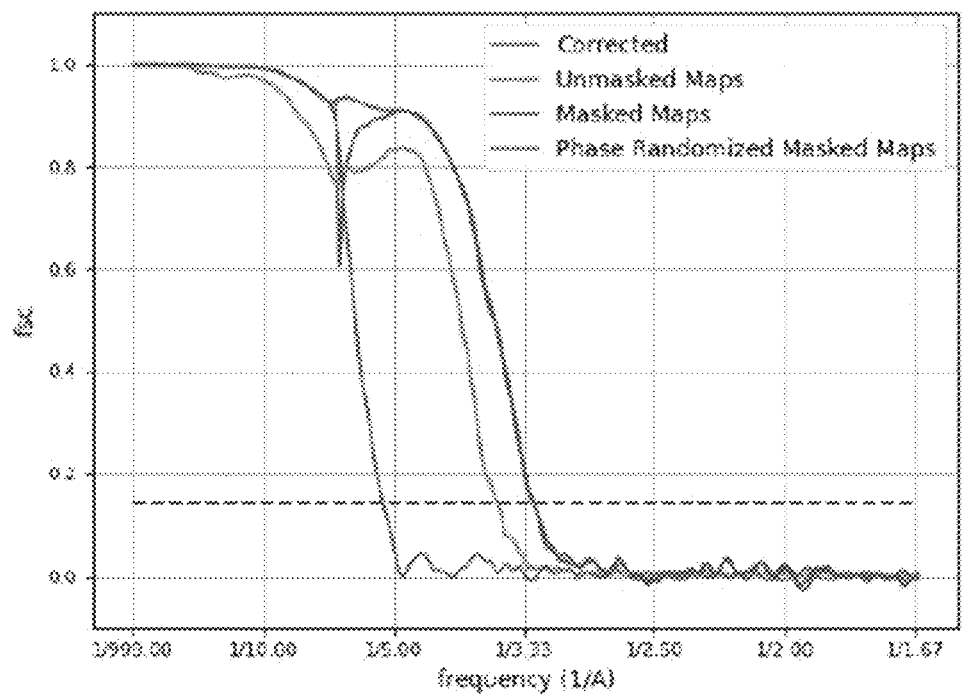
Figure 29A:
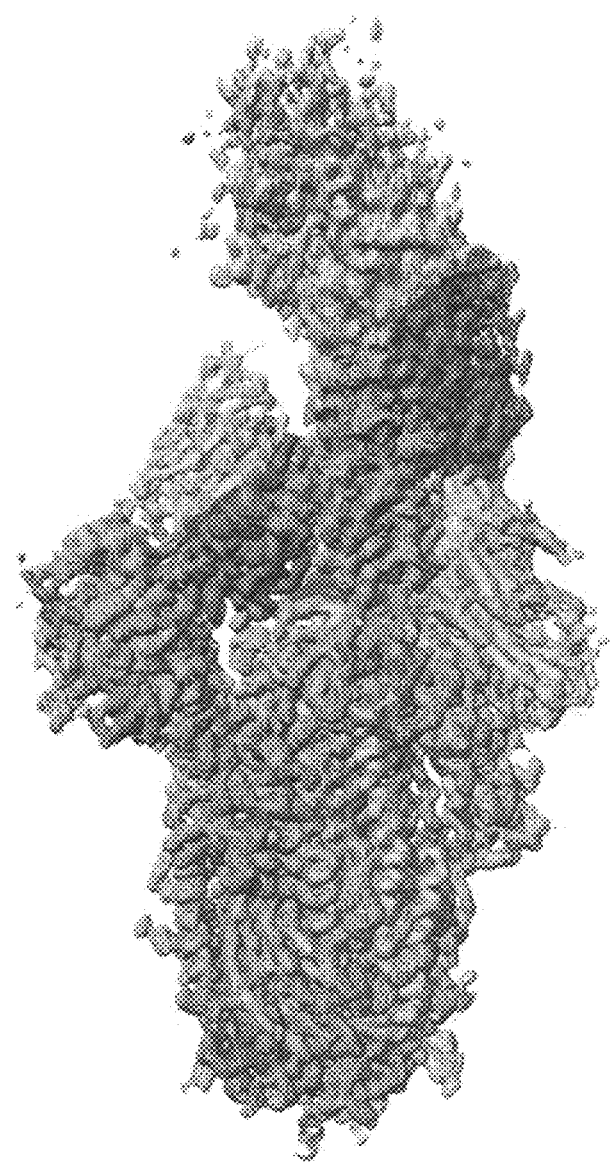
Figure 29B:
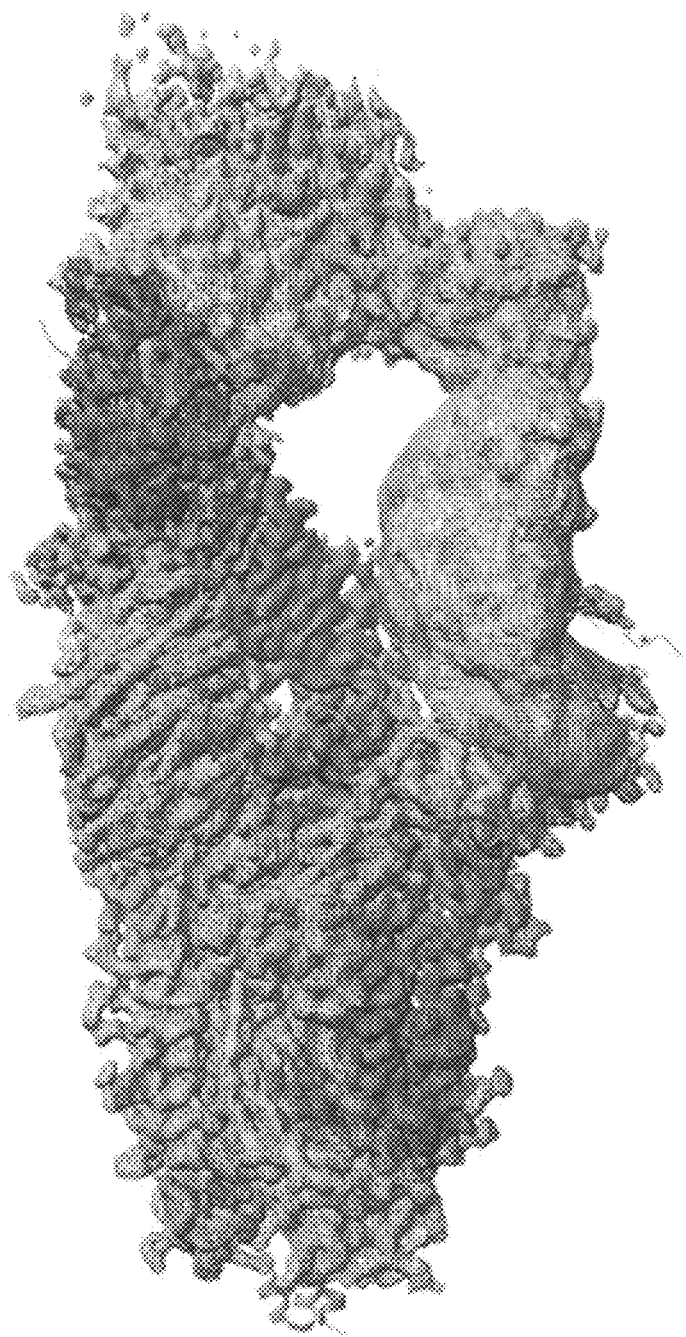
Figure 29C:
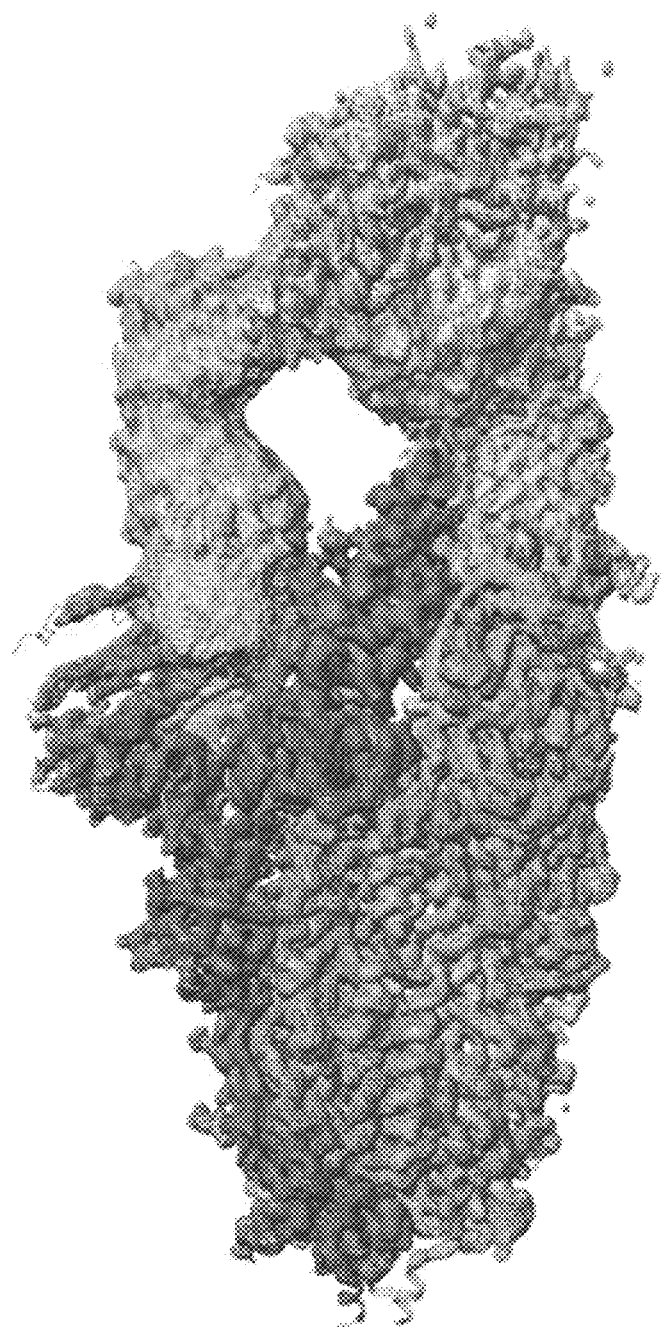
Figure 29D:
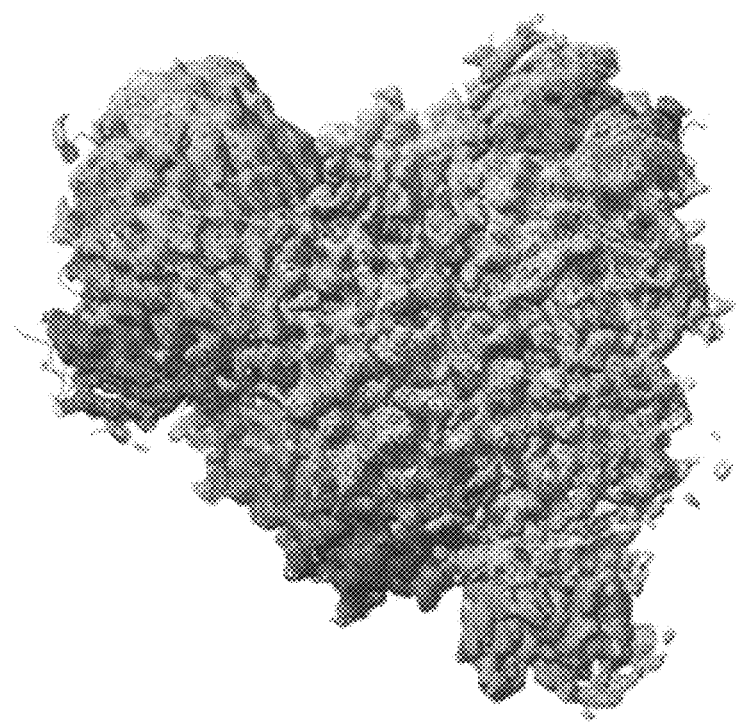

The ability of bispecific antibody 1 to inhibit the binding interaction between ACE2 and various forms of SARS-CoV-2 spike protein was determined quantitatively using AlphaLISA. To develop the assay conditions, the optimal concentrations of ACE2-muFc and biotinylated SARS-CoV-2 spike RBD (Ancestral) for complex formation were determined using a cross-titration experiment in a matrix format (FIG. 26). Based on the results from this experiment, binding of ACE2-muFc (11 nM, highlighted by the vertical bar in the graph) with RBD (11 nM, highlighted in the legend) gave a 20-fold signal-to-noise (S/N) which was considered an optimal binding signal for setting up a subsequent inhibition assay. Similar cross-titration experiments between ACE2-muFc (11 nM) and biotinylated D614G SARS-CoV-2 spike trimer (11 nM) resulted in 30-fold S/N. ACE2-mu Fc (11 nM) binding to SARS-CoV-2 spike trimers for Delta and Omicron (B.1.1.529) variants (33 nM) resulted in 17-fold and 25-fold S/N respectively. These optimized binding conditions were utilized to prepare complexes of ACE2 with different variants of SARS-CoV-2 spike proteins to examine the inhibition of the interaction by RBT-0813, parent VHH-Fc fusions (TB339-031 and TB202-03) and positive controls (Anti-RBD neutralizing antibody and ACE2-His) (FIG. 27).

Bispecific antibody 1 showed comparable potency to the commercially sourced Control anti-RBD neutralizing antibody in inhibition of Ancestral spike RBD and D614G spike trimer. Unlike the Control anti-RBD antibody, bispecific antibody 1 also exhibited inhibition of the interaction of ACE2 to Delta and Omicron spike trimers (FIG. 27) and exhibited similar potency in comparison to ACE2-His (positive control). Parental antibody 6-3 showed weak inhibition of the Delta spike trimer (FIG. 27, Panel C) at high concentrations and TB339-031 showed no inhibition of Omicron spike trimer (FIG. 27, Panel D). In the case of inhibition of the Omicron variant, a residual 30% binding to ACE2 was observed even at the highest concentration of inhibitors (350 nM). This residual binding likely relates to heterogeneous quality of the commercially sourced protein.

Using a variety of in vitro binding assays (SPR, ELISA, and AlphaLISA), bispecific antibody 1 was shown to be a potent ACE2 inhibitor and retains intact Fc functionality consistent with that of a human IgG1 isotype. Bispecific antibody 1 is a potent bispecific inhibitor of SARS-CoV-2 spike recombinant proteins [Ancestral RBD and spike trimer (D614G)] that also inhibits Delta and Omicron variants of the spike trimer, with similar potency as ACE2-His (control). Bispecific antibody 1 showed similar binding to C1q as the human IgG1 isotype control, and will likely activate the complement pathway similarly to a human IgG1. Bispecific antibody 1 also showed similar affinity for interaction with Fcγ receptors and FcRn as the isotype-matched Control anti-RBD neutralizing antibody (human IgG1 Fc). This suggests that bispecific antibody 1 is likely to exhibit similar in vivo activity in terms of Fc effector function and exhibit the long serum half-life (via the FcRn recycle/rescue pathway) characteristic of a human IgG1.

Example 3: Bispecific Antibody 1 CryoEM Analysis

CryoEM analysis was performed on Bispecific Antibody 1 to determine its structural features.

Collected movies were subjected to a motion search algorithm and both motion-corrected and motion-corrected and dose-weighted micrographs were produced. Motion corrected-micrographs without dose-weighting were used for defocus estimation, while motion-corrected and dose-weighted micrographs were used for further processing. (FIGS. 28A-28D).

Particle picking was performed on denoised micrographs using deep learning-based approaches, selecting slightly over 7M potential particles. These potential particles were split into 71 sets of about 100k particles each and each set was subjected to a "cleaning" 3D classification against a spike-only (i.e. without antibody) initial model created earlier in the screening phase of the project, leaving about 1.4M particles showing clear antibody density. These particles were then split into 6 sets, each about 233k particles and each set was further subjected to two rounds of 2D classification (one standard, one suppressing low frequency CTF correction) to create a clean set of 588k particles. A first unmasked consensus refinement was performed on this set, yielding a 3.5 Å map of the spike with strong densities for VHH in position 1 (VHH1) and VHH in position 2 (VHH2) and weak density for VHH in position 3 (VHH3). Following this initial refinement up with bayesian polishing and per-particle defocus refinement improved the resolution to 3.2 Å. This map is referred to as an "initial consensus map".

Using the "initial consensus map", a masked 3D classification to 2 classes with local searches was performed, where the mask encapsulated the locations of VHH1 and VHH2 and their respective RBDs. This classification separated remaining unbound spike particles (class 1) and particles with strong VHH1 and VHH2 densities (class 2). This class 2, containing 348k particles, was then used for a masked 3D refinement with local searches, producing the 3.4 Å map used to build the majority of the VHH1 epitope/paratope. Since the density for VHH2 was still suboptimal, additional masked 3D refinement with local searches was performed but with mask specifically only around VHH2 and its corresponding RBD up location. This refinement produced the 3.3 Å map used to build the VHH2 epitope/paratope.

The VHH3 was clearly visible in the "initial consensus map" but too weak to interpret correctly. Thus the "initial consensus map" was used as a basis for no-align 3D classification to 6 classes. This 3D classification revealed 4 classes that represented either unbound, all RBD down spike or spike with very weak density at VHH position 3 and 2 classes with a stronger density around the VHH position 3. These 2 classes, comprising 274k particles, were then combined and subjected to an unmasked 3D refinement that yielded the 3.3 Å map referred to as the "global consensus map". Upon convergence, however, the density for the VHH3, was already misaligned due to the presence of the spike body. Indeed, 3.3 Å represents the resolution of the spike body, not the true resolution of the VHH3 part of the map. Most reliable fitting of the VHH3 density could be done using map from iteration 8 of this global consensus refinement, which yielded the 6 Å map used to assign the position of VHH3. Further attempts at improving the density of VHH3 using similar approaches as those used for VHH1 and VHH2 did not bring any improvement. The most likely reason being that while VHH1 and VHH2 are rigidly bound to their respective RBD domains, VHH3 appears to be only flexibly bound to its RBD domain and the mass of VHH3 itself is too small to refine properly on its own.

Finally, the "global consensus map" was used as a basis for multi-body refinement that encapsulated VHH1 and parts of its surrounding RBD domain and especially the N-term domain of the neighboring B chain as one body (with spike core being the second body). This multi-body refinement yielded the 3.7 Å map that resolved the N-term interface well and which was used to build the N-term B chain epitope of VHH in position 1.

Initially, pdb:6x2b was used to rigid-body fit the map densities. Afterwards, all relevant residues were manually remodeled to correspond to the map density. The sequence of 6x2b was corrected to include all the amino acids present in the spike construct, which also aligned it such that the amino acids numbers correspond to the provided mutagenesis numbering. The model building then proceeded iteratively combining restrained molecular dynamics with manual intervention to build stereochemically valid models with best possible correspondence to the density. Similar approach was adopted for building the VHH models, only here AlphaFold2 predictions of the N-term and C-term VHH domains of the bispecific construct were used as a starting point for the rigid body fitting and subsequent manual/molecular dynamics remodeling.

The structure reconstruction revealed densities for three out of the four VHHs present on the bispecific antibody, as well as a density corresponding to the constant fragment. The location or presence of the fourth VHH could not be confirmed. (FIGS. 29A-29D).

Two of the revealed VHHs are confirmed to be the N-terminal VHHs and are bound to RBD down (position 1) and an RBD up domain (position 2). Identity of the third one could not be confirmed directly but stoichiometry of the bispecific antibody, connection with the constant fragment, and expected binding site all suggest it is the C-terminal VHH of the same bispecific antibody.

The two N-terminal VHHs are bound to RBDs in different positions. Their epitopes do overlap to a large extent but are not completely identical. Specifically (but not only) VHH in position 1 also interacts with neighboring chain B via the chain's N-terminal domain. This interaction is not present in VHH in position 2 epitope and the epitope in position 2 is limited solely to the respective RBD on chain B. The small change in the epitope/paratope between position 1 and 2 also suggests that the N-term VHH tolerates change/loss of several of its interface residues without losing capacity to bind.

The epitope of the third VHH bound to the second RBD up domain could not be determined in detail but the general position of the VHH with respect to the RBD suggests it is different from VHH1 and 2 and possibly agrees with the mutagenesis studies.

To determine the interacting epitope/paratope, three complementary strategies were used. In one strategy, neighboring spike/VHH residues were manually inspected during model building, in the second approach residues were automatically verified using computational methods, which analyze residue interfacing based on solvent-accessible area, buried surface area, and solvation energy and in the third one residues were simply taken within 5 Å distance. The first two methods were used interchangeably, i.e. automatically determined residues were manually inspected for further undetected interactions and vice versa, manual residues were compared to the automatic list and if not present there, they were further examined in detail to confirm the interaction. Residues 450 and 490 were found to directly interact with the VHH. Residue 472 does not directly interact with the VHH but possibly serves as a stabilizer of interacting RBD loops, thereby contributing to the VHH/RBD interaction indirectly. (FIGS. 30-35, FIGS. 38-43, and FIG. 46).

Residue 490 is one of the important residues described as spike:VHH interacting residue. Residue 354 is possibly spike:VHH interacting residue. The other residues are far away from the spike: VHH interface and therefore cannot be confirmed as any interaction with VHH. In the case of residues 275, 685 these are not even included in the spike: VHH model. (FIGS. 36-37 and FIGS. 44-45).

The resolution of density around VHH3 (around 6 Å) was not detailed enough to allow for epitope/paratope mapping. Nevertheless the density correlation and interaction with the constant fragment allowed for an approximate assignment of its position and orientation. Also, the stoichiometry of the entire bispecific antibody complex, the putative location of the VHH N-term epitope, its distinctly different position with respect to the RBD domain, and its strong connection to the constant fragment in direction of VHH2, all suggest it is indeed the C-term VHH of the bispecific construct. (FIGS. 47A-47B).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A bispecific antibody or an antibody fragment thereof, comprising at least two binding domains to a spike glycoprotein or a receptor of the spike glycoprotein:

a first binding domain of the at least two binding domains comprising a first variable domain, heavy chain region (VH), wherein the first VH region comprises complementarity determining regions CDRH1, CDRH2, and CDRH3, and wherein (i) an amino acid sequence of CDRH1 is as set forth in SEQ ID NO: 1; (ii) an amino acid sequence of CDRH2 is as set forth in SEQ ID NO: 2; and (iii) an amino acid sequence of CDRH3 as set forth in SEQ ID NO: 3; and a second binding domain of the at least two binding domains comprising a first variable domain, heavy chain region (VH), wherein the first VH region comprises complementarity determining regions CDRH1, CDRH2, and CDRH3, and wherein (i) an amino acid sequence of CDRH1 is as set forth in SEQ ID NO: 4; (ii) an amino acid sequence of CDRH2 is as set forth in SEQ ID NO: 5; and (iii) an amino acid sequence of CDRH3 as set forth in SEQ ID NO: 6.

2. The bispecific antibody of claim 1, wherein the bispecific antibody is bivalent, trivalent, or tetravalent.

3. The bispecific antibody of claim 1, wherein the bispecific antibody is bivalent.

4. The bispecific antibody of claim 1, wherein the bispecific antibody is tetravalent.

5. The bispecific antibody of claim 1, wherein the bispecific antibody or antibody fragment thereof comprises a KD of less than 50 nM.

6. The bispecific antibody of claim 1, wherein the bispecific antibody or antibody fragment thereof comprises a KD of less than 25 nM.

* * * * *